United States Patent
Joung et al.

(10) Patent No.: US 11,041,155 B2
(45) Date of Patent: Jun. 22, 2021

(54) CCCTC-BINDING FACTOR VARIANTS

(71) Applicant: The General Hospital Corporation, Boston, MA (US)

(72) Inventors: J. Keith Joung, Winchester, MA (US); Rebecca Tayler Cottman, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 61 days.

(21) Appl. No.: 16/415,989

(22) Filed: May 17, 2019

(65) Prior Publication Data
US 2019/0382767 A1   Dec. 19, 2019

Related U.S. Application Data

(60) Provisional application No. 62/828,277, filed on Apr. 2, 2019, provisional application No. 62/672,682, filed on May 17, 2018.

(51) Int. Cl.
| C12N 15/113 | (2010.01) |
| C12N 15/63 | (2006.01) |
| C12N 15/10 | (2006.01) |

(52) U.S. Cl.
CPC ...... *C12N 15/1135* (2013.01); *C12N 15/1044* (2013.01); *C12N 15/63* (2013.01)

(58) Field of Classification Search
None
See application file for complete search history.

(56) References Cited

U.S. PATENT DOCUMENTS

| 2006/0246440 A1* | 11/2006 | Joung ............... C07K 14/4702 435/6.12 |
| 2007/0213269 A1 | 10/2007 | Barbas et al. |
| 2011/0294873 A1 | 12/2011 | Mermod et al. |
| 2012/0115227 A1 | 5/2012 | Cohen-Haguenauer et al. |
| 2012/0178647 A1* | 7/2012 | Joung ............... C12N 15/1093 506/9 |
| 2016/0215280 A1 | 7/2016 | Fanucchi et al. |
| 2017/0175136 A1 | 6/2017 | Stamatoyannopoulos et al. |

FOREIGN PATENT DOCUMENTS

WO   WO 2017/031370   2/2017

OTHER PUBLICATIONS

Filippova et al., Tumor-associated Zinc Finger Mutations in the CTCF Transcription Factor Selectively Alter Its DNA-binding Specificity. Cancer Research 62, 48-52, Jan. 1, 2002 (Year: 2002).*

Filippova et al., An Exceptionally Conserved Transcriptional Repressor, CTCF, Employs Different Combinations of Zinc Fingers to Bind Diverged Promoter Sequences of Avian and Mammalian c-myc Oncogenes. Molecular and Cellular Biology, Jun. 1996, vol. 16, p. 2802-2813 (Year: 1996).*

(Continued)

*Primary Examiner* — Arthur S Leonard
(74) *Attorney, Agent, or Firm* — Fish & Richardson P.C.

(57) ABSTRACT

Described herein are engineered CCCTC-binding factor (CTCF) variants that can bind to mutant CTCF binding sequences and method of using the same.

6 Claims, 46 Drawing Sheets

Specification includes a Sequence Listing.

(56) References Cited

OTHER PUBLICATIONS

Hurt et al., Highly specific zinc finger proteins obtained by directed domain shuffling and cell-based selection. Proc Natl Acad Sci U S A. Oct. 14, 2003;100(21):12271-6 (Year: 2003).*
Guo et al., CTCF/cohesin-mediated DNA looping is required for protocadherin a promoter choice. PNAS Dec. 18, 2012 109 (51) 21081-21086 (Year: 2012).*
Ali et al, "Insulators and domains of gene expression," Curr. Opin. Genet. Dev., 2016, 37:17-26.
Guo et al, "Mutation hotspots at CTCF binding sites coupled to chromosomal instability in gastrointestinal cancers," Nat. Commun., 2018, 18;9(1):1520.
Han et al, "CTCF participates in DNA damage response via poly(ADP-ribosyl) ation ," Sci Rep., 2017, 6;7:43530.
Hashimoto et al, "Structural basis for the versatile and methylation-dependent binding of CTCF to DNA," Mol. Cell., 2017, 1;66(5):711-720.e3.
Hilmi et al, "CTCF facilitates DNA double-strand break repair by enhancing homologous recombination repair," Sci. Adv., 2017, 24;3(5):e1601898.
Joung et al, "A bacterial two-hybrid selection system for studying protein—DNA and protein—protein interactions," Proc. Natl. Acad. Sci. USA, 2000, 20;97(13):7382-7387.
Kang et al, "Disruption of CTCF/cohesin-mediated high-order chromatin structures by DNA methylation downregulates PTGS2 expression ," Oncogene, 2015, 5;34(45):5677-84.
Maeder et al, "Rapid "open-source" engineering of customized zinc-finger nucleases for highly efficient gene modification," Mol. Cell., 2008, ;31(2):294-301.
Nakahashi et al, "A Genome-wide Map of CTCF Multivalency Redefines the CTCF Code," Cell Rep., 2013, 30;3(5):1678-1689.
Nora et al, "Spatial partitioning of the regulatory landscape of the X-inactivation centre," Nature, 2012, 11;485(7398):381-5.
Ong & Corces, "CTCF: an architectural protein bridging genome topology and function," Nat. Rev. Genet., 2014, 15(4):234-46.
Phillip-Cremins et al, "Architectural protein subclasses shape 3D organization of genomes during lineage commitment," Cell, 2013, 153(6): 1281-1295.
Phillips & Corces, "CTCF: master weaver of the genome," Cell, 2009, 26:137(7): 1194-1211.
Rao et al, "A 3D map of the human genome at kilobase resolution reveals principles of chromatin looping," Cell, 2014, 159(7):1665-1680.
Rhee & Pugh, "Comprehensive genome-wide protein-DNA interactions detected at single-nucleotide resolution," Cell, 2011, 9;147(6):1408-1419.
Sander et al, "Selection-Free Zinc-Finger Nuclease Engineering by Context-Dependent Assembly (CoDA)," Nat Methods. Jan. 2011;8(1):67-9.
Schuijers et al, "Transcriptional Dysregulation of MYC Reveals Common Enhancer-Docking Mechanism," Cell Reports, 2018, 10;23(2):349-360.
Shukla et al, "CTCF-promoted RNA polymerase II pausing links DN Amethylation to splicing," Nature, 2011, 3;479(7371):74-79.
Wright et al, "Standardized reagents and protocols for engineering zinc finger nucleases by modular assembly," Nat Protoc., 2006, 1(3):1637-52.
Li et al., "Identification of critical base pairs required for CTCF binding in motif M1 and M2," Protein & Cell, Mar. 2017, 8(7):544-549.
PCT International Search Report and Written Opinion in International Appln. No. PCT/US2019/032937, dated Oct. 17, 2019, 17 pages.

* cited by examiner

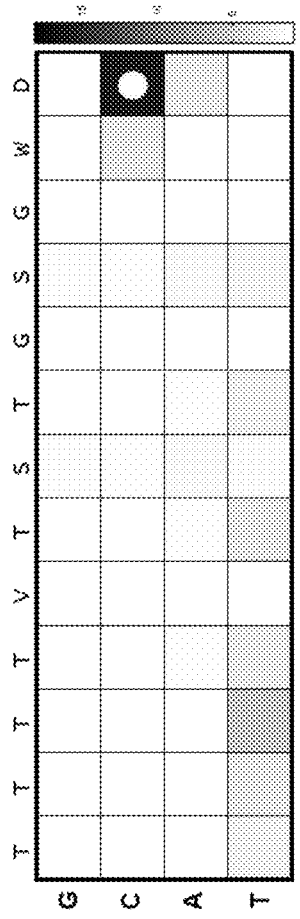
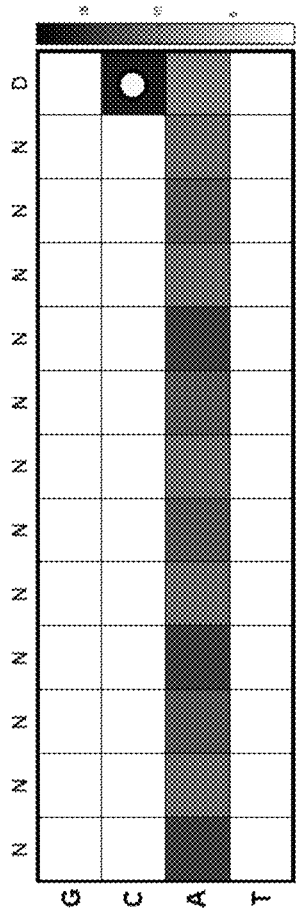
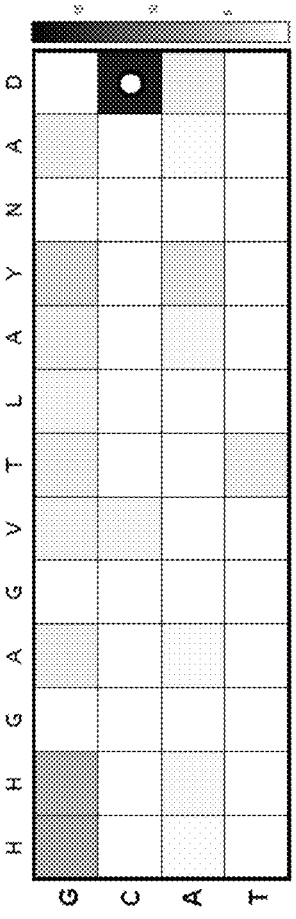
FIG. 7A
FIG. 7B
FIG. 7C
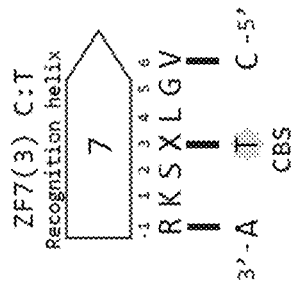
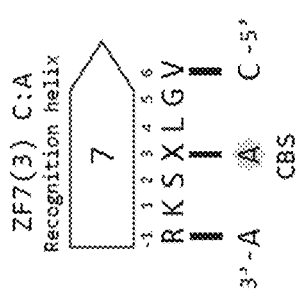
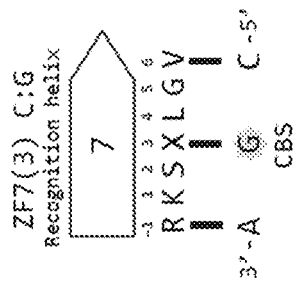

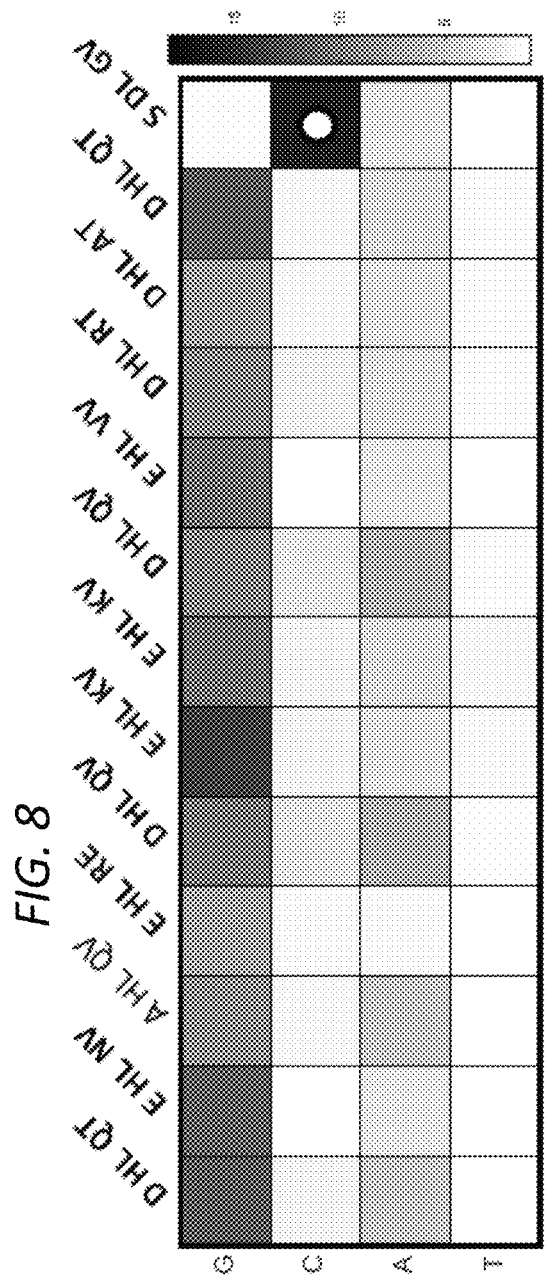
FIG. 8
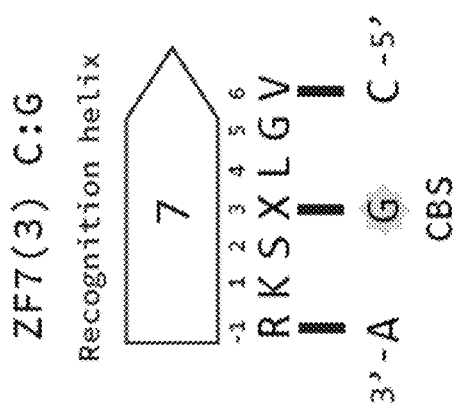

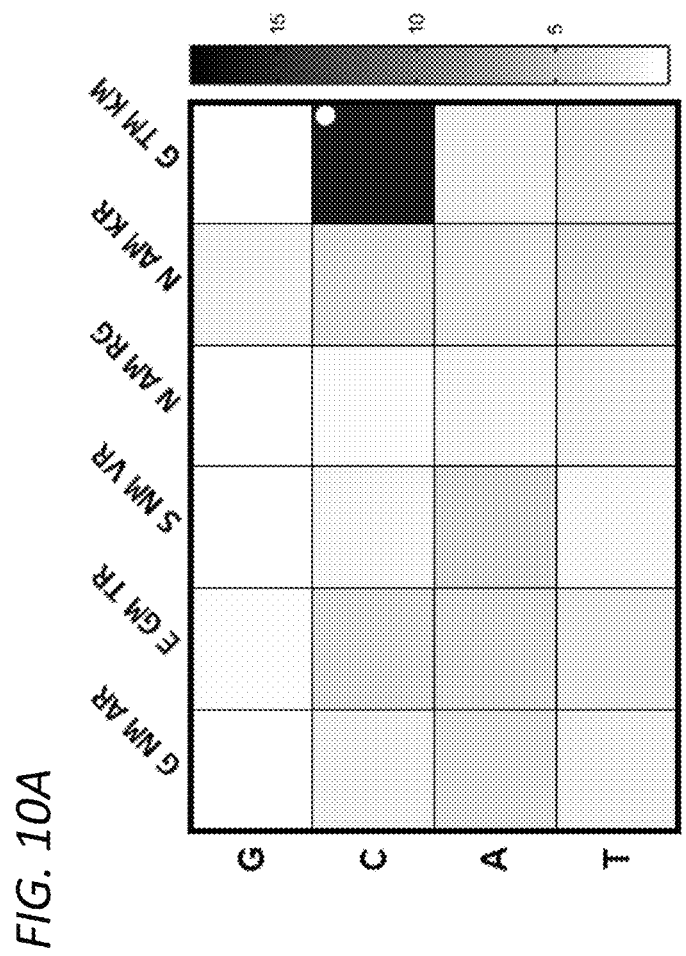
FIG. 10A
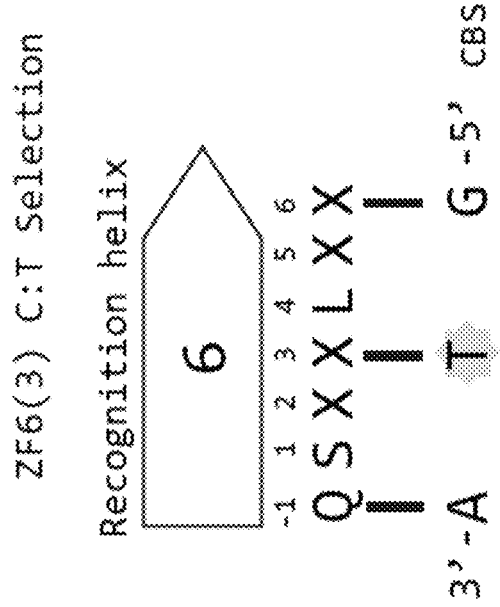

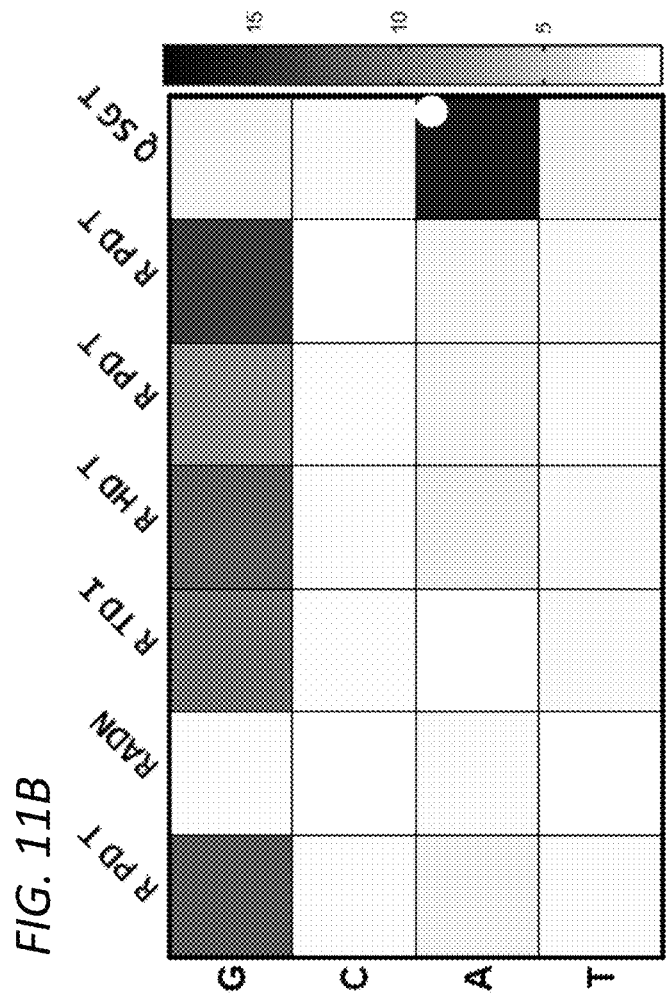
*FIG. 11B*
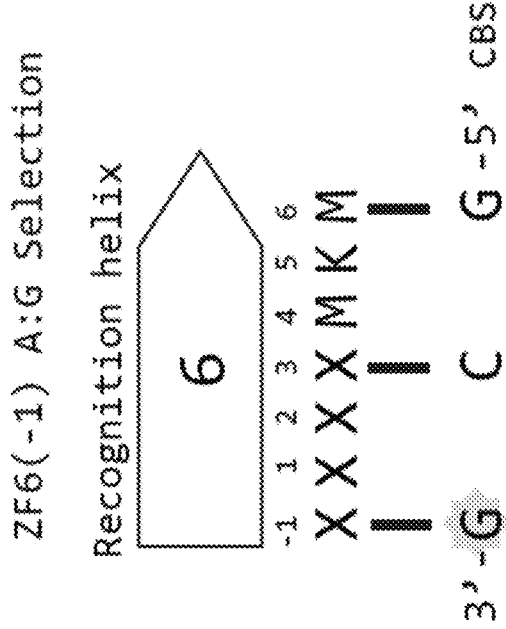

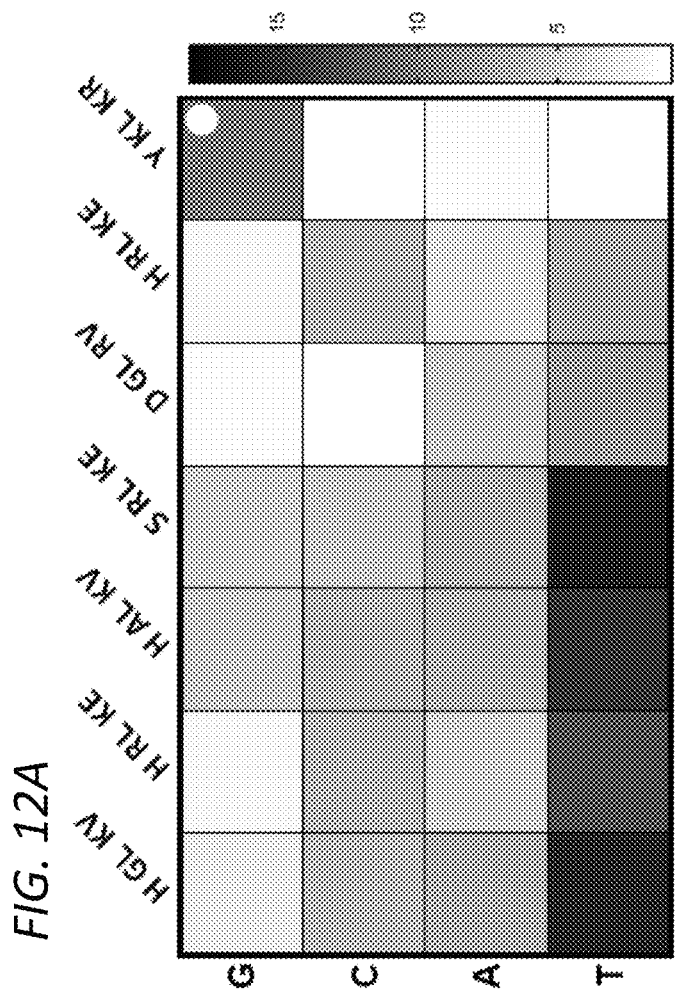
FIG. 12A
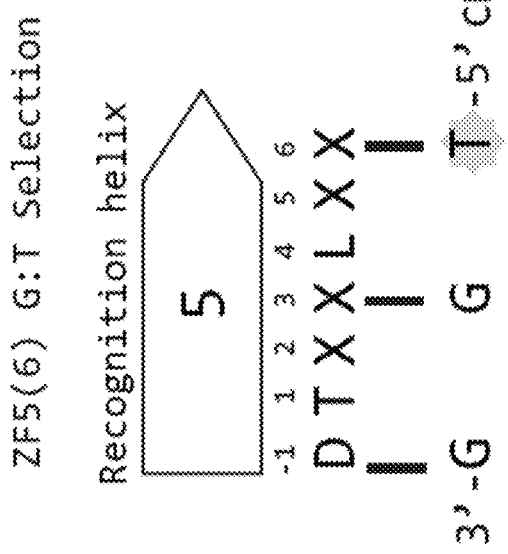

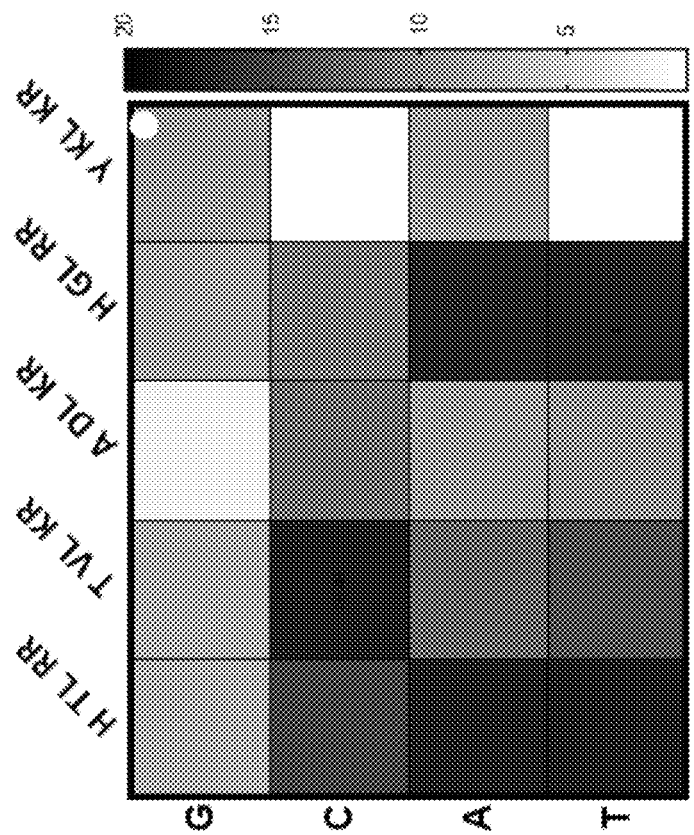
FIG. 13C
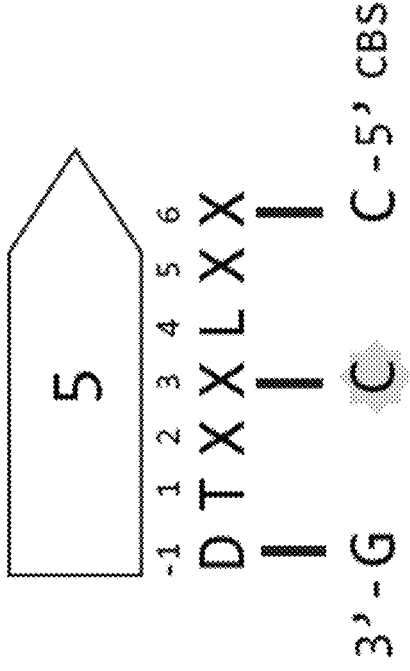

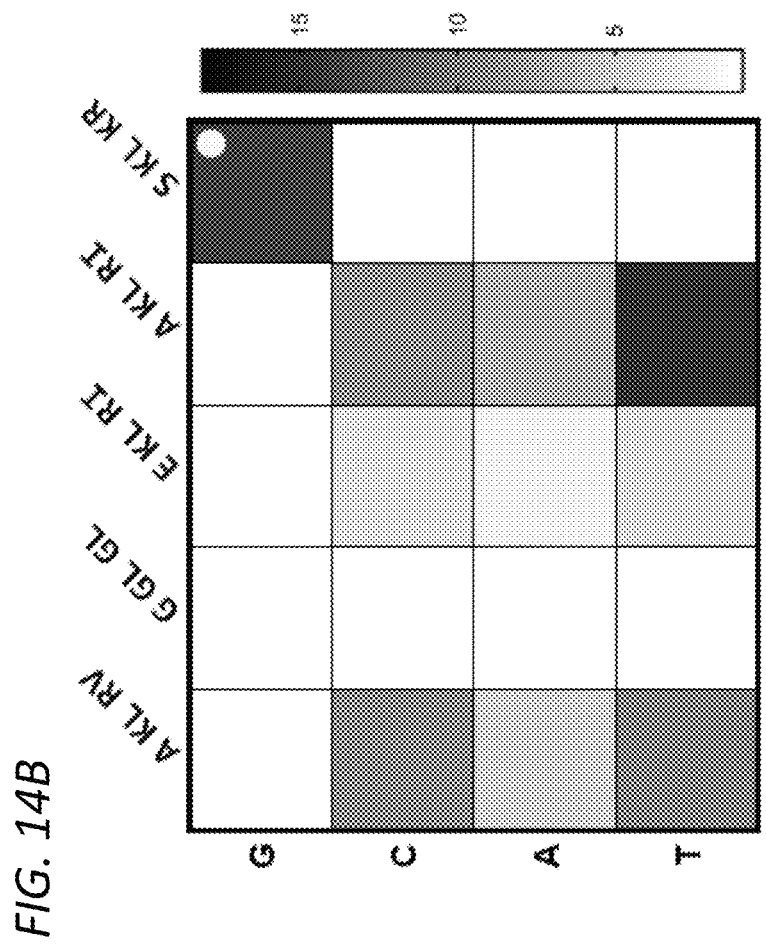
FIG. 14B
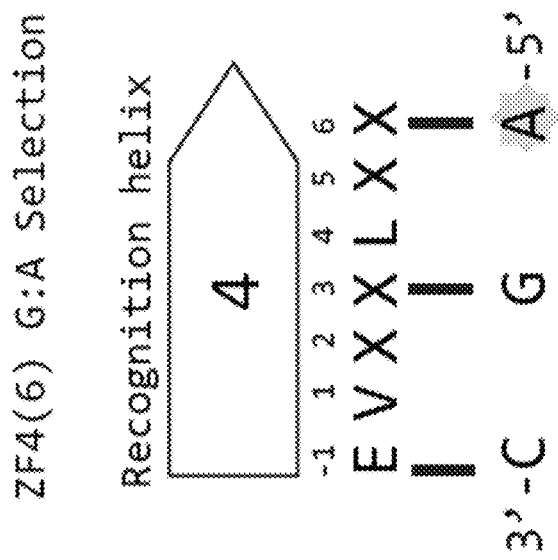

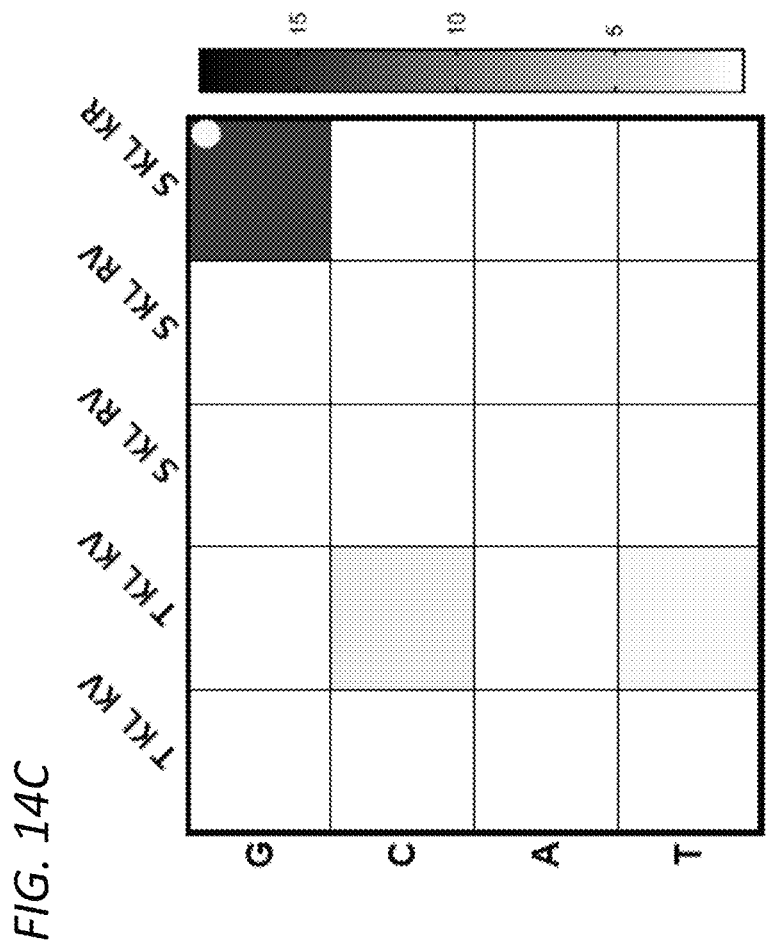
FIG. 14C
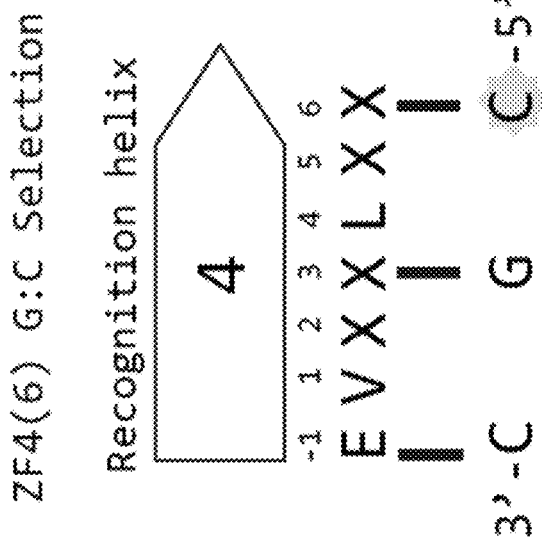

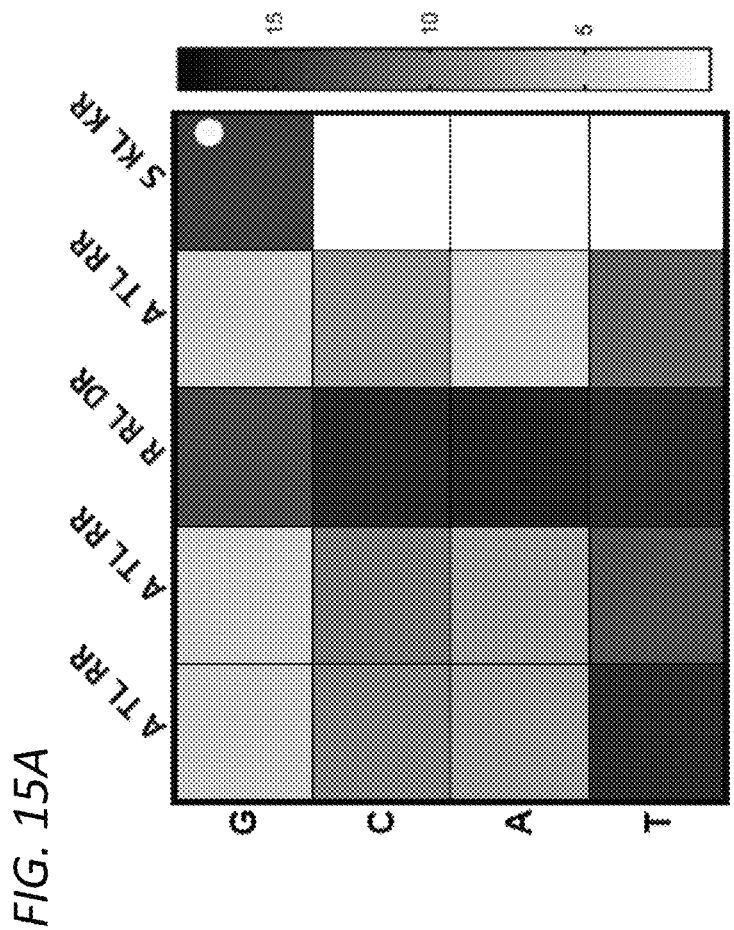
FIG. 15A
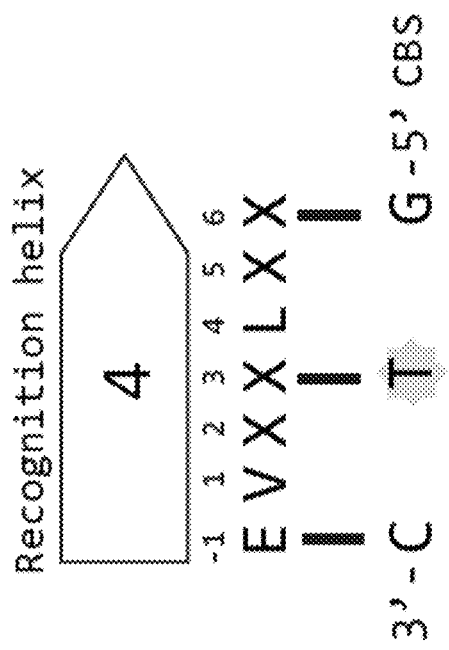

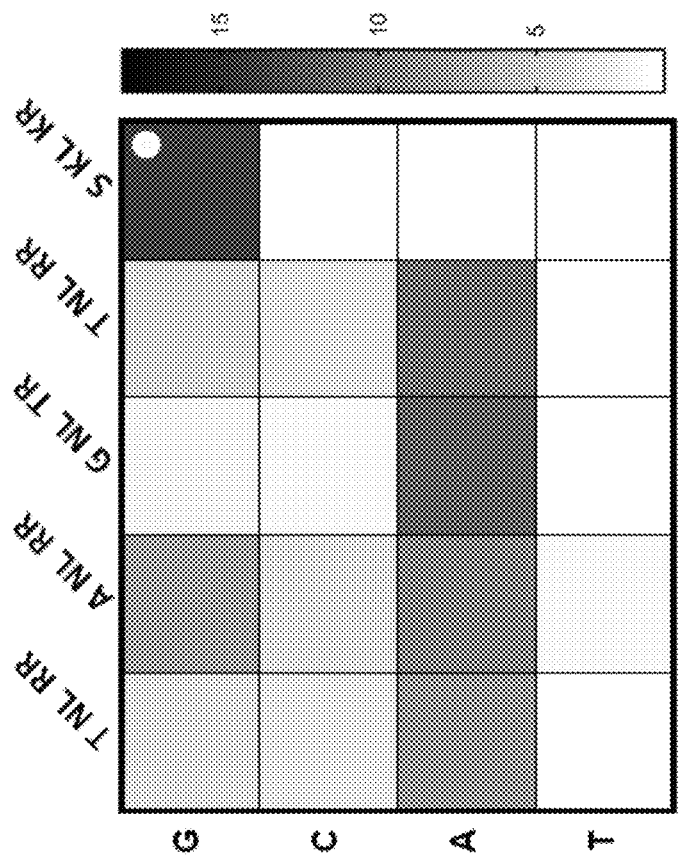
*FIG. 15B*
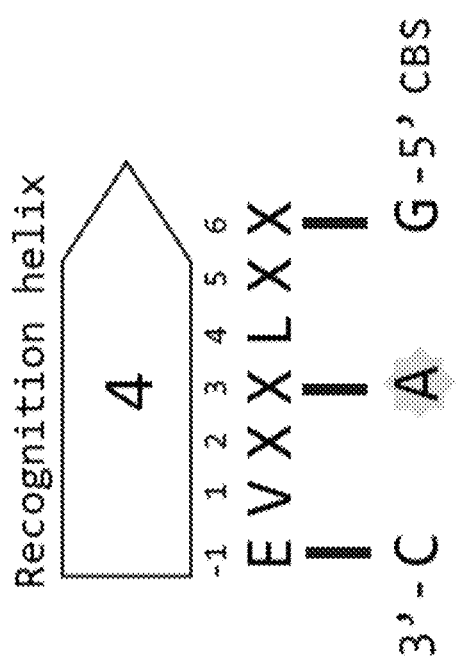

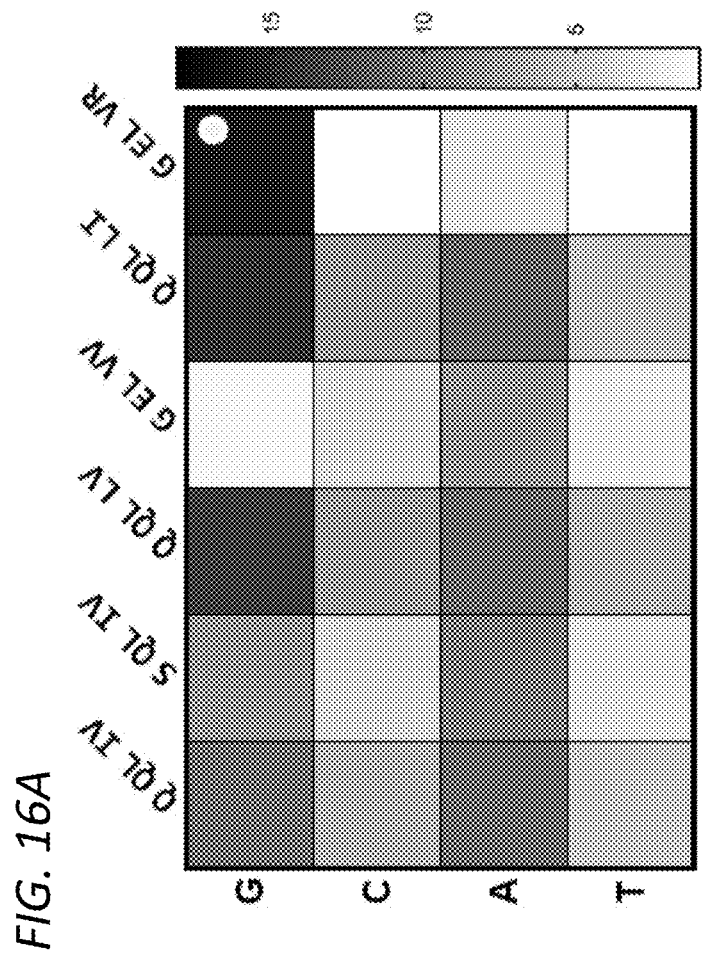
FIG. 16A
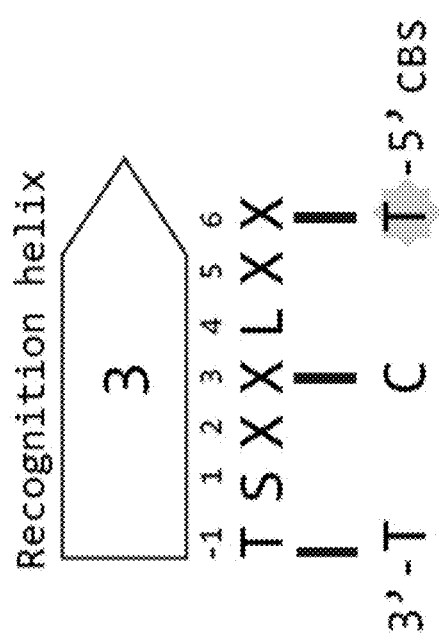

US 11,041,155 B2

CCCTC-BINDING FACTOR VARIANTS

CLAIM OF PRIORITY

This application claims the benefit of U.S. Provisional Patent Application Ser. No. 62/672,682, filed on May 17, 2018 and U.S. Provisional Patent Application Ser. No. 62/828,277, filed on Apr. 2, 2019. The entire contents of the foregoing are hereby incorporated by reference.

FEDERALLY SPONSORED RESEARCH OR DEVELOPMENT

This invention was made with Government support under Grant No. GM118158 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 20, 2019, is named 29539-0339WO1 SL.txt and is 1,104,397 bytes in size.

TECHNICAL FIELD

The invention relates, at least in part, to engineered CCCTC-binding factor variants with altered DNA-binding specificities.

BACKGROUND

CCCTC-binding factor (CTCF) is a multi-domain protein that acts as an essential genome organizer by maintaining higher-order chromatin structure while also having a role in cell differentiation and the promotion or repression of gene expression (Ong and Corces, Nature Reviews Genetics (2014); Phillips and Corces, Cell (2009)). CTCF maintains topologically associated domains (TADs) spanning MBs of the genome as well as smaller scale Sub-TADs leading to fine-tuned gene insulation or gene activation within gene clusters (Ali et al., Current Opinion in Genetics & Development (2016); Nora et al., Nature (2012); Rao et al., Cell (2014)). In addition, CTCF has been found to regulate mRNA splicing by influencing the rate of transcription and more recently been implicated in promoting homologous recombination repair at double-strand breaks (Shukla et al., Nature (2011); Hilmi et al., Science Advances (2017); Han et al., Scientific Reports (2016)). CTCF binds throughout the genome via an 11 finger zinc finger (ZF) array that recognizes CTCF binding sites (CBSs). The CBS is typically 40 bp in length with a highly conserved 15 bp core sequence.

SUMMARY

The present invention is based, at least in part, on the development of engineered CTCF variants that can bind to mutant CBSs with higher affinity than a wild-type CTCF.

The present invention relates to an engineered CCCTC-binding factor (CTCF) variant including at least one amino acid residue in at least one zinc finger that differs in sequence from the amino acid sequence of a wild-type CTCF, where the engineered CTCF variant binds to a mutant CTCF binding sequence (CBS) with a higher affinity than wild-type CTCF, the mutant CBS including at least one nucleotide base that differs in sequence from the nucleotide sequence of a consensus CBS, where the at least one amino acid residue that differs in sequence from the amino acid sequence of a wild-type CTCF is selected from the group consisting of the amino acid residues at the position(s) −1, +1, +2, +3, +5, and +6 of any of ZF7, ZF6, ZF5, ZF4, and ZF3 of the engineered CTCF variant.

In some embodiments, the engineered CTCF variant binds with a higher affinity than a wild-type CTCF to a mutant CTCF binding sequence (CBS) that has a Thymine (T), Adenine (A), or Guanine (G) residue at position 2 of the consensus CBS motif, the engineered CTCF including an amino acid residue threonine, asparagine, or histidine at ZF7 position +3.

In some embodiments, the engineered CTCF variant binds with a higher affinity than a wild-type CTCF to a mutant CBS that has a G residue at position 2 of the consensus CBS motif, the engineered CTCF including the amino acid sequence DHLQT (SEQ ID NO: 8), EHLNV (SEQ ID NO: 9), AHLQV (SEQ ID NO: 10), EHLRE (SEQ ID NO: 11), DHLQV (SEQ ID NO: 12), EHLKV (SEQ ID NO: 13), EHLVV (SEQ ID NO: 15), DHLRT (SEQ ID NO: 16), or DHLAT (SEQ ID NO: 17) at ZF7 positions +2 to +6.

In some embodiments, the engineered CTCF variant binds with a higher affinity than a wild-type CTCF to a mutant CBS that has a T, G, or C residue at position 3 of the consensus CBS motif, the engineered CTCF at ZF7 positions −1 to +3 including: the amino acid sequence RKHD (SEQ ID NO: 173) or RRSD (SEQ ID NO: 174), where the mutant CBS has a T residue at position 3 of the consensus CBS motif; the amino acid sequence RKAD (SEQ ID NO: 175), IPRI (SEQ ID NO: 176), RKHD (SEQ ID NO: 173), or RKDD (SEQ ID NO: 177), where the mutant CBS has a G residue at position 3 of the consensus CBS motif; or the amino acid sequence GIVN (SEQ ID NO: 178), ELLN (SEQ ID NO: 179), QALL (SEQ ID NO: 180) or PHRM (SEQ ID NO: 181), where the mutant CBS has a C residue at position 3 of the consensus CBS motif.

In some embodiments, the engineered CTCF variant binds with a higher affinity than a wild-type CTCF to a mutant CBS that has a T, G, or A residue at position 5 of the consensus CBS motif, the engineered CTCF at ZF6 positions +2 to +6 including: the amino acid sequence NAMKR (SEQ ID NO: 30), GNMAR (SEQ ID NO: 182), EGMTR (SEQ ID NO: 183), SNMVR (SEQ ID NO: 184), or NAMRG (SEQ ID NO: 185), where the mutant CBS has a T residue at position 5 of the consensus CBS motif; or the amino acid sequence EHMGR (SEQ ID NO: 31), DHMNR (SEQ ID NO: 32), THMKR (SEQ ID NO: 33), EHMRR (SEQ ID NO: 34), or THMNR (SEQ ID NO: 35), where the mutant CBS has a G residue at position 5 of the consensus CBS motif.

In some embodiments, the engineered CTCF variant binds with a higher affinity than a wild-type CTCF to a mutant CBS that has a T, G, or C residue at position 6 of the consensus CBS motif, the engineered CTCF at ZF6 positions −1 to +3 including: the amino acid sequence MNES (SEQ ID NO: 36) or HRES (SEQ ID NO: 37), where the mutant CBS has a T residue at position 6 of the consensus CBS motif; or the amino acid sequence RPDT (SEQ ID NO: 38), RTDI (SEQ ID NO: 39), or RHDT (SEQ ID NO: 40), where the mutant CBS has a G residue at position 6 of the consensus CBS motif.

In some embodiments, the engineered CTCF variant binds with a higher affinity than a wild-type CTCF to a mutant CBS that has a C, A, or T residue at position 7 of the consensus CBS motif, the engineered CTCF at ZF5 positions +2 to +6 including: the amino acid sequence HGLKV (SEQ ID NO: 41), HRLKE (SEQ ID NO: 42), HALKV (SEQ ID NO: 43), SRLKE (SEQ ID NO: 44), or DGLRV (SEQ ID NO: 45), where the mutant CBS has a T residue at position 7 of the consensus CBS motif; the amino acid sequence HTLKV (SEQ ID NO: 46), or HGLKV (SEQ ID NO: 41), where the mutant CBS has an A residue at position 7 of the consensus CBS motif; or the amino acid sequence SRLKE (SEQ ID NO: 44), HRLKE (SEQ ID NO: 42) or NRLKE (SEQ ID NO: 47), where the mutant CBS has a C residue at position 7 of the consensus CBS motif.

In some embodiments, the engineered CTCF variant binds with a higher affinity than a wild-type CTCF to a mutant CBS that has a C, A, or T residue at position 8 of the consensus CBS motif, the engineered CTCF at ZF5 positions +2 to +6 including: the amino acid sequence ATLKR (SEQ ID NO: 48), QALRR (SEQ ID NO: 49), GGLVR (SEQ ID NO: 50), or HGLIR (SEQ ID NO: 51), where the mutant CBS has a T residue at position 8 of the consensus CBS motif; the amino acid sequence ANLSR (SEQ ID NO: 52), TGLTR (SEQ ID NO: 53), HGLVR (SEQ ID NO: 54), or GGLTR (SEQ ID NO: 55), where the mutant CBS has an A residue at position 8 of the consensus CBS motif; the amino acid sequence HTLRR (SEQ ID NO: 56), TVLKR (SEQ ID NO: 57), ADLKR (SEQ ID NO: 58), or HGLRR (SEQ ID NO: 59), where the mutant CBS has a C residue at position 8 of the consensus CBS motif.

In some embodiments, the engineered CTCF variant binds with a higher affinity than a wild-type CTCF to a mutant CBS that has a T, A, or C residue at position 10 of the consensus CBS motif, the engineered CTCF at ZF4 positions +2 to +6 including: the amino acid sequence AHLRK (SEQ ID NO: 60), wherein the mutant CBS has a T residue at position 10 of the consensus CBS motif; the amino acid sequence AKLRV (SEQ ID NO: 61), EKLRI (SEQ ID NO: 186), or AKLRI (SEQ ID NO: 63), where the mutant CBS has an A residue at position 10 of the consensus CBS motif; or the amino acid sequence TKLKV (SEQ ID NO: 64), wherein the mutant CBS has a C residue at position 10 of the consensus CBS motif.

In some embodiments, the engineered CTCF variant binds with a higher affinity than a wild-type CTCF to a mutant CBS that has a T, A, or C residue at position 11 of the consensus CBS motif, the engineered CTCF at ZF4 positions +2 to +6 including: the amino acid sequence ATLRR (SEQ ID NO: 66) or RRLDR (SEQ ID NO: 67), where the mutant CBS has a T residue at position 11 of the consensus CBS motif; the amino acid sequence TNLRR (SEQ ID NO: 68), ANLRR (SEQ ID NO: 69), or GNLTR (SEQ ID NO: 70), where the mutant CBS has an A residue at position 11 of the consensus CBS motif; or the amino acid sequence AMLKR (SEQ ID NO: 71), HMLTR (SEQ ID NO: 72), AMLRR (SEQ ID NO: 73), or TMLRR (SEQ ID NO: 74), where the mutant CBS has a C residue at position 11 of the consensus CBS motif.

In some embodiments, the engineered CTCF variant binds with a higher affinity than a wild-type CTCF to a mutant CBS that has a T, A, or C residue at position 13 of the consensus CBS motif, the engineered CTCF at ZF3 positions +2 to +6 including: the amino acid sequence QQLIV (SEQ ID NO: 75), SQLIV (SEQ ID NO: 76), QQLLV (SEQ ID NO: 77), GELVV (SEQ ID NO: 78), or QQLLI (SEQ ID NO: 79), where the mutant CBS has a T residue at position 13 of the consensus CBS motif; the amino acid sequence GQLIV (SEQ ID NO: 80), GQLTV (SEQ ID NO: 81), GKLVT (SEQ ID NO: 187), TELII (SEQ ID NO: 82) or QGLLV (SEQ ID NO: 83), where the mutant CBS has an A residue at position 13 of the consensus CBS motif; or the amino acid sequence QQLLT (SEQ ID NO: 84), GQLLT (SEQ ID NO: 85), GELLT (SEQ ID NO: 86), or QQLLI (SEQ ID NO: 79), where the mutant CBS has a C residue at position 13 of the consensus CBS motif.

In some embodiments, the engineered CTCF variant binds with a higher affinity than a wild-type CTCF to a mutant CBS that has A, G, T, and T residues at positions 2, 6, 7, and 10 of the consensus CBS motif, respectively, the engineered CTCF including: (i) the amino acid sequence AKLKK (SEQ ID NO: 88), AKLRK (SEQ ID NO: 89), AHLRV (SEQ ID NO: 90), AKLRV (SEQ ID NO: 61), or SKLRL (SEQ ID NO: 92) at ZF4 positions +2 to +6 of the engineered CTCF; (ii) the amino acid sequence ERLRV (SEQ ID NO: 93), NRLKV (SEQ ID NO: 94), SRLKE (SEQ ID NO: 44), or NRLKV (SEQ ID NO: 94) at ZF5 positions +2 to +6 of the engineered CTCF; (iii) the amino acid sequence RPDT (SEQ ID NO: 38), RTET (SEQ ID NO: 98), or RADV (SEQ ID NO: 99) at ZF6 positions −1 to +3 of the engineered CTCF; and (iv) the amino acid sequence DNLLA (SEQ ID NO: 100), SNLLV (SEQ ID NO: 101), DNLMA (SEQ ID NO: 102), or DNLRV (SEQ ID NO: 103) at ZF7 positions +2 to +6 of the engineered CTCF.

In some embodiments, the engineered CTCF variant binds with a higher affinity than a wild-type CTCF to a mutant CBS that has G, G, T, and T residues at positions 2, 6, 7, and 10 of the consensus CBS motif, respectively, the engineered CTCF including: (i) the amino acid sequence GHLKK (SEQ ID NO: 158), AHLRK (SEQ ID NO: 60), or GKLRI (SEQ ID NO: 106) at ZF4 positions +2 to +6 of the engineered CTCF; (ii) the amino acid sequence SRLKE (SEQ ID NO: 44), DALRR (SEQ ID NO: 108), DGLKR (SEQ ID NO: 109), or TRLRE (SEQ ID NO: 110) at ZF5 positions +2 to +6 of the engineered CTCF; (iii) the amino acid sequence at RPDTMKR (SEQ ID NO: 188) or RTENMKM (SEQ ID NO: 189) at ZF6 positions −1 to +6 of the engineered CTCF; and (iv) the amino acid sequence EHLKV (SEQ ID NO: 13), DHLLA (SEQ ID NO: 114), or HHLDV (SEQ ID NO: 115) at ZF7 positions +2 to +6 of the engineered CTCF.

In some embodiments, the engineered CTCF variant binds with a higher affinity than a wild-type CTCF to a mutant CBS that has A, G, and A residues at positions 2, 5, and 11 of the consensus CBS motif, respectively, the engineered CTCF including: (i) the amino acid sequence SNLRR (SEQ ID NO: 116), GNLVR (SEQ ID NO: 117), GNLRR (SEQ ID NO: 118), GNLKR (SEQ ID NO: 119), ANLRR (SEQ ID NO: 69), NNLRR (SEQ ID NO: 121), or TNLRR (SEQ ID NO: 68) at ZF4 positions +2 to +6 of the engineered CTCF; (ii) the amino acid sequence EHMKR (SEQ ID NO: 123), EHMRR (SEQ ID NO: 34), THMKR (SEQ ID NO: 33), EHMNR (SEQ ID NO: 126), or EHMAR (SEQ ID NO: 127) at ZF6 positions +2 to +6 of the engineered CTCF; and (iii) the amino acid sequence DNLLT (SEQ ID NO: 128), DNLLV (SEQ ID NO: 129), DNLQT (SEQ ID NO: 130), DNLLA (SEQ ID NO: 100), DNLAT (SEQ ID NO: 132), DNLQA (SEQ ID NO: 133), DNLMA (SEQ ID NO: 102), or DNLMT (SEQ ID NO: 135) at ZF7 positions +2 to +6 of the engineered CTCF.

In some embodiments, the engineered CTCF variant binds with a higher affinity than a wild-type CTCF to a mutant CBS that has G, G, and A residues at positions 2, 5, and 11 of the consensus CBS motif, respectively, the engineered CTCF including: (i) the amino acid sequence GNLVR (SEQ ID NO: 117), GNLRR (SEQ ID NO: 118), GNLAR (SEQ ID NO: 138), GNLMR (SEQ ID NO: 139), ANLRR (SEQ ID NO: 69), SNLRR (SEQ ID NO: 116), or NNLRR (SEQ ID NO: 121) at ZF4 positions +2 to +6 of the engineered CTCF; (ii) the amino acid sequence EHMNR (SEQ ID NO: 126), EHMKR (SEQ ID NO: 123), EHMRR (SEQ ID NO: 34), SHMNR (SEQ ID NO: 146), SHMRR (SEQ ID NO: 147), THMKR (SEQ ID NO: 33), or DHMNR (SEQ ID NO: 32) at ZF6 positions +2 to +6 of the engineered CTCF; and (iii) the amino acid sequence EHLKV (SEQ ID NO: 13), EHLAE (SEQ ID NO: 151), STLNE (SEQ ID NO: 152), DHLQV (SEQ ID NO: 12), EHLNV (SEQ ID NO: 9), DHLNT (SEQ ID NO: 155), EHLQA (SEQ ID NO: 156), or HHLMH (SEQ ID NO: 157) at ZF7 positions +2 to +6 of the engineered CTCF.

In some embodiments, the engineered CTCF variant binds with a higher affinity than a wild-type CTCF to a mutant CBS that has G, T, and T residues at positions 6, 7, and 10 of the consensus CBS motif, respectively, the engineered CTCF including: (i) the amino acid sequence GHLKK (SEQ ID NO: 158), AHLKK (SEQ ID NO: 159), TKLRL (SEQ ID NO: 160), TKLKL (SEQ ID NO: 161), GHLRK (SEQ ID NO: 162), THLKK (SEQ ID NO: 163), or AHLRK (SEQ ID NO: 60) at ZF4 positions +2 to +6 of the engineered CTCF; (ii) the amino acid sequence TRLKE (SEQ ID NO: 165) or SRLKE (SEQ ID NO: 44) at ZF5 positions +2 to +6 of the engineered CTCF; and (iii) the amino acid sequence RADN (SEQ ID NO: 167), RHDT (SEQ ID NO: 40), RRDT (SEQ ID NO: 169), RPDT (SEQ ID NO: 38), RTSS (SEQ ID NO: 171), or RNDT (SEQ ID NO: 172) at ZF6 positions −1 to +3 of the engineered CTCF.

In some embodiments, the engineered CTCF variant includes at least one amino acid residue in at least one zinc finger that differs in sequence from the amino acid sequence of a wild-type CTCF, where the engineered CTCF variant binds to a mutant CTCF binding sequence (CBS) with a higher affinity than wild-type CTCF, the mutant CBS including at least one nucleotide base that differs in sequence from the nucleotide sequence of a consensus CBS, where the at least one amino acid residue that differs in sequence from the amino acid sequence of a wild-type CTCF is selected from the group consisting of the amino acid residues at the position(s) −1, +1, +2, +3, +5, and +6 of any of ZF7, ZF6, ZF5, ZF4, and ZF3 of the engineered CTCF variant.

In some embodiments, the engineered CCCTC-binding factor (CTCF) variant that binds with a higher affinity than a wild-type CTCF to a mutant CTCF binding sequence (CBS) that differs from a consensus CBS at position 2 of the consensus CBS motif, the engineered CTCF including an amino acid residue threonine, asparagine, or histidine at ZF7 +3 position.

In some embodiments, the engineered CTCF variant binds with a higher affinity than a wild-type CTCF to a mutant CBS that has a C-to-G mutation at position 2 of the consensus CBS motif, the engineered CTCF including the amino acid sequence DHLQT (SEQ ID NO: 8), EHLNV (SEQ ID NO: 9), AHLQV (SEQ ID NO: 10), EHLRE (SEQ ID NO: 11), DHLQV (SEQ ID NO: 12), EHLKV (SEQ ID NO: 13), DHLQV (SEQ ID NO: 12), EHLVV (SEQ ID NO: 15), DHLRT (SEQ ID NO: 16), DHLAT (SEQ ID NO: 17), or DHLQT (SEQ ID NO: 8) at ZF7 positions +2 to +6.

In some embodiments, the engineered CTCF variant binds with a higher affinity than a wild-type CTCF to a mutant CBS that differs from a consensus CBS at position 3 of the consensus CBS motif, the engineered CTCF including the amino acid sequence RKHD (SEQ ID NO: 173), RRSD (SEQ ID NO: 174), GIVN (SEQ ID NO: 178), ELLN (SEQ ID NO: 179), or PHRM (SEQ ID NO: 181) at ZF7 positions −1 to +3.

In some embodiments, the engineered CTCF variant binds with a higher affinity than a wild-type CTCF to a mutant CBS that differs from a consensus CBS at position 5 of the consensus CBS motif, the engineered CTCF including the amino acid sequence NAMKR (SEQ ID NO: 30), EHMGR (SEQ ID NO: 31), DHMNR (SEQ ID NO: 32), THMKR (SEQ ID NO: 33), EHMRR (SEQ ID NO: 34), or THMNR (SEQ ID NO: 35) at ZF6 positions +2 to +6.

In some embodiments, the engineered CTCF variant binds with a higher affinity than a wild-type CTCF to a mutant CBS that differs from a consensus CBS at position 6 of the consensus CBS motif, the engineered CTCF including the amino acid sequence MNES (SEQ ID NO: 36), HRES (SEQ ID NO: 37), RPDT (SEQ ID NO: 38), RTDI (SEQ ID NO: 39), or RHDT (SEQ ID NO: 40) at ZF6 positions −1 to +3.

In some embodiments, the engineered CTCF variant binds with a higher affinity than a wild-type CTCF to a mutant CBS that differs from a consensus CBS at position 7 of the consensus CBS motif, the engineered CTCF including the amino acid sequence HGLKV (SEQ ID NO: 41), HRLKE (SEQ ID NO: 42), HALKV (SEQ ID NO: 43), SRLKE (SEQ ID NO: 44), DGLRV (SEQ ID NO: 45), HTLKV (SEQ ID NO: 46), or NRLKE (SEQ ID NO: 47) at ZF5 positions +2 to +6.

In some embodiments, the engineered CTCF variant binds with a higher affinity than a wild-type CTCF to a mutant CBS that differs from a consensus CBS at position 8 of the consensus CBS motif, the engineered CTCF including the amino acid sequence ATLKR (SEQ ID NO: 48), QALRR (SEQ ID NO: 49), GGLVR (SEQ ID NO: 50), HGLIR (SEQ ID NO: 51), ANLSR (SEQ ID NO: 52), TGLTR (SEQ ID NO: 53), HGLVR (SEQ ID NO: 54), GGLTR (SEQ ID NO: 55), HTLRR (SEQ ID NO: 56), TVLKR (SEQ ID NO: 57), ADLKR (SEQ ID NO: 58), or HGLRR (SEQ ID NO: 59) at ZF5 positions +2 to +6.

In some embodiments, the engineered CTCF variant binds with a higher affinity than a wild-type CTCF to a mutant CBS that differs from a consensus CBS at position 10 of the consensus CBS motif, the engineered CTCF including the amino acid sequence AHLRK (SEQ ID NO: 60), AKLRV (SEQ ID NO: 61), GGLGL (SEQ ID NO: 62), AKLRI (SEQ ID NO: 63), TKLKV (SEQ ID NO: 64), or SKLRV (SEQ ID NO: 65) at ZF4 positions +2 to +6.

In some embodiments, the engineered CTCF variant binds with a higher affinity than a wild-type CTCF to a mutant CBS that differs from a consensus CBS at position 11 of the consensus CBS motif, the engineered CTCF including the amino acid sequence ATLRR (SEQ ID NO: 66), RRLDR (SEQ ID NO: 67), TNLRR (SEQ ID NO: 68), ANLRR (SEQ ID NO: 69), GNLTR (SEQ ID NO: 70), AMLKR (SEQ ID NO: 71), HMLTR (SEQ ID NO: 72), AMLRR (SEQ ID NO: 73), or TMLRR (SEQ ID NO: 74) at ZF4 positions +2 to +6.

In some embodiments, the engineered CTCF variant binds with a higher affinity than a wild-type CTCF to a mutant CBS that differs from a consensus CBS at position 13 of the consensus CBS motif, the engineered CTCF including the amino acid sequence QQLIV (SEQ ID NO: 75), SQLIV (SEQ ID NO: 76), QQLLV (SEQ ID NO: 77), GELVV (SEQ ID NO: 78), QQLLI (SEQ ID NO: 79), GQLIV (SEQ ID NO: 80), GQLTV (SEQ ID NO: 81), TELII (SEQ ID NO: 82), QGLLV (SEQ ID NO: 83), QQLLT (SEQ ID NO: 84), GQLLT (SEQ ID NO: 85), GELLT (SEQ ID NO: 86), or QQLLI (SEQ ID NO: 79) at ZF3 positions +2 to +6.

In some embodiments, the engineered CTCF variant binds with a higher affinity than a wild-type CTCF to a mutant CBS that differs from a consensus CBS at positions 2, 6, 7, and 10 of the consensus CBS motif, the engineered CTCF including:

(i) the amino acid sequence AKLKK (SEQ ID NO: 88), AKLRK (SEQ ID NO: 89), AHLRV (SEQ ID NO: 90), AKLRV (SEQ ID NO: 61), or SKLRL (SEQ ID NO: 92) at ZF4 positions +2 to +6;

(ii) the amino acid sequence ERLRV (SEQ ID NO: 93), NRLKV (SEQ ID NO: 94), SRLKE (SEQ ID NO: 44), or NRLKV (SEQ ID NO: 94) at ZF5 positions +2 to +6;

(iii) the amino acid sequence RPDT (SEQ ID NO: 38), RTET (SEQ ID NO: 98), or RADV (SEQ ID NO: 99) at ZF6 positions −1 to +3; and (iv) the amino acid sequence DNLLA (SEQ ID NO: 100), SNLLV (SEQ ID NO: 101), DNLMA (SEQ ID NO: 102), or DNLRV (SEQ ID NO: 103) at ZF7 positions +2 to +6.

In some embodiments, the engineered CTCF variant binds with a higher affinity than a wild-type CTCF to a mutant CBS that differs from a consensus CBS at positions 2, 6, 7, and 10 of the consensus CBS motif, the engineered CTCF including:

(i) the amino acid sequence GHLKK (SEQ ID NO: 158), AHLRK (SEQ ID NO: 60), or GKLRI (SEQ ID NO: 106) at ZF4 positions +2 to +6;

(ii) the amino acid sequence SRLKE (SEQ ID NO: 44), DALRR (SEQ ID NO: 108), DGLKR (SEQ ID NO: 109), or TRLRE (SEQ ID NO: 110) at ZF5 positions +2 to +6;

(iii) the amino acid sequence at RPDTMKR (SEQ ID NO: 188) or RTENMKM (SEQ ID NO: 189) at ZF6 positions −1 to +36; and (iv) the amino acid sequence EHLKV (SEQ ID NO: 13), DHLLA (SEQ ID NO: 114), or HHLDV (SEQ ID NO: 115) at ZF7 positions +2 to +6.

In some embodiments, the engineered CTCF variant binds with a higher affinity than a wild-type CTCF to a mutant CBS that differs from a consensus CBS at positions 2, 5, and 11 of the consensus CBS motif, the engineered CTCF including:

(i) the amino acid sequence SNLRR (SEQ ID NO: 116), GNLVR (SEQ ID NO: 117), GNLRR (SEQ ID NO: 118), GNLKR (SEQ ID NO: 119), ANLRR (SEQ ID NO: 69), NNLRR (SEQ ID NO: 121), or TNLRR (SEQ ID NO: 68) at ZF4 positions +2 to +6;

(ii) the amino acid sequence EHMKR (SEQ ID NO: 123), EHMRR (SEQ ID NO: 34), THMKR (SEQ ID NO: 33), EHMNR (SEQ ID NO: 126), or EHMAR (SEQ ID NO: 127) at ZF6 positions +2 to +6; and (iii) the amino acid sequence DNLLT (SEQ ID NO: 128), DNLLV (SEQ ID NO: 129), DNLQT (SEQ ID NO: 130), DNLLA (SEQ ID NO: 100), DNLAT (SEQ ID NO: 132), DNLQA (SEQ ID NO: 133), DNLMA (SEQ ID NO: 102), or DNLMT (SEQ ID NO: 135) at ZF7 positions +2 to +6.

In some embodiments, the engineered CTCF variant binds with a higher affinity than a wild-type CTCF to a mutant CBS that differs from a consensus CBS at positions 2, 5, and 11 of the consensus CBS motif, the engineered CTCF including:

(i) the amino acid sequence GNLVR (SEQ ID NO: 117), GNLRR (SEQ ID NO: 118), GNLAR (SEQ ID NO: 138), GNLMR (SEQ ID NO: 139), ANLRR (SEQ ID NO: 69), SNLRR (SEQ ID NO: 116), or NNLRR (SEQ ID NO: 121) at ZF4 positions +2 to +6;

(ii) the amino acid sequence EHMNR (SEQ ID NO: 126), EHMKR (SEQ ID NO: 123), EHMRR (SEQ ID NO: 34), SHMNR (SEQ ID NO: 146), SHMRR (SEQ ID NO: 147), THMKR (SEQ ID NO: 33), or DHMNR (SEQ ID NO: 32) at ZF6 positions +2 to +6; and (iii) the amino acid sequence EHLKV (SEQ ID NO: 13), EHLAE (SEQ ID NO: 151), STLNE (SEQ ID NO: 152), DHLQV (SEQ ID NO: 12), EHLNV (SEQ ID NO: 9), DHLNT (SEQ ID NO: 155), EHLQA (SEQ ID NO: 156), or HHLMH (SEQ ID NO: 157) at ZF7 positions +2 to +6.

In one embodiment, the engineered CTCF variant binds with a higher affinity than a wild-type CTCF to a mutant CBS that differs from a consensus CBS at positions 6, 7, and 10 of the consensus CBS motif, the engineered CTCF including:

(i) the amino acid sequence GHLKK (SEQ ID NO: 158), AHLKK (SEQ ID NO: 159), TKLRL (SEQ ID NO: 160), TKLKL (SEQ ID NO: 161), GHLRK (SEQ ID NO: 162), THLKK (SEQ ID NO: 163), or AHLRK (SEQ ID NO: 60) at ZF4 positions +2 to +6;

(ii) the amino acid sequence TRLKE (SEQ ID NO: 165) or SRLKE (SEQ ID NO: 44) at ZF5 positions +2 to +6; and (iii) the amino acid sequence RADN (SEQ ID NO: 167), RHDT (SEQ ID NO: 40), RRDT (SEQ ID NO: 169), RPDT (SEQ ID NO: 38), RTSS (SEQ ID NO: 171), or RNDT (SEQ ID NO: 172) at ZF6 positions −1 to +3.

In some embodiments, the engineered CTCF variant interacts with cohesion to mediate the formation of an enhancer-promoter loop to modulate gene expression.

In another aspect, the invention features a method of treating a subject in need thereof, the method including administering to the subject a therapeutically effective amount of an engineered CTCF variant described herein.

In some embodiments, the subject can have cancer.

In another aspect, the invention features a method of activating or repressing expression of a gene which is under the control of a CBS bearing one or more mutations, the method including contacting an engineered CTCF described herein with a sequence of interest in the gene, such that the expression of the gene is regulated.

In another aspect, the invention features a pharmaceutical composition including an engineered CTCF variant described herein.

In another aspect, the invention features a gene expression system for regulation of a gene, the system including a nucleic acid encoding an engineered CTCF variant according described herein.

In another aspect, the invention features a method of altering the structure of chromatin including contacting an engineered CTCF variant described herein with a sequence of interest to form a binding complex, such that the structure of the chromatin is altered.

In another aspect, the invention features a method of activating or repressing expression of a gene which is under the control of a CBS bearing one or more mutations, the method including contacting the CBS bearing one or more mutations with an engineered CTCF variant described herein.

In another aspect, the invention features a kit including an engineered CTCF variant described herein.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The following Detailed Description, given by way of example, but not intended to limit the invention to specific embodiment described, may be understood in conjunction with the accompanying figures, incorporated herein by reference.

FIG. 1 discloses SEQ ID NO: 5544.

FIG. 3 discloses SEQ ID NOS 5545-5548 and 5544, respectively, in order of appearance.

FIG. 4 discloses SEQ ID NO: 5544.

FIG. 5 discloses SEQ ID NOS 5549-5550 and 5544, respectively, in order of appearance.

FIGS. 7A-C: Binding activity of variants on altered CTCF binding sites. Variants picked from the high stringency gradient of the selective plates were tested for binding activity on sequences representing all four possible nucleotides at position 2 of the core sequence (gray star). Amino acid sequence of variants pulled out of the selection were listed above the heat map and the nucleotide present at position 2 of the core sequence was indicated on the y-axis. FIG. 7A: The nucleotide at position 2 is T. FIG. 7B: The nucleotide at position 2 is A. FIG. 7C: The nucleotide at Binding was quantified by the beta-galactosidase reporter system and colorimetric ONPG assay. Binding activity of wild-type CTCF zinc finger array on the wild-type binding site sequence was indicated by the white dot. A diagram of the ZF7 alpha recognition helix for each nucleotide change is on the left. It included the amino acid residues interacting with the triplet in the binding sequence. The amino acid at position 3 of the alpha helix was varied in the library and is indicated by an 'X'. FIGS. 7A-C disclose "RKSXLGV" as SEQ ID NO: 5551.

FIG. 8: Increasing the variation within the recognition helix produced stronger binders. Four amino acids were targeted for variance in the library to allow for more flexibility in the selection and generate stronger binders to the modified binding site of choice. ZF7 targeting a C:G change at position 2 (gray star) of the core sequence was selected for variants using the expanded approach. Each amino acid codon was replaced with 'VNS' codons at the indicated sites ('X'). Twelve colonies were picked from the high-stringency end of the selection and tested for their ability to bind to the CTCF binding site when the indicated nucleotide is at positon 2 of core sequence. Amino acid sequence of the variants selected are listed on the x-axis and the nucleotide at position two of the core sequence is on the y-axis. Wild-type zinc finger array binding activity on wild-type binding sequence is indicated by the white dot. FIG. 8 discloses "RKSXLGV" as SEQ ID NO: 5551, "AHLQV" as SEQ ID NO: 10, "DHLRT" as SEQ ID NO: 16, "DHLAT" as SEQ ID NO: 17, "DHLQT" as SEQ ID NO: 8, "DHLQV" as SEQ ID NO: 12, "SDLGV" as SEQ ID NO: 5552, "EHLKV" as SEQ ID NO: 13, "EHLVV" as SEQ ID NO: 15, "EHLNV" as SEQ ID NO: 9 and "EHLRE" as SEQ ID NO: 11.

FIGS. 9A-C disclose "RKSD" as SEQ ID NO: 711, "RKHD" as SEQ ID NO: 173, "RRSD" as SEQ ID NO: 174, "RKAD" as SEQ ID NO: 175, "IPRI" as SEQ ID NO: 176, "RKDD" as SEQ ID NO: 177, "QALL" as SEQ ID NO: 180, "PHRM" as SEQ ID NO: 181, "ELLN" as SEQ ID NO: 179 and "GIVN" as SEQ ID NO: 178.

FIGS. 10A-B: Selections performed targeting sequence changes at position 5 of the core motif in the CBS. Selections performed on library of variants centered around alterations in position 2 to 6 of the ZF6 recognition helix, leaving the 4th position unchanged. 'VNS' codons were introduced at positions indicated by 'X' and selected against three different nucleotide changes at position 5 of the core motif in the core motif of the CBS (gray star). Direct protein-DNA contacts were indicated by dashed lines. (A) Selections performed on C:T change in the binding site, (B) C:G change. No variants grew beyond the low stringency end of the gradient on selection plates for C:A change and were considered weak/insufficient binders. Most variants pulled out had relaxed binding specificity instead of altered specificity with the exception of THMKR' (SEQ ID NO: 33) targeting C:G change in the binding sequence. FIGS. 10A-B disclose "GNMAR" as SEQ ID NO: 182, "NAMKR" as SEQ ID NO: 30, "EGMTR" as SEQ ID NO: 183, "NAMRG" as SEQ ID NO: 185, "GTMKM" as SEQ ID NO: 1255, "SNMVR" as SEQ ID NO: 184, "DHMNR" as SEQ ID NO: 32, "EHMRR" as SEQ ID NO: 34, "EHMGR" as SEQ ID NO: 31, "THMNR" as SEQ ID NO: 35 and "THMKR" as SEQ ID NO: 33.

FIGS. 11A-C: Selections performed targeting sequence changes at position 6 of the core motif in the CBS. Selections performed on library of variants centered around alterations in position −1 to 3 of ZF6 recognition helix. 'VNS' codons were introduced at positions indicated by 'X' and selected against three different nucleotide changes at position 6 of the core motif in the CBS (gray star). Direct protein-DNA contacts are indicated by dashed lines. (A) Selections performed on A:T change in the binding site, (B) A:G change, (C) A:C change. Variants analyzed from the A:T selection had relaxed binding profile while variants from A:G selection showed strong binding for only the changed nucleotide. No good binders were identified in the A:C selection. FIGS. 11A-C disclose "NINES" as SEQ ID NO: 36, "QSGT" as SEQ ID NO: 1582, "HRES" as SEQ ID NO: 37, "RHDT" as SEQ ID NO: 40, "RPDT" as SEQ ID NO: 38, "RTDI" as SEQ ID NO: 39, "RADN" as SEQ ID NO: 167 and "ERKS" as SEQ ID NO: 1479.

FIGS. 12A-C: Selections performed targeting sequence changes at position 7 of the core motif in the CBS. Selections performed on library of variants centered around alterations in position 4 to 6 of ZF5 recognition helix, leaving the 4th position unchanged. 'VNS' codons were introduced at positions indicated by 'X' and selected against three different nucleotide changes at position 7 of the core motif in the CBS (gray star). Direct protein-DNA contacts are indicated by a line. (A) Selections performed on G:T change in the binding site, (B) G:A change, (C) G:C change. FIGS. 12A-C disclose "DGLRV" as SEQ ID NO: 45, "HGLKV" as SEQ ID NO: 41, "HRLKE" as SEQ ID NO: 42, "HALKV" as SEQ ID NO: 43, "YKLKR" as SEQ ID NO: 5553, "SRLKE" as SEQ ID NO: 44, "HTLKV" as SEQ ID NO: 46 and "NRLKE" as SEQ ID NO: 47.

FIGS. 13A-C: Selections performed targeting sequence changes at position 8 of the core motif in the CBS. Selections performed on library of variants centered around alterations in position 2 to 6 of ZF5 recognition helix, leaving the 4th position unchanged. 'VNS' codons were introduced at positions indicated by 'X' and selected against three different nucleotide changes at position 8 of the core motif in the CBS (gray star). Direct protein-DNA contacts are indicated by a line. (A) Selections performed on G:T change in the binding site, (B) G:A change, (C) G:C change. Note the different variants that appear with the same library being used to bind to the same changes in the sequence, but in a different position on the binding site. FIGS. 13A-C disclose "GGLVR" as SEQ ID NO: 50, "QALRR" as SEQ ID NO: 49, "HGLIR" as SEQ ID NO: 51, "YKLKR" as SEQ ID NO: 5553, "ATLKR" as SEQ ID NO: 48, "GGLTR" as SEQ ID NO: 55, "HGLVR" as SEQ ID NO: 54, "ANLSR" as SEQ ID NO: 52, "TGLTR" as SEQ ID NO: 53, "HGLRR"

as SEQ ID NO: 59, "ADLKR" as SEQ ID NO: 58, "HTLRR" as SEQ ID NO: 56 and "TVLKR" as SEQ ID NO: 57.

Figure 14A:
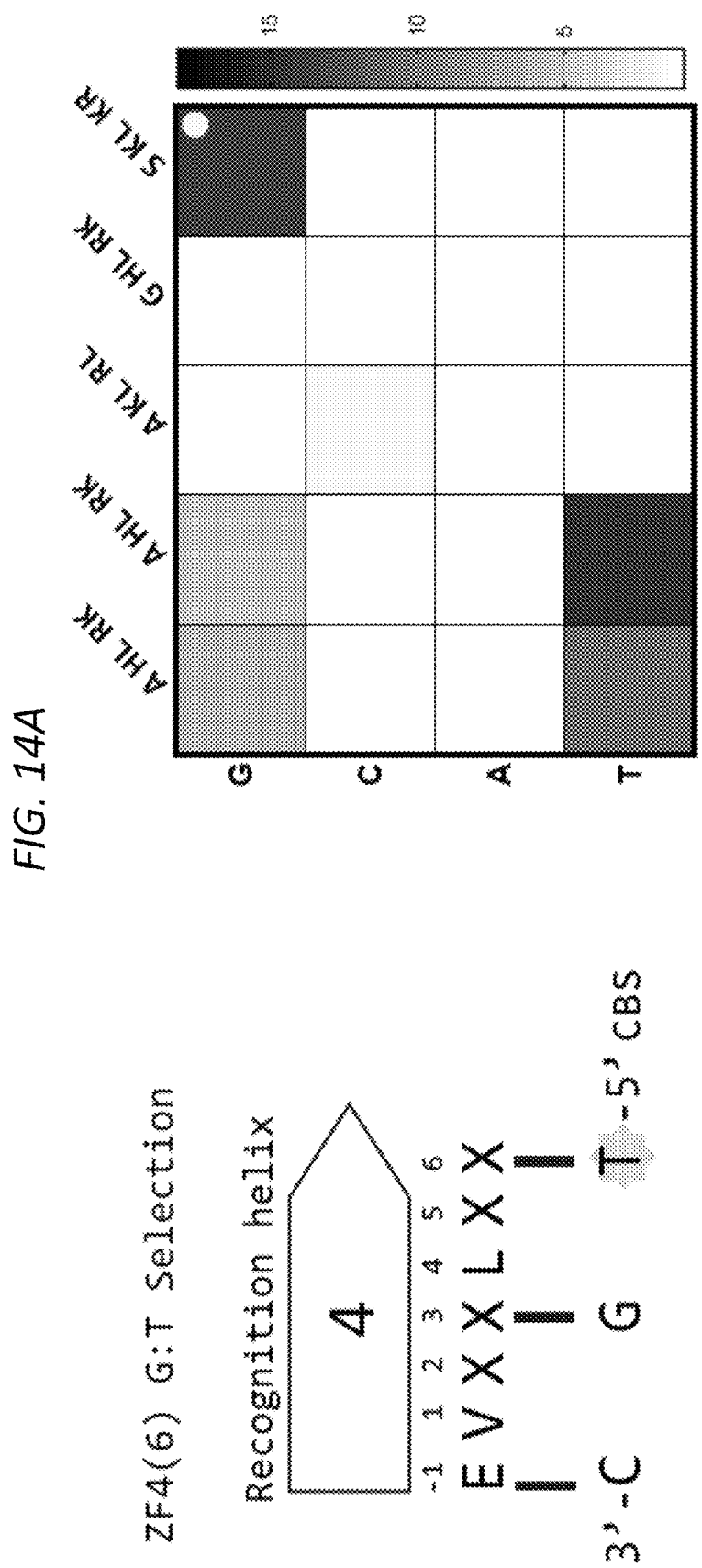
Figure 15C:
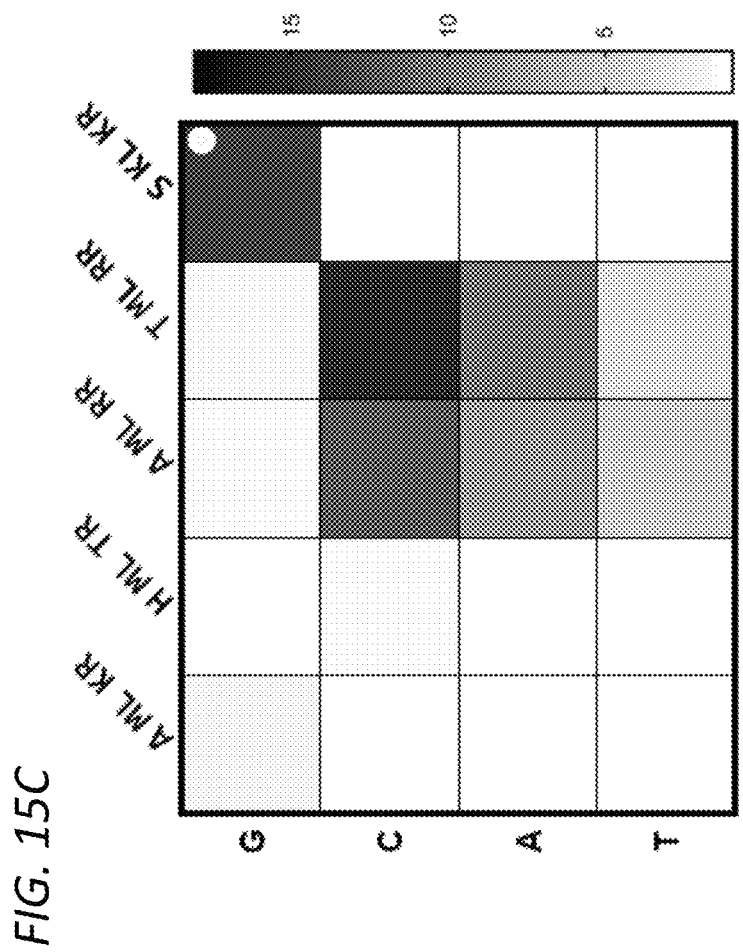
Figure 16B:
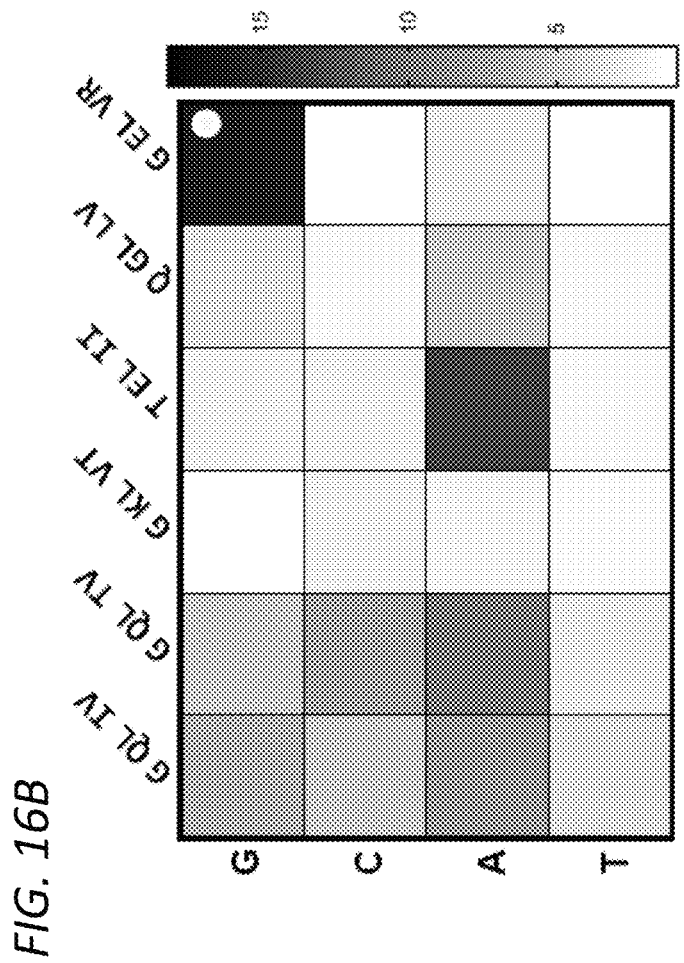
Figure 16C:
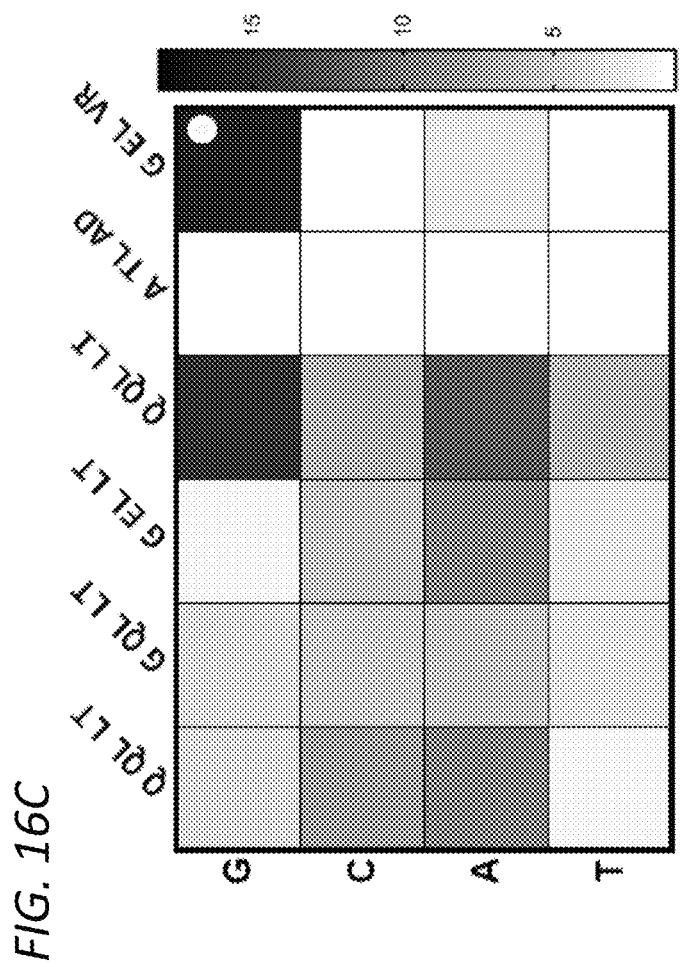
Figure 16C:
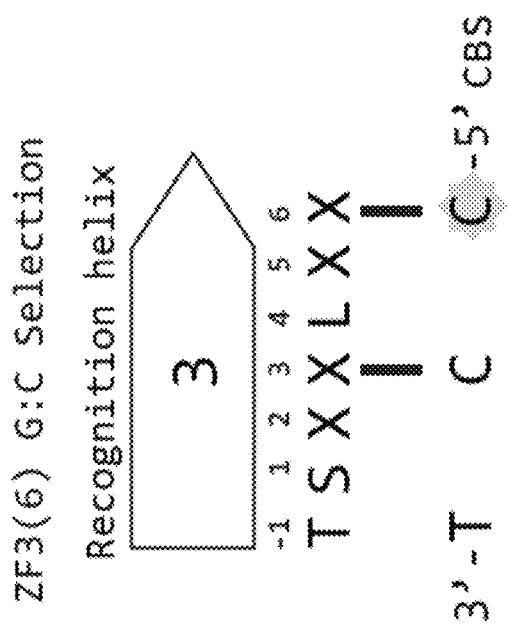
Figure 17:
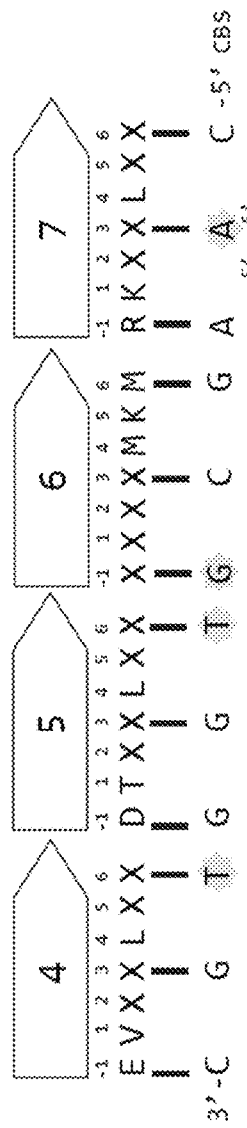
Figure 18:
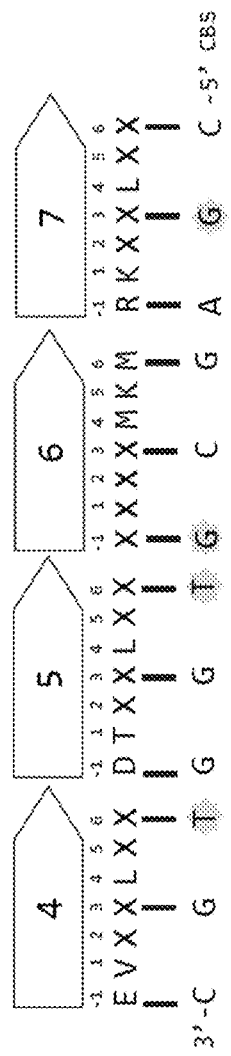
Figure 19:
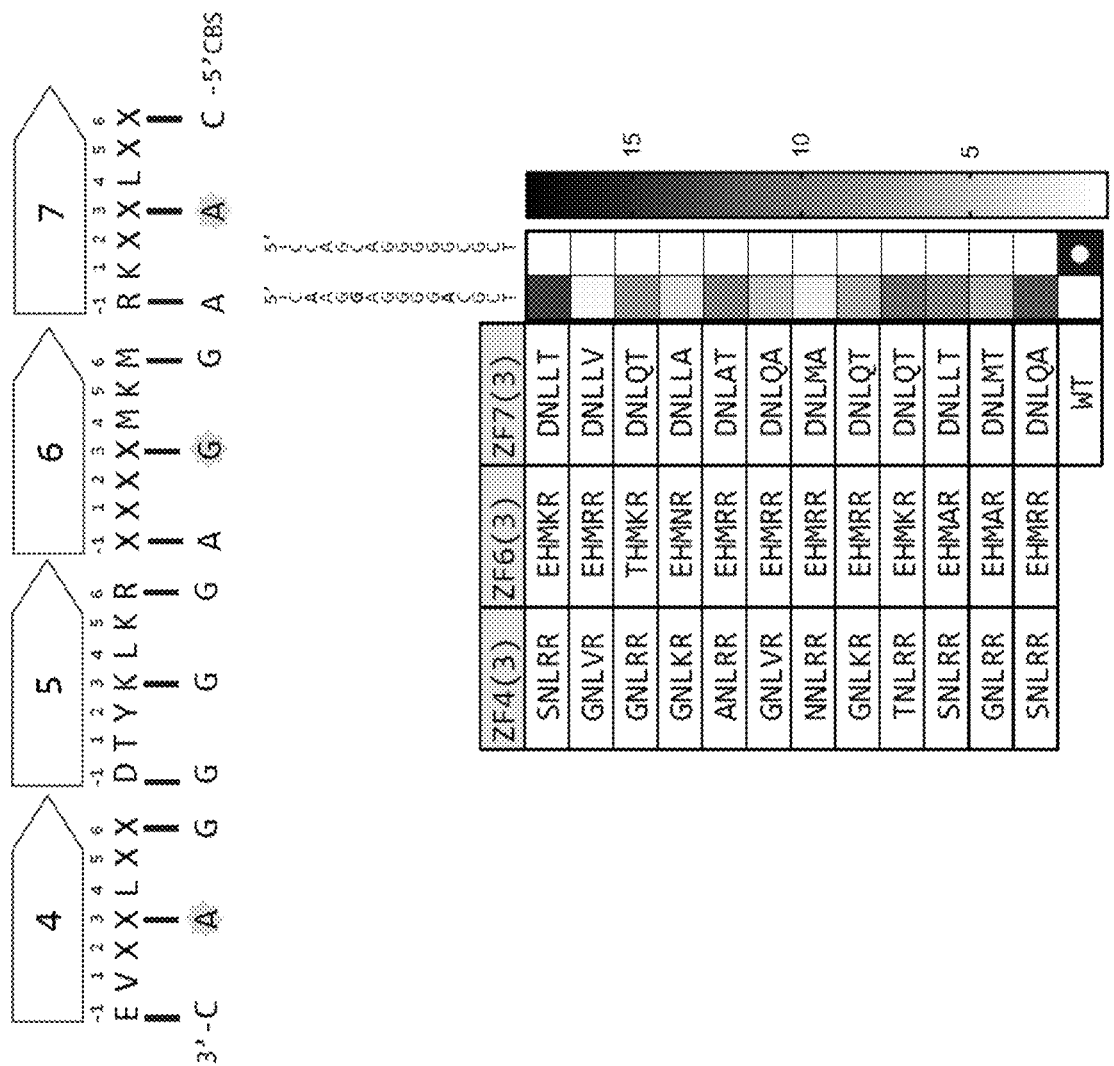

FIGS. 14A-C: Selections performed targeting sequence changes at position 10 of the core motif in the CBS. Selections performed on library of variants centered around alterations in position 2 to 6 of ZF4 recognition helix, leaving the 4th position unchanged. 'VNS' codons were introduced at positions indicated by 'X' and selected against three different nucleotide changes at position 10 of the core motif in the CBS (gray star). Direct protein-DNA contacts are indicated by a line. (A) Selections performed on G:T change in the binding site, (B) G:A change, (C) G:C change. G:C selection did not produce any growth at the high stringency end of the gradient selective plates. Binding data reflects colonies picked from mid-tier region, which is why they did not perform well as binders. White dot indicates wild-type CTCF zinc finger array binding activity on wild-type binding sequence. FIGS. 14A-C disclose "GHLRK" as SEQ ID NO: 162, "AKLRL" as SEQ ID NO: 3311, "AHLRK" as SEQ ID NO: 60, "SKLKR" as SEQ ID NO: 3470, "GGLGL" as SEQ ID NO: 62, "AKLRI" as SEQ ID NO: 63, "AKLRV" as SEQ ID NO: 61, "EKLRI" as SEQ ID NO: 186, "SKLRV" as SEQ ID NO: 65 and "TKLKV" as SEQ ID NO: 64.

FIGS. 15A-C: Selections performed targeting sequence changes at position 11 of the core motif in the CBS. Selections performed on library of variants centered around alterations in position 2 to 6 of ZF4 recognition helix, leaving the 4th position unchanged. 'VNS' codons were introduced at positions indicated by 'X' and selected against three different nucleotide changes at position 11 of the core motif in the CBS (gray star). Direct protein-DNA contacts are indicated by a line. (A) Selections performed on G:T change in the binding site, (B) G:A change, (C) G:C change. FIGS. 15A-C disclose "RRLDR" as SEQ ID NO: 67, "SKLKR" as SEQ ID NO: 3470, "ATLRR" as SEQ ID NO: 66, "GNLTR" as SEQ ID NO: 70, "ANLRR" as SEQ ID NO: 69, "TNLRR" as SEQ ID NO: 68, "AMLRR" as SEQ ID NO: 73, "AMLKR" as SEQ ID NO: 71, "HMLTR" as SEQ ID NO: 72 and "TMLRR" as SEQ ID NO: 74.

FIGS. 16A-C: Selections performed targeting sequence changes at position 13 of the core motif in the CBS. Selections performed on library of variants centered around alterations in position 2 to 6 of ZF3 recognition helix, leaving the 4th position unchanged. 'VNS' codons were introduced at positions indicated by 'X' and selected against three different nucleotide changes at position 13 of the core motif in the CBS (gray star). Direct protein-DNA contacts are indicated by a line. (A) Selections performed on G:T change in the binding site, (B) G:A change, (C) G:C change. FIGS. 16A-C disclose "QQLLI" as SEQ ID NO: 79, "QQLLV" as SEQ ID NO: 77, "QQLIV" as SEQ ID NO: 75, "GELVV" as SEQ ID NO: 78, "GELVR" as SEQ ID NO: 5554, "SQLIV" as SEQ ID NO: 76, "QGLLV" as SEQ ID NO: 83, "GQLTV" as SEQ ID NO: 81, "GQLIV" as SEQ ID NO: 80, "GKLVT" as SEQ ID NO: 187, "TELII" as SEQ ID NO: 82, "GQLLT" as SEQ ID NO: 85, "QQLLT" as SEQ ID NO: 84, "GELLT" as SEQ ID NO: 86 and "ATLAD" as SEQ ID NO: 5555.

FIG. 17: Binding activity of multi-finger variants on multiple sequence changes to the CBS. Diagram of the recognition helices of zinc finger 4-7 out of the 11 finger array, binding to their respective triplets in the core motif of the CBS. Altered amino acids are indicated by 'X' and nucleotide changes to the wild-type CBS are indicated by a gray star in the diagram and by bolded letters. ZF1-3 and ZF8-11 were unmodified in this library Protein-DNA contacts are indicated by lines between the ZF recognition helices and the CBS sequence. Wild-type CTCF 11-finger zinc finger array binding strength to wild-type CBS is indicated by a white dot. The amino acid sequence of each variant recognition helix in ZF4-7 are listed on the y-axis and binding activity on the modified CBS (changes in red) or the wild-type CBS are reflected by B2H β-gal reporter assay. FIG. 17 discloses "CGTGGTGCGAAC" as SEQ ID NO: 5556, "CAAGCGTGGTGCGCT" as SEQ ID NO: 5557, "CCAGCAGGGGGCGCT" as SEQ ID NO: 5558, "ERLRV" as SEQ ID NO: 93, "RPDT" as SEQ ID NO: 38, "DNLLA" as SEQ ID NO: 100, "AKLKK" as SEQ ID NO: 88, "AKLRK" as SEQ ID NO: 89, "NRLKV" as SEQ ID NO: 94, "RTET" as SEQ ID NO: 98, "SNLLV" as SEQ ID NO: 101, "AHLRV" as SEQ ID NO: 90, "SRLKE" as SEQ ID NO: 44, "DNLMA" as SEQ ID NO: 102, "AKLRV" as SEQ ID NO: 61, "SKLRL" as SEQ ID NO: 92, "RADV" as SEQ ID NO: 99 and "DNLRV" as SEQ ID NO: 103.

FIG. 18: Binding activity of multi-finger variants on multiple sequence changes to the CBS. The same selection as before except now there is a C:G change at position 2 of the CBS, where previously there was a C:A change. Variants pulled out of this selection had binding activity on the modified CBS without binding to the wild-type CBS. Wild-type 11-finger ZF array only showed binding activity on wild-type CBS (white dot) and no ability to bind to the modified CBS. Interestingly, the dominant variant selected for in the library contained a mutation that occurs at position 9 of the recognition helix that was either introduced during oligo synthesis (0.05% chance of the wrong nucleotide at each position) or through PCR while constructing these libraries. FIG. 18 discloses "CGTGGTGCGAGC" as SEQ ID NO: 5559, "CGAGCGTGGTGCGCT" as SEQ ID NO: 5560, "CCAGCAGGGGGCGCT" as SEQ ID NO: 5558, "GHLKK" as SEQ ID NO: 158, "SRLKE" as SEQ ID NO: 44, "EHLKV" as SEQ ID NO: 13, "RPDT(MK)R" as SEQ ID NO: 5561, "AHLRK" as SEQ ID NO: 60, "DALRR" as SEQ ID NO: 108, "RTEN" as SEQ ID NO: 112, "DHLLA" as SEQ ID NO: 114, "DGLKR" as SEQ ID NO: 109, "RPDT" as SEQ ID NO: 38, "HHLDV" as SEQ ID NO: 115, "GKLRI" as SEQ ID NO: 106 and "TRLRE" as SEQ ID NO: 110.

FIG. 19: Binding activity of multi-finger variants on multiple sequence changes to the CBS. Variants from individual pooled high stringency selections were stitched together and selected against three changes to the wild-type CBS (indicated by gray stars or bolded). Variants were assayed for binding on the modified CBS and the wild-type CBS alongside wild-type CTCF zinc finger array. The variants picked out of the selection were able to bind to the modified CBS, but not the wild-type sequence. Inversely, the wild-type zinc finger array was able to bind to the wild-type CBS, but not the modified one. FIG. 19 discloses "DTYKLKR" as SEQ ID NO: 3, "CAGGGGAGGAAC" as SEQ ID NO: 5562, "CAAGGAGGGGACGCT" as SEQ ID NO: 5563, "CCAGCAGGGGGCGCT" as SEQ ID NO: 5558, "SNLRR" as SEQ ID NO: 116, "EHMKR" as SEQ ID NO: 123, "DNLLT" as SEQ ID NO: 128, "GNLVR" as SEQ ID NO: 117, "EHMIRR" as SEQ ID NO: 34, "DNLLV" as SEQ ID NO: 129, "GNLRR" as SEQ ID NO: 118, "THMKR" as SEQ ID NO: 33, "DNLQT" as SEQ ID NO: 130, "GNLKR" as SEQ ID NO: 119, "EHMNR" as SEQ ID NO: 126, "DNLLA" as SEQ ID NO: 100, "ANLRR" as SEQ ID NO: 69, "DNLAT" as SEQ ID NO: 132, "DNLQA" as SEQ ID NO: 133, "NNLRR" as SEQ ID NO: 121, "DNLMA" as SEQ ID NO: 102, "TNLRR" as SEQ ID NO: 68, "EHMAR" as SEQ ID NO: 127 and "DNLMT" as SEQ ID NO: 135.

Figure 20:
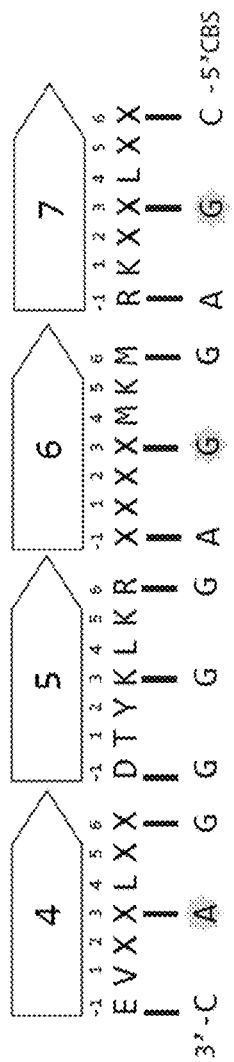

FIG. 20: Binding activity of multi-finger variants on multiple sequence changes to the CBS. Variants from individual pooled high stringency selections were stitched together and selected against three changes to the wild-type CBS (indicated by gray stars or bolded). Variants were assayed for binding on the modified CBS and the wild-type CBS alongside wild-type CTCF zinc finger array. The variants picked out of the selection were able to bind to the modified CBS, but not the wild-type sequence. Inversely, the wild-type zinc finger array was able to bind to the wild-type CBS, but not the modified one. FIG. 20 discloses "DTYKLKR" as SEQ ID NO: 3, "CAGGGGAGGAGC" as SEQ ID NO: 5564, "CGAGGAGGGGACGCT" as SEQ ID NO: 5565, "CCAGCAGGGGGCGCT" as SEQ ID NO: 5558, "GNLVR" as SEQ ID NO: 117, "EHMNR" as SEQ ID NO: 126, "EHLKV" as SEQ ID NO: 13, "GNLRR" as SEQ ID NO: 118, "EHMKR" as SEQ ID NO: 123, "EHLAE" as SEQ ID NO: 151, "GNLAR" as SEQ ID NO: 138, "EHMRR" as SEQ ID NO: 34, "STLNE" as SEQ ID NO: 152, "GNLMR" as SEQ ID NO: 139, "SHMNR" as SEQ ID NO: 146, "DHLQV" as SEQ ID NO: 12, "ANLRR" as SEQ ID NO: 69, "SHMRR" as SEQ ID NO: 147, "EHLNV" as SEQ ID NO: 9, "SNLRR" as SEQ ID NO: 116, "DHLNT" as SEQ ID NO: 155, "EHLQA" as SEQ ID NO: 156, "NNLRR" as SEQ ID NO: 121, "THMKR" as SEQ ID NO: 33, "DHMNR" as SEQ ID NO: 32 and "HHLMH" as SEQ ID NO: 157.

Figure 21:
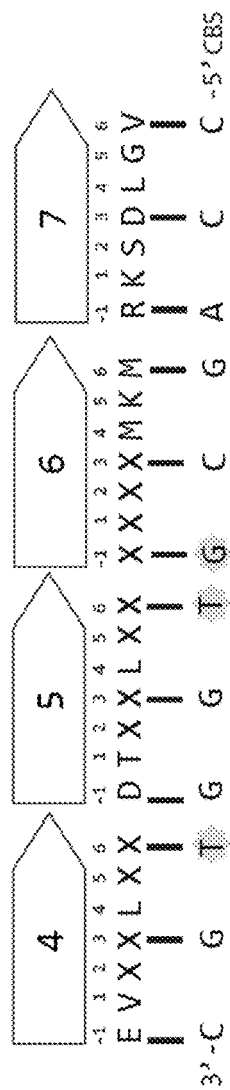

FIG. 21: Binding activity of multi-finger variants on multiple sequence changes to the CBS. Variants from individual pooled high stringency selections were stitched together and selected against three changes to the wild-type CBS (indicated by gray stars or bolded). Variants were assayed for binding on the modified CBS and the wild-type CBS alongside wild-type CTCF zinc finger array. The variants picked out of the selection were able to bind to the modified CBS, but not the wild-type sequence. Inversely, the wild-type zinc finger array was able to bind to the wild-type CBS (white dot), but not the modified one. FIG. 21 discloses "CGTGGTGCGACC" as SEQ ID NO: 5566, "RKSDLGV" as SEQ ID NO: 5, "CCAGCGTGGTGCGCT" as SEQ ID NO: 5567, "CCAGCAGGGGGCGCT" as SEQ ID NO: 5558, "GHLKK" as SEQ ID NO: 158, "TRLKE" as SEQ ID NO: 165, "RADN" as SEQ ID NO: 167, "AHLKK" as SEQ ID NO: 159, "RHDT" as SEQ ID NO: 40, "TKLRL" as SEQ ID NO: 160, "SRLKE" as SEQ ID NO: 44, "RRDT" as SEQ ID NO: 169, "TKLKL" as SEQ ID NO: 161, "RPDT" as SEQ ID NO: 38, "GHLRK" as SEQ ID NO: 162, "RTSS" as SEQ ID NO: 171, "RNDT" as SEQ ID NO: 172, "THLKK" as SEQ ID NO: 163 and "AHLRK" as SEQ ID NO: 60.

Figure 22:
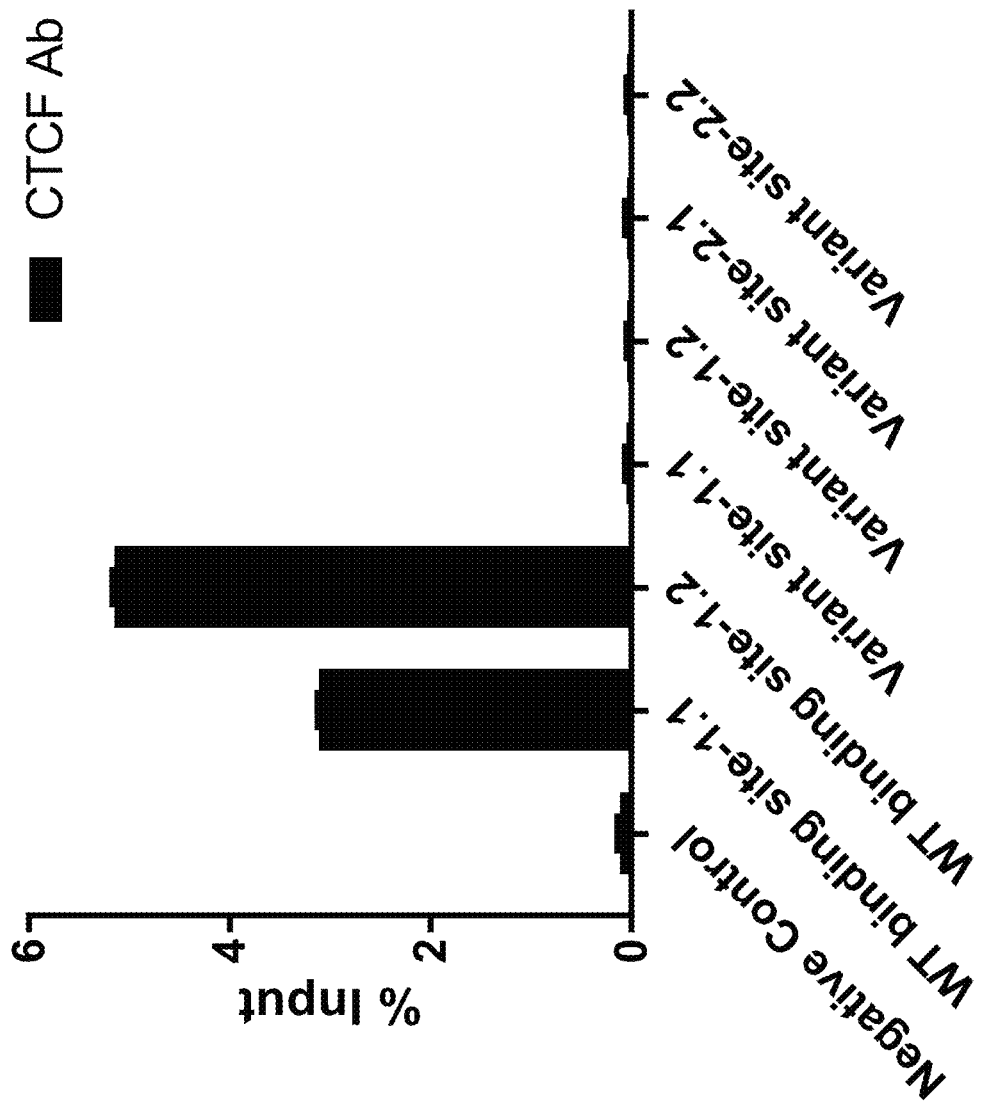
Figure 23A:
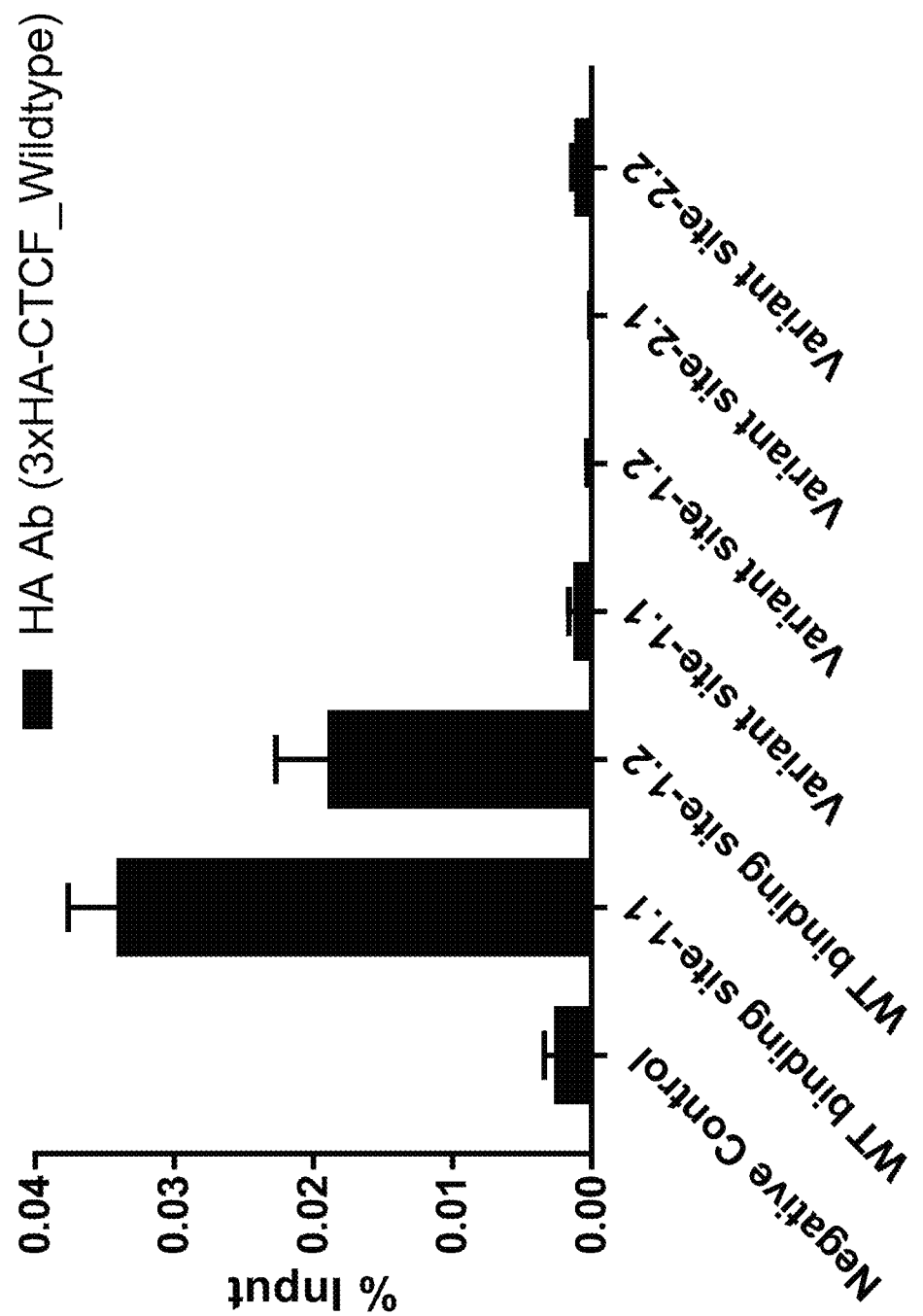
Figure 23B:
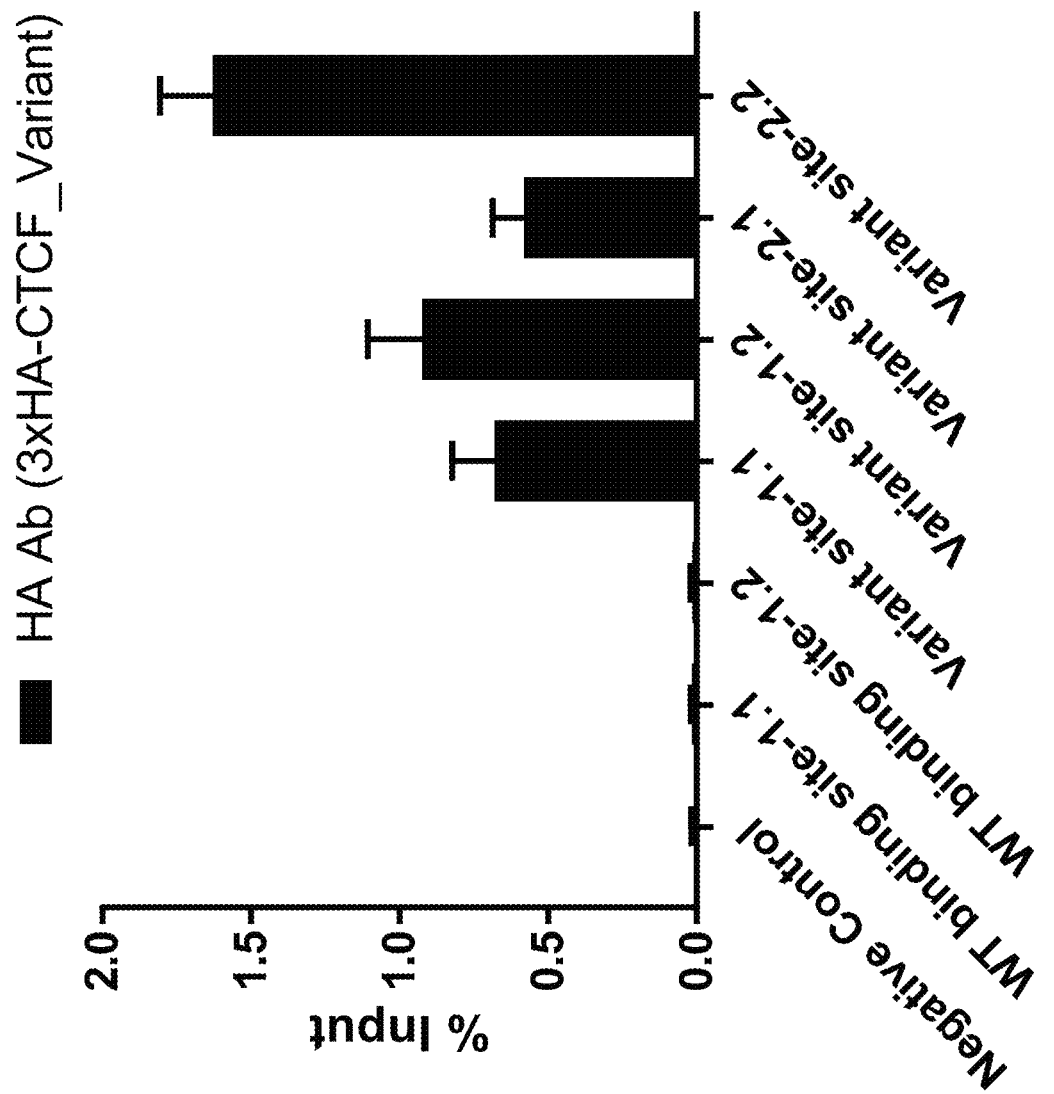

FIG. 22: Wild-type CTCF has binding activity to wild-type CTCF target site and no binding activity to two variant target sites. To confirm endogenous CTCF binds to the wild-type CBSs and not the variant binding sites, as seen in the B2H assay, in a human cell context, we harvested K562 cells, a human erythroleukemia cell line, and examined CTCF binding through ChIP-qPCR. CTCF was assayed for binding to a known CTCF target site and to two endogenous variant binding site sequences using a CTCF specific antibody to enrich for genomic DNA crosslinked to CTCF. Two sets of qPCR primers were designed for each binding site (indicated by 1.1, 1.2, etc). Binding was determined by enrichment of target site above 1% input of crosslinked and sonicated sample not treated with antibody, which is to represent the levels of the site of interest as a fold increase over the frequency of the site of interest in a sample unenriched with antibody. Antibody based enrichment of each sample is quantified by fold enrichment above untreated, and therefore unenriched, input. The negative control reflects background qPCR amplification levels of a target site that CTCF does not bind to. Anything above this negative level is considered enriched indicating CTCF binding while anything below is considered to not be unenriched, and therefore no binding by CTCF. Wild-type CTCF binds to the wild-type target site with no detectable binding to the variant binding sites as predicted by the bacterial B2H reporter assay FIGS. 23A-B: Exogenous wild-type and variant CTCF binding activity in human cells. Two endogenous variant binding site sequences, matching one of the five variant binding sites that CTCF variants were selected on, were identified in the human genome (Variant site 1 and Variant site 2). Both wild-type CTCF with a 3×HA tag and one of the 3×HA tagged engineered CTCF variants, selected to bind to the variant binding site sequence of Variant site 1 and Variant site 2, were assayed for binding in human cells through ChIP-qPCR. FIG. 23A: 3×HA tagged wild-type CTCF binds to wild-type CTCF binding site and does not bind to either variant binding site. Human K562 cells were transfected with plasmid expressing 3×HA tagged CTCF and processed with HA antibody to enrich specifically for the exogenous CTCF (3×HA tagged) and not endogenous CTCF (no tag) binding. A negative control is provided to show ChIP-qPCR levels with no enrichment for a region that is not occupied by CTCF. These results demonstrate exogenous wild-type CTCF has the same binding activity as endogenous CTCF. FIG. 23B: 3×HA tagged variant CTCF binds to variant binding sites and does not bind to wild-type CTCF binding site. K562 cells expressing variant CTCF tagged with 3×HA were analyzed by ChIP-qPCR and treated with HA specific antibody. The same sites as in FIGS. 22 and 23A were investigated for variant CTCF binding. The variant CTCF could bind to the variant sites as indicated by enrichment with variant specific HA antibody and no detectable binding was seen at the wild-type binding site as indicated by lack of HA antibody-based enrichment.

Figure 24A:
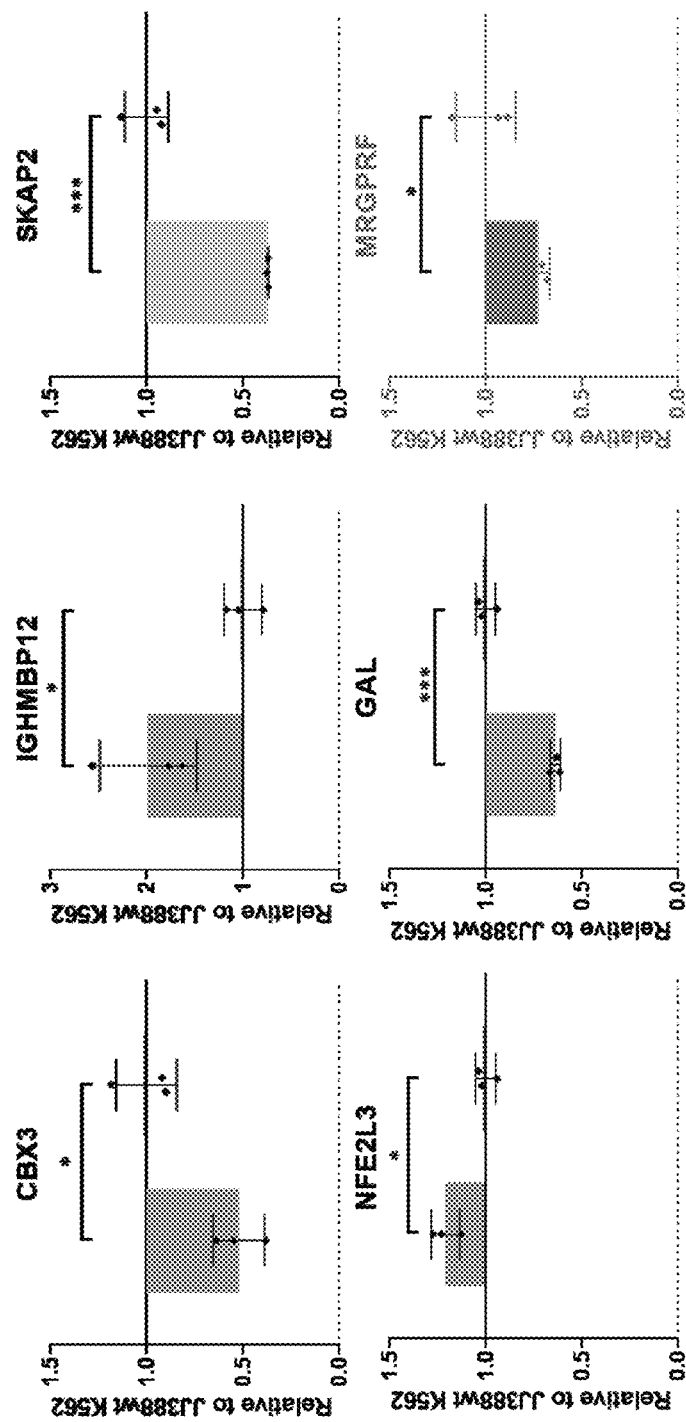
Figure 24B:
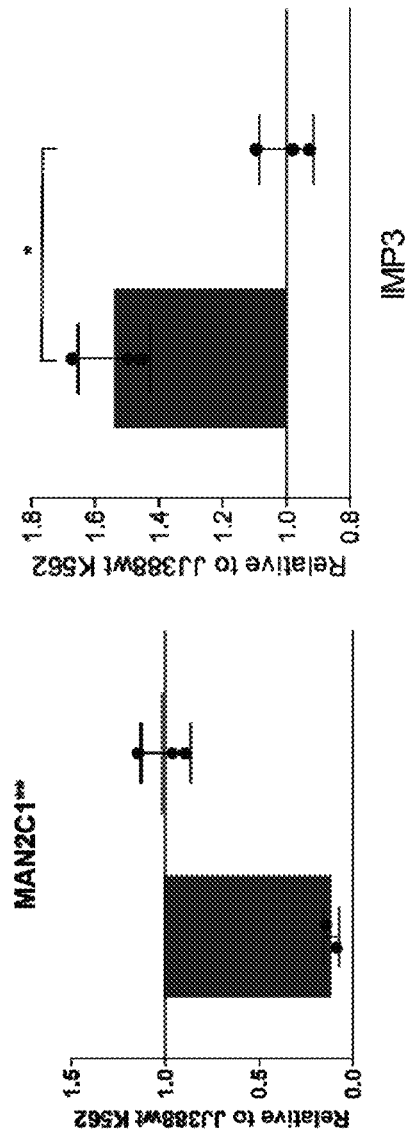

FIGS. 24A-B: Changes in gene expression relative to wild-type control of genes located around variant binding sites. A variant CTCF selected to the G3 binding site sequence and variant CTCF selected to the Other binding site sequence were expressed in wild-type K562s. The variant CTCFs were fused to GFP and RNA was isolated from GFP+ cells 72 hours post nucleofection. cDNA was generated from the RNA and quantified by RT-qPCR. Gene expression levels across samples were normalized to a house keeping gene (HPRT). Changes in gene expression are relative to gene expression levels in wild-type K562s expressing wild-type CTCF tagged with GFP. FIG. 24A. Changes in gene expression of genes around G3 variant binding site in the presence of variant CTCF relative to the wild-type CTCF control. FIG. 24B. Changes in gene expression of genes around Other variant binding site relative to the wild-type control.

Figure 25:
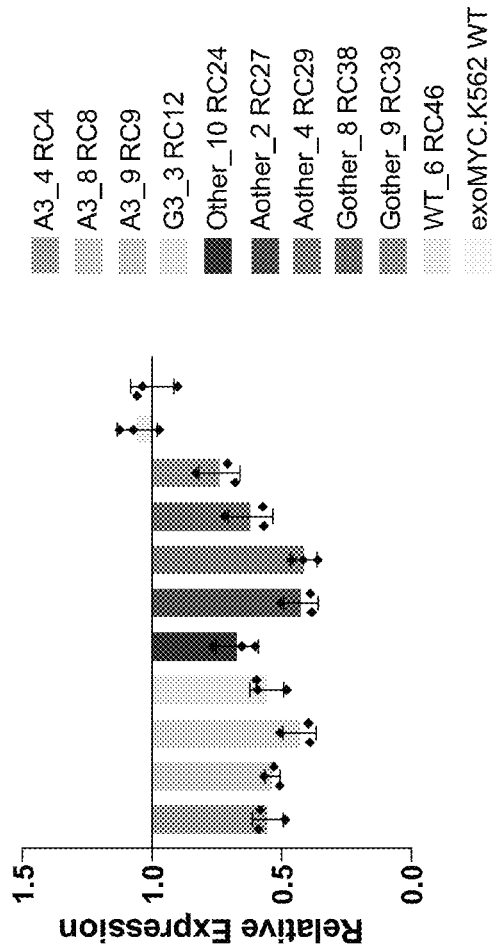

FIG. 25: Introduction of variant binding sites upstream of MYC leads to reduction of Endogenous MYC expression. The CTCF binding site ~2 kb upstream of the MYC TSS was replaced with one of six different sequences used for CTCF variant selections (listed in table). The introduction of these sequences with 4-6 nucleotide changes from the wild-type CTCF binding site sequence result in a reduction of endogenous MYC expression to the same levels as when the CTCF binding site is deleted and loop formation is disrupted. WT_6 sequence has 4 point mutations from the native CTCF binding site, but these changes should have no impact on wild-type CTCF binding as indicated by results from the B2H reporter assay. This appears to be the case as MYC expression levels in the WT_6 cell line are comparable to wild-type K562 MYC expression levels. Because K562 vitality is linked to MYC expression, all variant cell lines were generated in a K562 cell line with exogenous MYC expressed off of a separate PGK promoter (exoMYC.K562). FIG. 25 discloses SEQ ID NOS 5568-5573, respectively, in order of appearance.

Figure 26A:
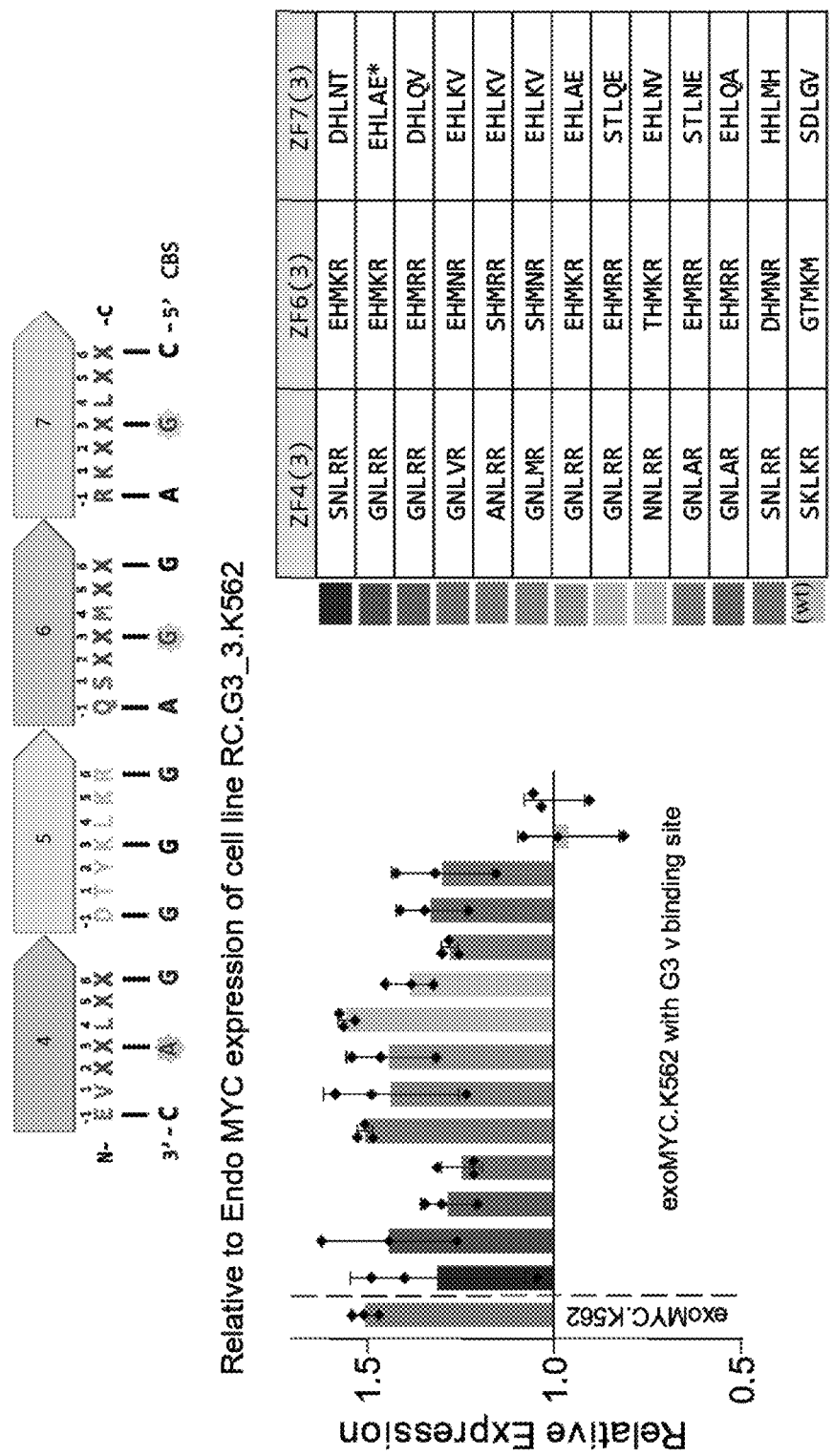
Figure 26B:
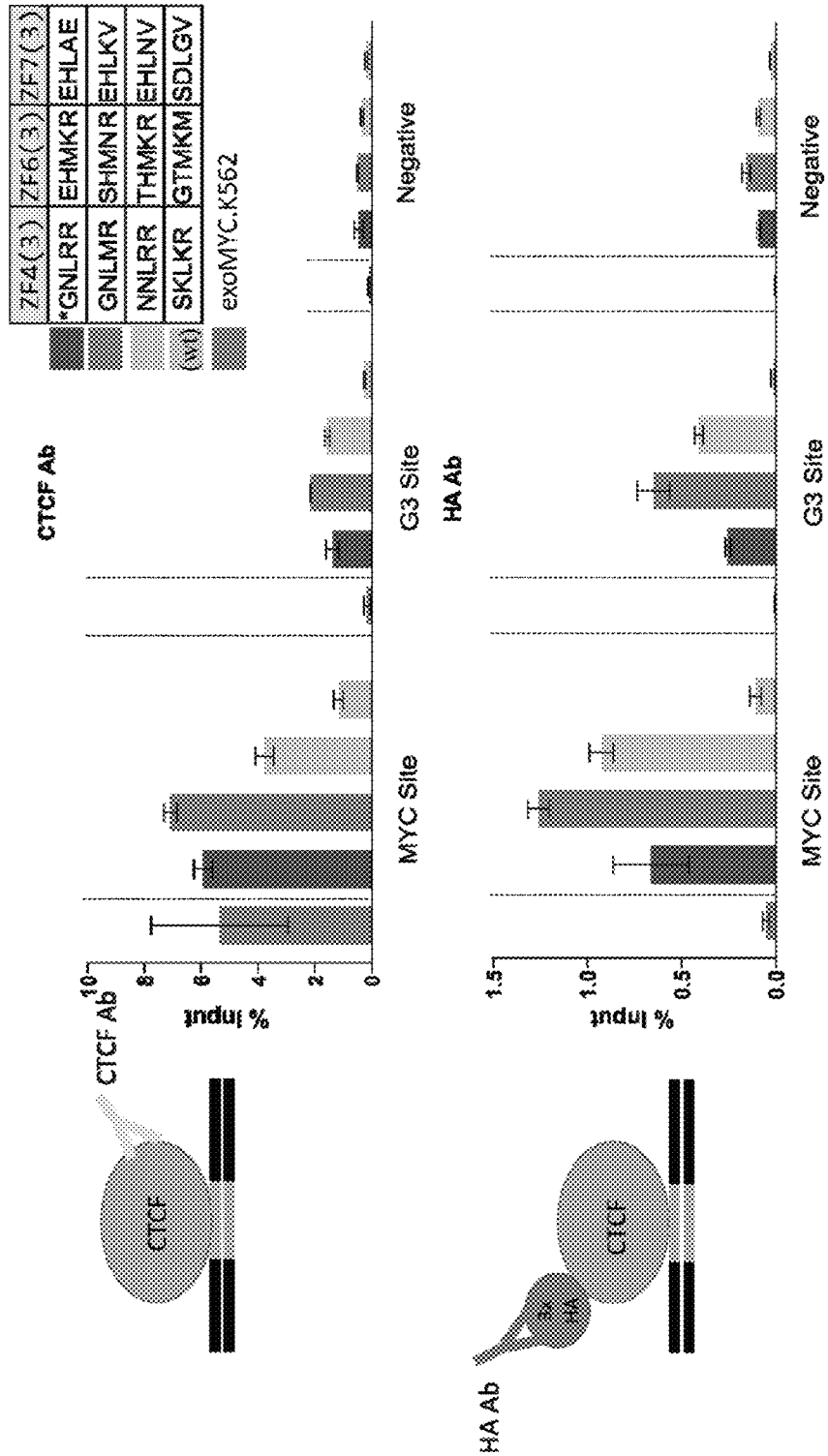

FIGS. 26A-B: Variant CTCFs are able to bind the engineered G3 variant binding site and recover MYC expression. CTCF variants selected to bind to the G3 variant binding site sequence were expressed in the G3_3.K562 cell line. Cells were analyzed for MYC expression and CTCF occupancy on the DNA 72 hours post nucleofection. Residues of ZF helix of the variant and wild-type (indicated by (wt) are listed in the legend. G3 binding site sequence and interacting recognition helix of the CTCF zinc finger array is also diagramed. FIG. 26A. Endogenous MYC levels are recovered to wild-type levels in the G3_3 cell line when CTCF variants are expressed. Endogenous MYC expression levels were quantified by RT-qPCR and are relative to reduced endogenous MYC levels of G3_3 cell line. Endogenous MYC levels from the exoMYC.K562 cell line without any alterations to the CTCF binding site is shown as a positive control (separated by dashed lines). FIG. 26B. CTCF variants are able to bind to the introduced variant binding site in G3_3 cell line while the wild-type CTCF does not. CTCF Ab specific enrichment captures both wild-type and variant CTCF while HA Ab will only detect HA-tagged CTCF (transiently expressed). exoMYC.K562 is included as a control for ChIP-qPCR and is separated by dashed line. exoMYC.K52 has the native sequence at the CTCF binding site upstream of MYC and should demonstrate wild-type CTCF binding. The exogenously expressed CTCFs (variant and wild-type) are HA tagged and expressed in the G3_3 cell line. ChIP-qPCR was performed to investigate CTCF binding to the variant CTCF site replacing the wild-type site ~2 kb upstream of MYC (MYC site). An endogenous G3 site elsewhere in the genome and a region with no known CTCF binding served as a positive and negative control respectively. The variant CTCFs are able to bind to the variant site as indicated by enrichment with both CTCF and HA antibody, while the wild-type CTCF does not. FIGS. 26A-B disclose "CAGGGGAGGAGC" as SEQ ID NO: 5564, "DTYKLKR" as SEQ ID NO: 3, "SNLRR" as SEQ ID NO: 116, "GNLRR" as SEQ ID NO: 118, "GNLVR" as SEQ ID NO: 117, "ANLRR" as SEQ ID NO: 69, "GNLMR" as SEQ ID NO: 139, "NNLRR" as SEQ ID NO: 121, "GNLAR" as SEQ ID NO: 138, "SKLKR" as SEQ ID NO: 3470, "EHMKR" as SEQ ID NO: 123, "EHMIRR" as SEQ ID NO: 34, "EHMNR" as SEQ ID NO: 126, "SHMRR" as SEQ ID NO: 147, "SHMNR" as SEQ ID NO: 146, "THMKR" as SEQ ID NO: 33, "DHMNR" as SEQ ID NO: 32, "GTMKM" as SEQ ID NO: 1255, "DHLNT" as SEQ ID NO: 155, "EHLAE" as SEQ ID NO: 151, "DHLQV" as SEQ ID NO: 12, "EHLKV" as SEQ ID NO: 13, "STLQE" as SEQ ID NO: 225, "EHLNV" as SEQ ID NO: 9, "STLNE" as SEQ ID NO: 152, "EHLQA" as SEQ ID NO: 156, "HHLMH" as SEQ ID NO: 157 and "SDLGV" as SEQ ID NO: 5552.

Figure 27A:
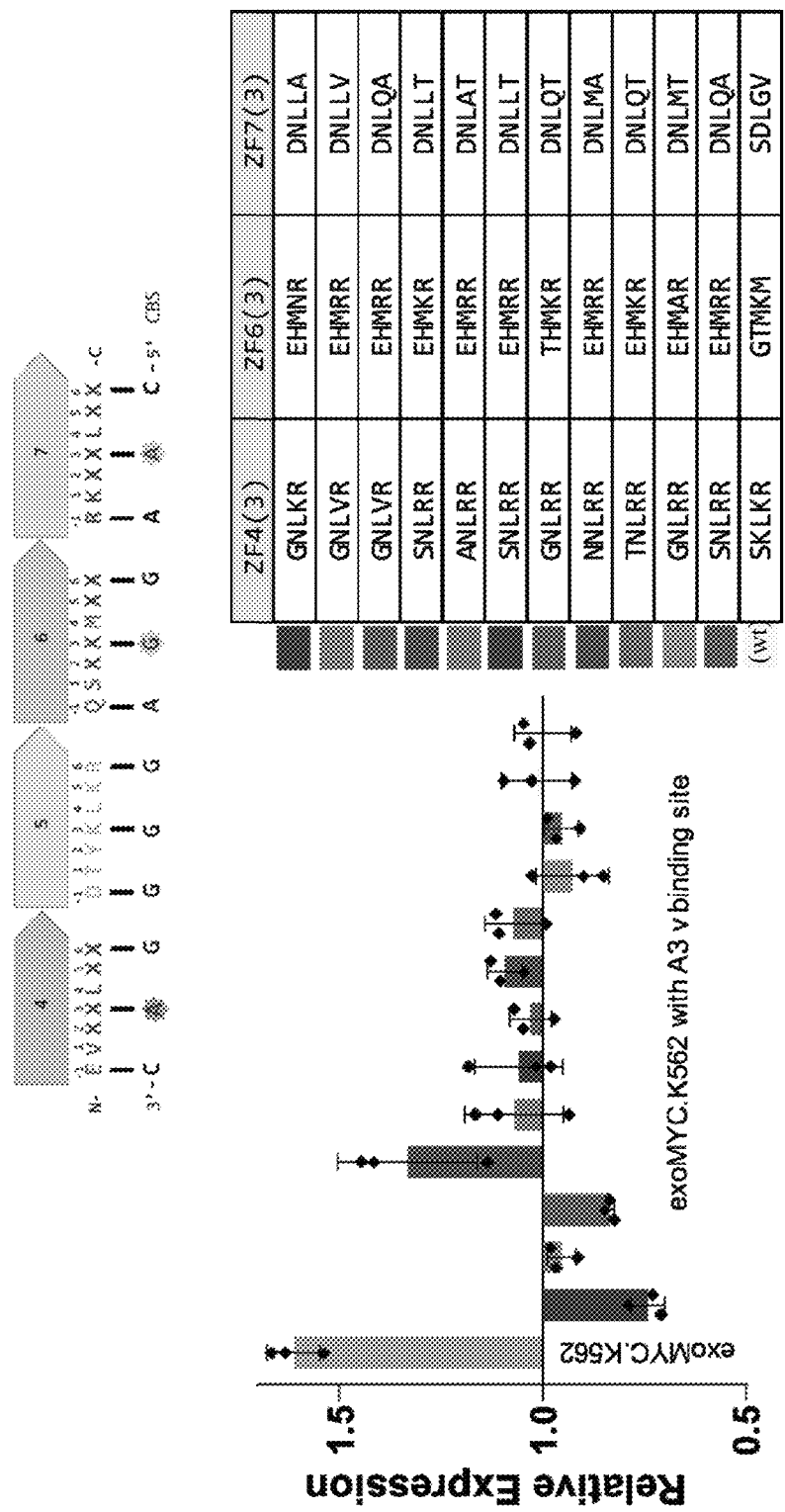
Figure 27B:
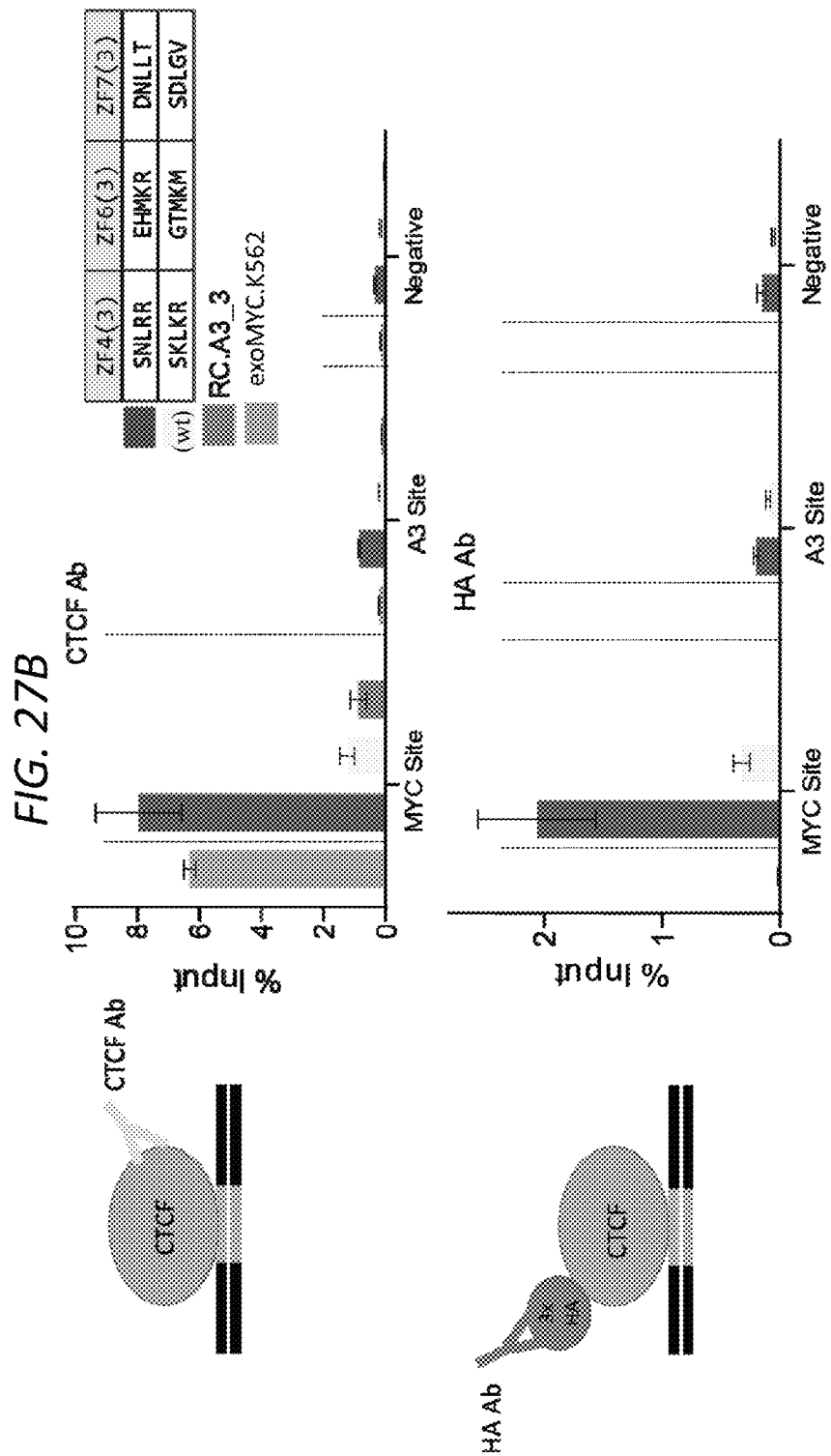

FIGS. 27A-B: Variant CTCFs are able to bind the engineered A3 variant binding site and recover MYC expression. CTCF variants selected to bind to the A3 variant binding site sequence were expressed in the A3_4.K562 cell line. Cells were analyzed for MYC expression and CTCF occupancy on the DNA 72 hours post nucleofection. Residues of ZF helix of the variant and wild-type (indicated by (wt) are listed in the legend. A3 binding site sequence and interacting recognition helix of the CTCF zinc finger array is also diagramed. FIG. 27A. Endogenous MYC levels are recovered to wild-type levels in the A3_4 cell line when CTCF variants are expressed. Endogenous MYC expression levels were quantified by RT-qPCR and are relative to reduced endogenous MYC levels of A3_4 cell line. Endogenous MYC levels from the exoMYC.K562 cell line without any alterations to the CTCF binding site is shown as a positive control (separated by dashed lines). FIG. 27B. CTCF variants are able to bind to the introduced variant binding site in A3_4 cell line while the wild-type CTCF does not. CTCF Ab specific enrichment captures both wild-type and variant CTCF while HAAb will only detect HA-tagged CTCF (transiently expressed). exoMYC.K562 is included as a control for ChIP-qPCR and is separated by dashed line. exoMYC.K52 has the native sequence at the CTCF binding site upstream of MYC and should demonstrate wild-type CTCF binding. The exogenously expressed CTCFs (variant and wild-type) are HA tagged and expressed in the A3_4 cell line. ChIP-qPCR was performed to investigate CTCF binding to the variant CTCF site replacing the wild-type site ~2 kb upstream of MYC (MYC site). An endogenous A3 site elsewhere in the genome and a region with no known CTCF binding served as a positive and negative control respectively. The variant CTCFs are able to bind to the variant site as indicated by enrichment with both CTCF and HA antibody above the negative control, while the wild-type CTCF does not bind. FIGS. 27A-B disclose "CAGGGGAGGAAC" as SEQ ID NO: 5562, "DTYKLKR" as SEQ ID NO: 3, "GNLKR" as SEQ ID NO: 119, "GNLVR" as SEQ ID NO: 117, "SNLRR" as SEQ ID NO: 116, "ANLRR" as SEQ ID NO: 69, "GNLRR" as SEQ ID NO: 118, "NNLRR" as SEQ ID NO: 121, "TNLRR" as SEQ ID NO: 68, "SKLKR" as SEQ ID NO: 3470, "EHMNR" as SEQ ID NO: 126, "EHMIRR" as SEQ ID NO: 34, "EHMKR" as SEQ ID NO: 123, "THMKR" as SEQ ID NO: 33, "EHMAR" as SEQ ID NO: 127, "GTMKM" as SEQ ID NO: 1255, "DNLLA" as SEQ ID NO: 100, "DNLLV" as SEQ ID NO: 129, "DNLQA" as SEQ ID NO: 133, "DNLLT" as SEQ ID NO: 128, "DNLAT" as SEQ ID NO: 132, "DNLQT" as SEQ ID NO: 130, "DNLMA" as SEQ ID NO: 102, "DNLMT" as SEQ ID NO: 135 and "SDLGV" as SEQ ID NO: 5552.

Figure 28:
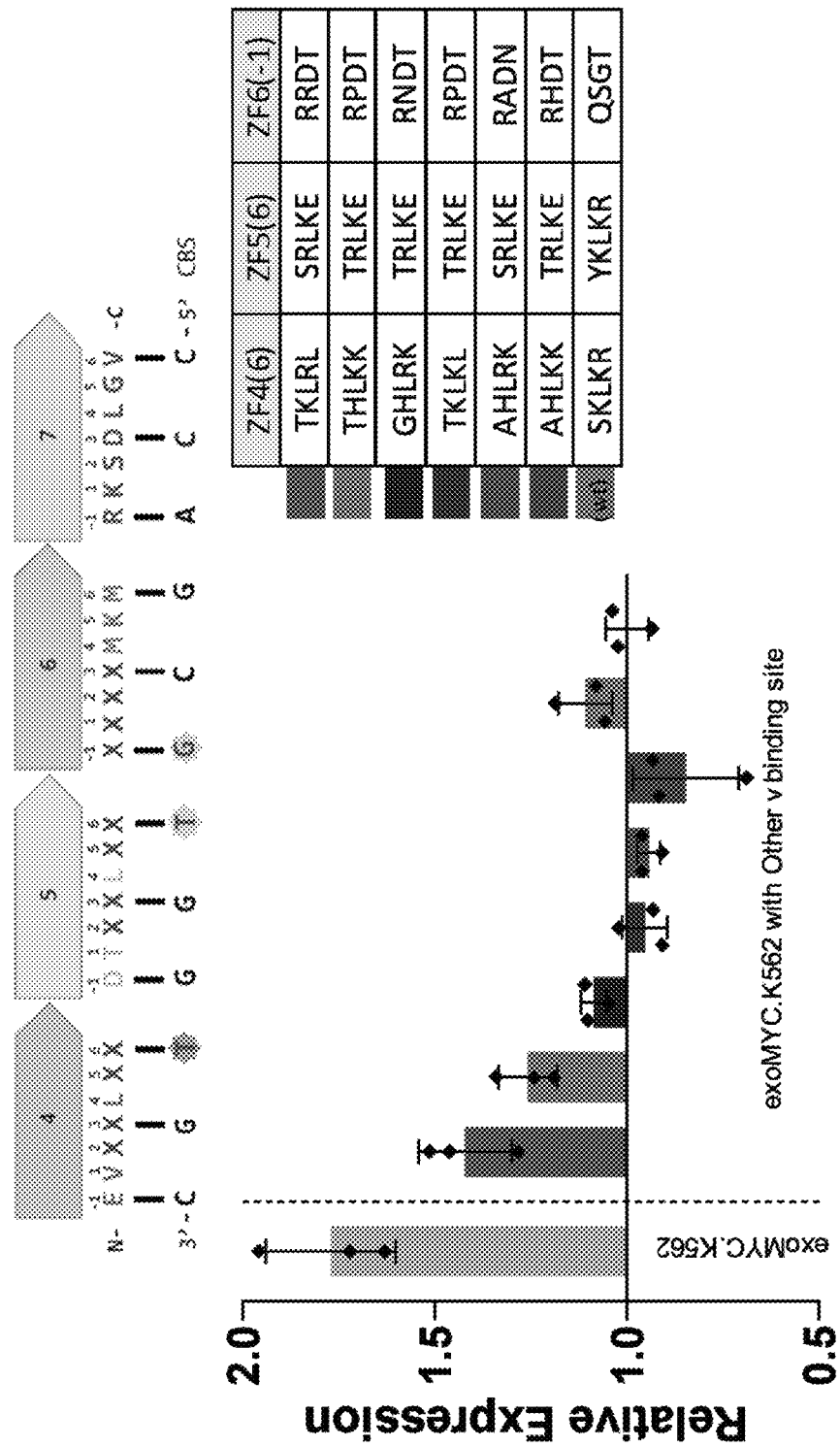

FIG. 28: Variant CTCFs recover MYC expression of the Other 10 variant binding site cell line. CTCF variants selected to bind to the Other variant binding site sequence were expressed in the Other 10.K562 cell line. Cells were analyzed for MYC expression 72 hours post nucleofection. Residues of ZF helix of the variant and wild-type CTCFs (indicated by (wt) are listed in the legend. Other binding site sequence and interacting recognition helix of the CTCF zinc finger array is also diagramed. A. Endogenous MYC levels are recovered to wild-type levels in the Other 10 cell line when CTCF variants are expressed. Endogenous MYC expression levels were quantified by RT-qPCR and are relative to reduced endogenous MYC levels of Other 10 cell line. Endogenous MYC levels from the exoMYC.K562 cell line without any alterations to the CTCF binding site is shown as a positive control (separated by dashed lines). FIG. 28 discloses "RKSDLGV" as SEQ ID NO: 5, "CGTGGTGCGACC" as SEQ ID NO: 5574, "TKLRL" as SEQ ID NO: 160, "THLKK" as SEQ ID NO: 163, "GHLRK" as SEQ ID NO: 162, "TKLKL" as SEQ ID NO: 161, "AHLRK" as SEQ ID NO: 60, "AHLKK" as SEQ ID NO: 159, "SKLKR" as SEQ ID NO: 3470, "SRLKE" as SEQ ID NO: 44, "TRLKE" as SEQ ID NO: 165, "YKLKR" as SEQ ID NO: 5553, "RRDT" as SEQ ID NO: 169, "RPDT" as SEQ ID NO: 38, "RNDT" as SEQ ID NO: 172, "RADN" as SEQ ID NO: 167, "RHDT" as SEQ ID NO: 40 and "QSGT" as SEQ ID NO: 1582.

Figure 29:
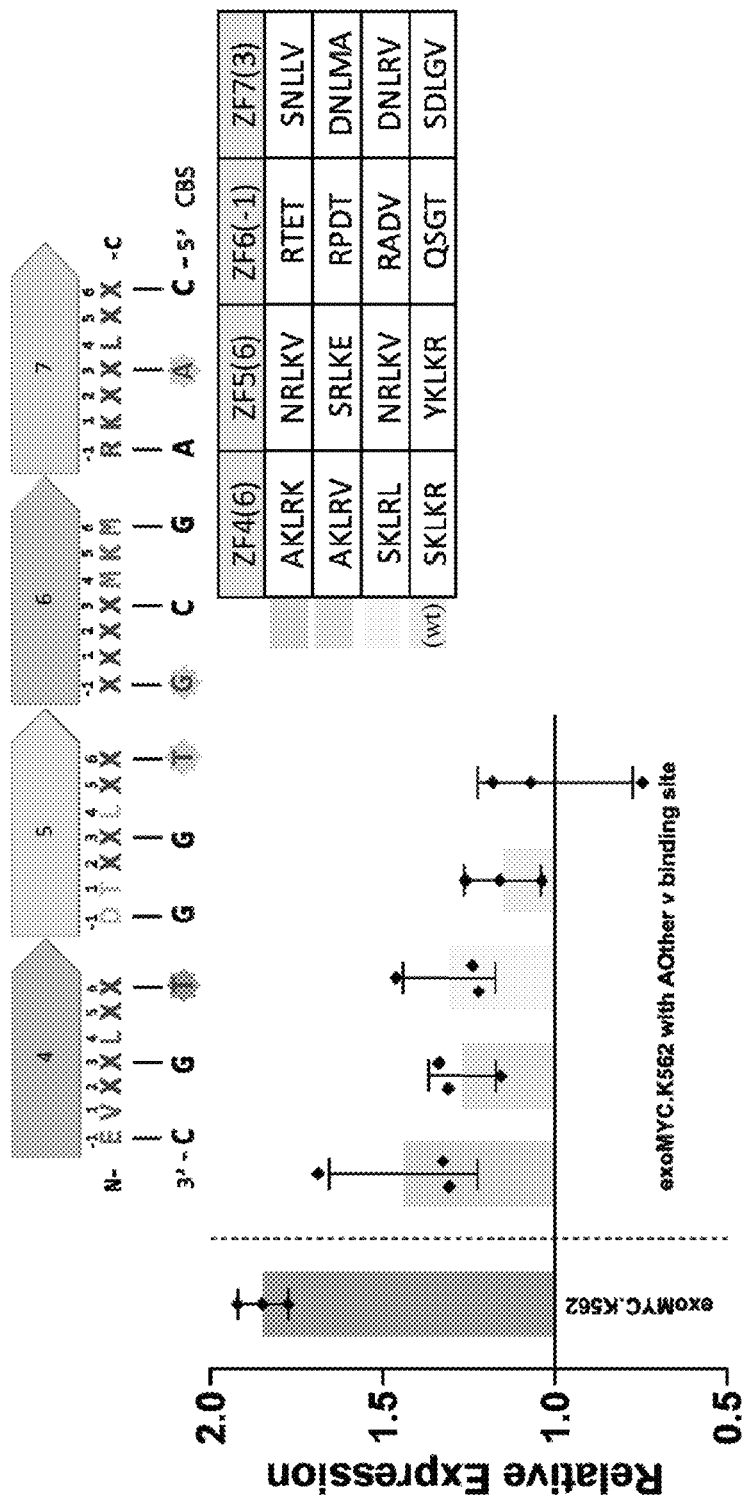

FIG. 29: Variant CTCFs recover MYC expression of the Aother_2 variant binding site cell line. CTCF variants selected to bind to the Aother variant binding site sequence were expressed in the Aother_2.K562 cell line. Cells were analyzed for MYC expression 72 hours post nucleofection. Residues of ZF helix of the variant and wild-type CTCFs (indicated by (wt) are listed in the legend. Aother binding site sequence and interacting recognition helix of the CTCF zinc finger array is also diagramed. A. Endogenous MYC levels are recovered to wild-type levels in the Aother_2 cell line when CTCF variants are expressed. Endogenous MYC expression levels were quantified by RT-qPCR and are relative to reduced endogenous MYC levels of Aother_2 cell line. Endogenous MYC levels from the exoMYC.K562 cell line without any alterations to the CTCF binding site is shown as a positive control (separated by dashed lines). FIG. 29 discloses "CGTGGTGCGAAC" as SEQ ID NO: 5575, "AKLRK" as SEQ ID NO: 89, "AKLRV" as SEQ ID NO: 61, "SKLRL" as SEQ ID NO: 92, "SKLKR" as SEQ ID NO: 3470, "NRLKV" as SEQ ID NO: 94, "SRLKE" as SEQ ID NO: 44, "YKLKR" as SEQ ID NO: 5553, "RTET" as SEQ ID NO: 98, "RPDT" as SEQ ID NO: 38, "RADV" as SEQ ID NO: 99, "QSGT" as SEQ ID NO: 1582, "SNLLV" as SEQ ID NO: 101, "DNLMA" as SEQ ID NO: 102, "DNLRV" as SEQ ID NO: 103 and "SDLGV" as SEQ ID NO: 5552.

DETAILED DESCRIPTION

To date, there are no engineered CTCF variants available that are designed to bind to mutant CBSs with higher affinity than wild-type CTCF. Therefore, there is a need for engineered CTCF variants that can bind to mutant CBSs with higher affinity than wild-type CTCF.

The present disclosure is based, at least in part, on the discovery that CTCF variants with alterations in the zinc finger array can be engineered to recognize CBSs that harbor one or more point mutations, i.e., mutant CBSs.

CTCF

CCCTC-binding factor (CTCF) is a multi-domain protein that acts as an essential genome organizer by maintaining higher-order chromatin structure while also having a role in cell differentiation and the promotion or repression of gene expression. CTCF maintains topologically associated domains (TADs) spanning megabases of the genome as well as smaller scale Sub-TADs leading to fine-tuned gene insulation or gene activation within gene clusters. In addition, CTCF has been found to regulate mRNA splicing by influencing the rate of transcription and more recently been implicated in promoting homologous recombination repair at double-strand breaks. Wild type CTCF binds throughout the genome via an 11 finger zinc finger array that recognizes canonical CTCF binding sites (CBSs).

Wild-type CTCF ZF arrays comprise the following sequences at ZFs 3-6 positions −1 to +6:

```
                                          (SEQ ID NO: 1)
    ZF3 positions -1 to +6: TSGELVR (SEQ ID NO: 2)
    ZF4 positions -1 to +6: EVSKLKR (SEQ ID NO: 3)
    ZF5 positions -1 to +6: DTYKLKR (SEQ ID NO: 4)
    ZF6 positions -1 to +6: QSGTMKM (SEQ ID NO: 5)
    ZF7 positions -1 to +6: RKSDLGV
```

A wild-type CTCF has an amino acid sequence that has greater than 80%, greater than 85%, greater than 90%, greater than 95%, greater than 96%, greater than 97%, greater than 98% or greater than 99% sequence identity as compared to the amino acid sequence shown below:

```
                                        (SEQ ID NO: 190)
MEGDAVEAIVEESETFIKGKERKTYQRRREGGQEEDACHLPQNQTDGGEV

VQDVNSSVQMVMMEQLDPTLLQMKTEVMEGTVAPEAEAAVDDTQIITLQV

VNMEEQPINIGELQLVQVPVPVTVPVATTSVEELQGAYENEVSKEGLAES

EPMICHTLPLPEGFQVVKVGANGEVETLEQGELPPQEDPSWQKDPDYQPP

AKKTKKTKKSKLRYTEEGKDVDVSVYDFEEEQQEGLLSEVNAEKVVGNMK

PPKPTKIKKKGVKKTFQCELCSYTCPRRSNLDRHMKSHTDERPHKCHLCG

RAFRTVTLLRNHLNTHTGTRPHKCPDCDMAFVTSGELVRHRRYKHTHEKP

FKCSMCDYASVEVSKLKRHIRSHTGERPFQCSLCSYASRDTYKLKRHMRT

HSGEKPYECYICHARFTQSGTMKMHILQKHTENVAKFHCPHCDTVIARKS

DLGVHLRKQHSYIEQGKKCRYCDAVFHERYALIQHQKSHKNEKRFKCDQC

DYACRQERHMIMHKRTHTGEKPYACSHCDKTFRQKQLLDMHFKRYHDPNF

VPAAFVCSKCGKTFTRRNTMARHADNCAGPDGVEGENGGETKKSKRGRKR

KMRSKKEDSSDSENAEPDLDDNEDEEEPAVEIEPEPEPQPVTPAPPPAKK

RRGRPPGRTNQPKQNQPTAIIQVEDQNTGAIENIIVEVKKEPDAEPAEGE

EEEAQPAATDAPNGDLTPEMILSMMDR
```

For the purpose of comparing two different nucleic acid or polypeptide sequences, one sequence (test sequence) may be described to be a specific percentage identical to another sequence (comparison sequence). The percentage identity can be determined by the algorithm of Karlin and Altschul, Proc. Natl. Acad. Sci. USA, 90:5873-5877 (1993), which is incorporated into various BLAST programs. The percentage identity can be determined by the "BLAST 2 Sequences" tool, which is available at the National Center for Biotechnology Information (NCBI) website. See Tatusova and Madden, FEMS Microbiol. Lett., 174(2):247-250 (1999). For pairwise DNA-DNA comparison, the BLASTN program is used with default parameters (e.g., Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP program can be employed using default parameters (e.g., Matrix: BLOSUM62; gap open: 11; gap extension: 1; x_dropoff: 15; expect: 10.0; and wordsize: 3, with filter).

Percent identity of two sequences is calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST is used to compare two sequences, it aligns the sequences and yields the percent identity over defined, aligned regions. If the two sequences are aligned across their entire length, the percent identity yielded by the BLAST is the percent identity of the two sequences. If BLAST does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence. Various versions of the BLAST programs can be used to compare sequences, e.g., BLAST 2.1.2 or BLAST+ 2.2.22.

CTCF Binding Sites (CBSs)

Figure 1:
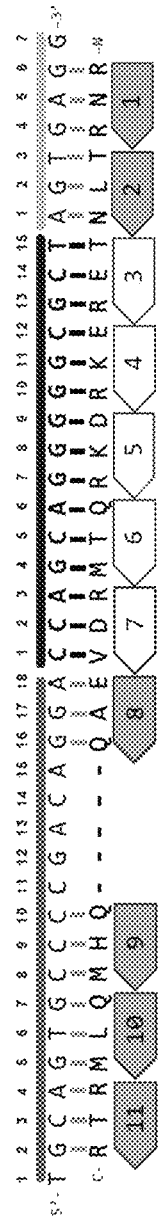
FIG. 1: Diagram of an exemplary 11-finger CTCF zinc finger array protein-DNA interactions at the CTCF binding site. Each zinc finger of the 11-finger array contained a recognition alpha-helix where protein-DNA base contacts were made by amino acids in position −1, 2, 3 and 6 of each alpha-helix. Here, position −1, 3, and 6 were only depicted as positon 2 makes a cross strand contact with the opposite strand of the binding site that is not shown here. The sequence for the binding site was derived from ChIP-seq data (Nakahashi et al., 2013). The binding site was partitioned into three segments: 5' flanking (gray-line), core (black-line), and 3' flanking (light gray line). The position of each nucleotide within each segment are numbered. Dashes indicate known DNA-protein contacts (black) and theoretical DNA-protein contacts (gray) between the zinc finger array and the binding site. Zinc fingers 3-7 of the array (white) make protein-DNA contacts with the core sequence (bold, black lined). There was a possible 5-6 base pair gap (represented by horizontal dashed lines) between zinc finger 8 and zinc fingers 9-11 as suggested by ChIP-exo and DNAse I footprinting of CTCF bound DNA fragments (Hashimoto, H. et al., 2017). Note CTCF binds to its target site in the 3'-5' direction with the N-terminal side of the protein binding to the 3' end of the binding site.

The CBS is typically 40 bp in length with a highly conserved 15 bp core sequence (or core motif). Sequence flanking the core sequence is significantly less well conserved, but still important for CTCF binding at sites throughout the genome (FIG. 1).

Wild type CTCF binds to a "consensus CBS motif" contains the following core sequence: 5'-NCDNHN-GRNGDNNNN-3' (SEQ ID NO: 191).

In one embodiment, the consensus CBS motif contains the following core sequence: 5'-CCAGCAGGGGGCGCT-3' (SEQ ID NO:6). Other core sequences that are known in the art.

It is not known if the nucleotides flanking the core sequence are bound by the 11 finger ZF array present within CTCF. Co-crystal structures of the 11-finger Zinc Finger (ZF) array bound to a consensus CTCF Binding Sequence (CBS) suggests that only ZFs 3-7 of the 11-finger ZF array appear to bind directly to the highly conserved core sequence while ZFs 8-11 and 1-2 do not appear to mediate sequence-specific contacts. Progressive truncations of the ZF array suggest that ZFs 8-11 and ZFs 1-2 may improve DNA-binding of CTCF to CBSs and DNaseI foot printing, as well as ChIP-Seq and ChIP-Exo data, suggests that ZFs 9-11 may make important protein-DNA contacts (Rhee and Pugh, Cell (2011); Nakahashi et al., Cell Reports (2013)). Interestingly, the co-crystal structure of the CTCF Z array bound to a CBS only contains zinc finger 2-9 with the other fingers not visible in the structure, consistent with the idea that zinc fingers interacting with flanking regions of the motif may not make stable contacts with the DNA (Hashimoto, et al., Molecular Cell (2017)). Thus, it remains unclear what impact all 11 fingers of the array have on DNA binding activity of CTCF and if all zinc fingers, or a subset, contact the DNA.

CTCF binding is sensitive to changes in the conserved 15 bp core motif of the CBS, where, in mice, single nucleotide changes at certain positions can lead to loss of CTCF binding (Nakahashi et al., Cell Reports (2013)). CTCF binding sites have been reported to be mutational hotspots in cancer with cancer-associated mutations localized to the core sequence of the CTCF binding site in primary samples from gastrointestinal cancer patients and with accompanying atypical gene expression profiles of oncogenic and tumor suppressor genes (Guo et al., Nature Communications (2018)). Small deletions of CTCF binding sites have also been shown to lead to loss of expression of genes such as MYC and PTGS2, which both play a role in cancer development (Schuijers et al., Cell Reports (2018); Kang et al., Oncogene (2015)).

Methods described herein can be used to select and generate engineered CTCF variants comprising a plurality of zinc fingers, where the selected polypeptide has at least one amino acid residue in at least one zinc finger that differs in sequence from a wild-type CTCF, and where the engineered CTCF variant binds to a DNA sequence of interest (e.g., CBS harboring at least one mutation in the consensus CBS sequence) but does not bind to a consensus CBS. Using methods of the present invention, a scaffold polypeptide is re-engineered into a new scaffold-based zinc-finger polypeptide that has different structural and functional features, such that the new polypeptide binds to a sequence of interest but does not bind to a naturally occurring DNA binding site of the scaffold protein.

The term "zinc finger" or "Zf" refers to a polypeptide having DNA binding domains that are stabilized by zinc. The individual DNA binding domains are typically referred to as "fingers." A Zf protein has at least one finger, preferably 2 fingers, 3 fingers, or 6 fingers. A Zf protein having two or more Zfs is referred to as a "multi-finger" or "multi-Zf" protein. Each finger typically comprises an approximately 30 amino acid, zinc-chelating, DNA-binding domain. An exemplary motif characterizing one class of these proteins is -Cys-(X) (2-4)-Cys-(X) (12)-His-(X) (3-5)-His (SEQ ID NO:7), where X is any amino acid, which is known as the "C(2)H(2)class." A single Zf of this class typically consists of an alpha helix containing the two invariant histidine residues co-ordinated with zinc along with the two cysteine residues.

The term "bind to" or "binding" with respect to a nucleic acid binding factor and its target nucleic acid, e.g., CTCF (variant or wild-type) and CBS, refers to sequence-dependent binding of the nucleic acid binding factor to the target nucleic acid sequence of a nucleic acid through intermolecular interactions, e.g., ionic, covalent, London dispersion, dipole-dipole, or hydrogen bonding, in such a way that the binding allows the nucleic acid binding factor to mediate a biologically significant function, e.g., transcriptional activation, recruitment of other proteins to the binding site, and/or alteration of chromatic structure. Such binding can result in modulation of expression of genes, such as activation, overexpression, suppression, or inactivation of gene expression.

The term "does not bind to" with respect to a nucleic acid binding factor and its target nucleic acid, e.g., CTCF (variant or wild-type) and CBS, refers to the lack of sequence-specific binding of the nucleic acid binding factor to a nucleic acid through intermolecular interactions, e.g., ionic, covalent, London dispersion, dipole-dipole, or hydrogen bonding, as a result of the lack of presence of a target sequence in the nucleic acid (e.g., due to one or more point-mutations in the CBS). Such non-binding does not allow the nucleic acid binding factor to mediate a biologically significant function, e.g., transcriptional activation, DNA modification, DNA cleavage, recruitment of other proteins to the binding site, and/or alteration of chromatic structure.

Each finger within a Zf protein binds to from about two to about five base pairs within a DNA sequence. Typically a single Zf within a Zf protein binds to a three or four base pair "subsite" within a DNA sequence. Accordingly, a "subsite" is a DNA sequence that is bound by a single zinc finger. A "multi-subsite" is a DNA sequence that is bound by more than one zinc finger, and comprises at least 4 bp, preferably 6 bp or more. A multi-Zf protein binds at least two, and typically three, four, five, six or more subsites, i.e., one for each finger of the protein.

Compositions and Methods

Described herein are engineered CTCF variants that can bind to mutant CBSs with higher affinity than wild-type CTCF. The engineered CTCF variants can be used in regulating genes that are under the control of mutant CBSs (CBSs having at least one nucleic acid that is different in sequence from the nucleic acid sequence of a consensus CBS). The CTCF variants have at least one amino acid residue in at least one zinc finger that differs in sequence from the amino acid sequence of a wild-type CTCF.

Exemplary engineered CTCF variants include those that contain:

(1) the amino acid sequence DHLQT (SEQ ID NO:8), EHLNV (SEQ ID NO:9), AHLQV (SEQ ID NO:10), EHLRE (SEQ ID NO:11), DHLQV (SEQ ID NO:12), EHLKV (SEQ ID NO:13), DHLQV (SEQ ID NO:14), EHLVV (SEQ ID NO:15), DHLRT (SEQ ID NO:16), DHLAT (SEQ ID NO:17), or DHLQT (SEQ ID NO:18) at ZF7 positions +2 to +6;

(2) the amino acid sequence DHLQT (SEQ ID NO:19), EHLNV (SEQ ID NO:20), AHLQV (SEQ ID NO:21), EHLRE(SEQ ID NO:22), DHLQV (SEQ ID NO:23), EHLKV (SEQ ID NO:24), DHLQV (SEQ ID NO:25), EHLVV (SEQ ID NO:26), DHLRT (SEQ ID NO:27), DHLAT (SEQ ID NO:28), or DHLQT (SEQ ID NO:29) at ZF7 positions +2 to +6;

(3) the amino acid sequence NAMKR (SEQ ID NO:30), EHMGR (SEQ ID NO:31), DHMNR (SEQ ID NO:32), THMKR (SEQ ID NO:33), EHMRR (SEQ ID NO:34), or THMNR (SEQ ID NO:35) at ZF6 positions +2 to +6;

(4) the amino acid sequence MNES (SEQ ID NO:36), HRES (SEQ ID NO:37), RPDT (SEQ ID NO:38), RTDI (SEQ ID NO:39), or RHDT (SEQ ID NO:40) at ZF6 positions −1 to +3;

(5) the amino acid sequence HGLKV (SEQ ID NO:41), HRLKE (SEQ ID NO:42), HALKV (SEQ ID NO:43), SRLKE (SEQ ID NO:44), DGLRV (SEQ ID NO:45), HTLKV (SEQ ID NO:46), or NRLKE (SEQ ID NO:47) at ZF5 positions +2 to +6;

(6) the amino acid sequence ATLKR (SEQ ID NO:48), QALRR (SEQ ID NO:49), GGLVR (SEQ ID NO:50), HGLIR (SEQ ID NO:51), ANLSR (SEQ ID NO:52), TGLTR (SEQ ID NO:53), HGLVR (SEQ ID NO:54), GGLTR(SEQ ID NO:55), HTLRR(SEQ ID NO:56), TVLKR (SEQ ID NO:57), ADLKR (SEQ ID NO:58), or HGLRR (SEQ ID NO:59) at ZF5 positions +2 to +6;

(7) the amino acid sequence AHLRK (SEQ ID NO:60), AKLRV (SEQ ID NO:61), GGLGL (SEQ ID NO:62), AKLRI (SEQ ID NO:63), TKLKV (SEQ ID NO:64), or SKLRV (SEQ ID NO:65) at ZF4 positions +2 to +6;

(8) the amino acid sequence ATLRR (SEQ ID NO:66), RRLDR (SEQ ID NO:67), TNLRR (SEQ ID NO:68), ANLRR (SEQ ID NO:69), GNLTR (SEQ ID NO:70), AMLKR (SEQ ID NO:71), HMLTR (SEQ ID NO:72), AMLRR (SEQ ID NO:73), or TMLRR (SEQ ID NO:74) at ZF4 positions +2 to +6;

(9) the amino acid sequence QQLIV (SEQ ID NO:75), SQLIV (SEQ ID NO:76), QQLLV (SEQ ID NO:77), GELVV (SEQ ID NO:78), QQLLI (SEQ ID NO:79), GQLIV (SEQ ID NO:80), GQLTV (SEQ ID NO:81), TELII (SEQ ID NO:82), QGLLV (SEQ ID NO:83), QQLLT (SEQ ID NO:84), GQLLT (SEQ ID NO:85), GELLT (SEQ ID NO:86), or QQLLI (SEQ ID NO:87) at ZF3 positions +2 to +6;

(10) the amino acid sequence AKLKK (SEQ ID NO:88), AKLRK (SEQ ID NO:89), AHLRV (SEQ ID NO:90), AKLRV (SEQ ID NO:91), or SKLRL (SEQ ID NO:92) at ZF4 positions +2 to +6; the amino acid sequence ERLRV (SEQ ID NO:93), NRLKV (SEQ ID NO:94), SRLKE (SEQ ID NO:95), or NRLKV (SEQ ID NO:96) at ZF5 positions +2 to +6; the amino acid sequence RPDT (SEQ ID NO:97), RTET (SEQ ID NO:98), or RADV (SEQ ID NO:99) at ZF6 positions −1 to +3; and the amino acid sequence DNLLA (SEQ ID NO:100), SNLLV (SEQ ID NO:101), DNLMA (SEQ ID NO:102), or DNLRV (SEQ ID NO:103) at ZF7 positions +2 to +6;

(11) the amino acid sequence GHLKK (SEQ ID NO:104), AHLRK (SEQ ID NO:105), or GKLRI (SEQ ID NO:106) at ZF4 positions +2 to +6; the amino acid sequence SRLKE (SEQ ID NO:107), DALRR (SEQ ID NO:108), DGLKR (SEQ ID NO:109), or TRLRE (SEQ ID NO:110) at ZF5 positions +2 to +6; the amino acid sequence at RPDT (SEQ ID NO:111) or RTEN (SEQ ID NO:112) at ZF6 positions −1 to +3; and the amino acid sequence EHLKV (SEQ ID NO:113), DHLLA (SEQ ID NO:114), or HHLDV (SEQ ID NO:115) at ZF7 positions +2 to +6;

(12) the amino acid sequence SNLRR (SEQ ID NO:116), GNLVR (SEQ ID NO:117), GNLRR (SEQ ID NO:118), GNLKR (SEQ ID NO:119), ANLRR (SEQ ID NO:120), NNLRR (SEQ ID NO:121), or TNLRR (SEQ ID NO:122) at ZF4 positions +2 to +6; the amino acid sequence EHMKR (SEQ ID NO:123), EHMRR (SEQ ID NO:124), THMKR (SEQ ID NO:125), EHMNR (SEQ ID NO:126), or EHMAR (SEQ ID NO:127) at ZF6 positions +2 to +6; and the amino acid sequence DNLLT (SEQ ID NO:128), DNLLV (SEQ ID NO:129), DNLQT (SEQ ID NO:130), DNLLA (SEQ ID NO:131), DNLAT (SEQ ID NO:132), DNLQA (SEQ ID NO:133), DNLMA (SEQ ID NO:134), or DNLMT (SEQ ID NO:135) at ZF7 positions +2 to +6;

(13) the amino acid sequence GNLVR (SEQ ID NO:136), GNLRR (SEQ ID NO:137), GNLAR (SEQ ID NO:138), GNLMR (SEQ ID NO:139), ANLRR (SEQ ID NO:140), SNLRR (SEQ ID NO:141), or NNLRR (SEQ ID NO:142) at ZF4 positions +2 to +6; the amino acid sequence EHMNR (SEQ ID NO:143), EHMKR (SEQ ID NO:144), EHMRR (SEQ ID NO:145), SHMNR (SEQ ID NO:146), SHMRR (SEQ ID NO:147), THMKR (SEQ ID NO:148), or DHMNR (SEQ ID NO:149) at ZF6 positions +2 to +6; and the amino acid sequence EHLKV (SEQ ID NO:150), EHLAE (SEQ ID NO:151), STLNE (SEQ ID NO:152), DHLQV (SEQ ID NO:153), EHLNV (SEQ ID NO:154), DHLNT (SEQ ID NO:155), EHLQA (SEQ ID NO:156), or HHLMH (SEQ ID NO:157) at ZF7 positions +2 to +6; or

(14) the amino acid sequence GHLKK (SEQ ID NO:158), AHLKK (SEQ ID NO:159), TKLRL (SEQ ID NO:160), TKLKL (SEQ ID NO:161), GHLRK (SEQ ID NO:162), THLKK (SEQ ID NO:163), or AHLRK (SEQ ID NO:164) at ZF4 positions +2 to +6; the amino acid sequence TRLKE (SEQ ID NO:165) or SRLKE (SEQ ID NO:166) at ZF5 positions +2 to +6; and the amino acid sequence RADN (SEQ ID NO:167), RHDT (SEQ ID NO:168), RRDT (SEQ ID NO:169), RPDT (SEQ ID NO:170), RTSS (SEQ ID NO:171), or RNDT (SEQ ID NO:172) at ZF6 positions −1 to +3.

In some embodiments, the engineered CTCF variants contain two or more combinations of the above-listed amino acid sequences.

In one embodiment of the present disclosure, mutations at certain positions within the consensus CBS substantially reduced binding by the wild-type CTCF zinc finger array in a bacterial two-hybrid system that was used to select for variants from randomized libraries that are capable of recognizing the mutated CBS sequence. Combining fingers together can be used to generate variant CTCF zinc finger arrays capable of recognizing CBSs harboring multiple point mutations. In some embodiments of the present disclosure, CTCF proteins harboring these zinc finger array variants are used to restore CTCF binding activity at sites bearing one or more mutations within a CBS (i.e., non-canonical CBSs). In some embodiments of the present disclosure, CTCF variants capable of recognizing alternative non-CBS sites in the genome. In some embodiments, such CTCF variants can be used to create artificial TADs and/or enhancer-promoter loops that can purposefully insulate genes and/or perturb the higher order structure of the genome and thereby alter expression of certain target genes of interest.

Diagnosis and Treatment of Diseases

The engineered CTCF variants described herein can be used for treating diseases where aberrant gene regulation due to mutant CBS is an underlying factor. The engineered CTCF variants described herein can, for example, bind to mutant CBSs that do not bind wild-type CTCFs, thereby altering or restoring gene regulation that can reverse or slow down progression of diseases. CTCF binding has been shown to regulate expression of oncogenes, such as MYC. Mutations accumulated in CTCF binding sites and loss of wild-type CTCF binding are associated to dysregulation of oncogenes and increased risk of carcinogenesis. Transcriptional dysregulation of MYC is one of the most frequent events in aggressive tumor cells and the dysregulation is a result of mutations in CTCF binding site disrupting enhancer-promoter loop. Engineered CTCF variants can bind to the mutated sites and restore normal gene expression levels, reducing risk of cancer development. In another case, Fragile X Syndrome is the result of a duplication in a repetitive region and the loss of FMR1 expression. Duplication of a repeat region in the X chromosome disrupts a CTCF binding site, leading to the loss of an enhancer-promoter loop driving the expression of FMR1. The engineered CTCF variants could restore the enhancer-promoter loop, leading to restoration of FMR1 expression. Human Papilloma Virus (HPV) and other integrating viruses (such as HIV) are often silenced by CTCF-mediated insulation of the viral genome from nearby enhancers. In the case of HPV18, there is a CTCF binding site in the promoter region of the viral genome. HPV18 that have mutations in the CTCF binding site are not silenced because these sequence mutations in the binding site can no longer be recognized by CTCF. Engineered CTCF variants would be able to bind to the mutated HPV integrated genomes and restore the insulating loop.

Kits

Also provided herein are kits comprising the engineered CTCF variant, and/or nucleic acids encoding an engineered CTCF variant as described herein and instructions for use.

Other Applications for the Engineered CTCF Variants

The engineered CTCF variants described herein can be used in a number of other applications, some of which are disclosed herein.

In some embodiments, the engineered CTCF variant, or nucleic acids encoding such engineered CTCF variant can be used to further elucidate the complex interactions of CTCF and other chromatin organization proteins. The structural maintenance of chromosomes is tightly regulated within cells and CTCF plays a major role. It still remains unclear how higher order structures are inherited across cell division and maintained through cell differentiation, the use of CTCF variants can help clarify that role. CTCF variants might be used to investigate how loops are formed across the genome and to modify or restore normal genomic architecture in a manner that impacts endogenous gene expression for research and therapeutic applications. They might also be used to re-establish ancestral CTCF binding sites so that we may better understand the evolutionary implications of TAD-based genome organization and epigenetic regulation of gene expression or to create alternative genomic architectures that impact endogenous gene expression for research and therapeutic applications.

EXAMPLES

Materials and Methods

The following materials and methods were used in the examples set forth below.

Construction of B2H Reporter Assay Components

The zinc-finger bacterial expression plasmid contained the CTCF zinc finger array (or variants) fused to gal11P. The amino-terminal end of all or part of the CTCF 11-finger zinc finger array was fused to the carboxy-terminal end of gal11P with a Flag tag linker between them. The zinc finger expression plasmid contains a Kanamycin resistance gene. The second plasmid, known as the bacterial reporter plasmid, contained CTCF binding site sequence that was introduced via BsaI restriction digest followed by T4 mediated ligation of annealed oligos containing the CTCF binding site. The reporter plasmid contained bacterial lac promoter that promoted the expression of lacZ when the CTCF binding site was bound. The reporter plasmid also has a Chloramphenicol resistance gene.

Bacterial-Two-Hybrid (B2H) Randomized Library Construction

Complimentary oligos were synthesized by IDT with 'VNS' or 'NNS' variation introduced in the sequence by design. Oligos were annealed and ligated into the zinc finger expression plasmid (previously digested with XbaI and BamHI) using T4 ligase. Ligation reaction was purified using Qiagen Minelute column and the purified substrate was electro-transformed into electro-competent XL1blue $E.$ $coli$ strain. After 1 hour recover in SOC at 37° C., the transformation was inoculated into 150 mL Luria broth (LB) with 50 ug/mL of Kanamycin. After the culture reached a OD600 of 0.400-0.600 (about 10 hours growth at 37° C.) the culture was spun down and the library was harvested using Qiagen Maxiprep kit.

Bacterial-Two-Hybrid (B2H) Reporter Assay 600 ng of gal11P-zinc finger expression plasmid and 600 ng of reporter plasmid with CTCF binding site of interest were chemically transformed into 150 uL of Δλ $E.$ $coli$ strain with an alpha N-terminal domain of RNA polymerase (α-NTD)-Gal4 fusion. Plasmid and cell mixture was incubated on ice for 30 minutes, heat shocked at 42° C. for 1 minute, recovered on ice for 2 minutes, followed by recovery in 500 uL of Luria Broth for 1 hour. Post-recovery, transformation was plated on Kanamycin (50 ug/mL), Chloramphenicol (12.5 ug/uL) selective LB agar plates. After 14-16 hours of growth at 37° C., colonies were picked and grown overnight in 1 mL of induction media (Luria broth with 50 ug/uL of Kanamycin, 12.5 ug/mL of Chloramphenicol, 10 ug/mL of ZnCl, and 500 ug/mL of IPTG). After 15-17 hours of growth, 25 uL of the overnight culture was sub-cultured into 1 mL of fresh induction media and grown for 2 hours at 37° C. or until cultures were between OD595 0.157-0.268 as measured by spectrophotometer. 100 uL of the subculture in then lysed for minimum of 15 minutes using 11 ul of a 1:10 mixture of lysozyme and PopCulture soap. 15 uL of the lysis mixture was then analyzed for fold activation of LacZ by previously described colorimetric ONPG assay. Binding was quantified by fold activation of LacZ. Fold activation was determined by calculating the fold increase of β-gal levels of a sample above the β-gal levels of the negative control (no zinc finger protein fused to gal11P).

Bacterial-Two-Hybrid (B2H) Selection Assay

Plasmids involved in the selection assay are the same as before with only one difference: The reporter plasmid is made to be a selective plasmid by swapping LacZ with BlaC, an antibiotic resistance gene for β-lactam ring class of antibiotics, such as Carbenicillin. Selections are carried out by constructing libraries of variants from a pool of oligos ligated into the zinc finger-gal11P expression plasmid. These are electro-transformed into electro-competent *E. coli* strain containing the selective plasmid with the CTCF binding site of interest. Cells are recovered in 1 mL of SOC for 1 hour at 37° C. followed by induction of selective plasmid for 3 additional hours at 37° C. in 4 mLs of induction media (previously described). After four total hours, transformations are plated on low stringency plates (LB agar with 50 ug/mL of Kanamycin, 12.5 ug/mL of chloramphenicol, 100 ug/mL of Carbenicillin, 10 ug/mL of zinc chloride, and 200 ug/mL, IPTG and 0.45 ug/mL of Clavulanic acid). Plates are grown overnight at 37° C. for 20-24 hours and then colonies are harvested off the surface with 2 mL of LB. 50 uL of the scrapped colonies are sub-cultured into 1 mL of terrific broth (TB) with 50 ug/mL of Kanamycin, and 12.5 ug/mL of Chloramphenicol and grown 14-16 hours at 37° C. The next day, plasmid is harvested from the overnight cultures and chemically transformed into chemically competent Δλ *E. coli* strain containing the same selective plasmid with the CTCF binding site of interest as before. The chemical transformation is performed as previously described with the addition of 2 hour growth in induction media following a 1 hour recovery at 37° C. After a total of 3 hours of growth, cells are plated on high stringency selective gradient plates. The high stringency gradient plates contains 50 ug/mL of Kanamycin, 12.5 ug/mL of Chloramphenicol, 100 ug/mL of Carbenicillin, 10 ug/mL of ZnCl, 200 ug/mL of IPTG with a gradient of Clavulanic acid starting from ~1 up to 40 ug/mL in concentration. Plates were incubated 20-24 hours at 37° C. Colonies that grew on the gradient with the highest levels of Clavulanic acid were picked and grown in 1mL of TB with 50 ug/mL of Kanamycin and grown overnight in order to harvest the plasmid. The variant plasmid was then Sanger sequenced as well as analyzed for binding activity in the B2H β-gal reporter assay.

High Stringency Gradient Plates

The high stringency gradient plates contains 50 ug/mL of Kanamycin, 12.5 ug/mL of Chloramphenicol, 100 ug/mL of Carbenicillin, 10 ug/mL of ZnCl, 200 ug/mL of IPTG with a gradient of Clavulanic acid starting from ~1 to 40 ug/mL in concentration. To obtain a gradient of Clavulanic acid, rectangle plates are elevated using a pipette tip so as to have a ~25° C. slope (enough of an angle so that the thin end of the wedge is only barely covered with LB agar). 20-25 mL of LB agar with 50 ug/mL of Kanamycin, 12.5 ug/mL of Chloramphenicol, 100 ug/mL of Carbenicillin, 10 ug/mL of ZnCl, 200 ug/mL of IPTG and 4 ug/mL of Clavulanic acid is added to the inclined plate to form the bottom wedge. Once solidified, the plates are laid flat and 20-25 mLs of LB agar with 50 ug/mL of Kanamycin, 12.5 ug/mL of Chloramphenicol, 100 ug/mL of Carbenicillin, 10 ug/mL of ZnCl, 200 ug/mL of IPTG (with no Clavulanic acid) is poured on top. This creates plates with a gradient of Clavulanic acid ranging from ~1 ug/mL up to 4.0 ug/mL.

CTCF Binding Assay Using ChIP-qPCR

K562 cells were seeded 18-24 hours in advance of transfection at a density of $3 \times 10^5$ cells/mL. 3 million K562s per variant were transfected using Lonza Kit V using the provided optimized protocol and pooled in a 10 cm dish. 5 ug of plasmid expressing HA epitope tagged CTCF (wild-type or variant) expressed by a pCAG promoter was used for each 1 million cell reaction. 72 hours post transfection, approximately 10 million cells were crosslinked with 1% Formaldehyde at 37° C. for 10 mins. Reaction was quenched with 1.2 mL of 2.5M Glycine for 5 mins at 37° C. Cells were pelleted at 430 g for 10 mins and sonicated on SFX250 Branson sonifier for 5.5 mins, 32% Amplitude, 1.3s off, 0.7s on. The samples were then split in half, one precipitated overnight, rotating at 4° C. with antibody specific to CTCF and the other precipitated overnight with HA specific antibody. The next day, antibody bound chromatin complexes were incubated with G-dynabeads for 2 hours at 4° C., rotating. Beads were washed three times in 1 mL of ice-cold RIPA 150 Wash Buffer (0.1% SDS, 0.1% DOC, 1% Triton X-100, 1 mM EDTA, 10 mM Tris-HCl pH 8, 150 mM NaCl), three time in 1 mL of ice-cold RIPA 500 wash buffer (0.1% SDS, 0.1% DOC, 1% Triton X-100, 1 mM EDTA, 10 mM Tris-HCl pH 8, 500 mM NaCl), three times in 1 mL of ice-cold LiCl wash buffer (10 mM Tris-HCl pH8, 250 mM LiCl, 0.5% Triton X-100, 0.5% DOC), and once in 1 mL of ice-cold 10 mM Tris-HCl pH 8.5. The antibody chromatin complex was eluted from the beads in 100 uL of Elution Buffer (10 mM Tris-HCl pH 8, 0.1% SDS, 150 mM NaCl) with 5 mM DTT added fresh. Beads were incubated with elution buffer at 65° C. for 1 hour, shaking at 900 rpm. Beads were pelleted by magnet and supernatant was moved to a clean tube where, after cooling to room temp, 1 uL of RNAse (Roche 11119915001) was added to the sample and incubated at 37° C. for 30 mins at 600 rpm. 3 uL of Proteinase K [20 mg/mL] was added to samples and incubated overnight at 65° C. (Lifetech #100005393). The next day, 100 uL of SPRI beads with 160 uL of PEG/NaCl (20% PEG, 2.5M NaCl) were added to samples, vortexed and incubated at room temp for 5 minutes before pelleting beads on a magnet. Pellet was washed twice with 80% ethanol and air dried for 5 minutes before final elution in 150 uL of 10 mM Tris-HCl pH 8. 3 uL of recovered supernatant was mixed with 5 uL of SYBR qPCR master mix and 2 uL of primer mix for quantification of fragment enrichment over 1% input untreated by antibody by Real Time-qPCR.

Generation of Variant Binding Site Cell Lines

Cell lines with the variant binding site introduced at the CTCF binding site ~2 kb upstream of MYC TSS were generated by nucleofecting exoMYC.K562 with SpCas9-P2A-GFP, gRNA targeting the CTCF binding site, and one of 6 distinct ssODNs as HDR templates to introduce the 6 different variant binding sites. exoMYC.K562 is K562 cell line transduced with exogenous MYC construct expressed off of PGK promoter. This was necessary as any reduction of endogenous MYC expression can impact the survival of K562 cells. GFP+ cells were sorted at a high dilution into a 96 well plate for single-cell clonal expansion. Once expanded, gDNA and RNA was extracted to genotype and phenotype the clonal cell population. Clonal lines that had a reduction of endogenous MYC and also appeared homozygous at the target site for the desired HDR event were used in the study.

Quantifying MYC Expression by RT-qPCR

Three million K562 cells genome edited to harbor the variant binding site upstream of MYC were nucleofected with 5 ug of plasmid expressing a variant CTCF following the Lonza Kit V protocol. 72 hours post nucleofection, 1 million cells were isolated for RNA extraction following the NucleoSpin RNA Plus RNA isolation protocol. The RNA was converted to cDNA via Thermo High-Capacity RNA-to-cDNA Kit. 3 uL of 1:20 dilution of cDNA was mixed with 5 uL of Thermo Fast SYBRgreen Master Mix and run on RT-qPCR machine following standard PCR amplification protocol.

Results

Single Nucleotide Substitution at CBS Affecting CTCF Binding Efficiency

Figure 2:
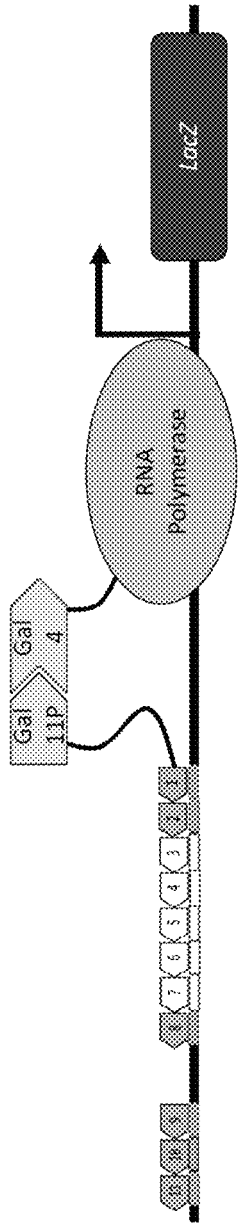
FIG. 2: Diagram of B2H Beta-galactosidase reporter assay. The B2H reporter assay used Gal11P-mediated recruitment of Gal4 to indicate binding. E. coli is transformed with two plasmids: one plasmid encoded for both a zinc finger-Gal11P fusion and an alpha N-terminal domain of RNA polymerase (α-NTD)-Gal4 fusion; the second plasmid contained a modifiable binding sequence upstream of a weak promoter that drives the expression of the lacZ gene, which encodes for β-galactosidase. A zinc finger-Gal11P fusion that was able to bind to the target sequence recruited the α-NTD-Gal4 fusion to the promoter, thereby inducing the expression of lacZ. This increase in β-galactosidase levels was detected by a simple colorimetric ONPG-based assay. The CTCF zinc finger array-gal11P fusion was bound to a CTCF binding site in this diagram, recruiting the α-NTD-Gal4 fusion to the promoter region upstream of lacZ, leading to expression.

We reasoned we could use a bacterial two-hybrid (B2H) system to evolve the zinc finger array of CTCF to bind to mutated CBSs bearing single or multiple sequence changes that disrupt wild-type CTCF binding (Wright et al. Nature Protocols (2006); Sander et al., Nature Methods (2010); Maeder et al. Molecular Cell. (2008)). We used a previously described bacterial-two-hybrid (B2H) system to systematically define the impact of single nucleotide substitutions within a previously defined consensus CBS site (Joung et al., PNAS (2000)). In the B2H system, the binding of a DNA-binding zinc finger array to a target site of interest can be configured to result in increased transcription of a reporter gene (e.g., beta-galactosidase or an antibiotic resistance gene) (FIG. 2). To do this, two fusions are expressed in an E. coli cell bearing a reporter construct. The first fusion consists of a zinc finger array fused to a fragment of the yeast Gal11P protein, which interacts with a fragment of the yeast Gal4 fusion. The second fusion consists of a fusion of the N-terminal domain of the E. coli RNA polymerase alpha subunit to the yeast Gal4 fragment (the α-Gal4 fusion). The reporter construct consists of a weak E. coli promoter that drives expression of the reporter gene of interest with a binding site for the zinc finger array positioned upstream of the promoter. Binding of the zinc finger-Gal11P fusion to the zinc finger binding site results in recruitment of RNA polymerase complexes harboring the alpha-Gal4 fusion, resulting in increased transcription of the reporter gene. If the reporter gene is lacZ, which encodes for β-galactosidase (β-gal), the level of beta-gal expression can be easily quantified using a well-established colorimetric ONPG-based assay (FIG. 2).

Figure 3:
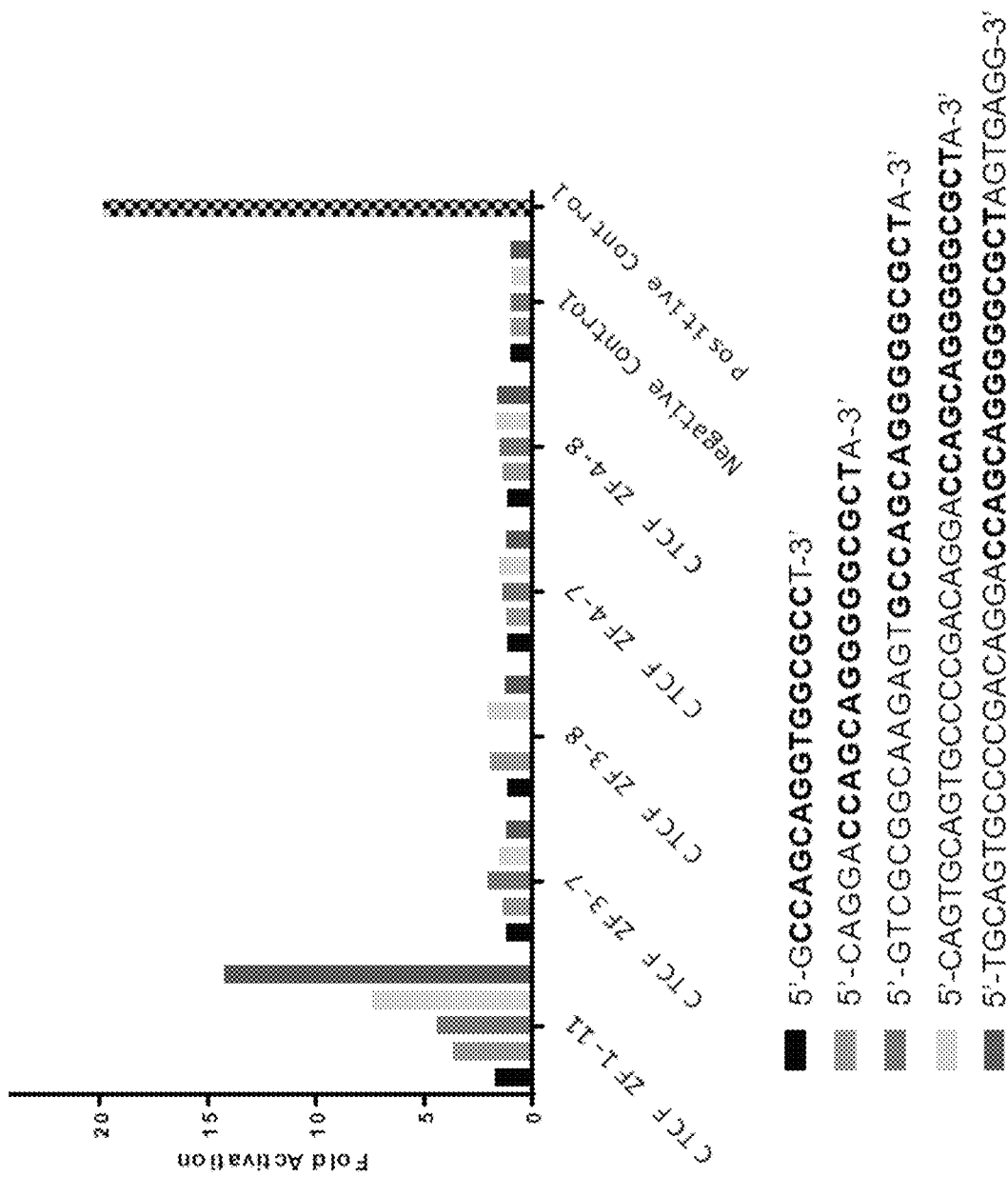
FIG. 3: Fold activation in the B2H B-gal assay was greatest when CTCF zinc fingers 1-11 of 11 finger array interacts with full length target site. Five target sites (sequence indicated in the legend) were tested along with the full CTCF zinc finger array and four different subsets (indicated on the x-axis). The core sequence (black and bolded) which is the most highly conserved sequence of CTCF binding sites was tested independently and with different quantities of flanking sequence as derived from Hashimoto, H. et al. Mol. Cell. 2017 (black and light gray); Persikov, A and Singh, M. NAR. 2014 (medium gray); and Nakahashi, H. et al., Cell Rep. 2013 (very light gray and dark gray). Positive control reflects binding activity of a known 3-finger zinc finger that binds strongly in bacterial and human contexts to a known sequence. The negative control reflects baseline beta-galactosidase levels when the alpha N-terminal domain of RNA polymerase (α-NTD)-Gal4 fusion is not directly recruited to the promoter of lacZ. This baseline was used to calculate fold activation when the CTCF zinc finger array is fused to gal11P.
Figure 4:
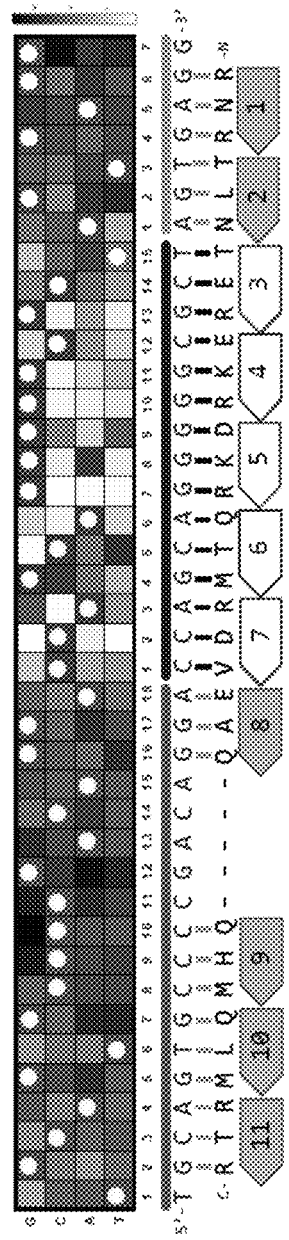
FIG. 4: CTCF zinc finger array is sensitive to sequence changes at certain positions of the core region within the CTCF binding site. Each of the four possible nucleotides at each position of the 40 bp reference CBS were tested for ability to bind the CTCF zinc finger array in the B2H y. Fold activation reflects binding activity above background β-galactosidase levels (Background β-gal levels are obtained from the levels of β-gal from samples with each binding site in the presence of the gal4-RNA polymerase fusion with no zinc finger array fused to gal11P). The reference sequence above is partitioned into three segments: 5' flanking (dark gray lined), core (black lined), and 3' flanking (gray lined). The position of each nucleotide within each segment are numbered. Dashes indicate known DNA-protein contacts (black) and theoretical DNA-protein contacts (gray) between the zinc finger array and the binding site. Core sequence 1-15 of the binding site (black, bold) interacts with zinc finger 3-7 of the array (white, black outline) and appear to be most sensitive to changes in the binding sequence. Alterations to the 5' flanking sequence as well as the 3' flanking sequence did not negatively impact binding.

In this B2H reporter assay, we determined the entire zinc finger array (ZF1-11) and the full CTCF binding site (CBS), not just the 15 bp consensus CBS sequence, was required for optimal expression of the lacZ gene (FIG. 3), which mimics observed CTCF binding requirements in human cells 10, 11. After optimizing positioning of the CBS site relative to the transcription start site, we then systematically introduce point mutations into the CBS and tested their impact on lacZ expression. These results demonstrated that mutation of nucleotides outside the 15 bp core sequence had little impact on lacZ expression. By contrast, binding, however certain sequences at certain positions within the core sequence resulted in no or reduced binding (FIG. 4). Our results closely match ChIP-Seq data for CTCF binding sites in human cells and reflect other studies in the literature in which point mutations in the CTCF core lead to loss of CTCF binding. Taken together, these results strongly suggest that binding activity of the CTCF zinc finger array in the B2H system mimics the binding activity of intact CTCF protein in human cells.

Figure 5:
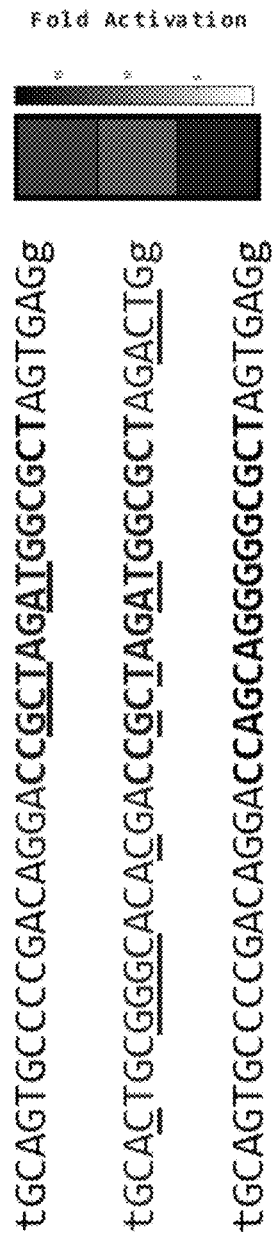
FIG. 5: Maximizing binding potential of the CTCF binding site. Modifications were made to the reference binding site (bottom) to combine nucleotide changes that, individually, showed increased binding activity of the CTCF zinc finger array. The core sequence motif is bold while changes made are underlined. Binding activity of the 11-finger CTCF zinc finger array was quantified in the B2H Beta-galactosidase reporter assay in triplicate. Fold activation reflects binding activity above background levels when no DNA binding protein is present.

Although most sequence changes in the flanking regions of the binding site had little impact on binding efficiency, certain alterations appeared to slightly improve the fold-activation of lacZ expression. Therefore, we tested whether a more "optimized" CBS bearing the "best" nucleotides as defined in the B2H assay might lead to higher-fold activation of lacZ expression but we did not observe any higher activity compared with the original consensus sequence (derived from Nakahashi et al. ChIP-seq data) (FIG. 5).

Figure 6:
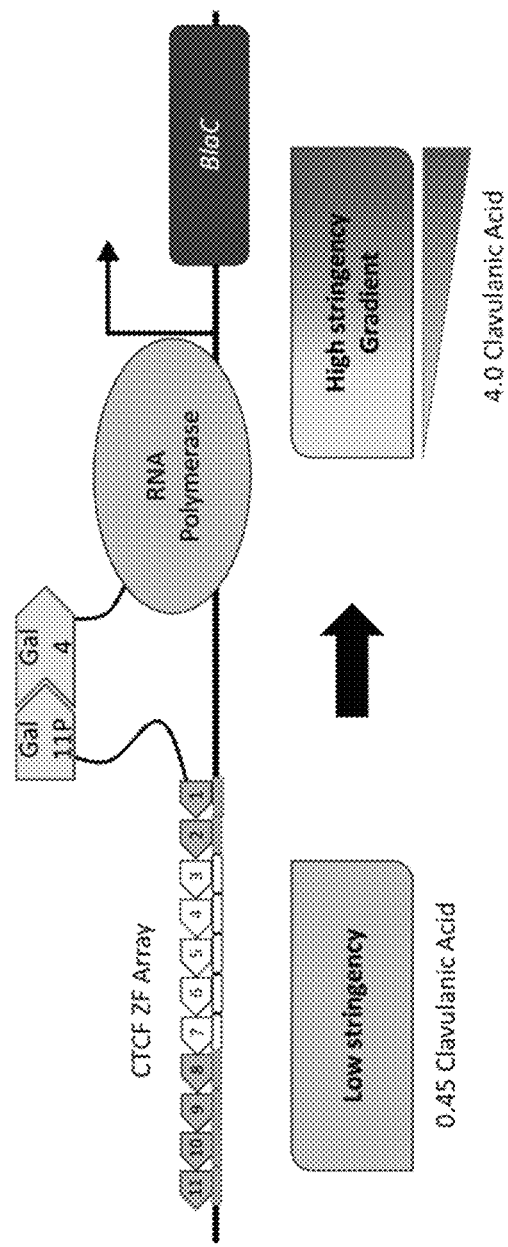
FIG. 6: Diagram of B2H Beta-lactamase inhibitor selection. The selection system contained the same components as the reporter system except successful binding of the zinc finger array to the CBS drove BlaC expression, an inhibitor of the beta-lactamase class of antibiotics, instead of lacZ. Expression of BlaC allowed for growth on Carbenicillin plates. The selection was driven by the addition of Clavulanic acid, an inhibitor of beta lactamase inhibitors. Low level expression of BlaC can result in growth on Carbenicillin plates, but the addition of clavulanic acid inhibits BlaC activity and results in the depletion of false positives and further enrichment of strong binders to any modification made to the binding site. Libraries of mutations in the zinc finger array fused to gal11P were selected for binders to an altered binding sequence through low stringency conditions followed by selection on a gradient of clavulanic acid. Growth on the highest stringency end of the gradient indicated variants in the zinc finger array that are strong binders to the new binding sequence.
Figure 9A:
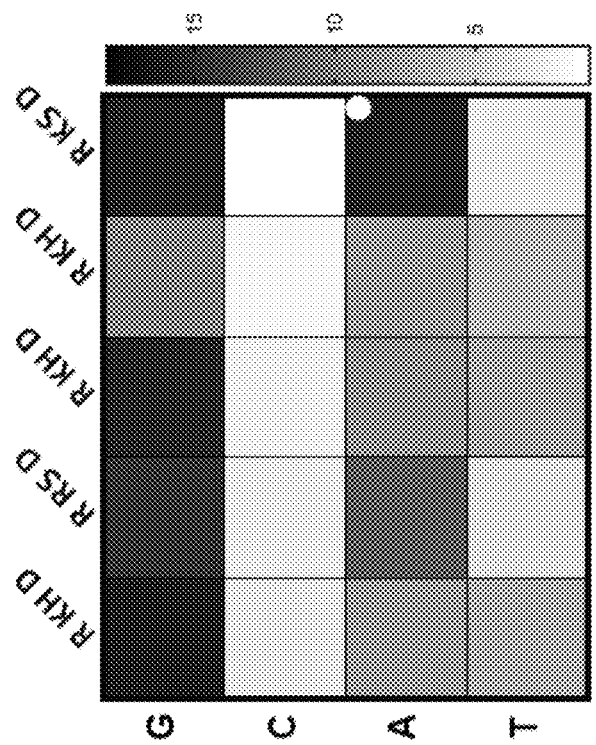
FIGS. 9A-C: Selected variants binding altered binding sites sequence at position 3 of core motif in CBS. Selections performed on library of variants centered around alterations in position −1 to 3 of recognition helix in ZF7 of the 11 finger CTCF zinc finger array. 'VNS' codons were introduced at positions indicated by 'X' and selected against three different nucleotide changes at position 3 of the core motif in the CBS (gray star). Direct protein-DNA contacts are indicated by dashed lines. (A) Selections performed on A:T change in the binding site, (B) A:G change, (C) A:C change. Most variants pulled out had relaxed binding specificity instead of altered specificity.
Figure 9A:
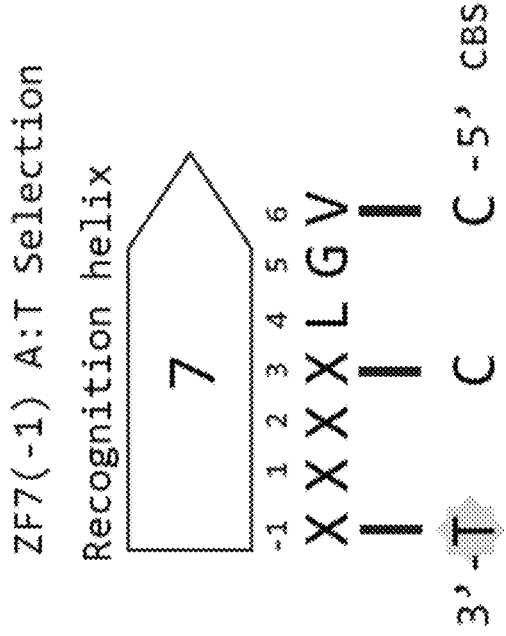
Figure 9B:
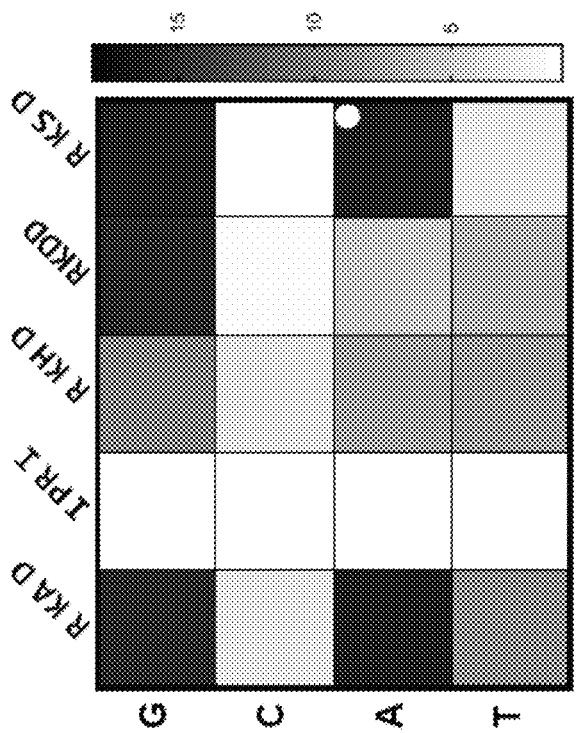
Figure 9C:
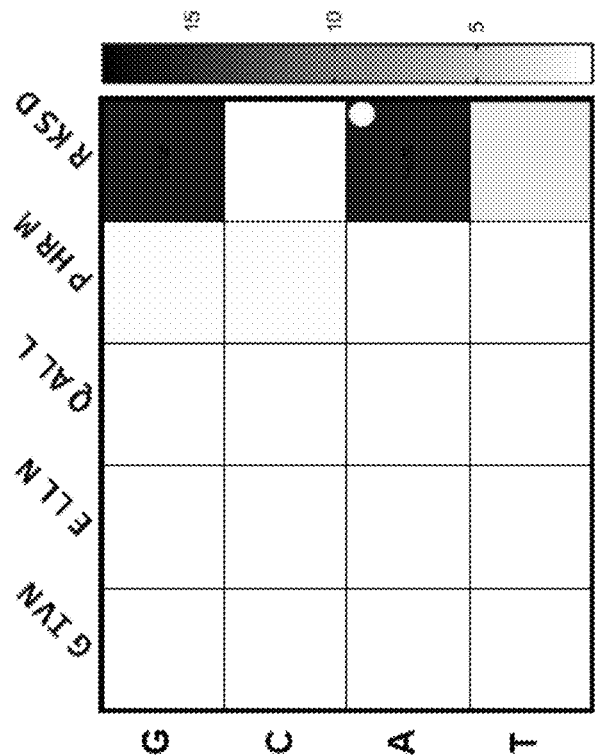
Figure 9C:
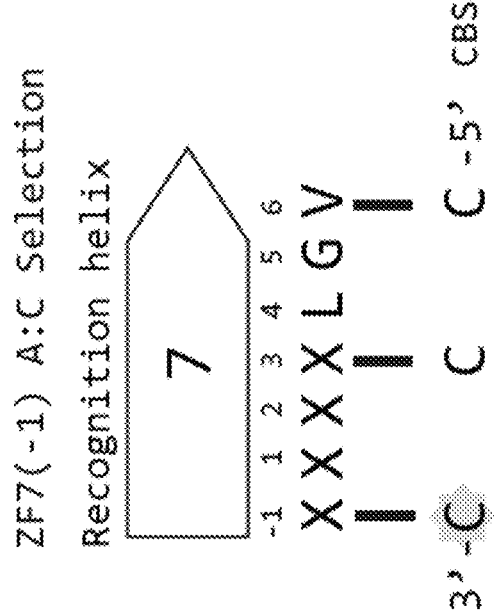
Figure 10B:
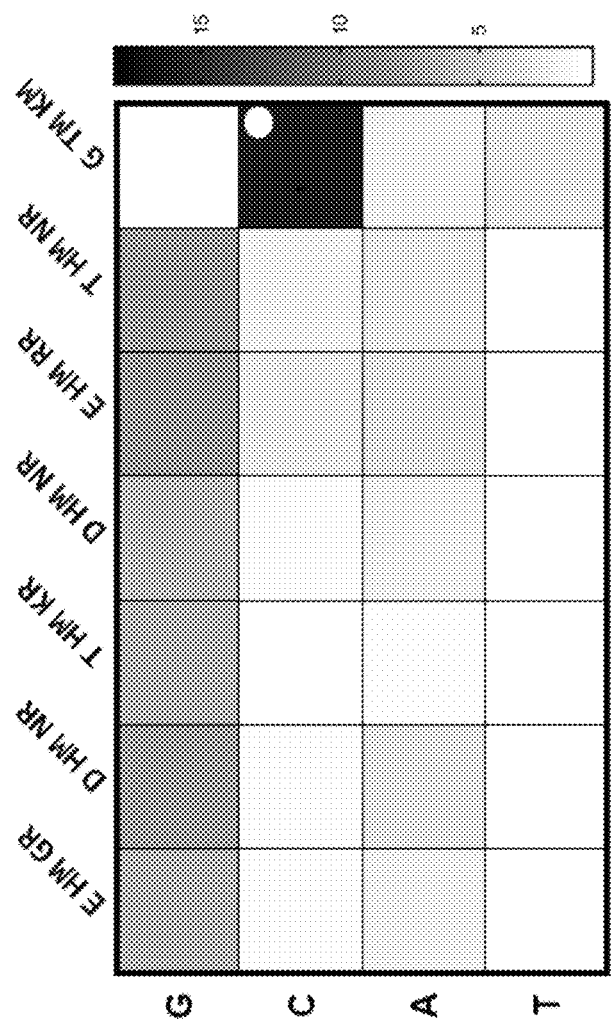
Figure 10B:
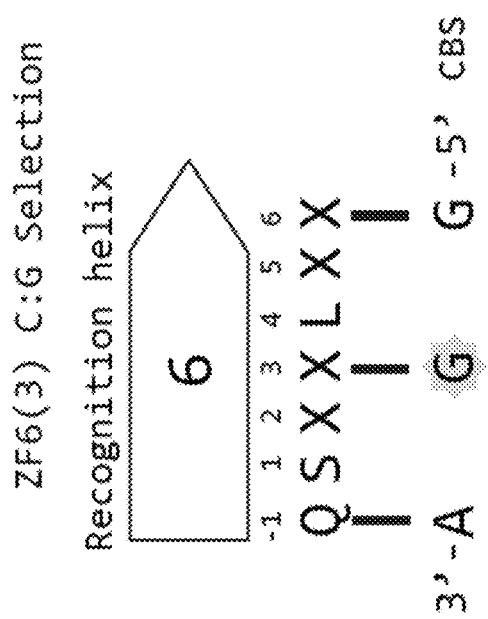
Figure 11A:
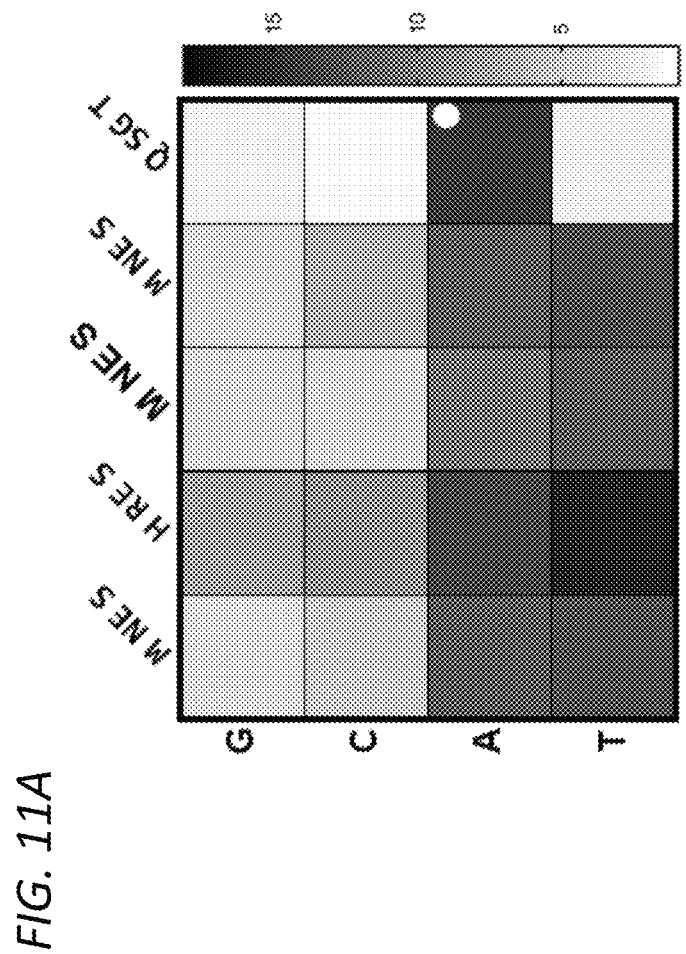
Figure 11A:
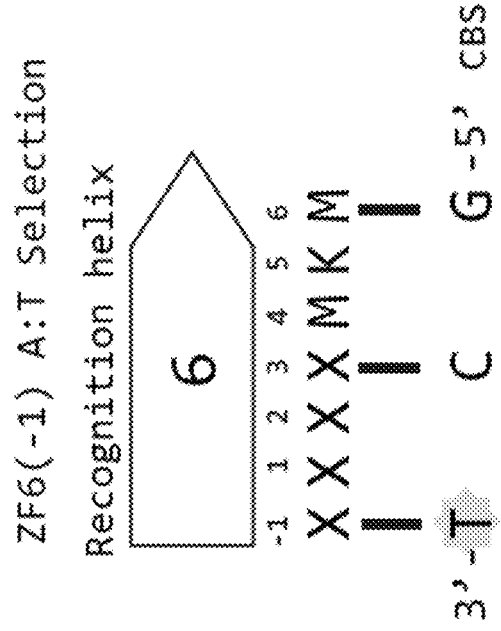
Figure 11C:
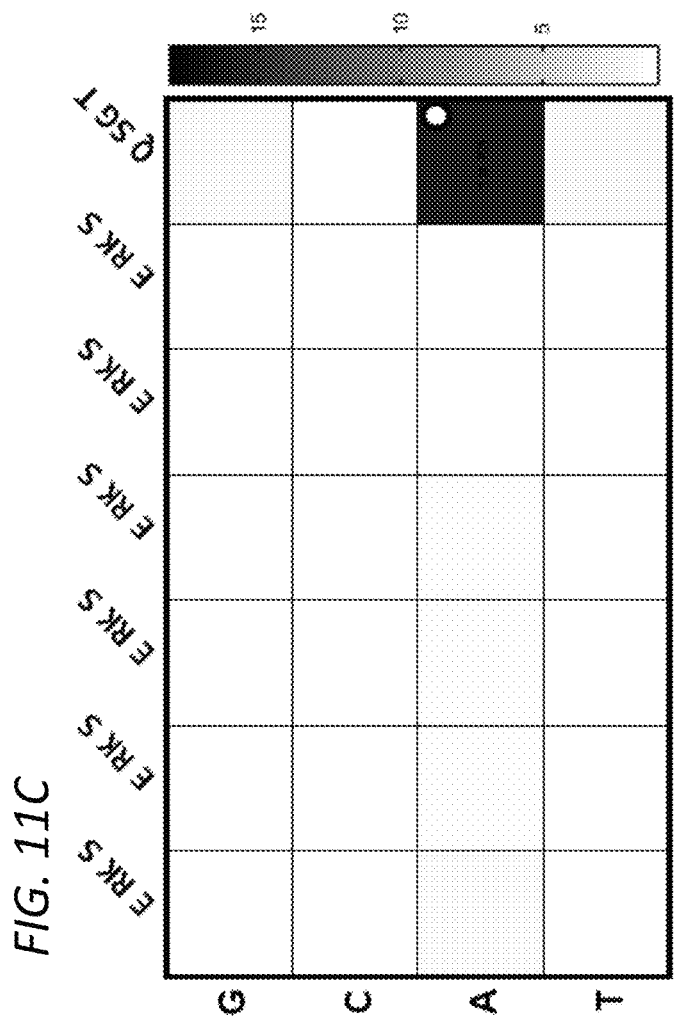
Figure 11C:
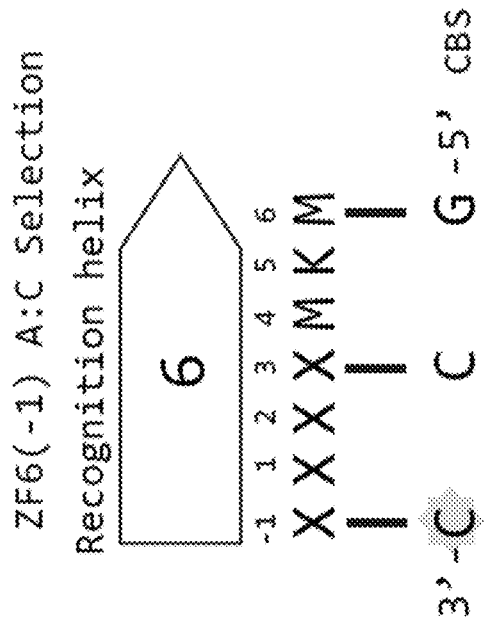
Figure 12B:
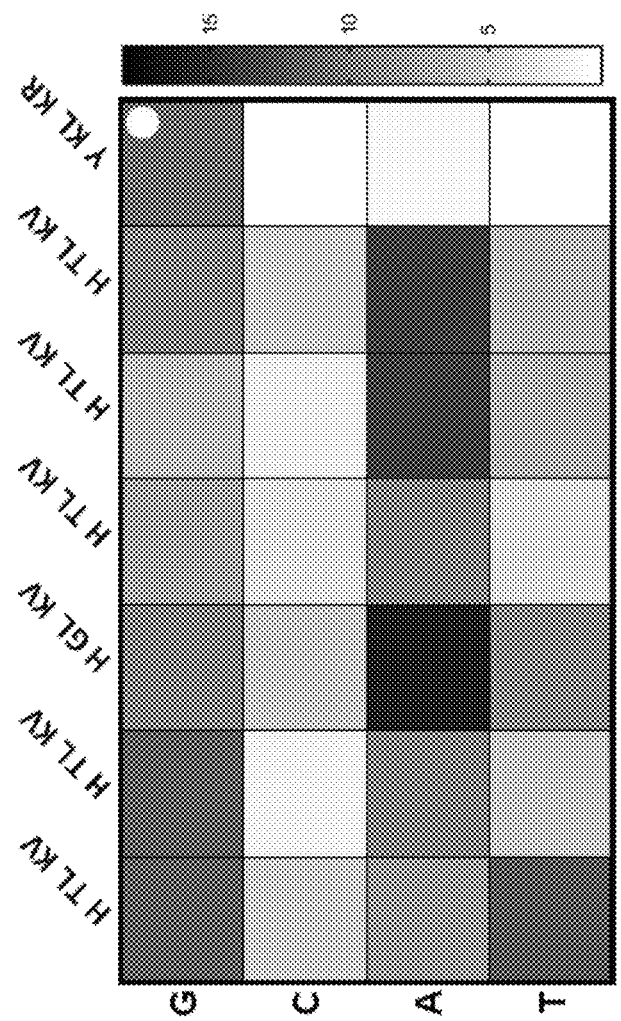
Figure 12B:
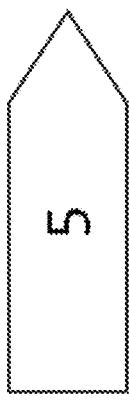
Figure 12C:
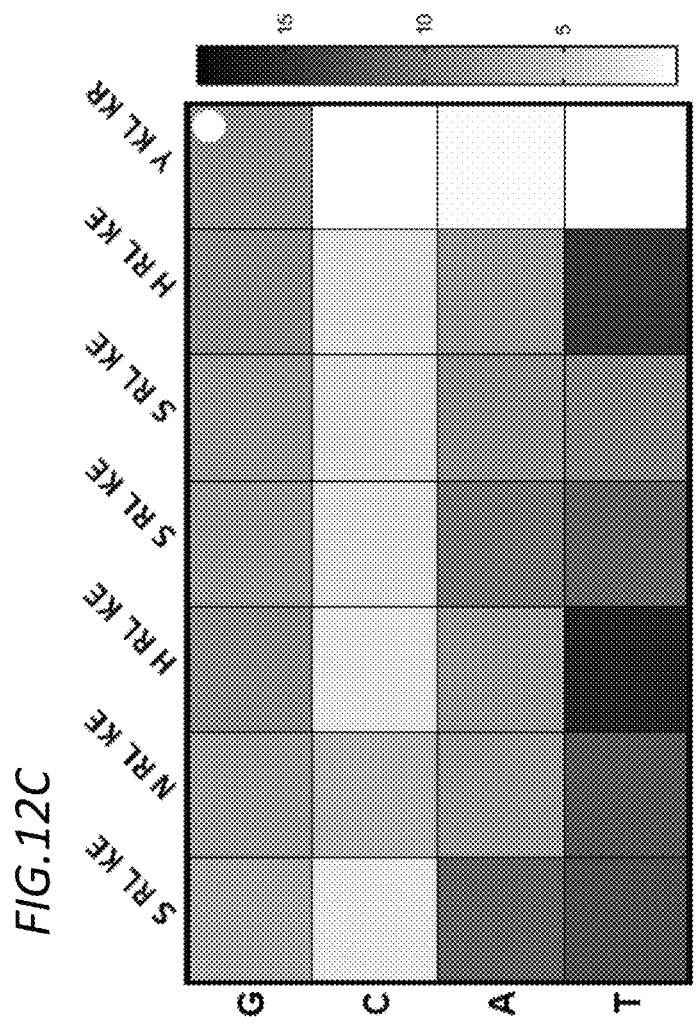
Figure 12C:
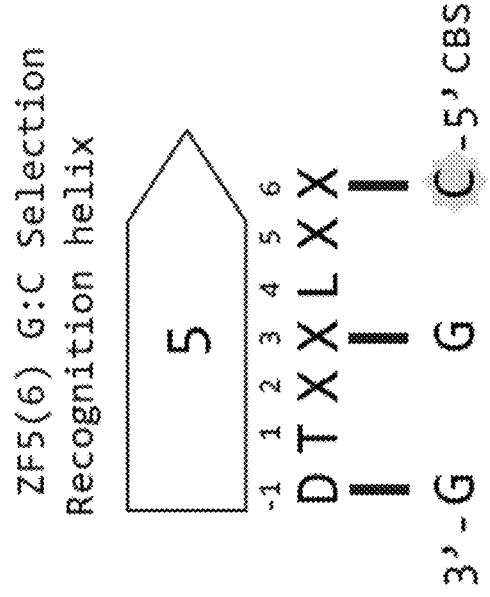
Figure 13A:
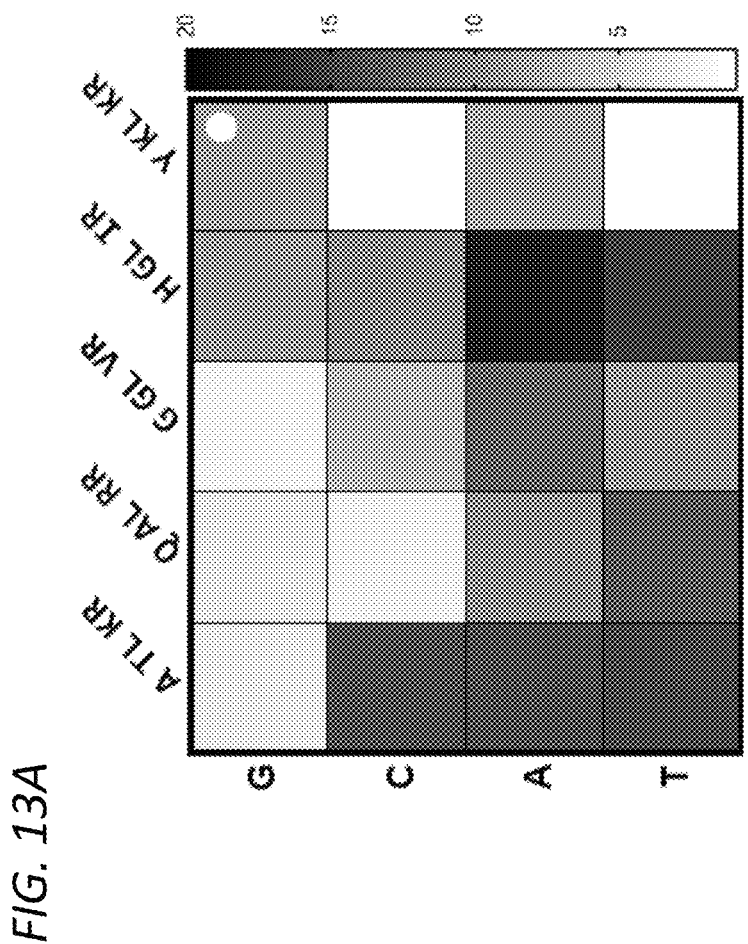
Figure 13A:
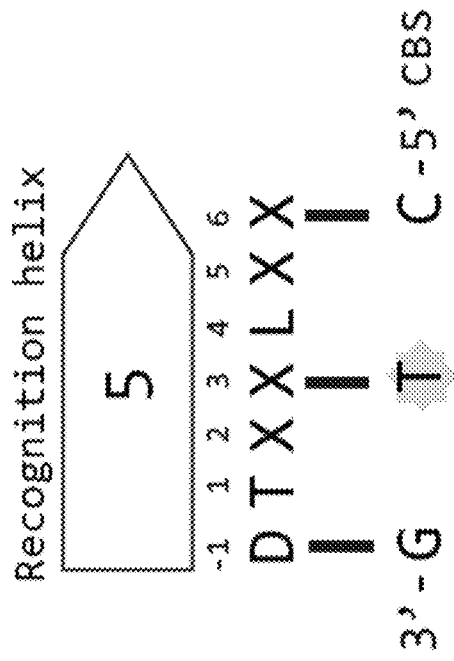
Figure 13B:
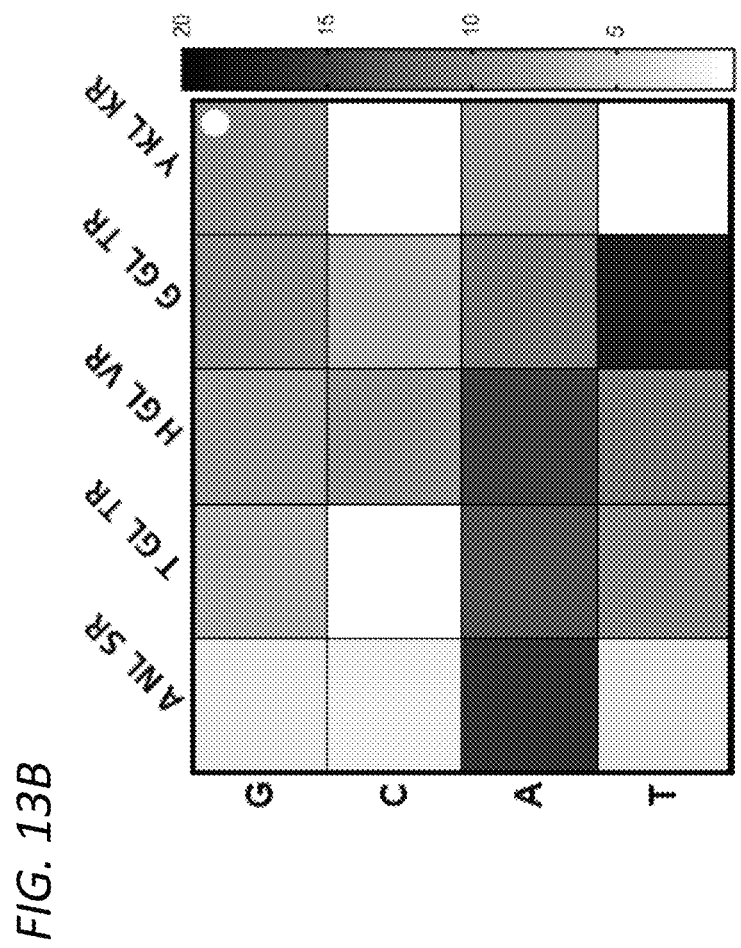
Figure 13B:
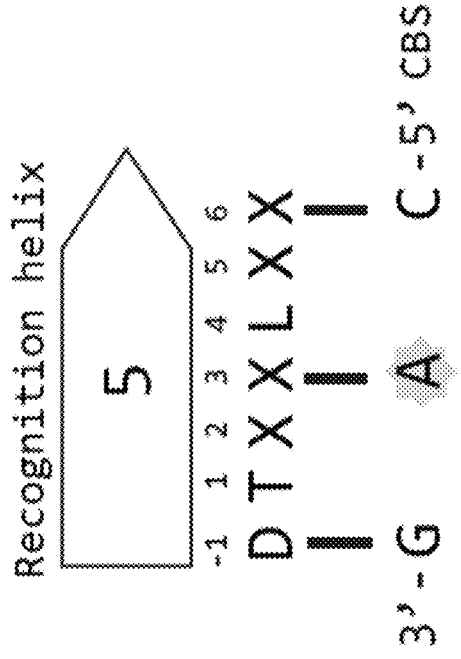

Generation of Engineered CTCF Variants That Bind to Mutated CBSs with Single Altered Nucleotide Next, we sought to determine if we could use the B2H system to select for CTCF zinc finger array variants capable of recognizing mutated CBSs not recognized by the wild-type CTCF zinc finger array. To do this, we modified the B2H reporter construct, replacing the lacZ gene with the blaC gene (FIG. 6), which encodes beta-lactamase and therefore confers resistance to beta-lactam antibiotics (e.g., carbenicillin). This modification enables us to select for cells that express a CTCF zinc finger array variant that can efficiently bind a mutant CBS positioned upstream of the weak promoter driving blaC expression. Increasingly higher levels of blaC expression can be selected for by using media containing carbenicillin and increasingly higher concentrations of the beta-lactamase inhibitor clavulanic acid. Gradients of clavulanic acid can be created within a single agar plate (FIG. 6; see Materials and Methods), thereby enabling sampling of cells at various concentrations of the inhibitor.

With this modified B2H selection system, we first sought to identify CTCF zinc finger array variants that can bind to CBSs bearing single point mutations that abolish binding by the wild-type CTCF zinc finger array in this system. In an initial set of selection experiments, we sought to identify CTCF zinc finger array variants that could bind to mutant CBSs bearing mutations of the C that is contacted by an aspartic acid (D) present at the third position (+3) of the alpha-helical recognition helix of ZF7 (shown by previously published co-crystal structures cited above). We created a randomized library of CTCF zinc finger array variants in which the codon encoding the ZF7 +3 position was randomized using a degenerate NNS codon (where N=G, A, C, or T and S=G or C). We then used the B2H selection system to interrogate this library to identify variants capable of recognizing CBSs bearing C to T, C to G, and C to A substitutions at the position contacted by ZF +3. Selections were initially performed on low stringency plates with clavulanic acid gradients ranging from 0 to 0.45 ug/ml) and surviving colonies harvested and plasmids encoding the variant zinc finger arrays were purified. This selected subset of variants was then subjected to high stringency selection in the B2H system on plates with carbenicillin and gradients of clavulanic acid ranging from 0 to 4 ug/ml). Plasmids encoding variant zinc finger arrays were purified from colonies that grew on the end of the gradient plate with highest concentration of clavulanic acid, sequenced, and then tested in the B2H reporter assay by beta-galactosidase assay.

As can be seen in FIGS. 7A-C, we obtained CTCF zinc finger array variants that showed preferential binding activity (as judged by the B2H reporter assay) for the mutated CBS compared with the original consensus CBS. These clones also showed selection for a particular amino acid at the ZF7 +3 position: for the C to T site, a threonine (T) was selected, for the C to A site, an asparagine (N) was selected, and for the C to G site a histidine (H) was selected. The identities of these amino acids is consistent with what might be expected to recognize the mutant nucleotide based on previous zinc finger selections using the Zif268 zinc finger array. However, although we successfully selected for mutants that had altered binding activity, in most cases, the binding activity of the variant for the mutated CBS was not as strong (as judged by the B2H reporter assay) as that of the wild-type CTCF zinc finger array for the consensus CBS (FIGS. 7A-C).

Based on our previous experience with re-engineering the DNA-binding specificities of the Zif268 zinc finger array, we hypothesized that obtaining stronger binding variants might require alteration of amino acids flanking the +3 position in ZF7. To test this idea, we created a larger library of variants in which we randomized positions +2, +3, +5 and +6 of ZF7 using degenerate VNS codons (where V=G, A, or C). Position +4 of ZF7 was not altered because it faces the internal core of the ZF domain and is not expected to make contacts to the DNA. We then performed B2H selections as described above using this library to identify variants that could identify a mutant CBS with a C to G mutation at the position contacted by ZF7 +3 in the wild-type CTCF zinc finger array. These selections identified variants that showed stronger binding activity for the mutant CBS and showed some degree of consensus in the identities of amino acids selected (FIG. 8).

Based on this success, we generated additional randomized libraries in which randomized positions −1, +1, +2, and +3 or +2, +3, +5 and +6 for ZF7, ZF6, ZF5, ZF4, and ZF3. We then performed selections as described above using these libraries against various matched mutant CBSs harboring nucleotide substitutions at positions expected to be contacted by residues randomized in the libraries (FIGS. 9-16). Analysis of variants from individual surviving colonies at the most selective end of the high stringency selection plates showed that many of these selections yielded variants with high activity for the mutant CBS of interest and sequencing of these clones showed that there was generally a degree of consensus in the amino acid sequences suggesting that selection was successfully occurring (FIGS. 9-16).

Generation of Engineered CTCF Variants That Bind to Mutated CBSs with Multiple Altered Nucleotides Having successfully identified CTCF zinc finger variants that could recognize CBSs with a single altered nucleotide position, we next sought to identify variants that could recognize CBSs bearing multiple mutated nucleotides. To do this, we sought to recombine ZF variants each selected to bind to different "subsites" within the CBS that bear individual mutations. However, because of well-known context-dependent effects that exist between ZFs in a multi-finger array, we undertook a strategy in which we recombined together pools of selected ZF variants (rather than a single variant) for any given altered subsite to identify the combinations of mutated ZFs that best work together to recognize a CBS bearing multiple mutations. To isolate pools of ZF variants for various mutated CBS subsites, we harvested all remaining clones from the high stringency selection plates we performed with the CBS sites bearing single mutations (depicted in FIGS. 9-16). Deep sequencing of the various selected clones in these pools yielded a variety of sequences with some degree of consensus within each selection as expected (Table 1).

We then recombined pools of variants for ZFs 4, 5, 6, and 7 to create CTCF zinc finger arrays that harbored various altered recognition helices for these positions and then performed B2H selections (see Materials and Methods) against five different mutated CBSs bearing combinations of various nucleotide substitutions in subsites for ZFs 4, 5, 6, and 7 (FIGS. 17-21). Sequencing of clones from these selections showed that certain recognition helix sequences for each finger were selected multiple times, suggesting that the selections were identifying combinations that work well together. Importantly, for all five of the multiply mutated CBSs, several of the CTCF zinc finger array variants identified showed good binding activity on the site for which they were selected as judged by B2H assay (FIGS. 17-21). In addition, for four of the five mutant CBS sites, we were able to identify variants that not only bind to the mutant CBS but also fail to bind to the original unmutated (consensus) CBS. Thus, we conclude that using our approach described here we are able to identify CTCF ZF array variants capable of recognizing multiply mutated CBSs that are not efficient bound by the original wild-type CTCF zinc finger array.

Binding Specificity of Engineered CTCF Variants to Mutant and Wild-Type CBSs in Human Cells Having successfully engineered variants that can recognize CBSs with multiple sequence changes across the motif, we next wanted to investigate whether the variants can bind to these same mutant binding sites in a human cell context while not binding to wild-type CBSs. First, we found a collection of sites in the human genome that matched the 15 bp core sequence for each of the five mutated binding sites that we had selected CTCF variants to bind (described in FIG. 17-21). We then looked at two variant binding sites with sequence that matched one of the five mutated binding sites (sequence depicted in FIG. 20) as well as known CBSs to determine if endogenous CTCF could bind to the wild-type CBS and not bind to the variant binding sites as the B2H reporter assay would suggest (FIG. 20). Human K562s, an erythroleukemia cell line, were harvested and analyzed by ChIP-qPCR using CTCF specific antibody to detect CTCF-DNA binding. Wild-type CTCF showed no detectable binding to two different target sites that matched the mutated CBS but showed great enrichment for wild-type CTCF binding site, supporting the results of the B2H reporter assay (FIG. 22). Next, we wanted to see if overexpressed, exogenous, 3×HA tagged wild-type CTCF delivered by plasmid transfection in K562s had the same binding profile observed with endogenous CTCF. Wild-type K562s were transfected with 3×HA-CTCF and 72 hours later were harvested and processed for ChIP-qPCR analysis with HA specific antibodies. Exogenous wild-type 3×HA-CTCF could bind to the wild-type CBSs and could not bind to the variant binding sites, same as endogenous wild-type CTCF, suggesting overexpression of CTCF by plasmid delivery reflects biologically relevant behavior (FIG. 23A). Based on these results, we next examined the ability of a variant CTCF to bind to the variant binding sites native to the human genome. The variant chosen was one pulled out from selection in the B2H selection assay and shown to bind to the variant site with the same sequence as variant site 1 and 2, used in FIGS. 22-23B, by the B2H reporter assay. K562s were transfected with the 3×HA-tagged CTCF variant and the same sites as before were examined for binding activity by ChIP-qPCR. Variant specific HA enrichment was present at the variant binding sites and lacking at the wild-type sites suggesting we successfully evolved a variant that can specifically bind to mutant CBS with as few as three nucleotide changes without binding native CBSs (FIG. 23B).

Gene Expression Regulation by Engineered CTCF Variants Via Looping

CTCF has the capacity to alter gene expression through CTCF-Cohesin mediated looping of the genome. We were curious to see if the variant CTCFs could reproduce the gene regulatory capacity of wild-type CTCF when bound to the endogenous variant binding sites. To investigate gene expression changes, we focused on genes within a 1 Mb region of the variant binding sites. Eleven genes were identified within 1 Mb region for Variant site 1.1 and 1.2 and another 10 genes were identified for Variant site 2.1 and 2.2. K562s were nucleofected with variant CTCFs fused to GFP that had the capacity to bind to Variant site 1 and Variant site 2. 72 hours post nucleofection, RNA was isolated from GFP+ cells and gene expression levels were compared to RNA extracted from K562s nucleofected with a wild-type CTCF control. Of the 11 genes for Variant site 1.1 and 1.2, 6 genes showed a change in gene expression relative to cells nucleofected with the wild-type CTCF control (JJ388) (FIG. 24A). 2 of the 10 genes identified for Variant site 2.1 and 2.2 had altered gene expression levels relative to wild-type control (FIG. 24B). This data suggests that not only do the variant CTCF proteins bind to their target sequence in human cells, but it also reproduces the biological role of native CTCF to regulate gene expression possibly through the formation of loops or sub-TADs.

Next we wanted to demonstrate that the CTCF variants could replicate the biological function of wild-type CTCF at a known CTCF binding site that creates an enhancer-promoter loop. MYC expression is maintained by a loop formed between a CTCF binding site ~2 kb upstream of the transcriptional start site (TSS) of MYC and a CTCF binding site ~1 kb downstream of the MYC TSS14. When CTCF Is bound to both sites, cohesin links both CTCFs via the CTCF's cohesin-interaction domain, creating a loop that maintains the expression of MYC. If one or both of the CTCF binding sites is disrupted the CTCF-mediated loop is lost and there is a reduction in MYC expression14. Five cell lines were generated containing the 5 different variant binding site sequences (defined in FIG. 25) at the CTCF binding site ~2 kb upstream of the MYC TSS. This was done in K562 background transduced with a lentiviral construct expressing exogenous MYC via phosphoglycerate kinase (PGK) promoter (exoMYC.K562) to compensate for any reduced cell fitness that reduction of endogenous MYC expression may cause. An additional sixth cell line was generated where point mutations to the CTCF binding site were made that should have no affect on wild-type CTCF binding as indicated by results from the B2H reporter assay. RNA was isolated from the clonal cell lines homozygous for the variant binding sites and endogenous MYC gene expression levels were assayed by reverse transcriptase Real Time qPCR (RT-qPCR). Each of the isolated cell lines with the variant CTCF binding site demonstrated a reduced level of MYC expression suggesting that the CTCF-mediated loop is disrupted (FIG. 25).

Based on this result, we wanted to see if expression of the variant CTCFs in these modified cell lines could bind to the engineered sites and restore MYC expression. HA tagged wild-type CTCF and HA tagged CTCF variants were expressed in the cell line that contained their matching variant binding site. Variants selected to bind to the G3 variant binding site were expressed in the G3_3 cell line, A3 variants in the A3_4 cell line, etc. HA-tagged wild-type CTCF was also tested in each of the variant cell lines for binding and for recovery of endogenous MYC expression. The level of endogenous MYC expression in exo-MYC.K562 served as wild-type control as there is no alteration to the CTCF binding site upstream of the MYC TSS. CTCF variants expressed in the engineered cell lines recovered endogenous MYC expression while expression of wild-type CTCF in these cell lines failed to recover MYC expression (FIGS. 26A-29). The same samples were analyzed for occupancy of the variant binding sites by wild-type CTCF or the variant CTCFs by ChIP-qPCR enriching for CTCF-bound DNA fragments with CTCF or HA antibody. Wild-type CTCF had a reduced occupancy of the variant binding sites, consistent with continued reduction of MYC expression, while variant CTCF proteins could bind to the variant site they were selected for as well as rescue MYC expression (FIG. 26-29). Together, this data suggests that we have evolved CTCF variants that can bind to novel sequences and still interact with cohesin to form loops that maintain gene expression profiles.

Tables

Amino acid sequence of variants selected for on different CTCF binding sites. All amino acids sequences are listed from N to C terminal. Colonies growing on the highest stringency of selection were scrapped off, pooled, and plasmid encoding for the zinc finger was isolated and deep sequenced. The number of reads reflects how prominent the variant was in the population pooled from selections performed in triplicate.

TABLE 1

ZF7 selection on C:G change at nt 2 of core motif in CBS. Sequences reflect position 2 through 6.

| SEQ ID NO: | Sequence | # reads |
|---|---|---|
| 8 | DHLQT | 2981 |
| 15 | EHLVV | 2413 |
| 155 | DHLNT | 1517 |
| 16 | DHLRT | 1442 |
| 13 | EHLKV | 1434 |
| 192 | KDLVV | 1357 |
| 193 | DHLQA | 1114 |
| 194 | DHLLV | 1076 |
| 195 | DHLLT | 881 |
| 196 | EHLTV | 803 |
| 197 | STLME | 786 |
| 17 | DHLAT | 777 |
| 9 | EHLNV | 736 |
| 12 | DHLQV | 574 |
| 198 | DHLKT | 541 |
| 199 | EHLKE | 517 |
| 200 | DHLLE | 506 |
| 201 | EHLRV | 503 |
| 202 | STLRE | 498 |
| 203 | DHLMV | 431 |
| 204 | DHLKV | 427 |

TABLE 1-continued

ZF7 selection on C:G change at nt 2 of core motif in CBS. Sequences reflect position 2 through 6.

| SEQ ID NO: | Sequence | # reads |
|---|---|---|
| 205 | DHLRV | 394 |
| 206 | DHLNV | 389 |
| 114 | DHLLA | 380 |
| 207 | DHLKE | 368 |
| 208 | DHLNE | 330 |
| 11 | EHLRE | 330 |
| 209 | STLLE | 323 |
| 210 | DHLMA | 305 |
| 211 | KDLTV | 296 |
| 212 | DHLVT | 284 |
| 213 | AHLNV | 270 |
| 214 | AHLTV | 268 |
| 215 | HTLME | 245 |
| 216 | DHLRA | 237 |
| 217 | DHLAV | 221 |
| 218 | HHLAE | 221 |
| 219 | GHLMD | 207 |
| 220 | DHLST | 199 |
| 221 | EHLMV | 197 |
| 222 | AHLVV | 196 |
| 223 | EHLAV | 192 |
| 224 | HTLAE | 187 |
| 225 | STLQE | 181 |
| 226 | DHLAE | 167 |
| 227 | AHLQE | 163 |
| 228 | SSLNE | 158 |
| 229 | GHLNV | 155 |
| 230 | EHLVE | 144 |
| 231 | DHLME | 143 |
| 232 | DHLRE | 134 |
| 233 | AHLNA | 120 |
| 234 | HTLVE | 120 |
| 235 | STLKE | 112 |
| 236 | EHLQV | 107 |
| 237 | GTLME | 106 |
| 238 | HHLAV | 102 |
| 239 | HSLME | 101 |
| 240 | HSLTE | 97 |
| 241 | EHLMA | 97 |
| 242 | DHLHT | 94 |
| 10 | AHLQV | 94 |
| 243 | DHLTV | 93 |
| 244 | EHLIV | 90 |
| 245 | SGLNE | 89 |
| 246 | AHLLV | 85 |
| 247 | EHLLV | 84 |
| 248 | VKLKI | 83 |
| 249 | DHLQE | 80 |
| 250 | HTLTE | 77 |
| 251 | STLHE | 76 |
| 252 | DHLVV | 76 |
| 253 | AGLAL | 70 |
| 254 | STLND | 69 |
| 255 | DHLKA | 68 |
| 256 | KDLTQ | 66 |
| 257 | DKLMN | 66 |
| 258 | GTLRE | 66 |
| 259 | GHLTV | 66 |
| 260 | RLLTA | 65 |
| 261 | SSLRE | 63 |
| 262 | HTLKE | 62 |
| 263 | GHLAV | 60 |
| 264 | RLLAQ | 58 |
| 265 | KDLAV | 57 |
| 266 | EHLQE | 57 |
| 267 | SHLNV | 57 |
| 268 | AGLPI | 57 |
| 269 | TTLME | 56 |
| 90 | AHLRV | 56 |
| 270 | AHLMV | 55 |

TABLE 1-continued

ZF7 selection on C:G change at nt 2 of core motif in CBS. Sequences reflect position 2 through 6.

| SEQ ID NO: | Sequence | # reads |
|---|---|---|
| 271 | EHLME | 55 |
| 272 | EHLQT | 55 |
| 273 | EVLNR | 55 |
| 274 | HHLVV | 54 |
| 275 | KDLSV | 54 |
| 276 | RHLVM | 53 |
| 277 | THLNE | 50 |
| 278 | RDLRT | 49 |
| 279 | LLLGS | 49 |
| 280 | MVLGN | 48 |
| 281 | KTLIE | 47 |
| 282 | AHLGV | 46 |
| 283 | SGLLA | 46 |
| 284 | DHLHV | 45 |
| 285 | EHLNT | 45 |
| 286 | STLLQ | 44 |
| 287 | AHLKV | 44 |
| 288 | AHLAV | 42 |
| 289 | TNLID | 41 |
| 290 | GTLNE | 41 |
| 291 | QVLTQ | 40 |
| 292 | SSLME | 39 |
| 293 | GHLVE | 38 |
| 294 | HSLLE | 38 |
| 295 | SGLLE | 38 |
| 296 | GGLLE | 36 |
| 297 | STLRV | 36 |
| 298 | HTLAD | 35 |
| 299 | SHLME | 35 |
| 300 | DHLAI | 35 |
| 301 | EHLLA | 35 |
| 302 | HNLLL | 34 |
| 303 | PHLVV | 34 |
| 304 | KALGT | 33 |
| 305 | PHLVI | 31 |
| 306 | VLLII | 30 |
| 307 | HHLRE | 29 |
| 308 | GALRM | 29 |
| 309 | RGLHE | 29 |
| 310 | AHLLE | 28 |
| 311 | EHLKA | 28 |
| 312 | DTLLV | 27 |
| 313 | EHLRT | 26 |
| 314 | SSLRD | 24 |
| 156 | EHLQA | 23 |
| 315 | EHLAT | 23 |
| 316 | SGLGE | 22 |
| 317 | ATLQE | 22 |
| 318 | DHLSA | 22 |
| 101 | SNLLV | 22 |
| 319 | SHLLV | 21 |
| 320 | KDLMV | 21 |
| 321 | DHLQQ | 20 |
| 322 | ATLME | 20 |
| 323 | GHLQA | 20 |
| 324 | RTLTE | 20 |
| 325 | RRLAH | 20 |
| 326 | DTLQA | 20 |
| 327 | GHLEV | 19 |
| 328 | HQLKL | 19 |
| 329 | EHLLT | 19 |
| 330 | DGLRT | 18 |
| 331 | THLRP | 18 |
| 132 | DNLAT | 18 |
| 332 | EHLNA | 17 |
| 333 | STLVV | 17 |
| 135 | DNLMT | 17 |
| 334 | DTLLA | 17 |
| 335 | STLDE | 16 |
| 336 | KDLVA | 15 |

TABLE 1-continued

ZF7 selection on C:G change at nt 2 of core motif in CBS. Sequences reflect position 2 through 6.

| SEQ ID NO: | Sequence | # reads |
|---|---|---|
| 337 | AHLHA | 15 |
| 338 | KDLQV | 15 |
| 339 | HHLTV | 15 |
| 340 | SGLLD | 15 |
| 341 | ANLME | 14 |
| 129 | DNLLV | 14 |
| 342 | EHLKT | 13 |
| 343 | GSLAI | 13 |
| 344 | EHLSV | 13 |
| 345 | EHLNE | 13 |
| 346 | EHLVI | 13 |
| 347 | KDLKV | 13 |
| 348 | EGLGT | 13 |
| 130 | DNLQT | 12 |
| 349 | STLMS | 12 |
| 350 | AHLMM | 12 |
| 351 | IKLDG | 12 |
| 352 | VLLGA | 12 |
| 353 | PGLSA | 12 |
| 354 | AELNR | 12 |
| 355 | HQLVI | 12 |
| 356 | GHLVV | 12 |
| 357 | PHLLV | 11 |
| 358 | PRLAL | 11 |
| 359 | DHLNA | 11 |
| 360 | KDLDV | 11 |
| 361 | AHLHV | 11 |
| 362 | RVLGG | 11 |
| 363 | AHLQA | 11 |
| 364 | RQLRT | 10 |
| 365 | AHLQT | 10 |
| 100 | DNLLA | 10 |
| 151 | EHLAE | 10 |
| 366 | EHLAM | 10 |
| 367 | DRLSI | 10 |
| 368 | GGLGA | 10 |
| 369 | GHLNT | 10 |
| 370 | AHLRT | 10 |
| 371 | DTLRV | 10 |
| 372 | MSLRG | 9 |
| 373 | DHLTI | 9 |
| 374 | THLIV | 9 |
| 375 | DTLMA | 9 |
| 376 | MKLQE | 9 |
| 377 | TALGT | 9 |
| 378 | GHLLV | 9 |
| 379 | GQLAI | 8 |
| 380 | ANLES | 8 |
| 381 | AHLNT | 8 |
| 382 | EHLLE | 8 |
| 383 | SNLTV | 8 |
| 384 | STLLV | 8 |
| 385 | STLMV | 8 |
| 386 | GTLVS | 7 |
| 387 | DNLKT | 7 |
| 388 | GHLQT | 7 |
| 128 | DNLLT | 7 |
| 389 | EHLVT | 7 |
| 390 | GALRE | 7 |
| 391 | SSLAE | 7 |
| 392 | DTLRQ | 7 |
| 393 | KALLG | 7 |
| 394 | AMLNP | 6 |
| 395 | DTLHQ | 6 |
| 396 | DNLLQ | 6 |
| 397 | EHLAH | 6 |
| 398 | AHLKE | 6 |
| 399 | ATLAE | 6 |
| 400 | EHLMD | 6 |
| 401 | STLHM | 6 |

TABLE 1-continued

ZF7 selection on C:G change at nt 2 of core motif in CBS. Sequences reflect position 2 through 6.

| SEQ ID NO: | Sequence | # reads |
|---|---|---|
| 402 | DTLAV | 6 |
| 403 | DHLVE | 6 |
| 404 | PTLGE | 6 |
| 405 | KGLPL | 6 |
| 406 | DTLLQ | 6 |
| 407 | AHLNE | 6 |
| 408 | AHLAE | 6 |
| 409 | GHLKV | 6 |
| 410 | SGLQV | 5 |
| 411 | HHLLV | 5 |
| 412 | EPLLP | 5 |
| 413 | DNLAV | 5 |
| 414 | AHLLT | 5 |
| 415 | AHLST | 5 |
| 133 | DNLQA | 5 |
| 416 | DNLRT | 5 |
| 417 | DTLAL | 5 |
| 418 | DTLQV | 5 |
| 419 | EHLRA | 5 |
| 420 | SNLQV | 5 |
| 421 | KDLRV | 5 |
| 422 | DTLAT | 5 |
| 423 | DTLRA | 5 |
| 424 | QHLRV | 4 |
| 425 | SSLLE | 4 |
| 426 | SNLMV | 4 |
| 427 | SDLGG | 4 |
| 428 | DNLHT | 4 |
| 429 | DNLTA | 4 |
| 430 | DTLMV | 4 |
| 431 | EHLST | 4 |
| 432 | DTLSV | 4 |
| 102 | DNLMA | 4 |
| 433 | EHLVM | 4 |
| 434 | STLAE | 4 |

TABLE 1-continued

ZF7 selection on C:G change at nt 2 of core motif in CBS. Sequences reflect position 2 through 6.

| SEQ ID NO: | Sequence | # reads |
|---|---|---|
| 435 | KDLAE | 4 |
| 436 | SSLNV | 4 |
| 437 | SSLLV | 4 |
| 438 | AHLKT | 4 |
| 439 | AHLRE | 4 |
| 440 | KDLLV | 4 |

TABLE 2

ZF7 selection on C:T change at nt 2 of core motif in CBS. Sequences reflect position 2 through 6.

| SEQ ID NO: | Sequence | Read # |
|---|---|---|
| 312 | DTLLV | 3772 |
| 334 | DTLLA | 1720 |
| 406 | DTLLQ | 1681 |
| 326 | DTLQA | 1340 |
| 371 | DTLRV | 1048 |
| 418 | DTLQV | 715 |
| 423 | DTLRA | 643 |
| 375 | DTLMA | 620 |
| 430 | DTLMV | 538 |
| 402 | DTLAV | 451 |
| 422 | DTLAT | 406 |
| 441 | DSLLV | 373 |
| 432 | DTLSV | 359 |
| 442 | DTLLM | 339 |
| 392 | DTLRQ | 334 |
| 443 | DTLLI | 306 |
| 444 | DTLTQ | 300 |
| 434 | STLAE | 269 |
| 445 | DTLAA | 268 |
| 395 | DTLHQ | 246 |
| 446 | DTLSA | 227 |
| 447 | DTLKA | 216 |

TABLE 2-continued

ZF7 selection on C:T change at nt 2 of core motif in CBS. Sequences reflect position 2 through 6.

| SEQ ID NO: | Sequence | Read # |
|---|---|---|
| 384 | STLLV | 213 |
| 448 | STLQQ | 201 |
| 449 | DTLQQ | 200 |
| 450 | DTLLL | 194 |
| 451 | DTLMQ | 189 |
| 225 | STLQE | 189 |
| 452 | DTLNA | 180 |
| 453 | STLLA | 176 |
| 454 | DTLKV | 163 |
| 455 | STLNA | 162 |
| 456 | DTLRE | 161 |
| 457 | DTLTA | 152 |
| 458 | DTLQD | 146 |
| 459 | DTLVA | 137 |
| 460 | DTLLS | 123 |
| 461 | STLTQ | 122 |
| 462 | DSLLA | 116 |
| 463 | DTLRT | 116 |
| 464 | DTLQI | 115 |
| 465 | DTLMN | 114 |
| 466 | STLSE | 114 |
| 467 | SSLQV | 112 |
| 468 | TNLAV | 109 |
| 469 | DTLVV | 108 |
| 470 | DTLHA | 107 |
| 471 | DTLMT | 107 |
| 437 | SSLLV | 107 |
| 209 | STLLE | 107 |
| 472 | DSLRV | 106 |
| 473 | DTLAE | 105 |
| 474 | STLNV | 105 |
| 475 | DTLRN | 101 |
| 476 | DTLNV | 100 |
| 477 | DTLRD | 99 |
| 478 | DSLAV | 94 |
| 479 | DTLVQ | 94 |
| 480 | DTLQE | 93 |
| 481 | STLLD | 92 |
| 482 | DTLTH | 89 |
| 483 | SSLND | 88 |
| 484 | STLTV | 88 |
| 385 | STLMV | 87 |
| 485 | DTLML | 86 |
| 286 | STLLQ | 85 |
| 202 | STLRE | 85 |
| 486 | STLQA | 84 |
| 487 | DTLLD | 83 |
| 488 | DTLKQ | 82 |
| 489 | DTLLT | 81 |
| 417 | DTLAL | 76 |
| 490 | DTLII | 75 |
| 491 | DTLLN | 75 |
| 492 | DSLLQ | 73 |
| 493 | STLEQ | 73 |
| 494 | DTLGV | 71 |
| 495 | DVLRE | 67 |
| 496 | STLSA | 66 |
| 497 | DSLSV | 65 |
| 498 | DTLLE | 63 |
| 499 | STLAA | 63 |
| 500 | DTLKI | 62 |
| 501 | DTLKM | 62 |
| 502 | DTLQN | 60 |
| 197 | STLME | 60 |
| 503 | TTLMT | 60 |
| 504 | TTLAE | 59 |
| 505 | STLTE | 58 |
| 506 | VELVQ | 57 |
| 507 | TTLNQ | 56 |
| 508 | DTLMI | 54 |
| 509 | TTLMD | 54 |

TABLE 2-continued

ZF7 selection on C:T change at nt 2 of core motif in CBS. Sequences reflect position 2 through 6.

| SEQ ID NO: | Sequence | Read # |
|---|---|---|
| 510 | STLMA | 51 |
| 511 | DVLLA | 50 |
| 512 | DVLLT | 49 |
| 235 | STLKE | 49 |
| 513 | TTLNE | 49 |
| 514 | MTLPT | 48 |
| 292 | SSLME | 48 |
| 251 | STLHE | 48 |
| 515 | HTLVV | 47 |
| 269 | TTLME | 46 |
| 516 | ATLTQ | 45 |
| 517 | STLAS | 45 |
| 333 | STLVV | 44 |
| 425 | SSLLE | 43 |
| 518 | SSLVE | 42 |
| 519 | DALQA | 41 |
| 520 | DVLDA | 41 |
| 521 | GSLMQ | 41 |
| 522 | DTLTM | 40 |
| 523 | STLAQ | 39 |
| 524 | STLMI | 38 |
| 525 | DTLAM | 37 |
| 526 | DTLHT | 37 |
| 527 | DTLQL | 37 |
| 528 | DSLKQ | 36 |
| 529 | DSLRA | 36 |
| 530 | STLHV | 35 |
| 531 | STLMQ | 35 |
| 532 | DGLMA | 34 |
| 533 | DTLRL | 34 |
| 534 | SSLLT | 34 |
| 535 | DSLQA | 33 |
| 536 | DTLRI | 33 |
| 537 | STLGE | 33 |
| 538 | DALKE | 32 |
| 539 | STLRA | 31 |
| 540 | DTLHH | 30 |
| 541 | DTLRG | 30 |
| 542 | DTLRM | 30 |
| 543 | DVLMT | 30 |
| 544 | DTLEI | 29 |
| 228 | SSLNE | 29 |
| 545 | DTLHV | 28 |
| 546 | GTLDE | 28 |
| 547 | SSLAV | 28 |
| 548 | STLKQ | 28 |
| 549 | DTLMD | 27 |
| 550 | GTLQT | 27 |
| 551 | SSLVQ | 27 |
| 297 | STLRV | 27 |
| 552 | LMLMG | 25 |
| 553 | STLRQ | 25 |
| 554 | STLTA | 25 |
| 8 | DHLQT | 24 |
| 555 | DSLVA | 23 |
| 556 | SSLRV | 23 |
| 557 | DSLRE | 22 |
| 558 | GRLQD | 22 |
| 559 | MALQD | 22 |
| 560 | STLLH | 21 |
| 561 | STLVQ | 21 |
| 562 | VRLTA | 21 |
| 563 | AVLGD | 20 |
| 564 | PILVT | 20 |
| 565 | STLDD | 20 |
| 566 | DSLMI | 19 |
| 567 | STLID | 19 |
| 568 | TKLDT | 19 |
| 569 | ATLVA | 18 |
| 570 | DTLIA | 18 |
| 571 | DTLTE | 18 |

TABLE 2-continued

ZF7 selection on C:T change at nt 2 of core motif in CBS. Sequences reflect position 2 through 6.

| SEQ ID NO: | Sequence | Read # |
|---|---|---|
| 572 | GTLNH | 17 |
| 573 | STLAI | 17 |
| 282 | AHLGV | 16 |
| 129 | DNLLV | 16 |
| 574 | DQLVQ | 16 |
| 575 | MPLIL | 16 |
| 576 | TTLHQ | 16 |
| 577 | TTLQV | 16 |
| 578 | ATLLE | 15 |
| 579 | DVLHE | 15 |
| 580 | ETLRA | 15 |
| 581 | KVLRS | 15 |
| 101 | SNLLV | 15 |
| 135 | DNLMT | 14 |
| 582 | DSLRQ | 14 |
| 583 | DTLAN | 14 |
| 584 | GTLNV | 14 |
| 585 | HNLMV | 14 |
| 586 | QTLQA | 14 |
| 587 | RQLTT | 14 |
| 588 | DTLSI | 13 |
| 589 | DRLVG | 12 |
| 590 | ETLRQ | 12 |
| 591 | SSLGE | 12 |
| 592 | SSLVV | 12 |
| 193 | DHLQA | 11 |
| 128 | DNLLT | 11 |
| 593 | DTLME | 11 |
| 594 | DTLTV | 11 |
| 595 | DTLVG | 11 |
| 596 | ETLKA | 11 |
| 597 | GVLSQ | 11 |
| 598 | LALMR | 11 |
| 599 | RTLVE | 11 |
| 600 | TTLLI | 11 |
| 601 | TTLNV | 11 |

TABLE 2-continued

ZF7 selection on C:T change at nt 2 of core motif in CBS. Sequences reflect position 2 through 6.

| SEQ ID NO: | Sequence | Read # |
|---|---|---|
| 602 | DTLSE | 10 |
| 391 | SSLAE | 10 |
| 603 | STLAV | 10 |

TABLE 3

ZF7 selection on C:A change at nt 2 of core motif in CBS. Sequences reflect position 2 through 6.

| SEQ ID NO: | Sequence | # read |
|---|---|---|
| 100 | DNLLA | 2659 |
| 101 | SNLLV | 2616 |
| 135 | DNLMT | 2555 |
| 130 | DNLQT | 1983 |
| 129 | DNLLV | 1945 |
| 128 | DNLLT | 1922 |
| 132 | DNLAT | 1457 |
| 604 | DNLRA | 1117 |
| 102 | DNLMA | 1038 |
| 605 | DNLMV | 901 |
| 606 | DNLQV | 845 |
| 607 | DNLQQ | 841 |
| 396 | DNLLQ | 813 |
| 387 | DNLKT | 582 |
| 133 | DNLQA | 571 |
| 420 | SNLQV | 565 |
| 608 | DNLRQ | 494 |
| 426 | SNLMV | 459 |
| 383 | SNLTV | 458 |
| 609 | DNLNT | 412 |
| 428 | DNLHT | 389 |
| 610 | SNLVV | 349 |
| 611 | SNLQQ | 334 |
| 429 | DNLTA | 323 |
| 612 | DNLLS | 322 |

TABLE 3-continued

ZF7 selection on C:A change at nt 2 of core motif in CBS. Sequences reflect position 2 through 6.

| SEQ ID NO: | Sequence | # read |
| --- | --- | --- |
| 413 | DNLAV | 316 |
| 416 | DNLRT | 309 |
| 613 | DNLTT | 300 |
| 614 | DNLAA | 295 |
| 615 | SNLLA | 295 |
| 616 | SNLLQ | 278 |
| 617 | SNLAV | 257 |
| 618 | DNLNA | 240 |
| 619 | DNLGT | 240 |
| 103 | DNLRV | 239 |
| 620 | DNLKA | 167 |
| 621 | DNLMQ | 156 |
| 622 | DNLKV | 148 |
| 623 | SNLNV | 132 |
| 624 | SNLMA | 128 |
| 625 | SVLQD | 113 |
| 626 | DNLQS | 110 |
| 627 | DNLSA | 105 |
| 628 | DNLAQ | 103 |
| 629 | DNLMS | 98 |
| 630 | DNLSQ | 95 |
| 631 | DNLNV | 87 |
| 632 | DNLGV | 87 |
| 633 | SNLLT | 87 |
| 634 | DNLIA | 83 |
| 635 | DNLNQ | 83 |
| 636 | SNLQT | 80 |
| 637 | SNLRV | 79 |
| 638 | SNLIV | 79 |
| 639 | DNLSV | 74 |
| 640 | SNLQA | 60 |
| 641 | SNLLL | 57 |
| 642 | SNLDV | 56 |
| 643 | DNLVQ | 54 |
| 644 | SNLLI | 54 |
| 645 | TGLAL | 52 |
| 646 | SNLMQ | 51 |
| 647 | DQLKI | 40 |
| 648 | GDLGT | 40 |
| 649 | SNLKV | 39 |
| 650 | VPLVD | 38 |
| 651 | DNLRI | 37 |
| 652 | DNLLI | 37 |
| 653 | TNLDV | 36 |
| 654 | HDLKI | 35 |
| 655 | DNLVV | 35 |
| 312 | DTLLV | 32 |
| 656 | DNLTV | 31 |
| 657 | DNLVT | 31 |
| 658 | SNLAQ | 30 |
| 659 | DNLIV | 28 |
| 660 | SNLMT | 27 |
| 465 | DTLMN | 25 |
| 661 | SNLTQ | 23 |
| 662 | EILRI | 23 |
| 663 | IGLEA | 22 |
| 664 | HRLGG | 22 |
| 8 | DHLQT | 21 |
| 665 | DNLST | 20 |
| 666 | MRLHV | 19 |
| 667 | SNLTT | 18 |
| 668 | SNLGV | 16 |
| 669 | SNLAT | 16 |
| 15 | EHLVV | 16 |
| 670 | ANLMV | 14 |
| 671 | HVLVG | 14 |
| 672 | SNLRA | 13 |
| 673 | HNLQL | 12 |
| 674 | DNLVA | 12 |
| 675 | SNLTA | 12 |
| 676 | KGLRM | 12 |

TABLE 3-continued

ZF7 selection on C:A change at nt 2 of core motif in CBS. Sequences reflect position 2 through 6.

| SEQ ID NO: | Sequence | # read |
|---|---|---|
| 334 | DTLLA | 12 |
| 677 | PMLGV | 11 |
| 678 | GVLVA | 11 |
| 679 | DNLQD | 11 |
| 680 | MKLGT | 11 |
| 406 | DTLLQ | 11 |

TABLE 4

ZF7 selection on A:T change at nt 3 of core motif in CBS. Sequences reflect position −1 to 3.

| SEQ ID NO: | Sequence | # Reads |
|---|---|---|
| 173 | RKHD | 4641 |
| 175 | RKAD | 1938 |
| 174 | RRSD | 1299 |
| 681 | RRHD | 868 |
| 682 | RKTD | 182 |
| 683 | NVSM | 146 |
| 684 | RQSD | 76 |
| 685 | RKND | 69 |
| 686 | SENV | 69 |
| 687 | VDHR | 60 |
| 688 | AQIV | 58 |
| 689 | KTPH | 56 |
| 690 | PKIV | 51 |
| 691 | GAEP | 42 |
| 692 | MLVE | 40 |
| 693 | VVGN | 40 |
| 694 | KGPE | 36 |
| 695 | GKVM | 33 |
| 696 | TEPG | 33 |
| 697 | TPHN | 32 |
| 698 | MPGG | 31 |
| 699 | DLEK | 28 |
| 700 | GTDN | 27 |

TABLE 4-continued

ZF7 selection on A:T change at nt 3 of core motif in CBS. Sequences reflect position −1 to 3.

| SEQ ID NO: | Sequence | # Reads |
|---|---|---|
| 701 | ISRL | 25 |
| 702 | ATGL | 21 |
| 703 | ASNP | 19 |
| 704 | GAPT | 17 |
| 705 | HSPN | 17 |
| 706 | RPVA | 16 |
| 177 | RKDD | 6 |
| 707 | MLVD | 4 |
| 708 | RHRK | 3 |
| 709 | RKHV | 3 |
| 710 | RKQD | 3 |
| 711 | RKSD | 3 |
| 712 | DHHT | 2 |
| 713 | GKHD | 2 |
| 714 | MKAD | 2 |
| 715 | RKAE | 2 |
| 716 | RRAD | 2 |
| 717 | APIG | 1 |
| 718 | AQNR | 1 |
| 719 | DMDA | 1 |
| 720 | EAPM | 1 |
| 721 | EEMM | 1 |
| 722 | EPIR | 1 |
| 723 | GALE | 1 |
| 724 | GENV | 1 |
| 725 | GKAD | 1 |
| 726 | GKVD | 1 |
| 727 | GPLA | 1 |
| 728 | GRIE | 1 |
| 729 | IEKL | 1 |
| 730 | KAAS | 1 |
| 731 | KEEH | 1 |
| 732 | LKVD | 1 |
| 733 | LLVE | 1 |
| 734 | LMTQ | 1 |
| 735 | MASL | 1 |

TABLE 4-continued

ZF7 selection on A:T change at nt 3 of core motif in CBS.
Sequences reflect position -1 to 3.

| SEQ ID NO: | Sequence | # Reads |
|---|---|---|
| 736 | MGIG | 1 |
| 737 | MPGD | 1 |
| 738 | MSLG | 1 |
| 739 | NDMT | 1 |
| 740 | NMHT | 1 |
| 741 | NRIV | 1 |
| 742 | PENA | 1 |
| 743 | QKHD | 1 |
| 744 | QVPD | 1 |
| 745 | RASD | 1 |
| 746 | REHD | 1 |
| 747 | RGHD | 1 |
| 748 | RKHA | 1 |
| 749 | RKHY | 1 |
| 750 | RKLD | 1 |
| 751 | RKPD | 1 |
| 752 | RKVD | 1 |
| 753 | RKYD | 1 |
| 754 | RMSD | 1 |
| 755 | RRLD | 1 |
| 756 | RRND | 1 |
| 757 | RRRD | 1 |
| 758 | RRSG | 1 |
| 759 | RWHD | 1 |
| 760 | SHRL | 1 |
| 761 | SQHV | 1 |
| 762 | SSHD | 1 |
| 763 | TTHV | 1 |
| 764 | VHHV | 1 |
| 765 | WKAD | 1 |
| 766 | WKHD | 1 |

TABLE 5

ZF7 selection on A:G change at nt 3 of core motif in CBS.
Sequences reflect position -1 to 3.

| SEQ ID NO: | Sequence | Read # |
|---|---|---|
| 174 | RRSD | 2997 |
| 173 | RKHD | 2731 |
| 175 | RKAD | 1867 |
| 177 | RKDD | 667 |
| 682 | RKTD | 475 |
| 767 | HADA | 411 |
| 710 | RKQD | 376 |
| 768 | RKWD | 296 |
| 745 | RASD | 265 |
| 681 | RRHD | 169 |
| 685 | RKND | 126 |
| 754 | RMSD | 40 |
| 769 | RKGD | 5 |
| 743 | QKHD | 3 |
| 757 | RRRD | 3 |
| 711 | RKSD | 3 |
| 752 | RKVD | 2 |
| 180 | QALL | 2 |
| 753 | RKYD | 2 |
| 756 | RRND | 2 |
| 720 | EAPM | 1 |
| 770 | RRCD | 1 |
| 771 | MLPA | 1 |
| 772 | RATD | 1 |
| 773 | RKDV | 1 |
| 774 | KKPV | 1 |
| 775 | GEHG | 1 |
| 776 | HPVR | 1 |
| 777 | RQHD | 1 |
| 778 | RMMQ | 1 |
| 779 | RRGD | 1 |
| 780 | GREV | 1 |
| 781 | REQD | 1 |
| 782 | DRDM | 1 |
| 783 | SKHD | 1 |
| 784 | RLSD | 1 |

TABLE 5-continued

ZF7 selection on A:G change at nt 3 of core motif in CBS.
Sequences reflect position -1 to 3.

| SEQ ID NO: | Sequence | Read # |
|---|---|---|
| 785 | VPTV | 1 |
| 786 | HKWD | 1 |
| 787 | KKND | 1 |
| 788 | RRSE | 1 |
| 749 | RKHY | 1 |
| 789 | READ | 1 |
| 790 | RNTD | 1 |
| 791 | MVRA | 1 |
| 792 | RKED | 1 |
| 793 | KTMG | 1 |
| 794 | NEPN | 1 |
| 795 | RGSD | 1 |
| 796 | RKRD | 1 |
| 797 | RWSD | 1 |
| 798 | TPLP | 1 |
| 799 | RKAN | 1 |
| 800 | RKAY | 1 |
| 801 | QLPL | 1 |
| 709 | RKHV | 1 |
| 802 | QGTS | 1 |
| 803 | DTMV | 1 |
| 804 | LKWD | 1 |
| 805 | MNTL | 1 |
| 806 | HADV | 1 |
| 697 | TPHN | 1 |
| 750 | RKLD | 1 |
| 807 | GRAH | 1 |
| 704 | GAPT | 1 |
| 808 | MKHD | 1 |
| 809 | HEDA | 1 |
| 712 | DHHT | 1 |
| 810 | RMLS | 1 |
| 811 | WRSD | 1 |
| 812 | DDAT | 1 |
| 735 | MASL | 1 |
| 730 | KAAS | 1 |

TABLE 6

ZF7 selection on A:C change at nt 3 of core motif in CBS.
Sequences reflect position -1 to 3.

| SEQ ID NO: | Sequence | Read # |
|---|---|---|
| 173 | RKHD | 9 |
| 813 | DTEN | 6 |
| 775 | GEHG | 5 |
| 814 | STKN | 5 |
| 815 | NIEI | 5 |
| 801 | QLPL | 4 |
| 780 | GREV | 4 |
| 712 | DHHT | 4 |
| 782 | DRDM | 4 |
| 816 | MVIN | 4 |
| 817 | VPDT | 4 |
| 818 | NIVP | 4 |
| 819 | MVPS | 4 |
| 820 | PNHP | 4 |
| 821 | KTDV | 4 |
| 794 | NEPN | 3 |
| 760 | SHRL | 3 |
| 736 | MGIG | 3 |
| 822 | HIKM | 3 |
| 823 | ILQI | 3 |
| 741 | NRIV | 3 |
| 824 | IVMQ | 3 |
| 825 | QTNS | 3 |
| 826 | ENMD | 3 |
| 827 | TVER | 3 |
| 828 | THDR | 3 |
| 829 | IRSP | 3 |
| 771 | MLPA | 3 |
| 721 | EEMM | 2 |
| 830 | ARIA | 2 |
| 785 | VPTV | 2 |
| 831 | EELI | 2 |
| 832 | KPLR | 2 |
| 812 | DDAT | 2 |
| 833 | NRLS | 2 |
| 834 | PTLR | 2 |

TABLE 6-continued

ZF7 selection on A:C change at nt 3 of core motif in CBS.
Sequences reflect position -1 to 3.

| SEQ ID NO: | Sequence | Read # |
|---|---|---|
| 835 | MHIL | 2 |
| 836 | GGGP | 2 |
| 837 | MVEN | 2 |
| 719 | DMDA | 2 |
| 838 | IVAT | 2 |
| 839 | TLDR | 2 |
| 840 | MEPL | 2 |
| 841 | DTGV | 2 |
| 842 | TSRS | 2 |
| 843 | VLSI | 2 |
| 844 | STVQ | 2 |
| 845 | GPAQ | 2 |
| 846 | VEQP | 2 |
| 847 | MTKK | 2 |
| 848 | PLIM | 2 |
| 802 | QGTS | 2 |
| 849 | AMTV | 2 |
| 850 | SPMR | 2 |
| 851 | EPNV | 2 |
| 735 | MASL | 2 |
| 852 | MQIN | 2 |
| 853 | ALDE | 2 |
| 728 | GRIE | 2 |
| 854 | ALEH | 2 |
| 855 | REKD | 2 |
| 856 | ELLA | 2 |
| 857 | GVAR | 2 |
| 858 | VDTL | 2 |
| 859 | GHEN | 2 |
| 730 | KAAS | 2 |
| 860 | ELES | 2 |
| 861 | DPDT | 2 |
| 862 | SLEL | 2 |
| 863 | TMNV | 2 |
| 764 | VHHV | 2 |
| 864 | IQPV | 2 |

TABLE 6-continued

ZF7 selection on A:C change at nt 3 of core motif in CBS.
Sequences reflect position -1 to 3.

| SEQ ID NO: | Sequence | Read # |
|---|---|---|
| 865 | MLQE | 1 |
| 866 | VMTV | 1 |
| 867 | MVEE | 1 |
| 868 | VARP... | 1 |
| 869 | KAIG | 1 |
| 870 | DRSM | 1 |
| 871 | KNSI | 1 |
| 872 | DDVS | 1 |
| 873 | KPQP | 1 |
| 874 | PHVP | 1 |
| 875 | DTLQ | 1 |
| 876 | KLGT | 1 |
| 877 | IDPH | 1 |
| 878 | HPNT | 1 |
| 879 | KSRG | 1 |
| 880 | RQMA | 1 |
| 881 | KKEN | 1 |
| 882 | QVLD | 1 |
| 722 | EPIR | 1 |
| 883 | RRQM | 1 |
| 798 | TPLP | 1 |
| 884 | ILKN | 1 |
| 885 | HQMK | 1 |
| 179 | ELLN | 1 |
| 886 | MDGG | 1 |
| 887 | AAGS | 1 |
| 888 | STVV | 1 |
| 889 | PARA | 1 |
| 890 | ALQG | 1 |
| 891 | SAPG | 1 |
| 892 | PVLN | 1 |
| 742 | PENA | 1 |
| 893 | TSLL | 1 |
| 731 | KEEH | 1 |
| 894 | HLDV | 1 |
| 895 | IHIR | 1 |

TABLE 6-continued

ZF7 selection on A:C change at nt 3 of core motif in CBS. Sequences reflect position -1 to 3.

| SEQ ID NO: | Sequence | Read # |
|---|---|---|
| 896 | SVTL | 1 |
| 897 | VKDR | 1 |
| 898 | KMTI | 1 |
| 899 | AGEM | 1 |
| 900 | GDSE | 1 |
| 901 | QPVK | 1 |
| 902 | KVEA | 1 |
| 903 | EQER | 1 |
| 729 | IEKL | 1 |
| 904 | GHHV | 1 |
| 905 | GMHL | 1 |
| 906 | RLRR | 1 |
| 907 | ATIR | 1 |
| 908 | RMDI | 1 |
| 909 | SVIH | 1 |
| 910 | MDIG | 1 |
| 911 | LART | 1 |
| 912 | RLMA | 1 |
| 913 | RQPP | 1 |
| 914 | MTMT | 1 |
| 915 | EDTR | 1 |
| 739 | NDMT | 1 |
| 916 | MRGR | 1 |
| 917 | ELHA | 1 |
| 918 | TNGQ | 1 |
| 919 | VNLT | 1 |
| 920 | MHIR | 1 |
| 921 | MLLQ | 1 |
| 922 | GRGE | 1 |
| 923 | NLRG | 1 |
| 924 | HIML | 1 |
| 807 | GRAH | 1 |
| 805 | MNTL | 1 |
| 763 | TTHV | 1 |
| 793 | KTMG | 1 |
| 925 | MTSV | 1 |
| 926 | RLSM | 1 |
| 803 | DTMV | 1 |
| 720 | EAPM | 1 |
| 927 | DMGM | 1 |
| 928 | MLMM | 1 |
| 929 | LMEM | 1 |
| 930 | QAVS | 1 |
| 931 | SRVL | 1 |
| 932 | DEDP | 1 |
| 933 | SGDR | 1 |
| 934 | MMNC | 1 |
| 935 | NIGM | 1 |
| 936 | MVQR | 1 |
| 937 | APHR | 1 |
| 938 | LDAG | 1 |
| 939 | RLAN | 1 |
| 940 | MKGS | 1 |
| 941 | KKLV | 1 |
| 942 | VNQE | 1 |
| 943 | ILKQ | 1 |
| 944 | PVIP | 1 |
| 945 | VESL | 1 |
| 946 | IKQN | 1 |
| 947 | EDNI | 1 |
| 948 | THRD | 1 |
| 949 | IPAG | 1 |
| 950 | GLNH | 1 |
| 951 | VDGR | 1 |
| 181 | PHRM | 1 |
| 952 | RTGA | 1 |
| 953 | VSPD | 1 |
| 954 | KVGD | 1 |

TABLE 7

ZF6 selection on C:T change at nt 5 of core motif in CBS.
Sequences reflect position 2 to 6.

| SEQ ID NO: | Sequence | Read # |
|---|---|---|
| 955 | GHMRR | 29 |
| 956 | GHMNR | 23 |
| 34 | EHMRR | 23 |
| 957 | THMRR | 19 |
| 33 | THMKR | 17 |
| 126 | EHMNR | 17 |
| 958 | GHMKR | 12 |
| 127 | EHMAR | 11 |
| 959 | EHMQR | 10 |
| 147 | SHMRR | 10 |
| 960 | SAMRR | 9 |
| 961 | ENMGR | 8 |
| 962 | SHMKR | 8 |
| 35 | THMNR | 7 |
| 963 | NHMRR | 7 |
| 964 | EGMRR | 7 |
| 965 | GNMGR | 7 |
| 146 | SHMNR | 6 |
| 966 | NGMRI | 6 |
| 967 | EGMAR | 6 |
| 968 | ESMRR | 6 |
| 969 | GHMSR | 5 |
| 970 | EGMHR | 5 |
| 971 | TAMRR | 5 |
| 972 | TNMQR | 5 |
| 973 | VNMRR | 5 |
| 974 | AHMKR | 4 |
| 975 | NGMTA | 4 |
| 976 | DGMRR | 4 |
| 977 | GHMTR | 4 |
| 978 | EHMSR | 4 |
| 123 | EHMKR | 4 |
| 979 | GSMRR | 4 |
| 980 | TNMLR | 4 |
| 981 | NHMKR | 4 |
| 982 | ENMLR | 4 |
| 983 | SPMGV | 3 |
| 984 | TNMGR | 3 |
| 985 | SSMAR | 3 |
| 986 | GGMRR | 3 |
| 987 | GGMKL | 3 |
| 988 | SGMVR | 3 |
| 989 | EHMHR | 3 |
| 990 | THMSR | 3 |
| 991 | GSMKI | 3 |
| 992 | EKMKE | 3 |
| 993 | NGMAR | 3 |
| 994 | QNMVR | 3 |
| 995 | DNMRR | 3 |
| 996 | ENMER | 3 |
| 997 | NSMRR | 3 |
| 998 | SGMKR | 3 |
| 999 | ANMQR | 3 |
| 1000 | GHMQR | 3 |
| 1001 | ANMGR | 3 |
| 1002 | DNMVR | 3 |
| 1003 | QAMRE | 2 |
| 1004 | GNMSR | 2 |
| 1005 | ESMQR | 2 |
| 1006 | TPMKV | 2 |
| 1007 | SNMGR | 2 |
| 1008 | GAMRI | 2 |
| 1009 | ANMNR | 2 |
| 1010 | DNMMR | 2 |
| 1011 | GSMKM | 2 |
| 31 | EHMGR | 2 |
| 1012 | GNMAQ | 2 |
| 1013 | EGMKG | 2 |
| 1014 | SSMKI | 2 |
| 1015 | TSMRR | 2 |
| 1016 | DGMKR | 2 |
| 1017 | DNMAR | 2 |

TABLE 7-continued

ZF6 selection on C:T change at nt 5 of core motif in CBS.
Sequences reflect position 2 to 6.

| SEQ ID NO: | Sequence | Read # |
|---|---|---|
| 1018 | SSMRR | 2 |
| 1019 | GNMMR | 2 |
| 185 | NAMRG | 2 |
| 1020 | THMKL | 2 |
| 1021 | ENMAR | 2 |
| 1022 | NNMVR | 2 |
| 1023 | TGMKR | 2 |
| 1024 | TAMKR | 2 |
| 1025 | AHMNR | 2 |
| 1026 | QNMGR | 2 |
| 1027 | TNMVR | 2 |
| 1028 | NHMNR | 2 |
| 1029 | EHMTR | 2 |
| 1030 | GNMIR | 2 |
| 1031 | SGMRR | 2 |
| 1032 | NHMSR | 2 |
| 1033 | GGMRL | 2 |
| 1034 | SPMKV | 2 |
| 1035 | TNMRR | 2 |
| 1036 | GNMRE | 2 |
| 1037 | ENMMR | 2 |
| 1038 | THMER | 1 |
| 1039 | QKMRT | 1 |
| 1040 | GAMRR | 1 |
| 1041 | TPMEV | 1 |
| 1042 | GGMRE | 1 |
| 1043 | GDMDR | 1 |
| 1044 | GAMRA | 1 |
| 1045 | PNMSR | 1 |
| 1046 | EGMGR | 1 |
| 1047 | EGTHR | 1 |
| 1048 | QSMRE | 1 |
| 1049 | THMKG | 1 |
| 1050 | NNMGR | 1 |
| 1051 | GHMNS | 1 |
| 1052 | IDMKG | 1 |

TABLE 7-continued

ZF6 selection on C:T change at nt 5 of core motif in CBS.
Sequences reflect position 2 to 6.

| SEQ ID NO: | Sequence | Read # |
|---|---|---|
| 1053 | ESMTR | 1 |
| 1054 | SHMKI | 1 |
| 1055 | HNMMR | 1 |
| 184 | SNMVR | 1 |
| 1056 | TAMKV | 1 |
| 1057 | DSMKR | 1 |
| 1058 | SNMAR | 1 |
| 1059 | ESMGR | 1 |
| 1060 | EAMRR | 1 |
| 1061 | GNMVR | 1 |
| 1062 | ANMRR | 1 |
| 1063 | DGMKI | 1 |
| 1064 | SHMHR | 1 |
| 1065 | GAMKE | 1 |
| 1066 | ESMRE | 1 |
| 1067 | GSMLR | 1 |
| 1068 | THMEV | 1 |
| 1069 | TSMGR | 1 |
| 1070 | EAMSK | 1 |
| 1071 | NAMRQ | 1 |
| 1072 | EGMRT | 1 |
| 1073 | SHMQR | 1 |
| 1074 | NGMKR | 1 |
| 1075 | ESMKE | 1 |
| 1076 | ANMHR | 1 |
| 1077 | DHTKR | 1 |
| 1078 | NGMRE | 1 |
| 1079 | GSMRA | 1 |
| 1080 | EGMNQ | 1 |
| 1081 | GGMRM | 1 |
| 1082 | PNMKR | 1 |
| 1083 | NGMKI | 1 |
| 1084 | SNMLR | 1 |
| 1085 | SNMRR | 1 |
| 1086 | SHMTR | 1 |
| 1087 | TGMRR | 1 |

TABLE 7-continued

ZF6 selection on C:T change at nt 5 of core motif in CBS.
Sequences reflect position 2 to 6.

| SEQ ID NO: | Sequence | Read # |
|---|---|---|
| 1088 | SGMRI | 1 |
| 1089 | DNMGR | 1 |
| 183 | EGMTR | 1 |

TABLE 8

ZF6 selection on C:A change at nt 5 of core motif in CBS.
Sequences reflect position 2 to 6.

| SEQ ID NO: | Sequence | Read # |
|---|---|---|
| 965 | GNMGR | 873 |
| 968 | ESMRR | 784 |
| 964 | EGMRR | 772 |
| 967 | EGMAR | 672 |
| 970 | EGMHR | 648 |
| 994 | QNMVR | 597 |
| 980 | TNMLR | 556 |
| 998 | SGMKR | 486 |
| 975 | NGMTA | 479 |
| 979 | GSMRR | 453 |
| 1003 | QAMRE | 452 |
| 961 | ENMGR | 434 |
| 960 | SAMRR | 431 |
| 993 | NGMAR | 401 |
| 1079 | GSMRA | 390 |
| 996 | ENMER | 389 |
| 1007 | SNMGR | 378 |
| 1046 | EGMGR | 376 |
| 1017 | DNMAR | 368 |
| 1063 | DGMKI | 347 |
| 999 | ANMQR | 342 |
| 1040 | GAMRR | 322 |
| 973 | VNMRR | 297 |
| 997 | NSMRR | 295 |
| 1005 | ESMQR | 293 |

TABLE 8-continued

ZF6 selection on C:A change at nt 5 of core motif in CBS.
Sequences reflect position 2 to 6.

| SEQ ID NO: | Sequence | Read # |
|---|---|---|
| 1018 | SSMRR | 289 |
| 1087 | TGMRR | 289 |
| 1009 | ANMNR | 279 |
| 1044 | GAMRA | 275 |
| 183 | EGMTR | 273 |
| 126 | EHMNR | 265 |
| 1004 | GNMSR | 263 |
| 971 | TAMRR | 260 |
| 972 | TNMQR | 257 |
| 1010 | DNMMR | 253 |
| 976 | DGMRR | 241 |
| 1026 | QNMGR | 240 |
| 1082 | PNMKR | 228 |
| 1089 | DNMGR | 226 |
| 1090 | ETMRR | 225 |
| 1091 | DNMKI | 224 |
| 1014 | SSMKI | 224 |
| 995 | DNMRR | 221 |
| 1053 | ESMTR | 214 |
| 1042 | GGMRE | 214 |
| 984 | TNMGR | 211 |
| 1031 | SGMRR | 204 |
| 986 | GGMRR | 203 |
| 1022 | NNMVR | 201 |
| 1092 | TNMER | 197 |
| 1083 | NGMKI | 195 |
| 1021 | ENMAR | 194 |
| 1059 | ESMGR | 194 |
| 1019 | GNMMR | 193 |
| 1036 | GNMRE | 193 |
| 1002 | DNMVR | 187 |
| 1093 | TNMAR | 186 |
| 34 | EHMRR | 182 |
| 1066 | ESMRE | 181 |
| 1027 | TNMVR | 181 |

TABLE 8-continued

ZF6 selection on C:A change at nt 5 of core motif in CBS. Sequences reflect position 2 to 6.

| SEQ ID NO: | Sequence | Read # |
|---|---|---|
| 1015 | TSMRR | 175 |
| 988 | SGMVR | 173 |
| 1024 | TAMKR | 170 |
| 1030 | GNMIR | 169 |
| 985 | SSMAR | 163 |
| 991 | GSMKI | 159 |
| 1094 | EHMKQ | 149 |
| 982 | ENMLR | 149 |
| 1016 | DGMKR | 144 |
| 1012 | GNMAQ | 139 |
| 1095 | SGMQR | 138 |
| 1084 | SNMLR | 133 |
| 1061 | GNMVR | 130 |
| 1001 | ANMGR | 129 |
| 1096 | HNMRR | 129 |
| 1050 | NNMGR | 128 |
| 1081 | GGMRM | 127 |
| 1033 | GGMRL | 124 |
| 1097 | QNMER | 124 |
| 1057 | DSMKR | 122 |
| 1035 | TNMRR | 122 |
| 1008 | GAMRI | 115 |
| 1058 | SNMAR | 115 |
| 1056 | TAMKV | 114 |
| 1098 | VSMKR | 113 |
| 966 | NGMRI | 112 |
| 1099 | TNMMR | 110 |
| 1013 | EGMKG | 109 |
| 1071 | NAMRQ | 108 |
| 123 | EHMKR | 107 |
| 1032 | NHMSR | 106 |
| 1100 | GAMRM | 102 |
| 1070 | EAMSK | 100 |
| 1101 | TAMNQ | 99 |

TABLE 8-continued

ZF6 selection on C:A change at nt 5 of core motif in CBS. Sequences reflect position 2 to 6.

| SEQ ID NO: | Sequence | Read # |
|---|---|---|
| 1102 | ESMSR | 96 |
| 1103 | GGMNQ | 95 |
| 1048 | QSMRE | 95 |
| 185 | NAMRG | 92 |
| 1104 | GGMKR | 89 |
| 184 | SNMVR | 84 |
| 1105 | ESMRL | 83 |
| 1075 | ESMKE | 81 |
| 1106 | SAMRE | 80 |
| 1107 | GGMQM | 76 |
| 1023 | TGMKR | 73 |
| 1037 | ENMMR | 69 |
| 1108 | NSMKM | 69 |
| 1109 | ESMKN | 66 |
| 1072 | EGMRT | 64 |
| 987 | GGMKL | 64 |
| 1110 | TNMSR | 63 |
| 1111 | DAMRV | 61 |
| 1112 | GNMER | 60 |
| 1113 | GAMRE | 59 |
| 182 | GNMAR | 54 |
| 1114 | EGMRK | 53 |
| 1011 | GSMKM | 50 |
| 1115 | SGMAR | 50 |

TABLE 9

ZF6 selection on C:G change at nt 5 of core motif in CBS. Sequences reflect position 2 to 6.

| SEQ ID NO: | Sequence | # Read |
|---|---|---|
| 34 | EHMRR | 3207 |
| 955 | GHMRR | 2397 |
| 957 | THMRR | 2025 |
| 956 | GHMNR | 1880 |

TABLE 9-continued

ZF6 selection on C:G change at nt 5 of core motif in CBS.
Sequences reflect position 2 to 6.

| SEQ ID NO: | Sequence | # Read |
|---|---|---|
| 33 | THMKR | 1415 |
| 35 | THMNR | 1341 |
| 958 | GHMKR | 1208 |
| 978 | EHMSR | 1038 |
| 127 | EHMAR | 927 |
| 962 | SHMKR | 771 |
| 959 | EHMQR | 764 |
| 126 | EHMNR | 676 |
| 146 | SHMNR | 646 |
| 147 | SHMRR | 579 |
| 123 | EHMKR | 511 |
| 1029 | EHMTR | 460 |
| 963 | NHMRR | 436 |
| 992 | EKMKE | 381 |
| 32 | DHMNR | 374 |
| 981 | NHMKR | 342 |
| 983 | SPMGV | 322 |
| 977 | GHMTR | 318 |
| 1028 | NHMNR | 285 |
| 1116 | DHMKR | 264 |
| 969 | GHMSR | 258 |
| 1025 | AHMNR | 247 |
| 989 | EHMHR | 232 |
| 974 | AHMKR | 227 |
| 31 | EHMGR | 210 |
| 1117 | GHMHR | 129 |
| 1118 | THMKV | 129 |
| 1020 | THMKL | 117 |
| 1006 | TPMKV | 110 |
| 1000 | GHMQR | 105 |
| 1119 | DHMRR | 105 |
| 990 | THMSR | 97 |
| 1120 | AHMRR | 92 |
| 1121 | EKMRE | 86 |
| 1122 | GHMAR | 84 |
| 1074 | NGMKR | 81 |
| 1123 | VHMNR | 77 |
| 1052 | IDMKG | 72 |
| 1124 | NHMTR | 65 |
| 1032 | NHMSR | 64 |
| 964 | EGMRR | 57 |
| 1125 | THMTR | 57 |
| 1126 | GHMKI | 56 |
| 1073 | SHMQR | 52 |
| 1127 | EHMVR | 43 |
| 1086 | SHMTR | 43 |
| 1128 | TKMKE | 42 |
| 1129 | EHMER | 38 |
| 1130 | THMKT | 37 |
| 1043 | GDMDR | 36 |
| 1131 | NGMRR | 35 |
| 1132 | EPMLM | 34 |
| 1133 | GHMVR | 31 |
| 1134 | THMRT | 29 |
| 968 | ESMRR | 28 |
| 1135 | PHMKR | 26 |
| 1136 | EHMRQ | 24 |
| 1137 | EHMRT | 23 |
| 1138 | DHMSR | 22 |
| 1039 | QKMRT | 22 |
| 1139 | ETMMI | 21 |
| 1034 | SPMKV | 21 |
| 1140 | SHMKL | 21 |
| 1141 | TPMKL | 21 |
| 1142 | GHMKM | 20 |
| 965 | GNMGR | 19 |
| 1143 | RQMLI | 19 |
| 1144 | GHMRM | 18 |
| 1145 | EGMKR | 17 |
| 1146 | EHMKA | 17 |
| 1147 | QIMPL | 17 |
| 1148 | SHMKV | 16 |

TABLE 9-continued

ZF6 selection on C:G change at nt 5 of core motif in CBS.
Sequences reflect position 2 to 6.

| SEQ ID NO: | Sequence | # Read |
|---|---|---|
| 1149 | SGMNR | 16 |
| 1150 | THMAR | 16 |
| 1151 | QGMKR | 15 |
| 960 | SAMRR | 14 |
| 1152 | TKMEG | 14 |
| 1153 | RPMGR | 14 |
| 1154 | VHMRR | 13 |
| 1155 | THMRV | 13 |
| 1068 | THMEV | 12 |
| 1156 | NHMKS | 11 |
| 1049 | THMKG | 11 |
| 1157 | AAMST | 11 |
| 980 | TNMLR | 11 |
| 996 | ENMER | 10 |
| 1158 | GKMRD | 10 |
| 1159 | THMEL | 10 |
| 998 | SGMKR | 10 |
| 1160 | TPMRV | 10 |
| 1161 | SPMRV | 10 |
| 1104 | GGMKR | 10 |
| 967 | EGMAR | 10 |
| 1162 | THMGV | 9 |
| 971 | TAMRR | 9 |
| 995 | DNMRR | 9 |
| 966 | NGMRI | 9 |
| 961 | ENMGR | 9 |
| 1163 | MGMGR | 8 |
| 973 | VNMRR | 8 |
| 1164 | GKPSM | 8 |
| 975 | NGMTA | 8 |
| 1165 | SHMRV | 8 |
| 1166 | SPMNR | 8 |
| 1167 | SAMNR | 8 |
| 1168 | SHMSR | 8 |
| 1169 | NGMPR | 8 |
| 972 | TNMQR | 8 |
| 1170 | SPMRR | 8 |
| 994 | QNMVR | 8 |
| 970 | EGMHR | 8 |
| 1017 | DNMAR | 7 |
| 1026 | QNMGR | 7 |
| 1171 | GHMGV | 7 |
| 1172 | THMRL | 7 |
| 979 | GSMRR | 7 |
| 1173 | QHMKR | 7 |
| 1174 | THMGR | 7 |
| 976 | DGMRR | 7 |
| 1175 | THMQR | 6 |
| 1038 | THMER | 6 |
| 1021 | ENMAR | 6 |
| 1176 | RHMKR | 6 |
| 1018 | SSMRR | 6 |
| 1177 | EHMRV | 6 |
| 1178 | KHMKR | 6 |
| 1179 | QHMNR | 6 |
| 1180 | RAMKV | 6 |
| 993 | NGMAR | 6 |
| 984 | TNMGR | 6 |
| 1002 | DNMVR | 6 |
| 1066 | ESMRE | 6 |
| 1181 | GHMRV | 6 |
| 982 | ENMLR | 6 |
| 185 | NAMRG | 5 |
| 1014 | SSMKI | 5 |
| 1182 | TPMGV | 5 |
| 1040 | GAMRR | 5 |
| 1183 | GHMKV | 5 |
| 1184 | RHMNR | 5 |
| 1009 | ANMNR | 5 |
| 1185 | TPMEL | 5 |
| 1022 | NNMVR | 5 |
| 988 | SGMVR | 5 |

TABLE 9-continued

ZF6 selection on C:G change at nt 5 of core motif in CBS.
Sequences reflect position 2 to 6.

| SEQ ID NO: | Sequence | # Read |
|---|---|---|
| 1186 | SPMKL | 5 |
| 1187 | SPMKR | 5 |
| 1035 | TNMRR | 5 |
| 1082 | PNMKR | 5 |
| 1188 | LAMEE | 5 |
| 1044 | GAMRA | 5 |
| 1100 | GAMRM | 5 |
| 1046 | EGMGR | 5 |
| 1033 | GGMRL | 5 |
| 1189 | PGMMS | 5 |
| 986 | GGMRR | 5 |
| 991 | GSMKI | 5 |
| 1089 | DNMGR | 5 |
| 183 | EGMTR | 4 |
| 1190 | SHMEV | 4 |
| 1004 | GNMSR | 4 |
| 1191 | GMMLT | 4 |
| 1003 | QAMRE | 4 |
| 997 | NSMRR | 4 |
| 1087 | TGMRR | 4 |
| 1192 | TPMKG | 4 |
| 1041 | TPMEV | 4 |
| 1193 | THMHR | 4 |
| 1194 | SHMGV | 4 |
| 1063 | DGMKI | 4 |
| 1016 | DGMKR | 4 |
| 1195 | THMKS | 4 |
| 1196 | THMRG | 4 |
| 1197 | GHMKT | 4 |
| 1015 | TSMRR | 4 |
| 1019 | GNMMR | 4 |
| 999 | ANMQR | 4 |
| 1079 | GSMRA | 4 |
| 1036 | GNMRE | 4 |
| 1083 | NGMKI | 4 |
| 1008 | GAMRI | 4 |
| 1050 | NNMGR | 4 |
| 1198 | THMRS | 4 |
| 1013 | EGMKG | 4 |
| 1199 | NHMQR | 4 |
| 1007 | SNMGR | 4 |
| 1200 | SHMAR | 3 |
| 1061 | GNMVR | 3 |
| 1201 | EAMKR | 3 |
| 1202 | GSMRE | 3 |
| 1203 | SPMEL | 3 |
| 1204 | AHMAR | 3 |
| 1057 | DSMKR | 3 |
| 1205 | PPMMV | 3 |
| 1027 | TNMVR | 3 |
| 1096 | HNMRR | 3 |
| 1206 | KHMNR | 3 |
| 1030 | GNMIR | 3 |
| 1084 | SNMLR | 3 |
| 1207 | TPMKR | 3 |
| 1208 | QSMKR | 3 |
| 1209 | RHMRR | 3 |
| 1075 | ESMKE | 3 |
| 1210 | DHMQR | 3 |
| 1056 | TAMKV | 3 |
| 1211 | AHMSR | 3 |
| 1212 | EHMRS | 3 |
| 1213 | AHMTR | 3 |
| 1214 | GHINR | 3 |
| 1048 | QSMRE | 3 |
| 1093 | TNMAR | 3 |
| 1215 | EYMRR | 3 |
| 1216 | GQMNR | 3 |
| 1217 | GHMKE | 3 |
| 1011 | GSMKM | 3 |
| 1064 | SHMHR | 3 |
| 1059 | ESMGR | 3 |

TABLE 9-continued

ZF6 selection on C:G change at nt 5 of core motif in CBS.
Sequences reflect position 2 to 6.

| SEQ ID NO: | Sequence | # Read |
|---|---|---|
| 1005 | ESMQR | 3 |
| 1051 | GHMNS | 3 |
| 1058 | SNMAR | 3 |
| 1012 | GNMAQ | 3 |
| 1023 | TGMKR | 3 |
| 1031 | SGMRR | 3 |
| 1001 | ANMGR | 3 |
| 987 | GGMKL | 3 |
| 1218 | EHMMR | 2 |
| 1219 | SHMRL | 2 |
| 1072 | EGMRT | 2 |
| 1107 | GGMQM | 2 |
| 1220 | GGMKA | 2 |
| 1070 | EAMSK | 2 |
| 1221 | EHMPR | 2 |
| 1222 | AHMKS | 2 |
| 1223 | AHMQR | 2 |
| 1224 | GHTRR | 2 |
| 1225 | GHMKG | 2 |
| 1226 | EPMKV | 2 |
| 1227 | EHMAK | 2 |
| 1228 | GYMNR | 2 |
| 1229 | THMSS | 2 |
| 1230 | GDMNR | 2 |
| 1231 | GHMRT | 2 |
| 1094 | EHMKQ | 2 |
| 1232 | QRMGV | 2 |
| 1233 | GSMRQ | 2 |
| 1234 | DHMTR | 2 |
| 1235 | VEMER | 2 |
| 1236 | SPMEV | 2 |
| 1237 | GPMKV | 2 |
| 1238 | TPMER | 2 |
| 1239 | EHMDR | 2 |
| 1240 | EHVRR | 2 |
| 1091 | DNMKI | 2 |
| 1241 | GGMAR | 2 |
| 1242 | HHMKR | 2 |
| 1243 | GHMRS | 2 |
| 1244 | EYMAR | 2 |
| 1245 | KHMRR | 2 |
| 1246 | EHMSS | 2 |
| 1247 | TPMRL | 2 |
| 1248 | GHMSL | 2 |
| 1249 | VHMKR | 2 |
| 1250 | GHTNR | 2 |
| 1251 | GPMRT | 2 |
| 1081 | GGMRM | 2 |
| 1092 | TNMER | 2 |
| 1109 | ESMKN | 2 |
| 1252 | EQMRR | 2 |
| 1053 | ESMTR | 2 |
| 1253 | EHMKS | 2 |
| 1254 | THMKM | 2 |
| 1065 | GAMKE | 2 |
| 1024 | TAMKR | 2 |
| 1010 | DNMMR | 2 |
| 985 | SSMAR | 2 |
| 1037 | ENMMR | 2 |
| 1255 | GTMKM | 1 |
| 1256 | VHRIR | 1 |
| 1257 | DHMNK | 1 |
| 1258 | TPMNM | 1 |
| 1259 | RQMII | 1 |
| 1260 | EHMRW | 1 |
| 1261 | SPMRL | 1 |
| 1262 | GVMRA | 1 |
| 1263 | GHMQV | 1 |
| 1264 | GPMKL | 1 |
| 1265 | IDMKR | 1 |
| 1266 | PGMMG | 1 |
| 1267 | KHMER | 1 |

TABLE 9-continued

ZF6 selection on C:G change at nt 5 of core motif in CBS.
Sequences reflect position 2 to 6.

| SEQ ID NO: | Sequence | # Read |
|---|---|---|
| 1268 | TPMNV | 1 |
| 1269 | EHVQR | 1 |
| 1270 | ENMKE | 1 |
| 1271 | DHMKM | 1 |
| 1272 | SHMNQ | 1 |
| 1108 | NSMKM | 1 |
| 1273 | GLMKR | 1 |
| 1274 | APMNL | 1 |
| 1275 | RHMSR | 1 |
| 1276 | EHMRG | 1 |
| 1277 | DWMRR | 1 |
| 1278 | GHMRH | 1 |
| 1279 | QNMHR | 1 |
| 1280 | CHMRR | 1 |
| 1281 | ERMRR | 1 |
| 1282 | EHMKE | 1 |
| 1283 | EPMKR | 1 |
| 1284 | AHINR | 1 |
| 1285 | SHMRT | 1 |
| 1286 | PHMNR | 1 |
| 1287 | AHMKV | 1 |
| 1288 | THMGM | 1 |
| 1289 | NGMKM | 1 |
| 1290 | EKMKR | 1 |
| 1291 | EHMIR | 1 |
| 1292 | NNMHR | 1 |
| 1293 | GNMNR | 1 |
| 1294 | KRMQR | 1 |
| 1295 | EKMRR | 1 |
| 1296 | TQMKQ | 1 |
| 1297 | EHMKV | 1 |
| 1298 | DHMKE | 1 |
| 1299 | EHTTR | 1 |
| 1300 | SPMRM | 1 |
| 1301 | GKMNR | 1 |
| 1302 | TNMKR | 1 |
| 1303 | THKRR | 1 |
| 1304 | SQTNR | 1 |
| 1305 | THLKR | 1 |
| 1306 | SHMQS | 1 |
| 1307 | THMSV | 1 |
| 1308 | THMRH | 1 |
| 1309 | DPMKV | 1 |
| 1310 | PHMMS | 1 |
| 1311 | SHVKR | 1 |
| 1102 | ESMSR | 1 |
| 1312 | SHMGL | 1 |
| 1313 | TDMVA | 1 |
| 1314 | PQMMS | 1 |
| 1315 | KHMQR | 1 |
| 1316 | EHMQL | 1 |
| 1317 | EHISR | 1 |
| 1318 | SHMKK | 1 |
| 1319 | EQMTR | 1 |
| 1320 | TPMRG | 1 |
| 1321 | GHISR | 1 |
| 1322 | GPMGV | 1 |
| 1323 | GYMRR | 1 |
| 1324 | GHMTV | 1 |
| 1325 | APMIM | 1 |
| 1326 | THINR | 1 |
| 1327 | DHMMS | 1 |
| 1328 | GHMKL | 1 |
| 1329 | EKMEE | 1 |
| 1330 | DPMRM | 1 |
| 1331 | SHMKT | 1 |
| 1332 | SPMGL | 1 |
| 1333 | SPMGE | 1 |
| 1334 | DHISR | 1 |
| 1335 | TPMKQ | 1 |
| 1336 | GHMKW | 1 |
| 1337 | EHMCR | 1 |

TABLE 9-continued

ZF6 selection on C:G change at nt 5 of core motif in CBS.
Sequences reflect position 2 to 6.

| SEQ ID NO: | Sequence | # Read |
| --- | --- | --- |
| 1338 | NNMKR | 1 |
| 1339 | ESMKR | 1 |
| 1340 | TEMLI | 1 |
| 1341 | SHMKM | 1 |
| 1342 | EHVNR | 1 |
| 1343 | GHMER | 1 |
| 1344 | NHMDR | 1 |
| 1345 | GHMWR | 1 |
| 1346 | THMKI | 1 |
| 1347 | QKMKE | 1 |
| 1348 | THMNK | 1 |
| 1349 | AHMKQ | 1 |
| 1350 | DHMGR | 1 |
| 1351 | EGMKW | 1 |
| 1352 | TQMKE | 1 |
| 1353 | TRMRR | 1 |
| 1354 | AHMGR | 1 |
| 1355 | TRMKR | 1 |
| 1356 | KNLTR | 1 |
| 1357 | PEMMS | 1 |
| 1358 | EHLTL | 1 |
| 1359 | RHMKV | 1 |
| 1360 | PGMIR | 1 |
| 1361 | THTKR | 1 |
| 1362 | EHIRR | 1 |
| 1363 | THMPR | 1 |
| 1364 | GKMKQ | 1 |
| 1365 | GPMRV | 1 |
| 1366 | AHVNR | 1 |
| 1367 | EPMSR | 1 |
| 1368 | PRMMV | 1 |
| 1369 | ELMSR | 1 |
| 1090 | ETMRR | 1 |
| 1370 | SNMNR | 1 |
| 1371 | TSMKT | 1 |
| 1372 | GNMHR | 1 |
| 1373 | TQMRR | 1 |
| 1374 | SHMKG | 1 |
| 1375 | DHMRT | 1 |
| 1376 | EHMRE | 1 |
| 1377 | SQLNR | 1 |
| 1378 | SHMGR | 1 |
| 1379 | GHKNR | 1 |
| 1380 | THMNL | 1 |
| 1381 | GYMKR | 1 |
| 1382 | SNMKV | 1 |
| 1383 | GHMRC | 1 |
| 1384 | NHMRV | 1 |
| 1385 | SGMKT | 1 |
| 1386 | EHLRR | 1 |
| 1387 | VPMRR | 1 |
| 1388 | DLMKR | 1 |
| 1389 | TSMKL | 1 |
| 1390 | APMTV | 1 |
| 1105 | ESMRL | 1 |
| 1391 | EHMLM | 1 |
| 1392 | EKMNR | 1 |
| 1393 | THRRR | 1 |
| 1111 | DAMRV | 1 |
| 1394 | ERMNR | 1 |
| 1395 | NHMHR | 1 |
| 1396 | DLMNR | 1 |
| 1397 | GQMQR | 1 |
| 1398 | RGMMI | 1 |
| 1399 | TQMKR | 1 |
| 1400 | EHMGV | 1 |
| 1401 | AHMTQ | 1 |
| 1402 | TPMMV | 1 |
| 1403 | GHKRR | 1 |
| 1404 | GPMER | 1 |
| 1405 | EPMQV | 1 |
| 1101 | TAMNQ | 1 |

TABLE 9-continued

ZF6 selection on C:G change at nt 5 of core motif in CBS.
Sequences reflect position 2 to 6.

| SEQ ID NO: | Sequence | # Read |
|---|---|---|
| 1406 | GDMRR | 1 |
| 1407 | EHLKR | 1 |
| 1408 | DHMKK | 1 |
| 1409 | GDIDR | 1 |
| 1410 | GHMKK | 1 |
| 1411 | TQMMI | 1 |
| 1412 | SGMKA | 1 |
| 1413 | TPMRM | 1 |
| 1414 | SPMKG | 1 |
| 1415 | KQLNR | 1 |
| 1416 | NHMKT | 1 |
| 1417 | TKMRE | 1 |
| 1098 | VSMKR | 1 |
| 1418 | EHMAV | 1 |
| 1419 | EHMNS | 1 |
| 1420 | DHMHR | 1 |
| 1421 | AHMVR | 1 |
| 1422 | GRMRR | 1 |
| 1423 | GHMNV | 1 |
| 1424 | GHMNL | 1 |
| 1425 | GHVSR | 1 |
| 1426 | GQMHR | 1 |
| 1427 | EKMAR | 1 |
| 1428 | NHMGL | 1 |
| 1429 | EHMKG | 1 |
| 1430 | EPMAL | 1 |
| 1431 | AHLTR | 1 |
| 1432 | KHMTR | 1 |
| 1433 | GHMTM | 1 |
| 1434 | EPMSG | 1 |
| 1435 | NHMNM | 1 |
| 1436 | GQMKR | 1 |
| 1437 | TPMEG | 1 |
| 1438 | KHMRV | 1 |
| 1439 | SLMKR | 1 |
| 1440 | DGMRN | 1 |
| 1441 | RQMHI | 1 |
| 1442 | EPMRV | 1 |
| 1113 | GAMRE | 1 |
| 1443 | SHMRM | 1 |
| 1444 | EQMAR | 1 |
| 1445 | SHMRS | 1 |
| 1446 | EHMQV | 1 |
| 1447 | EPMPM | 1 |
| 1448 | IDMNR | 1 |
| 1449 | TKMKQ | 1 |
| 1450 | RQMLS | 1 |
| 1451 | ATMML | 1 |
| 1452 | PQMMI | 1 |
| 1453 | NAMKI | 1 |
| 1454 | GHMQS | 1 |
| 1455 | EAMKK | 1 |
| 1456 | THMRK | 1 |
| 1457 | PHMRR | 1 |
| 1458 | GHMKA | 1 |
| 1459 | AHMNH | 1 |
| 1460 | EYMSR | 1 |
| 1461 | EHMAW | 1 |
| 1462 | NHMGR | 1 |
| 1463 | GHMKS | 1 |
| 1464 | EHMRL | 1 |
| 1465 | ENMTR | 1 |
| 1099 | TNMMR | 1 |
| 1466 | QAMRV | 1 |
| 1467 | EHMQP | 1 |
| 1468 | THMSM | 1 |
| 1469 | IDMKE | 1 |
| 1047 | EGTHR | 1 |
| 1055 | HNMMR | 1 |
| 1045 | PNMSR | 1 |
| 184 | SNMVR | 1 |
| 1062 | ANMRR | 1 |

TABLE 9-continued

ZF6 selection on C:G change at nt 5 of core motif in CBS.
Sequences reflect position 2 to 6.

| SEQ ID NO: | Sequence | # Read |
|---|---|---|
| 1042 | GGMRE | 1 |
| 1060 | EAMRR | 1 |
| 1067 | GSMLR | 1 |
| 1054 | SHMKI | 1 |
| 1076 | ANMHR | 1 |
| 1069 | TSMGR | 1 |
| 1077 | DHTKR | 1 |
| 1078 | NGMRE | 1 |
| 1071 | NAMRQ | 1 |
| 1080 | EGMNQ | 1 |
| 1085 | SNMRR | 1 |
| 1088 | SGMRI | 1 |

TABLE 10

ZF6 selection on A:C change at nt 6 of core motif in CBS.
Sequences reflect position -1 to 3.

| SEQ ID NO: | Sequence | Read # |
|---|---|---|
| 37 | HRES | 6362 |
| 36 | MNES | 5959 |
| 1470 | VKES | 3337 |
| 1471 | LRDS | 2986 |
| 1472 | HLES | 1799 |
| 1473 | TRES | 1285 |
| 1474 | MREA | 648 |
| 1475 | VRET | 601 |
| 1476 | MRET | 284 |
| 1477 | LLES | 222 |
| 1478 | MRTS | 192 |
| 1479 | ERKS | 122 |
| 1480 | IKES | 111 |
| 38 | RPDT | 95 |
| 1481 | VRVT | 61 |
| 1482 | RNES | 51 |
| 1483 | HVES | 41 |
| 98 | RTET | 40 |
| 1484 | LSHT | 33 |
| 1485 | RPES | 33 |
| 1486 | SRES | 32 |
| 1487 | ENKA | 25 |
| 167 | RADN | 24 |
| 1488 | TREN | 23 |
| 1489 | DSPQ | 21 |
| 1490 | RRES | 20 |
| 1491 | RGEN | 17 |
| 1492 | VRES | 17 |
| 1493 | HRDS | 15 |
| 1494 | HREA | 15 |
| 1495 | LRDT | 15 |
| 1496 | RVES | 15 |
| 1497 | EKKS | 14 |
| 1498 | GRES | 13 |
| 1499 | RMES | 13 |
| 1500 | LRES | 12 |
| 1501 | RTDN | 12 |
| 1502 | HADH | 12 |
| 1503 | VNES | 12 |
| 1504 | ANES | 12 |
| 112 | RTEN | 12 |
| 1505 | RNEH | 11 |
| 1506 | MNET | 11 |
| 1507 | RLDT | 11 |
| 99 | RADV | 10 |
| 1508 | RLET | 9 |
| 1509 | HRET HMR... | 9 9 |
| 1510 | NRES | 8 |
| 1511 | TGEA | 8 |
| 1512 | TGES | 8 |
| 1513 | RHET | 8 |
| 1514 | MRES | 7 |
| 172 | RNDT | 7 |

TABLE 10-continued

ZF6 selection on A:C change at nt 6 of core motif in CBS.
Sequences reflect position −1 to 3.

| SEQ ID NO: | Sequence | Read # |
|---|---|---|
| 1515 | LVES | 7 |
| 1516 | VGSS | 7 |
| 40 | RHDT | 7 |
| 1517 | RIDT | 7 |
| 1518 | VREA | 6 |
| 1519 | HMES | 6 |
| 1520 | ERKN | 5 |
| 1521 | RPEA | 5 |
| 1522 | TPPI | 5 |
| 1523 | RREA | 5 |
| 1524 | RQEN | 5 |
| 1525 | VKDS | 4 |
| 1526 | RKES | 4 |
| 1527 | MLGL... | 4 |
| 1528 | DRPN | 4 |
| 1529 | RKEA | 4 |
| 1530 | VMLGL... | 4 |
| 1531 | TRDS | 4 |
| 1532 | HLET | 4 |
| 1533 | HLDS | 4 |
| 1534 | PPAT | 4 |
| 1535 | ENAS | 4 |
| 1536 | VKET | 4 |
| 1537 | GREA | 4 |
| 1538 | TREA H... | 4 4 |
| 1539 | IRDS | 3 |
| 1540 | MNDS | 3 |
| 1541 | LLDS | 3 |
| 1542 | RTES | 3 |
| 1543 | RPET | 3 |
| 1544 | IDVH | 3 |
| 1545 | RTEH | 3 |
| 1546 | TRET | 3 |
| 1547 | HGES | 3 |
| 1548 | TMES | 3 |
| 1549 | LRVS | 2 |
| 1550 | PREA | 2 |
| 1551 | EGKN | 2 |
| 1552 | TSES | 2 |
| 1553 | VKFGHIFCVL L*NV... | 2 |
| 1554 | YRES | 2 |
| 1555 | MKES | 2 |
| 39 | RTDI | 2 |
| 1556 | MNEG | 2 |
| 1557 | MIES | 2 |
| 1558 | QRES | 2 |
| 1559 | MMEA | 2 |
| 1560 | MNER RGS | 2 2 |
| 171 | RTSS | 2 |
| 1561 | RNAS | 2 |
| 1562 | RTDT | 2 |
| 1563 | TRVS | 1 |
| 1564 | TFNV | 1 |
| 1565 | VRVS | 1 |
| 1566 | FRDS | 1 |
| 1567 | IKER | 1 |
| 1568 | RLEN | 1 |
| 1569 | IKET | 1 |
| 1570 | HRVS | 1 |
| 1571 | DRKG | 1 |
| 1572 | VKEC | 1 |
| 1573 | MSEA | 1 |
| 1574 | LRDR | 1 |
| 1575 | INES | 1 |
| 1576 | MSES | 1 |
| 1577 | NLES | 1 |
| 1578 | LQDS | 1 |
| 1579 | HAPT HRR... | 1 1 |
| 1580 | HRKA | 1 |
| 1581 | LRGS | 1 |

TABLE 10-continued

ZF6 selection on A:C change at nt 6 of core motif in CBS.
Sequences reflect position -1 to 3.

| SEQ ID NO: | Sequence | Read # |
|---|---|---|
| 1582 | QSGT | 1 |
| 1583 | HQES | 1 |
| 1584 | ETGS | 1 |
|  | SGT... | 1 |
| 1585 | MLGF... | 1 |
| 1586 | MNGS | 1 |
| 1587 | MRED | 1 |
| 1588 | TKES | 1 |
| 1589 | RPDH | 1 |
| 1590 | HRGS | 1 |
| 1591 | GNES | 1 |
| 1592 | LWDS | 1 |
| 1593 | MRDS | 1 |
| 1594 | IHES | 1 |
| 1595 | LRDG | 1 |
| 1596 | LRDC | 1 |
| 1597 | MYES | 1 |
| 1598 | RPNI | 1 |
| 1599 | EGRS | 1 |
|  | TRR... | 1 |
| 1600 | RLES | 1 |
| 1601 | LGLPTGR... | 1 |
| 1602 | ARES | 1 |
| 1603 | HLGS | 1 |
| 1604 | HSES | 1 |
| 1605 | PRTS | 1 |
| 1606 | MNKS | 1 |
| 1607 | RRDS | 1 |
| 1608 | RREN | 1 |
| 1609 | QGES | 1 |
| 1610 | LREA | 1 |
| 1611 | LLET | 1 |
| 1612 | MREV | 1 |
| 1613 | VEES | 1 |
| 1614 | MNEA | 1 |
| 1615 | RNEN | 1 |
| 1616 | HWES | 1 |
| 1617 | RHEA | 1 |
| 1618 | MTES | 1 |
| 1619 | GRDS | 1 |
| 1620 | VSET | 1 |
| 1621 | MRKA | 1 |
| 1622 | FKES | 1 |
| 1623 | ERKG | 1 |
|  | VKR... | 1 |
| 1624 | RNDH | 1 |
| 1625 | VPDA | 1 |
|  | TGR... | 1 |
| 1626 | RKDA | 1 |
| 1627 | SPDT | 1 |
| 1628 | TTTL | 1 |
| 1629 | RKDS | 1 |
| 1630 | RRLT | 1 |
| 1631 | RTSN | 1 |
|  | LRT... | 1 |
| 1632 | RQSA | 1 |
| 1633 | ARFT | 1 |
| 1634 | DRKS | 1 |
| 169 | RRDT | 1 |
| 1635 | RMDS | 1 |
| 1636 | HRKS | 1 |
| 1637 | GTTP | 1 |
| 1638 | DKRN | 1 |
| 1639 | RPERE... | 1 |
| 1640 | SGDS | 1 |
|  | TAG | 1 |
|  | GR... | 1 |
|  | T... | 1 |
| 1582 | ...QSGT... | 0 |

TABLE 11

ZF6 selection on A:G change at nt 6 of core motif in CBS.
Sequences reflect position −1 to 3.

| SEQ ID NO: | Sequence | # Reads |
|---|---|---|
| 38 | RPDT | 6216 |
| 1482 | RNES | 2750 |
| 98 | RTET | 1736 |
| 1485 | RPES | 1565 |
| 167 | RADN | 1412 |
| 112 | RTEN | 973 |
| 1499 | RMES | 860 |
| 1507 | RLDT | 734 |
| 1490 | RRES | 690 |
| 1501 | RTDN | 588 |
| 1496 | RVES | 584 |
| 1505 | RNEH | 575 |
| 1517 | RIDT | 557 |
| 1521 | RPEA | 516 |
| 1491 | RGEN | 467 |
| 99 | RADV | 455 |
| 172 | RNDT | 452 |
| 1513 | RHET | 413 |
| 1529 | RKEA | 340 |
| 1508 | RLET | 297 |
| 1543 | RPET | 263 |
| 1523 | RREA | 252 |
| 40 | RHDT | 247 |
| 37 | HRES | 239 |
| 1526 | RKES | 231 |
| 1524 | RQEN | 199 |
| 1641 | RGSA | 186 |
| 171 | RTSS | 154 |
| 39 | RTDI | 152 |
| 1479 | ERKS | 123 |
| 36 | MNES | 104 |
| 1561 | RNAS | 90 |
| 1608 | RREN | 88 |
| 1642 | RLDP | 82 |
| 169 | RRDT | 80 |
| 1545 | RTEH | 80 |

TABLE 11-continued

ZF6 selection on A:G change at nt 6 of core motif in CBS.
Sequences reflect position −1 to 3.

| SEQ ID NO: | Sequence | # Reads |
|---|---|---|
| 1626 | RKDA | 63 |
| 1470 | VKES | 61 |
| 1643 | RRET | 53 |
| 1471 | LRDS | 44 |
| 1562 | RTDT | 36 |
| 1568 | RLEN | 35 |
| 1564 | TFNV | 29 |
| 1644 | RADT | 28 |
| 1472 | HLES | 28 |
| 1473 | TRES | 27 |
| 1645 | RKET | 24 |
| 1646 | ATNM | 23 |
| 1647 | RREH | 22 |
| 1648 | RTDH | 21 |
| 1632 | RQSA | 21 |
| 1542 | RTES | 20 |
| 1649 | RNET | 20 |
| 1650 | RPDN | 19 |
| 1651 | THVP | 19 |
| 1633 | ARFT | 18 |
| 1487 | ENKA | 18 |
| 1637 | GTTP | 17 |
| 1652 | EASN | 16 |
| 1653 | RMEG | 14 |
| 1654 | RTAA | 14 |
| 1589 | RPDH | 14 |
| 1627 | SPDT | 14 |
| 1489 | DSPQ | 14 |
| 1497 | EKKS | 13 |
| 1474 | MREA | 13 |
| 1655 | RNEP | 12 |
| 1656 | VHDN | 12 |
| 1657 | RKEN | 12 |
| 1658 | RPYT | 12 |
| 1659 | RQES | 11 |
| 1660 | RSGS | 11 |

TABLE 11-continued

ZF6 selection on A:G change at nt 6 of core motif in CBS.
Sequences reflect position −1 to 3.

| SEQ ID NO: | Sequence | # Reads |
|---|---|---|
| 1661 | RPDS | 10 |
| 1475 | VRET | 10 |
| 1662 | MTGN | 7 |
| 1530 | VMLGL... | 7 |
| 1615 | RNEN | 7 |
| 1663 | RGET | 6 |
| 1664 | RKGS | 6 |
| 1600 | RLES | 5 |
| 1476 | MRET | 5 |
| 1624 | RNDH | 5 |
| 1665 | RNDS | 5 |
| 1666 | STET | 5 |
| 1537 | GREA | 5 |
| 1667 | SNES | 5 |
| 1668 | RPDA | 4 |
| 1669 | RNER | 4 |
| 1670 | RPEN | 4 |
| 1671 | RVET | 4 |
| 1672 | RAET | 4 |
| 1673 | SHET | 4 |
| 1674 | RSDTQ... | 4 |
| 1535 | ENAS | 3 |
| 1675 | LPDT | 3 |
| 1676 | MMES | 3 |
| 1677 | SPES | 3 |
| 1678 | RMEN | 3 |
| 1679 | RVEI | 3 |
| 1607 | RRDS | 3 |
| 1680 | RMET | 3 |
| 1681 | SADN | 3 |
| 1682 | RAES | 3 |
| 1683 | RPDV | 3 |
| 1684 | RTEA | 3 |
| 1685 | RHES | 3 |
| 1686 | RQEA | 3 |
| 1478 | MRTS | 3 |
| 1520 | ERKN | 3 |
| 1687 | RNRS | 2 |
| 1688 | RAEA | 2 |
| 1689 | RVDN | 2 |
| 1690 | RNEG | 2 |
| 1691 | RVEG | 2 |
| 1692 | RAEN | 2 |
| 1693 | RVDT | 2 |
| 1694 | RDDN | 2 |
| 1695 | RLEA | 2 |
| 1696 | RPNT | 2 |
| 1697 | RGES | 2 |
| 1698 | SPEA | 2 |
| 1699 | RTAG | 2 |
| 1700 | MKEA | 2 |
| 1486 | SRES | 2 |
| 1701 | WNES | 2 |
| 1591 | GNES | 2 |
| 1629 | RKDS | 2 |
| 1628 | TTTL | 2 |
| 1702 | RVEN | 2 |
| 1635 | RMDS | 2 |
| 1703 | RMEH | 2 |
| 1630 | RRLT | 2 |
| 1704 | RKEH | 1 |
| 1705 | ENRS | 1 |
| 1706 | RNKS | 1 |
| 1707 | RPGE... | 1 |
| 1708 | RKDT | 1 |
| 1625 | VPDA | 1 |
| 1709 | RGEA | 1 |
| 1710 | WIDT | 1 |
| 1711 | RNEY | 1 |
| 1712 | RADI | 1 |
| 1713 | RADY | 1 |
| 1714 | RTDD | 1 |

TABLE 11-continued

ZF6 selection on A:G change at nt 6 of core motif in CBS.
Sequences reflect position −1 to 3.

| SEQ ID NO: | Sequence | # Reads |
|---|---|---|
| 1715 | RVDS | 1 |
| 1716 | HTET | 1 |
| 1717 | HTEN | 1 |
| 1718 | SGEN | 1 |
| 1719 | RTST | 1 |
| 1720 | RAGR... | 1 |
| 1721 | SNAS | 1 |
| 1722 | RPGT | 1 |
| 1723 | RAEH | 1 |
| 1724 | MHDT | 1 |
| 1725 | REDN | 1 |
| 1726 | REEV | 1 |
|  | RRR... | 1 |
| 1727 | RMEW | 1 |
| 1728 | RRER | 1 |
| 1729 | RLDN | 1 |
|  | RPT... | 1 |
| 1730 | MVES | 1 |
| 1510 | NRES | 1 |
| 1731 | RIPA | 1 |
| 1732 | RMEA | 1 |
| 1733 | RHNT | 1 |
| 1734 | RNSS | 1 |
| 1735 | LPES | 1 |
| 1736 | SLDP | 1 |
| 1737 | STEN | 1 |
| 1738 | RPKS | 1 |
|  | ATS... | 1 |
| 1739 | MIDT | 1 |
| 1740 | PPDT | 1 |
| 1741 | GLDA | 1 |
| 1742 | RPEGE... | 1 |
| 1743 | RHYT | 1 |
| 1744 | RTEI | 1 |
| 1745 | SPEN | 1 |
|  | APR... | 1 |
|  | LSL... | 1 |
| 1746 | RHEN | 1 |
| 1747 | REDV | 1 |
| 1748 | RLKT | 1 |
| 1749 | RIET | 1 |
| 1750 | RIES | 1 |
| 1477 | LLES | 1 |
| 1751 | RPDI | 1 |
| 1752 | MNDT | 1 |
| 1753 | RLYT | 1 |
| 1504 | ANES | 1 |
| 1754 | RAYN | 1 |
| 1755 | RADS | 1 |
| 1756 | KNES | 1 |
| 1757 | RVSA | 1 |
| 1758 | RPED | 1 |
| 1759 | RGEH | 1 |
| 1728 | RRER... | 1 |
| 1760 | LTET | 1 |
| 1761 | LADN | 1 |
|  | GTR... | 1 |
| 1762 | RPER... | 1 |
| 1763 | MLGLPGTR... | 1 |
| 1764 | RPDP | 1 |
| 1765 | QADV | 1 |
| 1599 | EGRS | 1 |
|  | RGR... | 1 |
| 1766 | MADV | 1 |
| 1767 | HTDN | 1 |
| 1768 | RKEV | 1 |
| 1769 | RADA | 1 |
| 1770 | RDAS | 1 |
| 1771 | MLDT | 1 |
| 1772 | RPGS | 1 |
| 1773 | RTEY | 1 |
| 1774 | SLDT | 1 |
| 1775 | RWES | 1 |
| 1776 | ERKA | 1 |
| 1777 | RIYT | 1 |

TABLE 11-continued

ZF6 selection on A:G change at nt 6 of core motif in CBS.
Sequences reflect position -1 to 3.

| SEQ ID NO: | Sequence | # Reads |
|---|---|---|
| 1778 | TPVP | 1 |
| 1779 | RQDA | 1 |
| 1780 | RMER | 1 |
| 1631 | RTSN | 1 |
|  | LRT... | 1 |
| 1559 | MMEA | 1 |
| 1481 | VRVT | 1 |
| 1634 | DRKS | 1 |
| 1488 | TREN | 1 |
| 1636 | HRKS | 1 |
| 1500 | LRES | 1 |
| 1639 | RPERE... | 1 |
| 1638 | DKRN | 1 |
| 1781 | VGTV | 1 |
| 1582 | ...QSGT... | 0 |

TABLE 12

ZF6 selection on A:C change at nt 6 of core motif in CBS.
Sequences reflect position -1 to 3.

| SEQ ID NO: | Sequence | # Reads |
|---|---|---|
| 37 | HRES | 7487 |
| 1479 | ERKS | 7125 |
| 1489 | DSPQ | 876 |
| 1487 | ENKA | 801 |
| 1497 | EKKS | 508 |
| 1473 | TRES | 141 |
| 38 | RPDT | 126 |
| 1520 | ERKN | 120 |
| 1537 | GREA | 112 |
| 1535 | ENAS | 103 |
| 1471 | LRDS | 95 |
| 36 | MNES | 89 |
| 1504 | ANES | 84 |
| 1571 | DRKG | 73 |
| 1634 | DRKS | 72 |

TABLE 12-continued

ZF6 selection on A:C change at nt 6 of core motif in CBS.
Sequences reflect position -1 to 3.

| SEQ ID NO: | Sequence | # Reads |
|---|---|---|
| 1599 | EGRS | 69 |
| 1584 | ETGS | 67 |
| 1482 | RNES | 60 |
| 1470 | VKES | 57 |
| 1486 | SRES | 50 |
| 98 | RTET | 42 |
| 1625 | VPDA | 39 |
| 1630 | RRLT | 37 |
| 167 | RADN | 30 |
| 1485 | RPES | 30 |
| 1782 | ERGG | 27 |
| 1472 | HLES | 25 |
| 1638 | DKRN | 25 |
| 112 | RTEN | 21 |
| 1628 | TTTL | 19 |
| 1636 | HRKS | 19 |
| 1490 | RRES | 19 |
| 1499 | RMES | 18 |
| 1551 | EGKN | 17 |
| 1623 | ERKG | 16 |
| 1491 | RGEN | 16 |
| 1705 | ENRS | 15 |
| 1498 | GRES | 15 |
| 1501 | RTDN | 15 |
| 1507 | RLDT | 13 |
| 1496 | RVES | 13 |
| 1517 | RIDT | 13 |
| 1510 | NRES | 13 |
| 1505 | RNEH | 12 |
| 1783 | EKGT | 11 |
| 1513 | RHET | 11 |
| 1474 | MREA | 10 |
| 1543 | RPET | 9 |
|  | QGK | 9 |
| 1519 | HMES | 9 |
| 1475 | VRET | 9 |

TABLE 12-continued

ZF6 selection on A:C change at nt 6 of core motif in CBS.
Sequences reflect position -1 to 3.

| SEQ ID NO: | Sequence | # Reads |
|---|---|---|
| 99 | RADV HMR... | 9 9 |
| 1784 | ERNS | 8 |
| 1524 | RQEN | 8 |
| 172 | RNDT | 8 |
| 40 | RHDT | 8 |
| 1493 | HRDS | 7 |
| 171 | RTSS | 7 |
| 1529 | RKEA | 7 |
| 1785 | ENNS | 6 |
| 1776 | ERKA | 6 |
| 1523 | RREA RGS QEK... | 5 5 5 |
| 1478 | MRTS | 5 |
| 1500 | LRES | 4 |
| 1526 | RKES | 4 |
| 1786 | HREN | 4 |
| 1521 | RPEA | 4 |
| 1547 | HGES | 4 |
| 39 | RTDI | 4 |
| 1508 | RLET | 4 |
| 1477 | LLES | 3 |
| 1626 | RKDA | 3 |
| 1476 | MRET | 3 |
| 1590 | HRGS | 3 |
| 1787 | ERKR | 3 |
| 1561 | RNAS | 3 |
| 1788 | ERKI | 3 |
| 1789 | ERRS | 2 |
| 1642 | RLDP | 2 |
| 1604 | HSES | 2 |
| 1790 | YSPQ | 2 |
| 1791 | EGKS | 2 |
| 1792 | HRER QVK... | 2 2 |
| 1793 | DRKA | 2 |

TABLE 12-continued

ZF6 selection on A:C change at nt 6 of core motif in CBS.
Sequences reflect position -1 to 3.

| SEQ ID NO: | Sequence | # Reads |
|---|---|---|
| 1794 | ESGN QG... | 2 2 |
| 1795 | ERES | 2 |
| 1796 | HKES | 2 |
| 1797 | ESKS | 2 |
| 1558 | QRES | 2 |
| 1798 | EMKS | 2 |
| 1627 | SPDT | 2 |
| 169 | RRDT | 2 |
| 1527 | MLGL... | 2 |
| 1633 | ARFT | 2 |
| 1562 | RTDT | 2 |
| 1799 | KRKS | 1 |
| 1652 | EASN | 1 |
| 1800 | TGDA | 1 |
| 1801 | NRKS RGK | 1 1 |
| 1802 | EKNS HRE... | 1 1 |
| 1803 | QGKS | 1 |
| 1662 | MTGN | 1 |
| 1804 | DSTQ TGE... | 1 1 |
| 1805 | VRKS | 1 |
| 1509 | HRET | 1 |
| 1806 | ENKV | 1 |
| 1568 | RLEN | 1 |
| 1732 | RMEA | 1 |
| 1494 | HREA | 1 |
| 1692 | RAEN | 1 |
| 1774 | SLDT R... | 1 1 |
| 1512 | TGES | 1 |
| 1644 | RADT QAK... | 1 1 |
| 1807 | DIPQ QGT... | 1 1 |
| 1808 | ERKC | 1 |
| 1809 | HSPQ | 1 |

TABLE 12-continued

ZF6 selection on A:C change at nt 6 of core motif in CBS.
Sequences reflect position -1 to 3.

| SEQ ID NO: | Sequence | # Reads |
|---|---|---|
| 1542 | RTES | 1 |
| 1538 | TREA | 1 |
| 1810 | RTAT | 1 |
|  | QGR... | 1 |
| 1811 | TRKS | 1 |
| 1812 | GRKS | 1 |
| 1813 | ESKA | 1 |
|  | ERK... | 1 |
| 1554 | YRES | 1 |
| 1814 | EKRN | 1 |
|  | MGK... | 1 |
| 1815 | DSPH | 1 |
| 1816 | ERNG | 1 |
| 1817 | VSPQ | 1 |
|  | QWK... | 1 |
| 1818 | EKKC | 1 |
| 1601 | LGLPTGR... | 1 |
| 1819 | ERNN | 1 |
| 1643 | RRET | 1 |
| 1820 | TNES | 1 |
| 1821 | HRKN | 1 |
|  | RLF... | 1 |
| 1822 | DKSN | 1 |
| 1823 | DRNS | 1 |
|  | KRN | 1 |
| 1824 | ERMS | 1 |
| 1608 | RREN | 1 |
| 1825 | EIAS | 1 |
| 1826 | HREC | 1 |
| 1827 | ERKT | 1 |
| 1828 | ETGN | 1 |
| 1632 | RQSA | 1 |
| 1631 | RTSN | 1 |
| 1635 | RMDS | 1 |
| 1545 | RTEH | 1 |
| 1559 | MMEA | 1 |
| 1629 | RKDS | 1 |
|  | LRT... | 1 |
| 1481 | VRVT | 1 |
| 1488 | TREN | 1 |

TABLE 12-continued

ZF6 selection on A:C change at nt 6 of core motif in CBS.
Sequences reflect position -1 to 3.

| SEQ ID NO: | Sequence | # Reads |
|---|---|---|
| 1639 | RPERE... | 1 |
| 1637 | GTTP | 1 |
| 1640 | SGDS | 1 |
| 1582 | ...QSGT... | 0 |

TABLE 13

ZF5 selection on G:T change at nt 7 of core motif in CBS.
Sequences reflect position 2 to 6.

| SEQ ID NO: | Sequence | # Read |
|---|---|---|
| 165 | TRLKE | 2129 |
| 42 | HRLKE | 1938 |
| 44 | SRLKE | 1530 |
| 110 | TRLRE | 1078 |
| 1829 | HRLRE | 1073 |
| 47 | NRLKE | 1015 |
| 1830 | QRLRE | 769 |
| 1831 | DALKR | 700 |
| 109 | DGLKR | 681 |
| 1832 | SRLRE | 534 |
| 43 | HALKV | 389 |
| 94 | NRLKV | 381 |
| 93 | ERLRV | 375 |
| 1833 | DGLKK | 374 |
| 41 | HGLKV | 335 |
| 1834 | HRLKV | 315 |
| 1835 | ERLRM | 295 |
| 1836 | QRLKE | 243 |
| 1837 | DGLVR | 235 |
| 46 | HTLKV | 233 |
| 1838 | NRLRE | 195 |
| 1839 | ARLRE | 168 |
| 108 | DALRR | 168 |
| 1840 | ERLRQ | 141 |
| 1841 | ARLKE | 135 |

TABLE 13-continued

ZF5 selection on G:T change at nt 7 of core motif in CBS.
Sequences reflect position 2 to 6.

| SEQ ID NO: | Sequence | # Read |
|---|---|---|
| 1842 | TRLRD | 125 |
| 1843 | DGLRR | 118 |
| 1844 | SRLNE | 118 |
| 1845 | TGLKV | 92 |
| 1846 | HRLSE | 91 |
| 1847 | HRLNE | 78 |
| 1848 | SHLKV | 75 |
| 1849 | TTLKV | 75 |
| 1850 | HRLGE | 68 |
| 1851 | STLKV | 66 |
| 1852 | DGLKV | 65 |
| 1853 | DGLRK | 61 |
| 1854 | HRLTE | 60 |
| 1855 | DRLKV | 59 |
| 1856 | HSLKV | 56 |
| 45 | DGLRV | 47 |
| 1857 | SRLKV | 45 |
| 1858 | QRLKV | 44 |
| 1859 | HGLTV | 43 |
| 1860 | HRLME | 43 |
| 1861 | RLLPN | 42 |
| 1862 | ERLKV | 41 |
| 1863 | NRLRV | 35 |
| 1864 | TRLKV | 34 |
| 1865 | DGLKE | 29 |
| 454 | DTLKV | 29 |
| 1866 | HGLRV | 29 |
| 1867 | SALKT | 28 |
| 1868 | HRLAE | 25 |
| 1869 | ERLIS | 23 |
| 1870 | DGLTR | 22 |
| 1871 | DALVR | 21 |
| 1872 | HRLKR | 21 |
| 1873 | ERLRE | 20 |
| 1874 | HQLKV | 20 |
| 1875 | TTLKQ | 18 |

TABLE 13-continued

ZF5 selection on G:T change at nt 7 of core motif in CBS.
Sequences reflect position 2 to 6.

| SEQ ID NO: | Sequence | # Read |
|---|---|---|
| 1876 | SRLKR | 17 |
| 1877 | DRLKQ | 16 |
| 1878 | HRLRV | 16 |
| 1879 | TRLKR | 16 |
| 1880 | TRLNE | 16 |
| 1881 | NRLKQ | 15 |
| 1882 | TRLKD | 14 |
| 1883 | TRLRV | 14 |
| 1884 | EALKR | 13 |
| 1885 | HTLKQ | 13 |
| 1886 | NALKV | 13 |
| 1887 | SALKV | 13 |
| 1888 | SRLKD | 13 |
| 1889 | DGLRE | 12 |
| 1890 | ERLKE | 12 |
| 488 | DTLKQ | 11 |
| 1891 | HKLKV | 11 |
| 1892 | GTLKV | 10 |
| 1893 | ERLRR | 9 |
| 1894 | HALKT | 9 |
| 1895 | HGLKE | 9 |
| 1896 | HHLVQ | 9 |
| 1897 | NGLKV | 9 |
| 538 | DALKE | 8 |
| 1898 | DALKV | 8 |
| 1899 | HALKE | 8 |
| 1900 | HHLKQ | 8 |
| 1901 | HHLKV | 8 |
| 1902 | TRLKK | 8 |
| 1903 | DRLRT | 7 |
| 1904 | DRLRV | 7 |
| 371 | DTLRV | 7 |
| 1905 | HRLKK | 7 |
| 262 | HTLKE | 7 |
| 1906 | NRLKK | 7 |
| 235 | STLKE | 7 |

TABLE 13-continued

ZF5 selection on G:T change at nt 7 of core motif in CBS.
Sequences reflect position 2 to 6.

| SEQ ID NO: | Sequence | # Read |
|---|---|---|
| 1907 | SRLIE | 6 |
| 1908 | TRLME | 6 |
| 1909 | ATLKV | 5 |
| 1910 | HGLVV | 5 |
| 1911 | HRLRM | 5 |
| 1912 | HRLRQ | 5 |
| 1913 | HTLKA | 5 |
| 1914 | NRLRD | 5 |
| 1915 | TGLKE | 5 |
| 1916 | TGLKT | 5 |
| 1917 | TRLRQ | 5 |
| 1918 | TTLKI | 5 |
| 1919 | TTLRV | 5 |
| 1920 | DRLKE | 4 |
| 1921 | HRLKA | 4 |
| 1922 | HRLKD | 4 |
| 1923 | HSLKE | 4 |
| 1924 | NRLKI | 4 |
| 1925 | NRLKR | 4 |
| 1926 | STLKA | 4 |
| 548 | STLKQ | 4 |
| 1927 | TRLKA | 4 |
| 1928 | TRLKQ | 4 |
| 1929 | TRLRR | 4 |
| 447 | DTLKA | 3 |
| 1930 | HALKR | 3 |
| 1931 | HGLKA | 3 |
| 1932 | HGLKR | 3 |
| 1933 | HPEG... | 3 |
| 1934 | HRLK... | 3 |
| 1935 | HRLRK | 3 |
| 1936 | HTLRV | 3 |
| 1937 | NTLKQ | 3 |
| 1938 | QRLRV | 3 |
| 1939 | SRLME | 3 |
| 1940 | SRPKE | 3 |
| 1941 | TQLKV | 3 |
| 1942 | TRLQE | 3 |
| 1943 | TRLR... | 3 |
| 1944 | ARLKR | 2 |
| 1945 | ARLKV | 2 |
| 1946 | ARLR... | 2 |
| 1947 | ARLRV | 2 |
| 1948 | ARLVR | 2 |
| 1949 | DALKK | 2 |
| 1950 | DALRV | 2 |
| 1951 | DAPKR | 2 |
| 1952 | DRLRE | 2 |
| 1953 | EGLKV | 2 |
| 1954 | ERLLV | 2 |
| 1955 | ERLRA | 2 |
| 1956 | ERMRM | 2 |
| 1957 | GGLKV | 2 |
| 1958 | GGLVT | 2 |
| 1959 | HALRE | 2 |
| 1960 | HGLRE | 2 |
| 1961 | HHLKE | 2 |
| 1962 | HILKA | 2 |
| 1963 | HRLQE | 2 |
| 1964 | HRLRR | 2 |
| 1965 | KRLKE | 2 |
| 1966 | KTLKQ | 2 |
| 1967 | NALKE | 2 |
| 1968 | NRLNE | 2 |
| 1969 | NTLKV | 2 |
| 1970 | QRLKR | 2 |
| 1971 | QRLRQ | 2 |
| 1972 | QSLIA | 2 |
| 1973 | QTLKV | 2 |
| 1974 | RKLRS | 2 |
| 1975 | RRLRE | 2 |
| 1976 | SALKE | 2 |

TABLE 13-continued

ZF5 selection on G:T change at nt 7 of core motif in CBS.
Sequences reflect position 2 to 6.

| SEQ ID NO: | Sequence | # Read |
|---|---|---|
| 1977 | SRLKK | 2 |
| 1978 | SRLRK | 2 |
| 1979 | SRLRV | 2 |
| 297 | STLRV | 2 |
| 1980 | TMLKE | 2 |
| 1981 | TRLKG | 2 |
| 1982 | TRLRM | 2 |
| 1983 | TRLTE | 2 |
| 1984 | TRRKE | 2 |
| 1985 | AALKR | 1 |
| 1986 | AGLKR | 1 |
| 1987 | AGLKV | 1 |
| 1988 | AGLVR | 1 |
| 1989 | ARLGE | 1 |
| 1990 | ARLME | 1 |
| 1991 | ARLNE | 1 |
| 1992 | ARLRD | 1 |
| 1993 | ARLRM | 1 |
| 1994 | CRLKE | 1 |
| 1995 | DALDR | 1 |
| 1996 | DALKT | 1 |
| 1997 | DALKW | 1 |
| 1998 | DALRK | 1 |
| 1999 | DALTV | 1 |
| 2000 | DELKR | 1 |
| 2001 | DELPG | 1 |
| 2002 | DGLK... | 1 |
| 2003 | DGLKG | 1 |
| 2004 | DGLKW | 1 |
| 2005 | DGLLR | 1 |
| 2006 | DGLRQ | 1 |
| 2007 | DGLTV | 1 |
| 2008 | DGLVW | 1 |
| 1016 | DGMKR | 1 |
| 2009 | DKLKQ | 1 |
| 2010 | DKLRQ | 1 |
| 2011 | DRLRK | 1 |
| 2012 | DTHAG... | 1 |
| 2013 | DTLKT | 1 |
| 2014 | DVLKK | 1 |
| 2015 | EAAG... | 1 |
| 2016 | EHLRQ | 1 |
| 2017 | ELLKV | 1 |
| 2018 | EPLRV | 1 |
| 2019 | ERLCV | 1 |
| 2020 | ERLKK | 1 |
| 1893 | ERLRR... | 1 |
| 2021 | ERLVR | 1 |
| 2022 | ERLWE | 1 |
| 2023 | ERPRM | 1 |
| 2024 | ERPRV | 1 |
| 2025 | ERQRM | 1 |
| 2026 | GGLKQ | 1 |
| 2027 | GGLKR | 1 |
| 2028 | GMLKV | 1 |
| 2029 | GRLKE | 1 |
| 2030 | GTLKQ | 1 |
| 2031 | HALKA | 1 |
| 2032 | HALKG | 1 |
| 2033 | HALPV | 1 |
| 2034 | HAPEV | 1 |
| 2035 | HGLKK | 1 |
| 2036 | HGLKQ | 1 |
| 2037 | HGLMV | 1 |
| 2038 | HGLPV | 1 |
| 2039 | HGLRD | 1 |
| 54 | HGLVR | 1 |
| 2040 | HGQKE | 1 |
| 2041 | HGRKV | 1 |
| 2042 | HGRRG | 1 |
| 2043 | HHLRV | 1 |
| 2044 | HILIA | 1 |

TABLE 13-continued

ZF5 selection on G:T change at nt 7 of core motif in CBS.
Sequences reflect position 2 to 6.

| SEQ ID NO: | Sequence | # Read |
|---|---|---|
| 2045 | HKLKE | 1 |
| 2046 | HKLRV | 1 |
| 2047 | HMLKR | 1 |
| 2048 | HMLRE | 1 |
| 2049 | HNLKV | 1 |
| 2050 | HPLKV | 1 |
| 2051 | HQLKE | 1 |
| 2052 | HQLRE | 1 |
| 2053 | HQLRV | 1 |
|  | HR*A... | 1 |
| 2054 | HRGCG... | 1 |
| 2055 | HRLDE | 1 |
| 2056 | HRLIE | 1 |
| 2057 | HRLKF | 1 |
| 2058 | HRLKG | 1 |
| 2059 | HRLKL | 1 |
| 2060 | HRLMV | 1 |
| 2061 | HRLN... | 1 |
| 2062 | HRLR... | 1 |
| 2063 | HRLRA | 1 |
| 2064 | HRLS... | 1 |
| 2065 | HRLVR | 1 |
| 2066 | HRMRE | 1 |
| 2067 | HRPKE | 1 |
| 2068 | HRPNE | 1 |
| 2069 | HRQRE | 1 |
| 2070 | HRRKE | 1 |
| 2071 | HRRME | 1 |
| 2072 | HRRRE | 1 |
| 2073 | HRVRE | 1 |
| 2074 | HSACG... | 1 |
| 2075 | HSLNV | 1 |
| 2076 | HSLRV | 1 |
| 2077 | HTLAQ | 1 |
| 2078 | HTLNV | 1 |
| 2079 | HTMKV | 1 |
| 2080 | HVLKV | 1 |
| 2081 | HWLRE | 1 |
| 2082 | KGLKQ | 1 |
| 2083 | MHLRS | 1 |
| 2084 | MRLRE | 1 |
| 2085 | MRLRM | 1 |
| 2086 | NALKR | 1 |
| 2087 | NGLKE | 1 |
| 2088 | NLLRE | 1 |
| 2089 | NMLKE | 1 |
| 2090 | NMLNV | 1 |
| 2091 | NPLRE | 1 |
| 2092 | NRFKE | 1 |
| 2093 | NRLIE | 1 |
| 2094 | NRLKA | 1 |
| 2095 | NRLKF | 1 |
| 2096 | NRLKL | 1 |
| 2097 | NRLKT | 1 |
| 2098 | NRLME | 1 |
| 2099 | NRLND | 1 |
| 2100 | NRLNV | 1 |
| 2101 | NRLQE | 1 |
| 2102 | NRLR... | 1 |
| 2103 | NRLRM | 1 |
| 2104 | NRLRQ | 1 |
| 2105 | NRMKE | 1 |
| 2106 | NRPKE | 1 |
| 2107 | NRPKV | 1 |
| 2108 | NRQKE | 1 |
| 2109 | NSLKE | 1 |
| 2110 | NTLTV | 1 |
| 2111 | PRLKE | 1 |
| 2112 | PRLLP | 1 |
| 2113 | PRLRE | 1 |
| 2114 | PRLTE | 1 |
| 2115 | QAEG... | 1 |
| 2116 | QRLIS | 1 |

TABLE 13-continued

ZF5 selection on G:T change at nt 7 of core motif in CBS. Sequences reflect position 2 to 6.

| SEQ ID NO: | Sequence | # Read |
|---|---|---|
| 2117 | QRLKK | 1 |
| 2118 | QRLME | 1 |
| 2119 | QRLRG | 1 |
| 2120 | QRLRM | 1 |
| 2121 | QRLTE | 1 |
| 2122 | QTA*R... | 1 |
| 2123 | QTAW... | 1 |
| 2124 | QTG*S...R... | 1 1 |
| 2125 | RGLKV | 1 |
| 2126 | RRLGD | 1 |
| 2127 | RRLKE | 1 |
| 2128 | RRLNE | 1 |
| 2129 | RRLTK | 1 |
| 2130 | SALKK | 1 |
| 2131 | SALKR | 1 |
| 2132 | SCLKE | 1 |
| 2133 | SGLAM | 1 |
| 2134 | SGLAV | 1 |
| 2135 | SGLKV | 1 |
| 2136 | SHLKE | 1 |
| 2137 | SKLKV | 1 |
| 649 | SNLKV | 1 |
| 2138 | SQLKV | 1 |
| 2139 | SRLIG | 1 |
| 2140 | SRLK... | 1 |
| 2141 | SRLKA | 1 |
| 2142 | SRLKG | 1 |
| 2143 | SRLQE | 1 |
| 2144 | SRLR... | 1 |
| 2145 | SRLRA | 1 |
| 2146 | SRLRM | 1 |
| 2147 | SRLRQ | 1 |
| 2148 | SRLTE | 1 |
| 2149 | SRQRE | 1 |
| 2150 | SSLKE | 1 |
| 2151 | SSLKV | 1 |
| 2152 | SSQRE | 1 |
| 2153 | STLKRTAG... | 1 1 |
| 2154 | TGLKG | 1 |
| 2155 | TGLKQ | 1 |
| 2156 | TGLKS | 1 |
| 2157 | TGLRV | 1 |
| 2158 | TGRRG | 1 |
| 2159 | TLLRE | 1 |
| 2160 | TMQKE | 1 |
| 2161 | TRL*L | 1 |
| 2162 | TRLAE | 1 |
| 2163 | TRLE... | 1 |
| 2164 | TRLEE | 1 |
| 2165 | TRLGE | 1 |
| 2166 | TRLK... | 1 |
| 2167 | TRLKY | 1 |
| 2168 | TRLRG | 1 |
| 2169 | TRLRK | 1 |
| 2170 | TRLSE | 1 |
| 2171 | TRPKE | 1 |
| 2172 | TRQRD | 1 |
| 2173 | TRRRD | 1 |
| 2174 | TRVRE | 1 |
| 2175 | TSLRE | 1 |
| 2176 | TTLKA | 1 |
| 2177 | TTLKE | 1 |
| 2178 | TTLKL | 1 |
| 2179 | TTLKT | 1 |
| 2180 | TTPRG | 1 |
| 2181 | TTRKQ | 1 |
| 2182 | TWLRE | 1 |
| 2183 | VRRKV | 1 |
| 2184 | YGLKR | 1 |

TABLE 13-continued

ZF5 selection on G:T change at nt 7 of core motif in CBS. Sequences reflect position 2 to 6.

| SEQ ID NO: | Sequence | # Read |
|---|---|---|
| 2185 | YRLKE | 1 |
| 2186 | YTLKV | 1 |

TABLE 14

ZF5 selection on G:C change at nt 7 of core motif in CBS. Sequences reflect position 2 to 6.

| SEQ ID NO: | Sequence | Read # |
|---|---|---|
| 44 | SRLKE | 2533 |
| 165 | TRLKE | 2146 |
| 42 | HRLKE | 1984 |
| 47 | NRLKE | 1528 |
| 1829 | HRLRE | 1001 |
| 1832 | SRLRE | 799 |
| 110 | TRLRE | 625 |
| 46 | HTLKV | 499 |
| 41 | HGLKV | 320 |
| 1830 | QRLRE | 299 |
| 1851 | STLKV | 249 |
| 1841 | ARLKE | 238 |
| 1836 | QRLKE | 135 |
| 235 | STLKE | 126 |
| 1849 | TTLKV | 102 |
| 447 | DTLKA | 95 |
| 1891 | HKLKV | 87 |
| 454 | DTLKV | 84 |
| 43 | HALKV | 82 |
| 1962 | HILKA | 80 |
| 1845 | TGLKV | 80 |
| 1839 | ARLRE | 78 |
| 1850 | HRLGE | 75 |
| 1838 | NRLRE | 75 |
| 1854 | HRLTE | 61 |
| 1861 | RLLPN | 55 |
| 1852 | DGLKV | 50 |

TABLE 14-continued

ZF5 selection on G:C change at nt 7 of core motif in CBS. Sequences reflect position 2 to 6.

| SEQ ID NO: | Sequence | Read # |
|---|---|---|
| 1834 | HRLKV | 46 |
| 1856 | HSLKV | 43 |
| 1931 | HGLKA | 37 |
| 94 | NRLKV | 30 |
| 1901 | HHLKV | 27 |
| 1972 | QSLIA | 26 |
| 371 | DTLRV | 25 |
| 1864 | TRLKV | 25 |
| 2177 | TTLKE | 25 |
| 262 | HTLKE | 24 |
| 1888 | SRLKD | 23 |
| 1948 | ARLVR | 20 |
| 2187 | SKLKE | 20 |
| 1855 | DRLKV | 19 |
| 93 | ERLRV | 19 |
| 1857 | SRLKV | 19 |
| 1831 | DALKR | 18 |
| 109 | DGLKR | 18 |
| 2029 | GRLKE | 18 |
| 1892 | GTLKV | 18 |
| 1842 | TRLRD | 17 |
| 1913 | HTLKA | 16 |
| 1868 | HRLAE | 15 |
| 488 | DTLKQ | 14 |
| 1895 | HGLKE | 14 |
| 2188 | HILKT | 14 |
| 1974 | RKLRS | 14 |
| 2133 | SGLAM | 12 |
| 1875 | TTLKQ | 12 |
| 1926 | STLKA | 11 |
| 1833 | DGLKK | 10 |
| 2126 | RRLGD | 10 |
| 1882 | TRLKD | 10 |
| 2189 | TSLKV | 10 |
| 1837 | DGLVR | 9 |
| 1835 | ERLRM | 9 |

TABLE 14-continued

ZF5 selection on G:C change at nt 7 of core motif in CBS.
Sequences reflect position 2 to 6.

| SEQ ID NO: | Sequence | Read # |
|---|---|---|
| 1961 | HHLKE | 9 |
| 1896 | HHLVQ | 9 |
| 1847 | HRLNE | 9 |
| 1885 | HTLKQ | 9 |
| 1880 | TRLNE | 9 |
| 2190 | HRLHE | 8 |
| 1848 | SHLKV | 8 |
| 2191 | SKLRM | 8 |
| 45 | DGLRV | 7 |
| 1862 | ERLKV | 7 |
| 2192 | GTLRV | 7 |
| 1921 | HRLKA | 7 |
| 2193 | HTLKS | 7 |
| 1844 | SRLNE | 7 |
| 1915 | TGLKE | 7 |
| 108 | DALRR | 6 |
| 2194 | HGLKT | 6 |
| 1859 | HGLTV | 6 |
| 2045 | HKLKE | 6 |
| 1860 | HRLME | 6 |
| 1887 | SALKV | 6 |
| 1909 | ATLKV | 5 |
| 2195 | DTLKE | 5 |
| 2196 | GILND | 5 |
| 2135 | SGLKV | 5 |
| 2141 | SRLKA | 5 |
| 1871 | DALVR | 4 |
| 2197 | ETLKV | 4 |
| 1846 | HRLSE | 4 |
| 1923 | HSLKE | 4 |
| 1936 | HTLRV | 4 |
| 1969 | NTLKV | 4 |
| 1858 | QRLKV | 4 |
| 2140 | SRLK... | 4 |
| 2198 | THLKE | 4 |
| 1928 | TRLKQ | 4 |
| 1945 | ARLKV | 3 |
| 1853 | DGLRK | 3 |
| 1843 | DGLRR | 3 |
| 1840 | ERLRQ | 3 |
| 1957 | GGLKV | 3 |
| 1960 | HGLRE | 3 |
| 1900 | HHLKQ | 3 |
| 1965 | KRLKE | 3 |
| 2199 | NALRV | 3 |
| 1897 | NGLKV | 3 |
| 2200 | NRLGE | 3 |
| 1906 | NRLKK | 3 |
| 1975 | RRLRE | 3 |
| 2132 | SCLKE | 3 |
| 2137 | SKLKV | 3 |
| 2201 | SRLRD | 3 |
| 1979 | SRLRV | 3 |
| 548 | STLKQ | 3 |
| 1927 | TRLKA | 3 |
| 1942 | TRLQE | 3 |
| 2186 | YTLKV | 3 |
| 2202 | APLLR | 2 |
| 2009 | DKLKQ | 2 |
| 2203 | DKLKV | 2 |
| 1920 | DRLKE | 2 |
| 1873 | ERLRE | 2 |
| 1899 | HALKE | 2 |
| 2043 | HHLRV | 2 |
| 2051 | HQLKE | 2 |
| 2204 | HRLEE | 2 |
| 1878 | HRLRV | 2 |
| 2205 | HTLKG | 2 |
| 1966 | KTLKQ | 2 |
| 2206 | MVLVV | 2 |
| 2094 | NRLKA | 2 |
| 2207 | NRLKD | 2 |

TABLE 14-continued

ZF5 selection on G:C change at nt 7 of core motif in CBS.
Sequences reflect position 2 to 6.

| SEQ ID NO: | Sequence | Read # |
|---|---|---|
| 1881 | NRLKQ | 2 |
| 2101 | NRLQE | 2 |
| 2108 | NRQKE | 2 |
| 2208 | NTLKA | 2 |
| 1938 | QRLRV | 2 |
| 1973 | QTLKV | 2 |
| 2127 | RRLKE | 2 |
| 2209 | SRLKQ | 2 |
| 2151 | SSLKV | 2 |
| 553 | STLRQ | 2 |
| 297 | STLRV | 2 |
| 1983 | TRLTE | 2 |
| 2175 | TSLRE | 2 |
| 1987 | AGLKV | 1 |
| 2210 | AQMKE | 1 |
| 1991 | ARLNE | 1 |
| 1992 | ARLRD | 1 |
| 2211 | ARRRE | 1 |
| 2212 | CRLM... | 1 |
| 2213 | CRLMV | 1 |
| 538 | DALKE | 1 |
| 1898 | DALKV | 1 |
| 2001 | DELPG | 1 |
| 1865 | DGLKE | 1 |
| 2010 | DKLRQ | 1 |
| 2214 | DRLKA | 1 |
| 2215 | DRLKT | 1 |
| 1952 | DRLRE | 1 |
| 1903 | DRLRT | 1 |
| 2013 | DTLKT | 1 |
| 2216 | DTPKA | 1 |
| 1869 | ERLIS | 1 |
| 1893 | ERLRR... | 1 |
| 2023 | ERPRM | 1 |
| 2026 | GGLKQ | 1 |
| 2028 | GMLKV | 1 |
| 2217 | GRLKA | 1 |
| 2218 | GRLKV | 1 |
| 2030 | GTLKQ | 1 |
| 2219 | GVLKE | 1 |
| 2220 | GVLTG | 1 |
| 2221 | HALDV | 1 |
| 2031 | HALKA | 1 |
| 2222 | HELKV | 1 |
| 2223 | HGLEA | 1 |
| 2036 | HGLKQ | 1 |
| 2224 | HGLRG | 1 |
| 2225 | HGMKA | 1 |
| 2226 | HGPKV | 1 |
| 2044 | HILIA | 1 |
| 2227 | HILKE | 1 |
| 2228 | HILKV | 1 |
| 2229 | HILNA | 1 |
| 2230 | HKLKG | 1 |
| 2231 | HKLKQ | 1 |
| 2046 | HKLRV | 1 |
| 2048 | HMLRE | 1 |
| 1933 | HPEG... | 1 |
| 2232 | HPLKE | 1 |
| 1874 | HQLKV | 1 |
| 2233 | HRLGV | 1 |
| 1922 | HRLKD | 1 |
| 2058 | HRLKG | 1 |
| 2059 | HRLKL | 1 |
| 1872 | HRLKR | 1 |
| 2234 | HRLLE | 1 |
| 2235 | HRLQG | 1 |
| 2063 | HRLRA | 1 |
| 2236 | HRLRS | 1 |
| 2237 | HRLTV | 1 |
| 2065 | HRLVR | 1 |
| 2066 | HRMRE | 1 |

TABLE 14-continued

ZF5 selection on G:C change at nt 7 of core motif in CBS.
Sequences reflect position 2 to 6.

| SEQ ID NO: | Sequence | Read # |
|---|---|---|
| 2072 | HRRRE | 1 |
| 2238 | HSG*G... | 1 |
| 2239 | HSLKQ | 1 |
| 2240 | HSLRE | 1 |
| 2241 | HSVKA | 1 |
| 2242 | HTG*R... | 1 |
| 2077 | HTLAQ | 1 |
| 2243 | HTLEV | 1 |
| 215 | HTLME | 1 |
| 2244 | HTLMV | 1 |
| 2245 | HTLQE | 1 |
| 2246 | HTLRQ | 1 |
| 2080 | HVLKV | 1 |
| 2247 | IRLKE | 1 |
| 2248 | IRQEE | 1 |
| 2082 | KGLKQ | 1 |
| 2249 | KRLKV | 1 |
| 2250 | LRLKK | 1 |
| 2251 | NKLKE | 1 |
| 2252 | NKLKG | 1 |
| 2092 | NRFKE | 1 |
| 2253 | NRLAE | 1 |
| 2254 | NRLEE | 1 |
| 1925 | NRLKR | 1 |
| 2255 | NRLKS | 1 |
| 2097 | NRLKT | 1 |
| 1914 | NRLRD | 1 |
| 2256 | NRLRG | 1 |
| 1863 | NRLRV | 1 |
| 2257 | NRLTE | 1 |
| 2109 | NSLKE | 1 |
| 1937 | NTLKQ | 1 |
| 2258 | PAEG... | 1 |
| 2259 | PPPPE | 1 |
| 2113 | PRLRE | 1 |
| 2115 | QAEG... | 1 |
| 2260 | QGRRE | 1 |
| 2261 | QRLEE | 1 |
| 2119 | QRLRG | 1 |
| 2262 | QSLGR | 1 |
| 2134 | SGLAV | 1 |
| 2263 | SKLK... | 1 |
| 2264 | SMLRE | 1 |
| 2265 | SRLAE | 1 |
| 2266 | SRLCE | 1 |
| 2142 | SRLKG | 1 |
| 2267 | SRLLE | 1 |
| 2143 | SRLQE | 1 |
| 2145 | SRLRA | 1 |
| 1978 | SRLRK | 1 |
| 1940 | SRPKE | 1 |
| 2149 | SRQRE | 1 |
| 2268 | SRRKE | 1 |
| 2150 | SSLKE | 1 |
| 2152 | SSQRE | 1 |
| 539 | STLRA | 1 |
| 202 | STLRE | 1 |
| 2155 | TGLKQ | 1 |
| 2269 | TGLRE | 1 |
| 2270 | THLKV | 1 |
| 2271 | TILYE | 1 |
| 2272 | TLLKE | 1 |
| 1981 | TRLKG | 1 |
| 1908 | TRLME | 1 |
| 1883 | TRLRV | 1 |
| 2273 | TRLTV | 1 |
| 2274 | TRMGE | 1 |
| 2275 | TRMKQ | 1 |
| 2176 | TTLKA | 1 |
| 1918 | TTLKI | 1 |
| 2178 | TTLKL | 1 |
| 2276 | YTLKE | 1 |

TABLE 15

ZF5 selection on G:A change at nt 7 of core motif in CBS. Sequences reflect position 2 to 6.

| SEQ ID NO: | Sequence | Read # |
|---|---|---|
| 46 | HTLKV | 3934 |
| 41 | HGLKV | 2682 |
| 1851 | STLKV | 2167 |
| 1861 | RLLPN | 1887 |
| 1849 | TTLKV | 1471 |
| 43 | HALKV | 923 |
| 454 | DTLKV | 888 |
| 1875 | TTLKQ | 754 |
| 1891 | HKLKV | 571 |
| 1885 | HTLKQ | 513 |
| 1845 | TGLKV | 482 |
| 1892 | GTLKV | 473 |
| 488 | DTLKQ | 462 |
| 1852 | DGLKV | 443 |
| 1856 | HSLKV | 352 |
| 1896 | HHLVQ | 298 |
| 1901 | HHLKV | 259 |
| 1834 | HRLKV | 210 |
| 42 | HRLKE | 190 |
| 371 | DTLRV | 189 |
| 44 | SRLKE | 186 |
| 165 | TRLKE | 178 |
| 1887 | SALKV | 177 |
| 1909 | ATLKV | 155 |
| 1900 | HHLKQ | 149 |
| 1926 | STLKA | 140 |
| 1897 | NGLKV | 136 |
| 47 | NRLKE | 124 |
| 548 | STLKQ | 118 |
| 1973 | QTLKV | 112 |
| 1874 | HQLKV | 94 |
| 2135 | SGLKV | 91 |
| 1829 | HRLRE | 89 |
| 1936 | HTLRV | 88 |
| 297 | STLRV | 78 |
| 447 | DTLKA | 75 |

TABLE 15-continued

ZF5 selection on G:A change at nt 7 of core motif in CBS. Sequences reflect position 2 to 6.

| SEQ ID NO: | Sequence | Read # |
|---|---|---|
| 1957 | GGLKV | 75 |
| 1928 | TRLKQ | 75 |
| 1966 | KTLKQ | 69 |
| 2277 | HTL*A | 66 |
| 1913 | HTLKA | 64 |
| 1832 | SRLRE | 61 |
| 110 | TRLRE | 58 |
| 1937 | NTLKQ | 56 |
| 2278 | SKLKQ | 55 |
| 1830 | QRLRE | 53 |
| 2203 | DKLKV | 51 |
| 1919 | TTLRV | 48 |
| 2151 | SSLKV | 43 |
| 1848 | SHLKV | 42 |
| 2030 | GTLKQ | 40 |
| 1864 | TRLKV | 40 |
| 2270 | THLKV | 38 |
| 1969 | NTLKV | 37 |
| 553 | STLRQ | 35 |
| 2279 | HALRV | 34 |
| 1931 | HGLKA | 33 |
| 2009 | DKLKQ | 32 |
| 109 | DGLKR | 29 |
| 1953 | EGLKV | 29 |
| 2197 | ETLKV | 29 |
| 2280 | GILKV | 28 |
| 1855 | DRLKV | 26 |
| 1866 | HGLRV | 24 |
| 2281 | SVLKQ | 23 |
| 1831 | DALKR | 22 |
| 93 | ERLRV | 22 |
| 2282 | GQLHV | 21 |
| 2283 | TTLRQ | 21 |
| 45 | DGLRV | 20 |
| 2284 | DTLKN | 20 |
| 2179 | TTLKT | 20 |

TABLE 15-continued

ZF5 selection on G:A change at nt 7 of core motif in CBS.
Sequences reflect position 2 to 6.

| SEQ ID NO: | Sequence | Read # |
|---|---|---|
| 2285 | GVLKV | 17 |
| 2010 | DKLRQ | 16 |
| 2286 | GTLKA | 16 |
| 2026 | GGLKQ | 15 |
| 2036 | HGLKQ | 15 |
| 2043 | HHLRV | 15 |
| 94 | NRLKV | 15 |
| 2192 | GTLRV | 14 |
| 262 | HTLKE | 14 |
| 2287 | SVLKV | 14 |
| 2155 | TGLKQ | 14 |
| 1835 | ERLRM | 13 |
| 1838 | NRLRE | 13 |
| 2137 | SKLKV | 13 |
| 649 | SNLKV | 13 |
| 2288 | TVLKV | 13 |
| 1841 | ARLKE | 12 |
| 1839 | ARLRE | 12 |
| 1833 | DGLKK | 12 |
| 2289 | HHLRQ | 12 |
| 2205 | HTLKG | 12 |
| 2080 | HVLKV | 12 |
| 1917 | TRLRQ | 12 |
| 2290 | NTLRQ | 11 |
| 2134 | SGLAV | 11 |
| 108 | DALRR | 10 |
| 2291 | QTLKQ | 10 |
| 2292 | RTLKQ | 10 |
| 235 | STLKE | 10 |
| 1987 | AGLKV | 9 |
| 2013 | DTLKT | 9 |
| 274 | HHLVV | 9 |
| 2049 | HNLKV | 9 |
| 1836 | QRLKE | 9 |
| 2293 | STLKG | 9 |
| 2294 | TVLKQ | 9 |
| 1837 | DGLVR | 8 |
| 2295 | GGLVV | 8 |
| 2296 | HGLQV | 8 |
| 1850 | HRLGE | 8 |
| 1854 | HRLTE | 8 |
| 2246 | HTLRQ | 8 |
| 1857 | SRLKV | 8 |
| 2297 | DTLKG | 7 |
| 2298 | GGLTV | 7 |
| 2299 | GVLKA | 7 |
| 2031 | HALKA | 7 |
| 2194 | HGLKT | 7 |
| 2176 | TTLKA | 7 |
| 2300 | GTLRQ | 6 |
| 2301 | HALKQ | 6 |
| 1844 | SRLNE | 6 |
| 2302 | STLKT | 6 |
| 1842 | TRLRD | 6 |
| 2303 | ATLKA | 5 |
| 2304 | ATLKQ | 5 |
| 2305 | DGLKQ | 5 |
| 1843 | DGLRR | 5 |
| 1862 | ERLKV | 5 |
| 2306 | GTLNA | 5 |
| 2307 | GVLKN | 5 |
| 1895 | HGLKE | 5 |
| 1910 | HGLVV | 5 |
| 2308 | TTLKG | 5 |
| 1853 | DGLRK | 4 |
| 1840 | ERLRQ | 4 |
| 2309 | ETLRV | 4 |
| 2310 | HGLKG | 4 |
| 2311 | HGLNV | 4 |
| 1859 | HGLTV | 4 |
| 1961 | HHLKE | 4 |
| 1846 | HRLSE | 4 |

TABLE 15-continued

ZF5 selection on G:A change at nt 7 of core motif in CBS.
Sequences reflect position 2 to 6.

| SEQ ID NO: | Sequence | Read # |
|---|---|---|
| 1886 | NALKV | 4 |
| 484 | STLTV | 4 |
| 2312 | VGLGE | 4 |
| 2186 | YTLKV | 4 |
| 2313 | AGLAT | 3 |
| 1948 | ARLVR | 3 |
| 2314 | D*LPG | 3 |
| 2003 | DGLKG | 3 |
| 2315 | DKLRV | 3 |
| 1899 | HALKE | 3 |
| 1860 | HRLME | 3 |
| 2239 | HSLKQ | 3 |
| 2078 | HTLNV | 3 |
| 2079 | HTMKV | 3 |
| 2316 | HTQKV | 3 |
| 2262 | QSLGR | 3 |
| 1974 | RKLRS | 3 |
| 474 | STLNV | 3 |
| 2177 | TTLKE | 3 |
| 1871 | DALVR | 2 |
| 2001 | DELPG | 2 |
| 2317 | DGLRA | 2 |
| 2318 | DVLKV | 2 |
| 2319 | GALRV | 2 |
| 2320 | GGLVQ | 2 |
| 2321 | GNLKV | 2 |
| 2322 | GPLKV | 2 |
| 2323 | GTLKG | 2 |
| 2324 | GVLKQ | 2 |
| 2325 | GVLRV | 2 |
| 678 | GVLVA | 2 |
| 2032 | HALKG | 2 |
| 2326 | HDLKV | 2 |
| 2327 | HGLEV | 2 |
| 2226 | HGPKV | 2 |
| 2328 | HHMVQ | 2 |
| 1962 | HILKA | 2 |
| 2329 | HKLKA | 2 |
| 2045 | HKLKE | 2 |
| 2231 | HKLKQ | 2 |
| 1921 | HRLKA | 2 |
| 2330 | HRLKQ | 2 |
| 1847 | HRLNE | 2 |
| 2082 | KGLKQ | 2 |
| 2331 | KTLKV | 2 |
| 2332 | PTLKV | 2 |
| 1972 | QSLIA | 2 |
| 2333 | RLLPY | 2 |
| 2334 | RLRPN | 2 |
| 2335 | RTLAQ | 2 |
| 2336 | RTLKV | 2 |
| 2337 | SALTV | 2 |
| 2338 | STLKL | 2 |
| 1916 | TGLKT | 2 |
| 2339 | TKLKQ | 2 |
| 1918 | TTLKI | 2 |
| 2340 | TTPKV | 2 |
| 2341 | AGLAS | 1 |
| 2342 | AGLKM | 1 |
| 2343 | APLKV | 1 |
| 1945 | ARLKV | 1 |
| 1992 | ARLRD | 1 |
| 2344 | ATLKG | 1 |
| 538 | DALKE | 1 |
| 1898 | DALKV | 1 |
| 2345 | DELRQ | 1 |
| 2346 | DGLKA | 1 |
| 1865 | DGLKE | 1 |
| 2347 | DGLKL | 1 |
| 2348 | DKLKG | 1 |
| 1877 | DRLKQ | 1 |
| 1952 | DRLRE | 1 |

TABLE 15-continued

ZF5 selection on G:A change at nt 7 of core motif in CBS.
Sequences reflect position 2 to 6.

| SEQ ID NO: | Sequence | Read # |
|---|---|---|
| 1904 | DRLRV | 1 |
| 2349 | DSLKV | 1 |
| 2195 | DTLKE | 1 |
| 2350 | DTLNQ | 1 |
| 326 | DTLQA | 1 |
| 423 | DTLRA | 1 |
| 533 | DTLRL | 1 |
| 2351 | DTLWQ | 1 |
| 2352 | DTMKV | 1 |
| 2353 | EGLKQ | 1 |
| 1955 | ERLRA | 1 |
| 1873 | ERLRE | 1 |
| 2023 | ERPRM | 1 |
| 2354 | ETLKE | 1 |
| 2355 | ETRRV | 1 |
| 2356 | GGLAV | 1 |
| 2357 | GGLRG | 1 |
| 2358 | GGLRV | 1 |
| 2359 | GHLKA | 1 |
| 2196 | GILND | 1 |
| 2028 | GMLKV | 1 |
| 2360 | GPLRA | 1 |
| 2361 | GQQHV | 1 |
| 2362 | GTLQA | 1 |
| 2363 | GTPKV | 1 |
| 2364 | HALES | 1 |
| 2365 | HALKF | 1 |
| 2366 | HALMV | 1 |
| 2033 | HALPV | 1 |
| 2367 | HAMKV | 1 |
| 2368 | HARKV | 1 |
| 2222 | HELKV | 1 |
| 2369 | HGLKD | 1 |
| 2370 | HGLKL | 1 |
| 2371 | HGLKM | 1 |
| 2372 | HGLKW | 1 |
| 2373 | HGRKI | 1 |
| 2041 | HGRKV | 1 |
| 2374 | HHLAQ | 1 |
| 2375 | HHLGQ | 1 |
| 2376 | HHLMQ | 1 |
| 2377 | HHMKV | 1 |
| 2044 | HILIA | 1 |
| 2228 | HILKV | 1 |
| 2230 | HKLKG | 1 |
| 2378 | HKLKM | 1 |
| 2379 | HKLNV | 1 |
| 2380 | HKLQE | 1 |
| 2046 | HKLRV | 1 |
| 2381 | HMLNV | 1 |
| 2382 | HPLDV | 1 |
| 2050 | HPLKV | 1 |
| 2383 | HPLQV | 1 |
| 2384 | HQLKA | 1 |
| 2385 | HQLKG | 1 |
| 2386 | HQLKT | 1 |
| 1868 | HRLAE | 1 |
| 2058 | HRLKG | 1 |
| 2059 | HRLKL | 1 |
| 1872 | HRLKR | 1 |
| 1912 | HRLRQ | 1 |
| 2065 | HRLVR | 1 |
| 2067 | HRPKE | 1 |
| 2387 | HSLKA | 1 |
| 1923 | HSLKE | 1 |
| 2388 | HSLKG | 1 |
| 2389 | HSLKL | 1 |
| 2241 | HSVKA | 1 |
| 2077 | HTLAQ | 1 |
| 2390 | HTLAV | 1 |
| 2243 | HTLEV | 1 |
| 2391 | HTLKN | 1 |

TABLE 15-continued

ZF5 selection on G:A change at nt 7 of core motif in CBS.
Sequences reflect position 2 to 6.

| SEQ ID NO: | Sequence | Read # |
|---|---|---|
| 2244 | HTLMV | 1 |
| 2392 | HTLNA | 1 |
| 2393 | HTLQV | 1 |
| 250 | HTLTE | 1 |
| 2394 | HTLTV | 1 |
| 2395 | HTPKV | 1 |
| 2396 | HTRKQ | 1 |
| 2397 | HVLKF | 1 |
| 2398 | HVMKV | 1 |
| 2399 | HWLKV | 1 |
| 2400 | KADTV | 1 |
| 2401 | KGLKG | 1 |
| 2402 | KRLKQ | 1 |
| 2403 | KTLAQ | 1 |
| 2404 | KTLRV | 1 |
| 2405 | KTLTQ | 1 |
| 2406 | LHLKV | 1 |
| 2407 | LTLKQ | 1 |
| 2408 | LTLKV | 1 |
| 2409 | MGLKV | 1 |
| 2410 | MPPK | 1 |
| 2411 | MRLKQ | 1 |
| 2412 | NAVTE | 1 |
| 2413 | NGLKG | 1 |
| 2414 | NGLKL | 1 |
| 2415 | NRLKG | 1 |
| 1914 | NRLRD | 1 |
| 1863 | NRLRV | 1 |
| 2416 | NTLRV | 1 |
| 2417 | PGLKV | 1 |
| 2418 | QGLKV | 1 |
| 1858 | QRLKV | 1 |
| 1938 | QRLRV | 1 |
| 2419 | QRQRV | 1 |
| 2420 | QTLKA | 1 |
| 2421 | QTLKG | 1 |

TABLE 15-continued

ZF5 selection on G:A change at nt 7 of core motif in CBS.
Sequences reflect position 2 to 6.

| SEQ ID NO: | Sequence | Read # |
|---|---|---|
| 2422 | QTLKK | 1 |
| 2423 | QTLKM | 1 |
| 2424 | QTLMV | 1 |
| 2125 | RGLKV | 1 |
| 2425 | RHLVQ | 1 |
| 2426 | RLLPT | 1 |
| 2427 | RLLSN | 1 |
| 2428 | RLMPD | 1 |
| 2429 | RMLPN | 1 |
| 2126 | RRLGD | 1 |
| 2430 | RSLKV | 1 |
| 2431 | RTLKG | 1 |
| 2432 | SALKQ | 1 |
| 2433 | SALRQ | 1 |
| 2434 | SELKV | 1 |
| 2435 | SFLKV | 1 |
| 2133 | SGLAM | 1 |
| 2436 | SGLKQ | 1 |
| 2437 | SHLKQ | 1 |
| 2438 | SKLKA | 1 |
| 2187 | SKLKE | 1 |
| 1888 | SRLKD | 1 |
| 2145 | SRLRA | 1 |
| 556 | SSLRV | 1 |
| 2152 | SSQRE | 1 |
| 2439 | STLKK | 1 |
| 2440 | STLKM | 1 |
| 385 | STLMV | 1 |
| 448 | STLQQ | 1 |
| 554 | STLTA | 1 |
| 2441 | STMKA | 1 |
| 2442 | STMKV | 1 |
| 2443 | TALKV | 1 |
| 2444 | TGLKA | 1 |
| 2445 | TGLKD | 1 |
| 1915 | TGLKE | 1 |

TABLE 15-continued

ZF5 selection on G:A change at nt 7 of core motif in CBS.
Sequences reflect position 2 to 6.

| SEQ ID NO: | Sequence | Read # |
|---|---|---|
| 2154 | TGLKG | 1 |
| 2446 | TGLMV | 1 |
| 2198 | THLKE | 1 |
| 2447 | THLKG | 1 |
| 2448 | THLKL | 1 |
| 2449 | THLKQ | 1 |
| 2450 | THLMV | 1 |
| 64 | TKLKV | 1 |
| 2451 | TPLQV | 1 |
| 1882 | TRLKD | 1 |
| 1981 | TRLKG | 1 |
| 2452 | TRLPQ | 1 |
| 1942 | TRLQE | 1 |
| 2453 | TTLEV | 1 |
| 2454 | TTLHV | 1 |
| 507 | TTLNQ | 1 |
| 577 | TTLQV | 1 |
| 2455 | TTLRG | 1 |
| 2456 | TTLYV | 1 |
| 2457 | TTMKV | 1 |
| 2458 | TVLRQ | 1 |
| 2459 | VGLGG | 1 |
| 2460 | VTLKV | 1 |

TABLE 16

ZF5 selection on G:A change position 8 of the CBS core motif.
Sequences reflect position 2 to 6.

| SEQ ID NO: | Sequence | # Read |
|---|---|---|
| 2461 | GGLRR | 341 |
| 50 | GGLVR | 336 |
| 2462 | TGLRR | 274 |
| 2463 | EGLRR | 267 |
| 1843 | DGLRR | 232 |
| 2464 | SGLRR | 206 |
| 2465 | AGLAR | 179 |
| 2466 | SGLAR | 178 |
| 2467 | GGLAR | 177 |
| 55 | GGLTR | 168 |
| 2468 | DGLAR | 152 |
| 1986 | AGLKR | 148 |
| 2469 | TGLAR | 135 |
| 1837 | DGLVR | 129 |
| 2470 | GGLQR | 127 |
| 70 | GNLTR | 124 |
| 117 | GNLVR | 123 |
| 2471 | HGLAR | 123 |
| 2027 | GGLKR | 111 |
| 2472 | TGLVR | 108 |
| 2473 | AGLTR | 105 |
| 2474 | SGLSR | 102 |
| 2475 | AGLRR | 100 |
| 2476 | GGLSR | 94 |
| 59 | HGLRR | 91 |
| 54 | HGLVR | 87 |
| 2477 | SGLTR | 84 |
| 2478 | NGLVR | 80 |
| 2479 | AGLQR | 79 |
| 118 | GNLRR | 79 |
| 2480 | AGLHR | 76 |
| 2481 | GNLER | 76 |
| 2482 | HNLLR | 76 |
| 138 | GNLAR | 73 |
| 1870 | DGLTR | 72 |
| 2483 | HALRR | 69 |
| 2484 | HGLQR | 69 |
| 2485 | NGLRR | 69 |
| 2486 | SGLVR | 68 |
| 2487 | SNLDR | 67 |
| 68 | TNLRR | 66 |
| 2488 | HGLTR | 63 |

TABLE 16-continued

ZF5
selection on G:A
change position 8 of the CBS core motif.
Sequences reflect position 2 to 6.

| SEQ ID NO: | Sequence | # Read |
|---|---|---|
| 2489 | SSLRR | 63 |
| 108 | DALRR | 61 |
| 2490 | EGLTR | 61 |
| 2491 | GGLER | 61 |
| 109 | DGLKR | 60 |
| 2492 | TGLQR | 60 |
| 56 | HTLRR | 59 |
| 1985 | AALKR | 58 |
| 1988 | AGLVR | 55 |
| 2493 | AGLIR | 54 |
| 1932 | HGLKR | 54 |
| 2494 | ANLVR | 53 |
| 2495 | EGLKR | 53 |
| 2496 | SNLLR | 51 |
| 2497 | EGLAR | 50 |
| 2498 | AGLSR | 49 |
| 2499 | DGLIR | 48 |
| 2500 | TGLKR | 48 |
| 2501 | SGLQR | 46 |
| 2502 | ETLKR | 45 |
| 2503 | HGLLR | 45 |
| 2504 | NGLQR | 45 |
| 2505 | TGLMR | 45 |
| 69 | ANLRR | 43 |
| 2506 | DNLVR | 42 |
| 2507 | TGLLR | 42 |
| 2508 | DGLMR | 41 |
| 2509 | ASLKR | 39 |
| 2510 | QGLRR | 38 |
| 2511 | TNLVR | 38 |
| 2512 | NGLTR | 37 |
| 2513 | SGLDR | 37 |
| 2514 | SGLHR | 37 |
| 2515 | TGLNR | 37 |
| 2516 | TGLSR | 37 |
| 2517 | GNLLR | 36 |
| 2518 | NNLVR | 36 |
| 2519 | TGLIR | 36 |
| 2520 | DMLRR | 35 |
| 2521 | GALKR | 35 |
| 2522 | GNLDR | 35 |
| 2523 | SALRR | 35 |
| 2524 | SNLAR | 35 |
| 2525 | SGLLR | 34 |
| 2526 | TNLNR | 33 |
| 2527 | AGLLR | 31 |
| 2528 | GGLIR | 31 |
| 2529 | DGLHR | 30 |
| 2530 | DTLRR | 30 |
| 2531 | HLLKR | 30 |
| 2532 | SALAR | 30 |
| 2533 | SMLAR | 30 |
| 2534 | VGLKR | 30 |
| 2535 | DNLLR | 28 |
| 2536 | GGLMR | 28 |
| 2537 | SGLMR | 28 |
| 2538 | AALRR | 27 |
| 2539 | ETLRR | 27 |
| 2540 | NGLAR | 27 |
| 2157 | TGLRV | 27 |
| 53 | TGLTR | 27 |
| 2541 | TNLQR | 27 |
| 2542 | ANLAR | 26 |
| 2543 | NNLAR | 26 |
| 2544 | SNLSR | 26 |
| 2545 | STLSR | 26 |
| 2546 | AALAR | 25 |
| 2547 | HALVR | 25 |
| 2548 | HGLSR | 25 |
| 2549 | SGLNR | 25 |
| 2550 | STLAR | 25 |

TABLE 16-continued

ZF5
selection on G:A
change position 8 of the CBS core motif.
Sequences reflect position 2 to 6.

| SEQ ID NO: | Sequence | # Read |
|---|---|---|
| 2551 | ANLIR | 24 |
| 2552 | DGLDR | 24 |
| 2553 | DGLSR | 24 |
| 2554 | GTLKR | 24 |
| 1884 | EALKR | 23 |
| 2555 | NGLSR | 23 |
| 2556 | SMLRR | 23 |
| 2557 | HNLHR | 22 |
| 2558 | HNLRR | 22 |
| 2559 | SGLKR | 22 |
| 2560 | TGLGR | 22 |
| 2561 | TNLMR | 22 |
| 1871 | DALVR | 21 |
| 2562 | GTLTR | 21 |
| 2563 | DGLNR | 20 |
| 2564 | SSLVR | 20 |
| 2565 | TGLER | 20 |
| 2566 | DTLKR | 19 |
| 2567 | GNLSR | 19 |
| 51 | HGLIR | 19 |
| 2568 | HSLVR | 19 |
| 2569 | AGLNR | 18 |
| 2570 | DALAR | 18 |
| 2571 | GGLHR | 18 |
| 2572 | NGLIR | 18 |
| 2573 | QGLTR | 18 |
| 2574 | QMLKR | 18 |
| 2575 | QNLRR | 18 |
| 1845 | TGLKV | 18 |
| 2576 | AILKR | 17 |
| 119 | GNLKR | 17 |
| 139 | GNLMR | 17 |
| 2577 | HNLTR | 17 |
| 2578 | HTLAR | 17 |
| 2579 | QGLKR | 17 |
| 2580 | SGLER | 17 |
| 2581 | SGLGR | 17 |
| 2582 | SNLVR | 17 |
| 2583 | EALRR | 16 |
| 2584 | GTLRR | 16 |
| 2585 | HGLGR | 16 |
| 2586 | HTLMR | 16 |
| 2587 | NTLRR | 16 |
| 2588 | TGLHR | 16 |
| 2589 | TSLRR | 16 |
| 2590 | TTLQR | 16 |
| 2591 | DNLKR | 15 |
| 2592 | GALTR | 15 |
| 2593 | QTLRR | 15 |
| 2594 | SGLIR | 15 |
| 2595 | TNLKR | 15 |
| 2596 | DGLGR | 14 |
| 2597 | DSLQR | 14 |
| 2598 | EGLNR | 14 |
| 2599 | ENLRR | 14 |
| 2600 | GSLRR | 14 |
| 2601 | NGLNR | 14 |
| 2602 | QALKR | 14 |
| 2603 | SALSR | 14 |
| 2604 | SSLGR | 14 |
| 2605 | VNLKR | 14 |
| 66 | ATLRR | 13 |
| 2005 | DGLLR | 13 |
| 2606 | EMLKR | 13 |
| 2607 | GALVR | 13 |
| 2608 | GNLGR | 13 |
| 2609 | GNLQR | 13 |
| 2610 | HALAR | 13 |
| 2611 | HSLIR | 13 |
| 2612 | HTLER | 13 |
| 2613 | HTLQR | 13 |

TABLE 16-continued

ZF5
selection on G:A
change position 8 of the CBS core motif.
Sequences reflect position 2 to 6.

| SEQ ID NO: | Sequence | # Read |
|---|---|---|
| 2614 | NGLER | 13 |
| 2615 | NGLMR | 13 |
| 2616 | QGLVR | 13 |
| 2617 | TALKR | 13 |
| 2618 | TTLMR | 13 |
| 2619 | VGLRR | 13 |
| 2620 | ANLKR | 12 |
| 2621 | ANLNR | 12 |
| 2622 | ATLTR | 12 |
| 2623 | DNLRR | 12 |
| 2624 | ENLKR | 12 |
| 2625 | GGLLR | 12 |
| 2626 | GTLVR | 12 |
| 2627 | HNLSR | 12 |
| 2628 | NTLKR | 12 |
| 2629 | SALER | 12 |
| 2630 | SSLTR | 12 |
| 2631 | TALVR | 12 |
| 52 | ANLSR | 11 |
| 2632 | DNLAR | 11 |
| 2633 | ENLSR | 11 |
| 2634 | ESLRR | 11 |
| 2635 | NALRR | 11 |
| 2636 | NGLKR | 11 |
| 2637 | NNLLR | 11 |
| 2418 | QGLKV | 11 |
| 116 | SNLRR | 11 |
| 2638 | STLRR | 11 |
| 2639 | VNLSR | 11 |
| 2640 | DMLKR | 10 |
| 2641 | GALRR | 10 |
| 2642 | GGLDR | 10 |
| 2643 | HGLMR | 10 |
| 2644 | HNLVR | 10 |
| 2645 | HQLIR | 10 |
| 2086 | NALKR | 10 |
| 1969 | NTLKV | 10 |
| 2646 | QNLQR | 10 |
| 1887 | SALKV | 10 |
| 2647 | SMLIR | 10 |
| 2648 | TALRV | 10 |
| 2649 | TNLAR | 10 |
| 2650 | TQLKR | 10 |
| 1849 | TTLKV | 10 |
| 2651 | TTLTR | 10 |
| 2652 | VGLQR | 10 |
| 2653 | AALSR | 9 |
| 2654 | ATLAR | 9 |
| 2655 | DALGR | 9 |
| 2656 | DTLNR | 9 |
| 2657 | EILKR | 9 |
| 2658 | ESLKR | 9 |
| 2659 | GGLNR | 9 |
| 2660 | GSLTR | 9 |
| 2661 | HNLAR | 9 |
| 2662 | MGLKR | 9 |
| 2663 | NGLHR | 9 |
| 2664 | NMLKR | 9 |
| 2665 | PNLKR | 9 |
| 2666 | SALTR | 9 |
| 2667 | SDLKR | 9 |
| 2668 | STLGR | 9 |
| 2669 | AGLER | 8 |
| 2670 | DILRR | 8 |
| 2671 | DMLNR | 8 |
| 2672 | DTLAR | 8 |
| 2673 | HALLR | 8 |
| 2674 | HALSR | 8 |
| 2675 | HNLGR | 8 |
| 2676 | NALVR | 8 |
| 2677 | SMLTR | 8 |

TABLE 16-continued

ZF5
selection on G:A
change position 8 of the CBS core motif.
Sequences reflect position 2 to 6.

| SEQ ID NO: | Sequence | # Read |
|---|---|---|
| 2678 | TALAR | 8 |
| 2679 | TNLER | 8 |
| 2680 | TNLGR | 8 |
| 2681 | TTLNR | 8 |
| 2682 | DALLR | 7 |
| 2683 | DSLAR | 7 |
| 2684 | GTLAR | 7 |
| 2685 | GTLLV | 7 |
| 2686 | HALIR | 7 |
| 2687 | HGLDR | 7 |
| 2688 | HGLER | 7 |
| 2689 | HTLLR | 7 |
| 2690 | NNLIR | 7 |
| 2691 | NNLMR | 7 |
| 2692 | QSLKR | 7 |
| 2693 | SALGR | 7 |
| 2694 | SALVR | 7 |
| 2695 | SNLMR | 7 |
| 2696 | SQLRR | 7 |
| 2697 | STLQR | 7 |
| 2698 | STLVR | 7 |
| 2699 | SVLKR | 7 |
| 2189 | TSLKV | 7 |
| 2700 | AALTR | 6 |
| 2701 | DSLKR | 6 |
| 2702 | DSLRR | 6 |
| 2703 | DTLMR | 6 |
| 2704 | EGLLR | 6 |
| 2705 | ENLAR | 6 |
| 2706 | GNLNR | 6 |
| 2707 | GTLQR | 6 |
| 2708 | HALDR | 6 |
| 2709 | HVLER | 6 |
| 2710 | IGLRR | 6 |
| 2711 | INLTR | 6 |

TABLE 16-continued

ZF5
selection on G:A
change position 8 of the CBS core motif.
Sequences reflect position 2 to 6.

| SEQ ID NO: | Sequence | # Read |
|---|---|---|
| 2712 | NMLRR | 6 |
| 2713 | QMLRR | 6 |
| 2714 | TNLHR | 6 |
| 2715 | TSLHR | 6 |
| 2716 | VGLAR | 6 |
| 2717 | AALQR | 5 |
| 2718 | AGLDR | 5 |
| 48 | ATLKR | 5 |
| 1833 | DGLKK | 5 |
| 2719 | DTLQR | 5 |
| 2720 | DVLKR | 5 |
| 2721 | GALSR | 5 |
| 2722 | GMLKR | 5 |
| 2723 | GTLSR | 5 |
| 2724 | HNLER | 5 |
| 2725 | NGLLV | 5 |
| 2726 | NNLTR | 5 |
| 2727 | QALAV | 5 |
| 2728 | QGLAR | 5 |
| 2729 | QNLHR | 5 |
| 2730 | SALMR | 5 |
| 2731 | SLLLR | 5 |
| 2732 | SVLAR | 5 |
| 2733 | SVLTR | 5 |
| 2734 | TALRR | 5 |
| 74 | TMLRR | 5 |
| 2735 | TQLRV | 5 |
| 2736 | TTLLR | 5 |
| 2737 | TTLRR | 5 |
| 2738 | AALNR | 4 |
| 2739 | ATLVR | 4 |
| 2740 | DALHR | 4 |
| 2741 | DALMR | 4 |
| 2742 | DGLER | 4 |
| 2743 | DGLQR | 4 |
| 45 | DGLRV | 4 |

TABLE 16-continued

ZF5
selection on G:A
change position 8 of the CBS core motif.
Sequences reflect position 2 to 6.

| SEQ ID NO: | Sequence | # Read |
|---|---|---|
| 2744 | DLLRR | 4 |
| 1855 | DRLKV | 4 |
| 2745 | GGLGR | 4 |
| 2746 | GNLHR | 4 |
| 1892 | GTLKV | 4 |
| 2747 | GTLNR | 4 |
| 2748 | HALHR | 4 |
| 2749 | HALMR | 4 |
| 2750 | HILTR | 4 |
| 2751 | HLLLR | 4 |
| 2752 | HNLQR | 4 |
| 2753 | HTLGR | 4 |
| 2754 | IGLTG | 4 |
| 2755 | NGLLR | 4 |
| 2756 | NSLRR | 4 |
| 2757 | PNLIR | 4 |
| 2758 | PNLRR | 4 |
| 2759 | SALIR | 4 |
| 2760 | SILGR | 4 |
| 2761 | SPLVR | 4 |
| 2762 | STLTR | 4 |
| 2763 | TALKT | 4 |
| 2764 | TALTR | 4 |
| 2765 | TGLDR | 4 |
| 2766 | TSLKR | 4 |
| 2767 | TTLVR | 4 |
| 2768 | VGLQN | 4 |
| 2769 | VNLRR | 4 |
| 2770 | AALVR | 3 |
| 58 | ADLKR | 3 |
| 2771 | ANLGR | 3 |
| 2772 | ATLSR | 3 |
| 2773 | DNLQR | 3 |
| 2774 | DNLTR | 3 |
| 2775 | DRLRR | 3 |
| 2776 | DTLVR | 3 |
| 2777 | EGLVR | 3 |
| 2778 | GALNR | 3 |
| 2779 | GDLKR | 3 |
| 2780 | GDLTR | 3 |
| 62 | GGLGL | 3 |
| 2781 | GSLQR | 3 |
| 1930 | HALKR | 3 |
| 2782 | HGLHR | 3 |
| 1866 | HGLRV | 3 |
| 2783 | HTLKR | 3 |
| 2784 | HVLKR | 3 |
| 2785 | NGLDR | 3 |
| 2786 | NMLAR | 3 |
| 2787 | NSLAR | 3 |
| 2788 | NTLAR | 3 |
| 2789 | QGLHR | 3 |
| 2134 | SGLAV | 3 |
| 2790 | SILTR | 3 |
| 2791 | SILVR | 3 |
| 2792 | SQLKR | 3 |
| 2793 | SSLQR | 3 |
| 2794 | TALHR | 3 |
| 2795 | TALNR | 3 |
| 2796 | TALSR | 3 |
| 2797 | AGLGR | 2 |
| 2798 | AGLMR | 2 |
| 2799 | ASLQR | 2 |
| 2800 | ASLVR | 2 |
| 2801 | ATLMR | 2 |
| 2802 | AVLKR | 2 |
| 2803 | DALNR | 2 |
| 2804 | DALQR | 2 |
| 2805 | DALSR | 2 |
| 1853 | DGLRK | 2 |
| 2806 | DHLHR | 2 |

TABLE 16-continued

ZF5
selection on G:A
change position 8 of the CBS core motif.
Sequences reflect position 2 to 6.

| SEQ ID NO: | Sequence | # Read |
|---|---|---|
| 2807 | DHLVR | 2 |
| 2808 | DNLSR | 2 |
| 2809 | DTLSR | 2 |
| 2810 | DTLTR | 2 |
| 2811 | DVLRR | 2 |
| 2812 | EGLIR | 2 |
| 2813 | EGLSR | 2 |
| 2814 | GAEE . . . | 2 |
| 2815 | GALQR | 2 |
| 2319 | GALRV | 2 |
| 2816 | GDLRR | 2 |
| 2817 | GDLVR | 2 |
| 1957 | GGLKV | 2 |
| 2358 | GGLRV | 2 |
| 2818 | GSLAR | 2 |
| 2819 | GSLKR | 2 |
| 2820 | HDLRR | 2 |
| 2821 | HGLNR | 2 |
| 2822 | HHLIR | 2 |
| 2047 | HMLKR | 2 |
| 2823 | HMLRR | 2 |
| 2824 | HQLVR | 2 |
| 2825 | HSLAR | 2 |
| 2826 | HSLHR | 2 |
| 2827 | HSLRR | 2 |
| 46 | HTLKV | 2 |
| 2828 | HTLNR | 2 |
| 2829 | HTLTR | 2 |
| 2830 | HTLVR | 2 |
| 2831 | IGLKR | 2 |
| 2832 | ITLKR | 2 |
| 2833 | MTLKR | 2 |
| 2834 | NALHR | 2 |
| 2835 | NALSR | 2 |
| 2836 | NGLGR | 2 |
| 2837 | NTLHR | 2 |
| 2838 | QDLKR | 2 |
| 2839 | QGLLR | 2 |
| 2840 | QNLLR | 2 |
| 2841 | QNLRW | 2 |
| 2842 | QSLRR | 2 |
| 2843 | QTLKR | 2 |
| 2131 | SALKR | 2 |
| 2844 | SALRV | 2 |
| 2845 | SSLAR | 2 |
| 2846 | SSLSR | 2 |
| 2847 | STLDR | 2 |
| 2848 | STLER | 2 |
| 2849 | STLHR | 2 |
| 1851 | STLKV | 2 |
| 2850 | STLMR | 2 |
| 2851 | TALGR | 2 |
| 2852 | TGLAT | 2 |
| 2853 | TGLSV | 2 |
| 2854 | TGLVT | 2 |
| 2855 | TNLKV | 2 |
| 2856 | TNLSR | 2 |
| 2857 | TTLAR | 2 |
| 2858 | TTLGR | 2 |
| 2859 | TTLIR | 2 |
| 2860 | TTLKR | 2 |
| 2179 | TTLKT | 2 |
| 2861 | TVLRM | 2 |
| 2862 | VQLAM | 2 |
| 2863 | VTLTR | 2 |
|  | A*S . . . | 1 |
| 2864 | AALLR | 1 |
| 2865 | AALMR | 1 |
| 2866 | AAPER | 1 |
| 2867 | ADLRR | 1 |
| 2868 | AGLAW | 1 |

TABLE 16-continued

ZF5
selection on G:A
change position 8 of the CBS core motif.
Sequences reflect position 2 to 6.

| SEQ ID NO: | Sequence | # Read |
|---|---|---|
| 2869 | AGLRW | 1 |
| 2870 | AGLTS | 1 |
| 2871 | AILTR | 1 |
| 71 | AMLKR | 1 |
| 2872 | ANLPR | 1 |
| 1944 | ARLKR | 1 |
| 2873 | ARLQR | 1 |
| 2874 | ARLTR | 1 |
| 2875 | ASLRR | 1 |
| 2876 | ASLTR | 1 |
| 2877 | ATLDR | 1 |
| 2878 | ATLER | 1 |
| 2879 | ATLIR | 1 |
| 2880 | ATLLR | 1 |
| 2881 | ATLQR | 1 |
| 2882 | AVLRR | 1 |
| 1831 | DALKR | 1 |
| 1950 | DALRV | 1 |
| 2883 | DGLSV | 1 |
| 2884 | DILHR | 1 |
| 2885 | DQLRR | 1 |
| 2886 | DSLSR | 1 |
| 2887 | DTLAK | 1 |
| 2888 | DVLLR | 1 |
| 2889 | EALNR | 1 |
| 2890 | EALTR | 1 |
| 1953 | EGLKV | 1 |
| 2891 | EGLMR | 1 |
| 2892 | EGLQR | 1 |
| 2893 | EGLRL | 1 |
| 2894 | EGLRV | 1 |
| 2895 | EGVRR | 1 |
| 2896 | ELLRR | 1 |
| 2897 | ENLER | 1 |
| 2898 | ETLLR | 1 |
| 2899 | GALHR | 1 |
| 2900 | GGHRR | 1 |
| 2901 | GGLAG | 1 |
| 2356 | GGLAV | 1 |
| 2902 | GGLDV | 1 |
| 2903 | GGLGS | 1 |
| 2904 | GGLQE | 1 |
| 2905 | GGLVL | 1 |
| 1958 | GGLVT | 1 |
| 2906 | GGPSH | 1 |
| 2907 | GGPSR | 1 |
| 2908 | GGQRR | 1 |
| 2909 | GGVRR | 1 |
| 2910 | GGWR . . . | 1 |
| 2911 | GILER | 1 |
| 2912 | GKLRR | 1 |
| 2913 | GMLAR | 1 |
| 2914 | GNLIR | 1 |
| 2915 | GSLER | 1 |
| 2916 | GSLVR | 1 |
| 2917 | GTLER | 1 |
| 2918 | GTLGR | 1 |
| 2919 | GTLHR | 1 |
| 2920 | GTQVR | 1 |
| 2921 | GVLRR | 1 |
| 2922 | GVLTR | 1 |
| 2923 | HALGR | 1 |
| 43 | HALKV | 1 |
| 2924 | HDLAK | 1 |
| 2925 | HGAAR | 1 |
| 2035 | HGLKK | 1 |
| 2371 | HGLKM | 1 |
| 41 | HGLKV | 1 |
| 2926 | HGLSV | 1 |
| 2927 | HGLTW | 1 |
| 2928 | HGPAR | 1 |

TABLE 16-continued

ZF5
selection on G:A
change position 8 of the CBS core motif.
Sequences reflect position 2 to 6.

| SEQ ID NO: | Sequence | # Read |
|---|---|---|
| 2929 | HKLAR | 1 |
| 2930 | HNLLS | 1 |
| 2931 | HRLSR | 1 |
| 2932 | HSLNR | 1 |
| 2933 | HSLSR | 1 |
| 2934 | HTLHR | 1 |
| 2935 | HVLAR | 1 |
| 2936 | INLSR | 1 |
| 2937 | NALAR | 1 |
| 2938 | NHLVQ | 1 |
| 2939 | NTLIR | 1 |
| 2940 | NTLNR | 1 |
| 2941 | NTLQR | 1 |
| 2942 | NVLKR | 1 |
| 2943 | PALKR | 1 |
| 2944 | PGLLR | 1 |
|  | PWS . . . | 1 |
| 2945 | QAAWG . . . | 1 |
| 2946 | QALAR | 1 |
| 2947 | QALTR | 1 |
| 2948 | QDLIR | 1 |
| 2949 | QTLAR | 1 |
| 2950 | QTLQR | 1 |
| 2951 | QVLRR | 1 |
| 2952 | RGLTR | 1 |
| 2953 | RGLVR | 1 |
| 2954 | SALDR | 1 |
| 2955 | SALMC | 1 |
| 2956 | SALNR | 1 |
| 2957 | SDLAR | 1 |
| 2958 | SDLQR | 1 |
| 2959 | SDLRR | 1 |
| 2960 | SGPRR | 1 |
| 2961 | SLLSD | 1 |
| 2962 | SMLHR | 1 |
| 2963 | SNLQR | 1 |
| 2964 | SSLIR | 1 |
| 2965 | SSLKR | 1 |
| 2966 | STLLR | 1 |
| 2967 | STLNR | 1 |
| 2968 | STLRK | 1 |
| 2969 | SVLGR | 1 |
| 2970 | SVLRR | 1 |
| 2971 | TALER | 1 |
| 2972 | TALRT | 1 |
| 2973 | TDLAR | 1 |
| 2974 | TDLRR | 1 |
| 2975 | TGLQV | 1 |
| 2976 | TGLVRR | 1 |
| 2977 | TGPAR | 1 |
| 2978 | TMLKR | 1 |
| 2979 | TNLPR | 1 |
| 2980 | TSLAR | 1 |
| 2981 | TSLGG | 1 |
| 2982 | TSLGR | 1 |
| 2983 | TSLQR | 1 |
| 2984 | TSLVR | 1 |
| 2985 | VALAR | 1 |
| 2986 | VALKR | 1 |
| 2987 | VALSR | 1 |
| 2988 | VGLKC | 1 |
| 2989 | VGLSR | 1 |
| 2990 | VGLTM | 1 |
| 2991 | VNLAR | 1 |
| 2992 | VNLIR | 1 |
| 2993 | VNLNR | 1 |
| 2994 | VTLGR | 1 |
| 2995 | VTLKR | 1 |
| 2996 | VTLMR | 1 |
| 2997 | VTLRR | 1 |
| 2998 | WGLER | 1 |

TABLE 17

ZF5
selection on G:C
change at nt 8 of core motif in CBS.
Sequences reflect position 2 to 6.

| SEQ ID NO: | Sequence | # Read |
|---|---|---|
| 1843 | DGLRR | 498 |
| 108 | DALRR | 388 |
| 2463 | EGLRR | 348 |
| 1871 | DALVR | 288 |
| 1837 | DGLVR | 262 |
| 2468 | DGLAR | 261 |
| 1986 | AGLKR | 257 |
| 1870 | DGLTR | 255 |
| 2462 | TGLRR | 237 |
| 2530 | DTLRR | 196 |
| 59 | HGLRR | 192 |
| 66 | ATLRR | 176 |
| 2539 | ETLRR | 149 |
| 2464 | SGLRR | 142 |
| 2584 | GTLRR | 136 |
| 50 | GGLVR | 132 |
| 2545 | STLSR | 132 |
| 2707 | GTLQR | 131 |
| 2553 | DGLSR | 127 |
| 2027 | GGLKR | 126 |
| 2684 | GTLAR | 123 |
| 2578 | HTLAR | 114 |
| 2486 | SGLVR | 111 |
| 2779 | GDLKR | 109 |
| 2593 | QTLRR | 107 |
| 2472 | TGLVR | 106 |
| 2668 | STLGR | 103 |
| 2776 | DTLVR | 102 |
| 2563 | DGLNR | 100 |
| 2811 | DVLRR | 100 |
| 2698 | STLVR | 100 |
| 2720 | DVLKR | 99 |
| 48 | ATLKR | 96 |
| 2461 | GGLRR | 93 |
| 2638 | STLRR | 93 |
| 2802 | AVLKR | 91 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2816 | GDLRR | 90 |
| 2554 | GTLKR | 89 |
| 1932 | HGLKR | 89 |
| 56 | HTLRR | 89 |
| 2492 | TGLQR | 87 |
| 2559 | SGLKR | 86 |
| 2672 | DTLAR | 84 |
| 2654 | ATLAR | 83 |
| 2848 | STLER | 81 |
| 2737 | TTLRR | 80 |
| 2495 | EGLKR | 79 |
| 2562 | GTLTR | 79 |
| 2469 | TGLAR | 75 |
| 2529 | DGLHR | 74 |
| 54 | HGLVR | 74 |
| 2828 | HTLNR | 73 |
| 2967 | STLNR | 71 |
| 2489 | SSLRR | 69 |
| 2516 | TGLSR | 68 |
| 2772 | ATLSR | 67 |
| 2656 | DTLNR | 67 |
| 2788 | NTLAR | 66 |
| 58 | ADLKR | 65 |
| 2570 | DALAR | 65 |
| 2626 | GTLVR | 64 |
| 2719 | DTLQR | 62 |
| 2739 | ATLVR | 61 |
| 2478 | NGLVR | 61 |
| 109 | DGLKR | 59 |
| 2467 | GGLAR | 59 |
| 2568 | HSLVR | 59 |
| 2804 | DALQR | 58 |
| 2507 | TGLLR | 58 |
| 2640 | DMLKR | 57 |
| 55 | GGLTR | 56 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2867 | ADLRR | 55 |
| 2474 | SGLSR | 55 |
| 2564 | SSLVR | 54 |
| 2500 | TGLKR | 53 |
| 2475 | AGLRR | 52 |
| 2550 | STLAR | 52 |
| 2783 | HTLKR | 51 |
| 2587 | NTLRR | 51 |
| 2857 | TTLAR | 51 |
| 2622 | ATLTR | 49 |
| 2817 | GDLVR | 49 |
| 2667 | SDLKR | 49 |
| 2767 | TTLVR | 49 |
| 2466 | SGLAR | 48 |
| 2847 | STLDR | 48 |
| 2850 | STLMR | 48 |
| 2515 | TGLNR | 48 |
| 2502 | ETLKR | 47 |
| 2970 | SVLRR | 47 |
| 2849 | STLHR | 46 |
| 2959 | SDLRR | 45 |
| 2699 | SVLKR | 44 |
| 2488 | HGLTR | 43 |
| 2702 | DSLRR | 42 |
| 2974 | TDLRR | 42 |
| 2471 | HGLAR | 40 |
| 2586 | HTLMR | 40 |
| 2477 | SGLTR | 40 |
| 2966 | STLLR | 40 |
| 2736 | TTLLR | 40 |
| 2636 | NGLKR | 39 |
| 2810 | DTLTR | 38 |
| 2598 | EGLNR | 37 |
| 2723 | GTLSR | 37 |
| 2978 | TMLKR | 37 |
| 2589 | TSLRR | 37 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2801 | ATLMR | 36 |
| 2999 | DALTR | 36 |
| 2697 | STLQR | 36 |
| 2762 | STLTR | 36 |
| 2780 | GDLTR | 35 |
| 2476 | GGLSR | 35 |
| 51 | HGLIR | 35 |
| 2509 | ASLKR | 34 |
| 2630 | SSLTR | 34 |
| 1985 | AALKR | 33 |
| 3000 | DALIR | 33 |
| 2859 | TTLIR | 33 |
| 2490 | EGLTR | 32 |
| 2753 | HTLGR | 32 |
| 2613 | HTLQR | 32 |
| 2692 | QSLKR | 32 |
| 2701 | DSLKR | 31 |
| 2131 | SALKR | 31 |
| 2845 | SSLAR | 31 |
| 2618 | TTLMR | 31 |
| 2878 | ATLER | 30 |
| 2086 | NALKR | 30 |
| 2594 | SGLIR | 30 |
| 2556 | SMLRR | 30 |
| 3001 | GVLKR | 29 |
| 53 | TGLTR | 29 |
| 2497 | EGLAR | 28 |
| 2612 | HTLER | 28 |
| 2766 | TSLKR | 28 |
| 3002 | GDLHR | 27 |
| 2644 | HNLVR | 27 |
| 1936 | HTLRV | 27 |
| 2465 | AGLAR | 26 |
| 3003 | GDLNR | 26 |
| 2503 | HGLLR | 26 |

TABLE 17-continued

ZF5
selection on G:C
change at nt 8 of core motif in CBS.
Sequences reflect position 2 to 6.

| SEQ ID NO: | Sequence | # Read |
|---|---|---|
| 3004 | SILKR | 26 |
| 2858 | TTLGR | 26 |
| 2499 | DGLIR | 25 |
| 2732 | SVLAR | 25 |
| 2590 | TTLQR | 25 |
| 2473 | AGLTR | 24 |
| 1988 | AGLVR | 24 |
| 2805 | DALSR | 24 |
| 3005 | DTLIR | 24 |
| 2777 | EGLVR | 24 |
| 2579 | QGLKR | 24 |
| 2820 | HDLRR | 23 |
| 2784 | HVLKR | 23 |
| 3006 | NTLTR | 23 |
| 2957 | SDLAR | 23 |
| 2965 | SSLKR | 23 |
| 2973 | TDLAR | 23 |
| 2803 | DALNR | 22 |
| 3007 | HTLIR | 22 |
| 2628 | NTLKR | 22 |
| 2838 | QDLKR | 22 |
| 2860 | TTLKR | 22 |
| 3008 | EVLRR | 21 |
| 3009 | GDLSR | 21 |
| 3010 | HVLRR | 21 |
| 2837 | NTLHR | 21 |
| 3011 | TDLTR | 21 |
| 2681 | TTLNR | 21 |
| 1833 | DGLKK | 20 |
| 2520 | DMLRR | 20 |
| 2919 | GTLHR | 20 |
| 2833 | MTLKR | 20 |
| 2980 | TSLAR | 20 |
| 3012 | ATLHR | 19 |
| 3013 | DSLVR | 19 |
| 3014 | GTLDR | 19 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2830 | HTLVR | 19 |
| 3015 | NTLLR | 19 |
| 2843 | QTLKR | 19 |
| 2634 | ESLRR | 18 |
| 3016 | HDLQR | 18 |
| 2821 | HGLNR | 18 |
| 2823 | HMLRR | 18 |
| 57 | TVLKR | 18 |
| 3017 | ATLNR | 17 |
| 2596 | DGLGR | 17 |
| 2485 | NGLRR | 17 |
| 2549 | SGLNR | 17 |
| 2501 | SGLQR | 17 |
| 3018 | STLIR | 16 |
| 2617 | TALKR | 16 |
| 2519 | TGLIR | 16 |
| 3019 | TTLSR | 16 |
| 3020 | DILKR | 15 |
| 3021 | ETLNR | 15 |
| 2916 | GSLVR | 15 |
| 3022 | MDLKR | 15 |
| 2504 | NGLQR | 15 |
| 2949 | QTLAR | 15 |
| 2964 | SSLIR | 15 |
| 2538 | AALRR | 14 |
| 2818 | GSLAR | 14 |
| 2484 | HGLQR | 14 |
| 2512 | NGLTR | 14 |
| 3023 | QDLRR | 14 |
| 2588 | TGLHR | 14 |
| 3024 | TSLTR | 14 |
| 71 | AMLKR | 13 |
| 3025 | ATLGR | 13 |
| 3026 | GDLQR | 13 |
| 2470 | GGLQR | 13 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2819 | GSLKR | 13 |
| 3027 | NTLVR | 13 |
| 3028 | SILRR | 13 |
| 2582 | SNLVR | 13 |
| 2846 | SSLSR | 13 |
| 2995 | VTLKR | 13 |
| 2880 | ATLLR | 12 |
| 2597 | DSLQR | 12 |
| 2659 | GGLNR | 12 |
| 2548 | HGLSR | 12 |
| 2525 | SGLLR | 12 |
| 2792 | SQLKR | 12 |
| 2505 | TGLMR | 12 |
| 2982 | TSLGR | 12 |
| 2479 | AGLQR | 11 |
| 2670 | DILRR | 11 |
| 3029 | DTLER | 11 |
| 3030 | DTLLR | 11 |
| 2917 | GTLER | 11 |
| 2689 | HTLLR | 11 |
| 2540 | NGLAR | 11 |
| 2663 | NGLHR | 11 |
| 3031 | SDLTR | 11 |
| 3032 | SMLKR | 11 |
| 1849 | TTLKV | 11 |
| 2879 | ATLIR | 10 |
| 2722 | GMLKR | 10 |
| 2600 | GSLRR | 10 |
| 3033 | GTLLR | 10 |
| 2510 | QGLRR | 10 |
| 2480 | AGLHR | 9 |
| 2498 | AGLSR | 9 |
| 2740 | DALHR | 9 |
| 2005 | DGLLR | 9 |
| 3034 | DTLGR | 9 |
| 3035 | GDLAR | 9 |
| 1930 | HALKR | 9 |
| 2782 | HGLHR | 9 |
| 46 | HTLKV | 9 |
| 3036 | HVLVR | 9 |
| 2664 | NMLKR | 9 |
| 2939 | NTLIR | 9 |
| 3037 | QDLAR | 9 |
| 2560 | TGLGR | 9 |
| 2875 | ASLRR | 8 |
| 2881 | ATLQR | 8 |
| 3038 | ETLAR | 8 |
| 2592 | GALTR | 8 |
| 2607 | GALVR | 8 |
| 2547 | HALVR | 8 |
| 2643 | HGLMR | 8 |
| 3039 | HILKR | 8 |
| 3040 | HMLVR | 8 |
| 2827 | HSLRR | 8 |
| 3041 | NTLSR | 8 |
| 2948 | QDLIR | 8 |
| 3042 | SDLVR | 8 |
| 2537 | SGLMR | 8 |
| 2677 | SMLTR | 8 |
| 2189 | TSLKV | 8 |
| 2651 | TTLTR | 8 |
| 2700 | AALTR | 7 |
| 3043 | ETLQR | 7 |
| 2521 | GALKR | 7 |
| 2641 | GALRR | 7 |
| 2528 | GGLIR | 7 |
| 117 | GNLVR | 7 |
| 3044 | HDLGR | 7 |
| 3045 | HDLTR | 7 |
| 2826 | HSLHR | 7 |
| 2934 | HTLHR | 7 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2942 | NVLKR | 7 |
| 2678 | TALAR | 7 |
| 3046 | TDLKR | 7 |
| 1845 | TGLKV | 7 |
| 3047 | TSLNR | 7 |
| 2983 | TSLQR | 7 |
| 3048 | VDLKR | 7 |
| 2014 | DVLKK | 6 |
| 3049 | GILKR | 6 |
| 2921 | GVLRR | 6 |
| 2610 | HALAR | 6 |
| 2483 | HALRR | 6 |
| 2531 | HLLKR | 6 |
| 3050 | HNLKR | 6 |
| 2834 | NALHR | 6 |
| 3051 | QDLQR | 6 |
| 2616 | QGLVR | 6 |
| 2532 | SALAR | 6 |
| 3052 | SDLGR | 6 |
| 2514 | SGLHR | 6 |
| 2302 | STLKT | 6 |
| 3053 | TDLSR | 6 |
| 2565 | TGLER | 6 |
| 2742 | DGLER | 5 |
| 3054 | DILVR | 5 |
| 2566 | DTLKR | 5 |
| 1884 | EALKR | 5 |
| 2657 | EILKR | 5 |
| 3055 | GVLVG | 5 |
| 3056 | HSLTR | 5 |
| 3057 | HTLDR | 5 |
| 2937 | NALAR | 5 |
| 2572 | NGLIR | 5 |
| 2555 | NGLSR | 5 |
| 3058 | QQLQR | 5 |
| 2523 | SALRR | 5 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2694 | SALVR | 5 |
| 2513 | SGLDR | 5 |
| 2581 | SGLGR | 5 |
| 2496 | SNLLR | 5 |
| 3059 | SVLLR | 5 |
| 3060 | TDLGR | 5 |
| 3061 | TDLQR | 5 |
| 2534 | VGLKR | 5 |
| 2493 | AGLIR | 4 |
| 2576 | AILKR | 4 |
| 3062 | ALLKR | 4 |
| 2683 | DSLAR | 4 |
| 2886 | DSLSR | 4 |
| 3063 | DTLRK | 4 |
| 3064 | ETLTR | 4 |
| 3065 | GELTR | 4 |
| 70 | GNLTR | 4 |
| 2660 | GSLTR | 4 |
| 2918 | GTLGR | 4 |
| 2748 | HALHR | 4 |
| 3066 | HDLNR | 4 |
| 2482 | HNLLR | 4 |
| 3067 | MTLRR | 4 |
| 2615 | NGLMR | 4 |
| 3068 | NTLER | 4 |
| 2956 | SALNR | 4 |
| 2958 | SDLQR | 4 |
| 3069 | SELKR | 4 |
| 2580 | SGLER | 4 |
| 2604 | SSLGR | 4 |
| 3070 | STLSM | 4 |
| 3071 | TDLMR | 4 |
| 68 | TNLRR | 4 |
| 2650 | TQLKR | 4 |
| 3072 | TSLLR | 4 |

TABLE 17-continued

ZF5
selection on G:C
change at nt 8 of core motif in CBS.
Sequences reflect position 2 to 6.

| SEQ ID NO: | Sequence | # Read |
|---|---|---|
| 3073 | TSLMR | 4 |
| 2984 | TSLVR | 4 |
| 3074 | TTLER | 4 |
| 3075 | TVLRR | 4 |
| 2738 | AALNR | 3 |
| 3076 | ADLTR | 3 |
| 2669 | AGLER | 3 |
| 2542 | ANLAR | 3 |
| 69 | ANLRR | 3 |
| 2877 | ATLDR | 3 |
| 2741 | DALMR | 3 |
| 3077 | DILTR | 3 |
| 3078 | DMLQR | 3 |
| 2632 | DNLAR | 3 |
| 2591 | DNLKR | 3 |
| 2809 | DTLSR | 3 |
| 3079 | DVLVR | 3 |
| 2583 | EALRR | 3 |
| 2813 | EGLSR | 3 |
| 3080 | ETLRK | 3 |
| 2481 | GNLER | 3 |
| 3081 | GTLMR | 3 |
| 2747 | GTLNR | 3 |
| 3082 | HAEG . . . | 3 |
| 3083 | HDLMR | 3 |
| 3084 | HMLQR | 3 |
| 2577 | HNLTR | 3 |
| 3085 | HSLKR | 3 |
| 2829 | HTLTR | 3 |
| 2935 | HVLAR | 3 |
| 2835 | NALSR | 3 |
| 2518 | NNLVR | 3 |
| 3086 | QSLNR | 3 |
| 3087 | SILAR | 3 |
| 2962 | SMLHR | 3 |
| 297 | STLRV | 3 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2733 | SVLTR | 3 |
| 3088 | SVLVR | 3 |
| 2734 | TALRR | 3 |
| 2981 | TSLGG | 3 |
| 2994 | VTLGR | 3 |
| 2546 | AALAR | 2 |
| 2864 | AALLR | 2 |
| 2770 | AALVR | 2 |
| 3089 | ADLVR | 2 |
| 2569 | AGLNR | 2 |
| 2494 | ANLVR | 2 |
| 3090 | ASLAR | 2 |
| 3091 | ASLIR | 2 |
| 2800 | ASLVR | 2 |
| 2655 | DALGR | 2 |
| 3552 | DGLDR | 2 |
| 2743 | DGLQR | 2 |
| 1853 | DGLRK | 2 |
| 2506 | DNLVR | 2 |
| 3092 | DVLMR | 2 |
| 3093 | DVLQR | 2 |
| 3094 | EGLGR | 2 |
| 3095 | EGLHR | 2 |
| 2892 | EGLQR | 2 |
| 2658 | ESLKR | 2 |
| 2536 | GGLMR | 2 |
| 138 | GNLAR | 2 |
| 139 | GNLMR | 2 |
| 3096 | HDLSR | 2 |
| 2687 | HGLDR | 2 |
| 2585 | HGLGR | 2 |
| 2371 | HGLKM | 2 |
| 3097 | HILMR | 2 |
| 2557 | HNLHR | 2 |
| 2627 | HNLSR | 2 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2611 | HSLIR | 2 |
| 3098 | HSLQR | 2 |
| 3099 | HVLHR | 2 |
| 3100 | IDLKR | 2 |
| 2755 | NGLLR | 2 |
| 3101 | NILVR | 2 |
| 2943 | PALKR | 2 |
| 3102 | PGLAR | 2 |
| 3103 | PTLMR | 2 |
| 2573 | QGLTR | 2 |
| 2574 | QMLKR | 2 |
| 2842 | QSLRR | 2 |
| 3104 | QTLSR | 2 |
| 2759 | SALIR | 2 |
| 2603 | SALSR | 2 |
| 3105 | SELRR | 2 |
| 2487 | SNLDR | 2 |
| 116 | SNLRR | 2 |
| 2544 | SNLSR | 2 |
| 2696 | SQLRR | 2 |
| 2153 | STLKR | 2 |
| 2968 | STLRK | 2 |
| 3106 | TDLHR | 2 |
| 3107 | TDLVR | 2 |
| 3108 | TGLKL | 2 |
| 2157 | TGLRV | 2 |
| 3109 | TMLNR | 2 |
| 2649 | TNLAR | 2 |
| 2595 | TNLKR | 2 |
| 2511 | TNLVR | 2 |
| 3110 | TSLIR | 2 |
| 2176 | TTLKA | 2 |
| 3111 | VDLRR | 2 |
| 3112 | VTLAR | 2 |
| 3113 | AALHR | 1 |
| 2717 | AALQR | 1 |
| 2866 | AAPER | 1 |
| 3114 | ADLNR | 1 |
| 3115 | ADLRV | 1 |
| 2868 | AGLAW | 1 |
| 3116 | AGLKK | 1 |
| 2527 | AGLLR | 1 |
| 3117 | AILRR | 1 |
| 2621 | ANLNR | 1 |
| 3118 | ASLKS | 1 |
| 2799 | ASLQR | 1 |
| 2876 | ASLTR | 1 |
| 3119 | ASMKR | 1 |
| 3120 | ATPVP | 1 |
| 2882 | AVLRR | 1 |
| 3121 | AVLTR | 1 |
| 3122 | CGLRR | 1 |
| 3123 | DAEA . . . | 1 |
| 3124 | DALER | 1 |
| 1831 | DALKR | 1 |
| 2682 | DALLR | 1 |
| 3125 | DALPR | 1 |
| 3126 | DARRR | 1 |
| 3127 | DDLNR | 1 |
| 3128 | DGAAE . . . | 1 |
| 1852 | DGLKV | 1 |
| 3129 | DGLWR | 1 |
| 3130 | DGPAR | 1 |
| 3131 | DGPKK | 1 |
| 3132 | DGRRR | 1 |
| 3133 | DGVRR | 1 |
| 3134 | DMLTR | 1 |
| 2535 | DNLLR | 1 |
| 2808 | DNLSR | 1 |
| 3135 | DSLNR | 1 |
| 3136 | DTLDR | 1 |

TABLE 17-continued

ZF5
selection on G:C
change at nt 8 of core motif in CBS.
Sequences reflect position 2 to 6.

| SEQ ID NO: | Sequence | # Read |
|---|---|---|
| 371 | DTLRV | 1 |
| 3137 | DVLRK | 1 |
| 3138 | DVLRS | 1 |
| 3139 | DVLSR | 1 |
| 3140 | DVQKR | 1 |
| 3141 | EALVR | 1 |
| 2812 | EGLIR | 1 |
| 3142 | EGLKM | 1 |
| 2704 | EGLLR | 1 |
| 2891 | EGLMR | 1 |
| 3143 | EGLQC | 1 |
| 3144 | EGLRS | 1 |
| 2894 | EGLRV | 1 |
| 3145 | EGRRR | 1 |
| 2895 | EGVRR | 1 |
| 3146 | EGWS . . . | 1 |
| 2705 | ENLAR | 1 |
| 2633 | ENLSR | 1 |
| 3147 | ESLAR | 1 |
| 3148 | ETGWG . . . | 1 |
| 3149 | ETLER | 1 |
| 3150 | ETLHR | 1 |
| 3151 | ETLVR | 1 |
| 3152 | ETRRR | 1 |
| 3153 | EVLKR | 1 |
| 2814 | GAEE . . . | 1 |
| 3154 | GALAR | 1 |
| 2778 | GALNR | 1 |
| 3155 | GDLYR | 1 |
| 3156 | GDPAP . . . | 1 |
| 2642 | GGLDR | 1 |
| 2745 | GGLGR | 1 |
| 2904 | GGLQE | 1 |
| 3157 | GGQTR | 1 |
| 3158 | GGVR | 1 |
| 3159 | GHLQR | 1 |
| 3160 | GILRR | 1 |
| 3161 | GMLRR | 1 |
| 2522 | GNLDR | 1 |
| 3162 | GNLLL | 1 |
| 2517 | GNLLR | 1 |
| 2609 | GNLQR | 1 |
| 3163 | GNLVM | 1 |
| 2685 | GTLLV | 1 |
| 2192 | GTLRV | 1 |
| 3164 | GTLRW | 1 |
| 3165 | GTPHR | 1 |
| 3166 | GVLAR | 1 |
| 3167 | GVLNR | 1 |
| 3168 | GVLVR | 1 |
| 3169 | GWLSR | 1 |
| 3170 | HAEA . . . | 1 |
| 43 | HALKV | 1 |
| 3171 | HDLKR | 1 |
| 3172 | HELTR | 1 |
| 3173 | HGLRW | 1 |
| 3174 | HGMRR | 1 |
| 3175 | HILIR | 1 |
| 3176 | HLLNR | 1 |
| 2661 | HNLAR | 1 |
| 3177 | HPAP . . . | 1 |
| 2645 | HQLIR | 1 |
| 2825 | HSLAR | 1 |
| 2933 | HSLSR | 1 |
| 3178 | HTLNK | 1 |
| 3179 | HTLRA | 1 |
| 3180 | HTLRG | 1 |
| 3181 | HTLSR | 1 |
| 2709 | HVLER | 1 |
| 3182 | HWLLR | 1 |
| 2710 | IGLRR | 1 |

TABLE 17-continued

ZF5
selection on G:C
change at nt 8 of core motif in CBS.
Sequences reflect position 2 to 6.

| SEQ ID NO: | Sequence | # Read |
|---|---|---|
| 2754 | IGLTG | 1 |
| 2711 | INLTR | 1 |
| 3183 | ITLTR | 1 |
| 3184 | KGLPG | 1 |
| 3185 | MDVKG | 1 |
| 3186 | MTLIR | 1 |
| 2635 | NALRR | 1 |
| 2676 | NALVR | 1 |
| 2614 | NGLER | 1 |
| 2938 | NHLVQ | 1 |
| 2786 | NMLAR | 1 |
| 2543 | NNLAR | 1 |
| 2637 | NNLLR | 1 |
| 2787 | NSLAR | 1 |
| 2940 | NTLNR | 1 |
| 2941 | NTLQR | 1 |
| 3187 | P*MGS | 1 |
| 3188 | PALKP | 1 |
| 3189 | PGWAG | 1 |
| 3190 | PTLKR | 1 |
| 3191 | PTLRR | 1 |
|  | PWS . . . | 1 |
| 2602 | QALKR | 1 |
| 2947 | QALTR | 1 |
| 3192 | QDLAT | 1 |
| 3193 | QDLVR | 1 |
| 2728 | QGLAR | 1 |
| 2729 | QNLHR | 1 |
| 2646 | QNLQR | 1 |
| 2575 | QNLRR | 1 |
| 2841 | QNLRW | 1 |
| 3194 | QPACV | 1 |
| 3195 | QTLHR | 1 |
| 2950 | QTLQR | 1 |
| 3196 | QTLTR | 1 |
| 3197 | RGLKR | 1 |

TABLE 17-continued

ZF5
selection on G:C
change at nt 8 of core motif in CBS.
Sequences reflect position 2 to 6.

| SEQ ID NO: | Sequence | # Read |
|---|---|---|
| 3198 | RPAA . . . | 1 |
| 2336 | RTLKV | 1 |
| 3199 | SALHR | 1 |
| 1887 | SALKV | 1 |
| 2955 | SALMC | 1 |
| 2730 | SALMR | 1 |
| 3200 | SDLKS | 1 |
| 3201 | SILKV | 1 |
| 3202 | SILNR | 1 |
| 2791 | SILVR | 1 |
| 2533 | SMLAR | 1 |
| 3203 | SMLLR | 1 |
| 3204 | SMLR | 1 |
| 2524 | SNLAR | 1 |
| 3205 | SNLHR | 1 |
| 2963 | SNLQR | 1 |
| 3206 | SPLHR | 1 |
| 3207 | SSLKW | 1 |
| 3208 | STPER | 1 |
| 3209 | STQVR | 1 |
| 3210 | SVLQR | 1 |
| 3211 | SVLSR | 1 |
| 2795 | TALNR | 1 |
| 2631 | TALVR | 1 |
| 2765 | TGLDR | 1 |
| 3212 | TGLKW | 1 |
| 3213 | TGLNV | 1 |
| 3214 | TGLQC | 1 |
| 3215 | TGLRQ | 1 |
| 2977 | TGPAR | 1 |
| 3216 | TGPNR | 1 |
| 3217 | TGQRR | 1 |
| 74 | TMLRR | 1 |
| 2561 | TNLMR | 1 |
| 2526 | TNLNR | 1 |
| 3218 | TRLVR | 1 |

TABLE 17-continued

ZF5
selection on G:C
change at nt 8 of core motif in CBS.
Sequences reflect position 2 to 6.

| SEQ ID NO: | Sequence | # Read |
|---|---|---|
| 3219 | TSLIS | 1 |
| 3220 | TTLDR | 1 |
| 3221 | TTLKK | 1 |
| 3222 | TTLRT | 1 |
| 1919 | TTLRV | 1 |
| 2861 | TVLRM | 1 |
| 2985 | VALAR | 1 |
| 3223 | VALRR | 1 |
| 3224 | VGLHR | 1 |
| 3225 | VGLNR | 1 |
| 2652 | VGLQR | 1 |
| 2619 | VGLRR | 1 |
| 2990 | VGLTM | 1 |
| 2605 | VNLKR | 1 |
| 3226 | YGLAR | 1 |
| 3227 | YGLVR | 1 |
| 3228 | YILRR | 1 |

TABLE 18

ZF5
selection on G:T
change at nt 8 of core motif in CBS.
Sequences reflect position 2 to 6.

| SEQ ID NO: | Sequence | Read # |
|---|---|---|
| 50 | GGLVR | 178 |
| 2538 | AALRR | 174 |
| 2607 | GALVR | 170 |
| 2462 | TGLRR | 162 |
| 2464 | SGLRR | 158 |
| 2461 | GGLRR | 152 |
| 2463 | EGLRR | 148 |
| 2475 | AGLRR | 143 |
| 2641 | GALRR | 126 |
| 56 | HTLRR | 125 |
| 2027 | GGLKR | 117 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2700 | AALTR | 111 |
| 2473 | AGLTR | 108 |
| 2521 | GALKR | 104 |
| 2465 | AGLAR | 102 |
| 54 | HGLVR | 101 |
| 1932 | HGLKR | 99 |
| 2610 | HALAR | 97 |
| 1986 | AGLKR | 96 |
| 59 | HGLRR | 96 |
| 1985 | AALKR | 94 |
| 2466 | SGLAR | 93 |
| 66 | ATLRR | 90 |
| 2539 | ETLRR | 90 |
| 2471 | HGLAR | 90 |
| 2495 | EGLKR | 83 |
| 2477 | SGLTR | 82 |
| 2488 | HGLTR | 79 |
| 1843 | DGLRR | 77 |
| 2592 | GALTR | 75 |
| 2467 | GGLAR | 74 |
| 2483 | HALRR | 74 |
| 2523 | SALRR | 71 |
| 2486 | SGLVR | 70 |
| 2734 | TALRR | 69 |
| 3154 | GALAR | 66 |
| 2500 | TGLKR | 66 |
| 55 | GGLTR | 63 |
| 2694 | SALVR | 61 |
| 2875 | ASLRR | 57 |
| 108 | DALRR | 57 |
| 2530 | DTLRR | 52 |
| 2819 | GSLKR | 50 |
| 2748 | HALHR | 46 |
| 2568 | HSLVR | 46 |
| 2546 | AALAR | 45 |
| 2131 | SALKR | 45 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2583 | EALRR | 44 |
| 2770 | AALVR | 42 |
| 1884 | EALKR | 42 |
| 2827 | HSLRR | 42 |
| 2532 | SALAR | 42 |
| 2666 | SALTR | 42 |
| 2489 | SSLRR | 41 |
| 2654 | ATLAR | 40 |
| 1930 | HALKR | 40 |
| 2587 | NTLRR | 40 |
| 2956 | SALNR | 40 |
| 2479 | AGLQR | 39 |
| 1837 | DGLVR | 38 |
| 2502 | ETLKR | 38 |
| 49 | QALRR | 38 |
| 2678 | TALAR | 36 |
| 2857 | TTLAR | 36 |
| 2737 | TTLRR | 36 |
| 2547 | HALVR | 35 |
| 2578 | HTLAR | 35 |
| 2476 | GGLSR | 34 |
| 2738 | AALNR | 33 |
| 2470 | GGLQR | 33 |
| 2564 | SSLVR | 33 |
| 2656 | DTLNR | 31 |
| 2600 | GSLRR | 31 |
| 2586 | HTLMR | 30 |
| 2559 | SGLKR | 30 |
| 2550 | STLAR | 30 |
| 2498 | AGLSR | 29 |
| 1988 | AGLVR | 29 |
| 2509 | ASLKR | 29 |
| 2684 | GTLAR | 29 |
| 3229 | QALVR | 29 |
| 2594 | SGLIR | 29 |
| 2545 | STLSR | 29 |
| 2472 | TGLVR | 29 |
| 2468 | DGLAR | 28 |
| 2701 | DSLKR | 28 |
| 2762 | STLTR | 28 |
| 2653 | AALSR | 27 |
| 2674 | HALSR | 27 |
| 2603 | SALSR | 27 |
| 2850 | STLMR | 26 |
| 2828 | HTLNR | 25 |
| 1870 | DGLTR | 24 |
| 51 | HGLIR | 24 |
| 2628 | NTLKR | 24 |
| 2589 | TSLRR | 24 |
| 2997 | VTLRR | 24 |
| 2569 | AGLNR | 23 |
| 2721 | GALSR | 23 |
| 2630 | SSLTR | 22 |
| 2480 | AGLHR | 21 |
| 2778 | GALNR | 21 |
| 2753 | HTLGR | 21 |
| 2593 | QTLRR | 21 |
| 53 | TGLTR | 21 |
| 2717 | AALQR | 20 |
| 2562 | GTLTR | 20 |
| 2643 | HGLMR | 20 |
| 2617 | TALKR | 20 |
| 2799 | ASLQR | 19 |
| 2739 | ATLVR | 19 |
| 1831 | DALKR | 19 |
| 2634 | ESLRR | 19 |
| 2659 | GGLNR | 19 |
| 2622 | ATLTR | 18 |
| 2528 | GGLIR | 18 |
| 2660 | GSLTR | 18 |
| 2554 | GTLKR | 18 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2707 | GTLQR | 18 |
| 2636 | NGLKR | 18 |
| 2667 | SDLKR | 18 |
| 2698 | STLVR | 18 |
| 2584 | GTLRR | 17 |
| 2525 | SGLLR | 17 |
| 2493 | AGLIR | 16 |
| 2800 | ASLVR | 16 |
| 2818 | GSLAR | 16 |
| 2934 | HTLHR | 16 |
| 2549 | SGLNR | 16 |
| 2474 | SGLSR | 16 |
| 1871 | DALVR | 15 |
| 2916 | GSLVR | 15 |
| 2782 | HGLHR | 15 |
| 2878 | ATLER | 14 |
| 3098 | HSLQR | 14 |
| 2501 | SGLQR | 14 |
| 2519 | TGLIR | 14 |
| 2516 | TGLSR | 14 |
| 2858 | TTLGR | 14 |
| 2767 | TTLVR | 14 |
| 2995 | VTLKR | 14 |
| 2772 | ATLSR | 13 |
| 2702 | DSLRR | 13 |
| 2759 | SALIR | 13 |
| 2631 | TALVR | 13 |
| 2736 | TTLLR | 13 |
| 2864 | AALLR | 12 |
| 3230 | HALTR | 12 |
| 2616 | QGLVR | 12 |
| 2469 | TGLAR | 12 |
| 2880 | ATLLR | 11 |
| 2563 | DGLNR | 11 |
| 2626 | GTLVR | 11 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2602 | QALKR | 11 |
| 3231 | SALLR | 11 |
| 3232 | SSLHR | 11 |
| 2967 | STLNR | 11 |
| 2492 | TGLQR | 11 |
| 2590 | TTLQR | 11 |
| 2876 | ASLTR | 10 |
| 109 | DGLKR | 10 |
| 2756 | NSLRR | 10 |
| 2692 | QSLKR | 10 |
| 2537 | SGLMR | 10 |
| 2849 | STLHR | 10 |
| 2638 | STLRR | 10 |
| 3113 | AALHR | 9 |
| 2879 | ATLIR | 9 |
| 3017 | ATLNR | 9 |
| 2672 | DTLAR | 9 |
| 2566 | DTLKR | 9 |
| 2484 | HGLQR | 9 |
| 2933 | HSLSR | 9 |
| 2943 | PALKR | 9 |
| 2964 | SSLIR | 9 |
| 2764 | TALTR | 9 |
| 2588 | TGLHR | 9 |
| 2881 | ATLQR | 8 |
| 3007 | HTLIR | 8 |
| 2829 | HTLTR | 8 |
| 2941 | NTLQR | 8 |
| 2579 | QGLKR | 8 |
| 2699 | SVLKR | 8 |
| 3047 | TSLNR | 8 |
| 3233 | AALIR | 7 |
| 2865 | AALMR | 7 |
| 2999 | DALTR | 7 |
| 2719 | DTLQR | 7 |
| 3234 | GSLHR | 7 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2781 | GSLQR | 7 |
| 2548 | HGLSR | 7 |
| 2478 | NGLVR | 7 |
| 2965 | SSLKR | 7 |
| 2848 | STLER | 7 |
| 2795 | TALNR | 7 |
| 48 | ATLKR | 6 |
| 2802 | AVLKR | 6 |
| 3038 | ETLAR | 6 |
| 2503 | HGLLR | 6 |
| 2830 | HTLVR | 6 |
| 2784 | HVLKR | 6 |
| 3235 | NALQR | 6 |
| 2485 | NGLRR | 6 |
| 3236 | NSLVR | 6 |
| 2580 | SGLER | 6 |
| 2514 | SGLHR | 6 |
| 2860 | TTLKR | 6 |
| 3237 | AALER | 5 |
| 3238 | AALGR | 5 |
| 3025 | ATLGR | 5 |
| 2598 | EGLNR | 5 |
| 2904 | GGLQE | 5 |
| 70 | GNLTR | 5 |
| 2086 | NALKR | 5 |
| 2788 | NTLAR | 5 |
| 2843 | QTLKR | 5 |
| 2950 | QTLQR | 5 |
| 2505 | TGLMR | 5 |
| 2515 | TGLNR | 5 |
| 2980 | TSLAR | 5 |
| 2743 | DGLQR | 4 |
| 2703 | DTLMR | 4 |
| 2777 | EGLVR | 4 |
| 2745 | GGLGR | 4 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2536 | GGLMR | 4 |
| 3239 | GSLIR | 4 |
| 3240 | GSLNR | 4 |
| 2673 | HALLR | 4 |
| 2783 | HTLKR | 4 |
| 46 | HTLKV | 4 |
| 2938 | NHLVQ | 4 |
| 2510 | QGLRR | 4 |
| 3241 | QVLKR | 4 |
| 3199 | SALHR | 4 |
| 2845 | SSLAR | 4 |
| 2668 | STLGR | 4 |
| 3018 | STLIR | 4 |
| 2966 | STLLR | 4 |
| 3242 | TALQR | 4 |
| 3073 | TSLMR | 4 |
| 3243 | AALDR | 3 |
| 2527 | AGLLR | 3 |
| 2542 | ANLAR | 3 |
| 69 | ANLRR | 3 |
| 3244 | ASLSR | 3 |
| 3012 | ATLHR | 3 |
| 2570 | DALAR | 3 |
| 2804 | DALQR | 3 |
| 2499 | DGLIR | 3 |
| 2553 | DGLSR | 3 |
| 2520 | DMLRR | 3 |
| 2497 | EGLAR | 3 |
| 2490 | EGLTR | 3 |
| 2658 | ESLKR | 3 |
| 2491 | GGLER | 3 |
| 2625 | GGLLR | 3 |
| 138 | GNLAR | 3 |
| 117 | GNLVR | 3 |
| 3245 | GSLSR | 3 |
| 3246 | HALQR | 3 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2577 | HNLTR | 3 |
| 3085 | HSLKR | 3 |
| 2613 | HTLQR | 3 |
| 2832 | ITLKR | 3 |
| 2833 | MTLKR | 3 |
| 2787 | NSLAR | 3 |
| 3247 | NSLSR | 3 |
| 2940 | NTLNR | 3 |
| 2947 | QALTR | 3 |
| 2573 | QGLTR | 3 |
| 3195 | QTLHR | 3 |
| 3248 | QTLVR | 3 |
| 2730 | SALMR | 3 |
| 2496 | SNLLR | 3 |
| 2604 | SSLGR | 3 |
| 2847 | STLDR | 3 |
| 2970 | SVLRR | 3 |
| 2507 | TGLLR | 3 |
| 2561 | TNLMR | 3 |
| 68 | TNLRR | 3 |
| 3249 | TSLER | 3 |
| 2618 | TTLMR | 3 |
| 2534 | VGLKR | 3 |
| 2718 | AGLDR | 2 |
| 2669 | AGLER | 2 |
| 2797 | AGLGR | 2 |
| 3250 | ASLMR | 2 |
| 3251 | ASLNR | 2 |
| 2552 | DGLDR | 2 |
| 2529 | DGLHR | 2 |
| 2591 | DNLKR | 2 |
| 2535 | DNLLR | 2 |
| 2623 | DNLRR | 2 |
| 2506 | DNLVR | 2 |
| 2683 | DSLAR | 2 |
| 3030 | DTLLR | 2 |
| 2809 | DTLSR | 2 |
| 2810 | DTLTR | 2 |
| 2720 | DVLKR | 2 |
| 2811 | DVLRR | 2 |
| 2890 | EALTR | 2 |
| 3043 | ETLQR | 2 |
| 3252 | GALDR | 2 |
| 2779 | GDLKR | 2 |
| 2780 | GDLTR | 2 |
| 3253 | GGPRR | 2 |
| 2917 | GTLER | 2 |
| 3254 | HALNR | 2 |
| 2820 | HDLRR | 2 |
| 2687 | HGLDR | 2 |
| 2585 | HGLGR | 2 |
| 2821 | HGLNR | 2 |
| 2482 | HNLLR | 2 |
| 2826 | HSLHR | 2 |
| 3255 | MPLTR | 2 |
| 2834 | NALHR | 2 |
| 2540 | NGLAR | 2 |
| 2572 | NGLIR | 2 |
| 2755 | NGLLR | 2 |
| 2504 | NGLQR | 2 |
| 2512 | NGLTR | 2 |
| 2837 | NTLHR | 2 |
| 2939 | NTLIR | 2 |
| 2942 | NVLKR | 2 |
| 2948 | QDLIR | 2 |
| 2838 | QDLKR | 2 |
| 2842 | QSLRR | 2 |
| 3004 | SILKR | 2 |
| 2556 | SMLRR | 2 |
| 2793 | SSLQR | 2 |
| 2697 | STLQR | 2 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2971 | TALER | 2 |
| 2851 | TALGR | 2 |
| 2157 | TGLRV | 2 |
| 2978 | TMLKR | 2 |
| 2511 | TNLVR | 2 |
| 2715 | TSLHR | 2 |
| 3019 | TTLSR | 2 |
| 2651 | TTLTR | 2 |
| 3256 | AALTG | 1 |
| 2866 | AAPER | 1 |
| 58 | ADLKR | 1 |
| 2868 | AGLAW | 1 |
| 3257 | AGVIR | 1 |
| 3258 | AGVTR | 1 |
| 71 | AMLKR | 1 |
| 2621 | ANLNR | 1 |
| 3090 | ASLAR | 1 |
| 3259 | ASLRG | 1 |
| 2801 | ATLMR | 1 |
| 3260 | ATLRM | 1 |
| 3261 | ATPRR | 1 |
| 3262 | AVLAR | 1 |
| 2882 | AVLRR | 1 |
| 3263 | AVLVR | 1 |
| 2803 | DALNR | 1 |
| 2596 | DGLGR | 1 |
| 1833 | DGLKK | 1 |
| 1853 | DGLRK | 1 |
| 3129 | DGLWR | 1 |
| 3264 | DGPAA . . . | 1 |
| 2640 | DMLKR | 1 |
| 2597 | DSLQR | 1 |
| 2776 | DTLVR | 1 |
| 2014 | DVLKK | 1 |
| 3265 | EALHR | 1 |

TABLE 18-continued

ZF5
selection on G:T
change at nt 8 of core motif in CBS.
Sequences reflect position 2 to 6.

| SEQ ID NO: | Sequence | Read # |
|---|---|---|
| 3266 | EALSR | 1 |
| 3095 | EGLHR | 1 |
| 2891 | EGLMR | 1 |
| 3267 | EGLRG | 1 |
| 2894 | EGLRV | 1 |
| 2705 | ENLAR | 1 |
| 2633 | ENLSR | 1 |
| 2814 | GAEE . . . | 1 |
| 3268 | GALER | 1 |
| 3269 | GALGK | 1 |
| 3270 | GALIR | 1 |
| 3271 | GALKV | 1 |
| 3272 | GALMR | 1 |
| 2815 | GALQR | 1 |
| 3273 | GAPRR | 1 |
| 3003 | GDLNR | 1 |
| 2817 | GDLVR | 1 |
| 2642 | GGLDR | 1 |
| 2571 | GGLHR | 1 |
| 3274 | GGPAR | 1 |
| 3275 | GGPVR | 1 |
| 3276 | GGQVR | 1 |
| 3277 | GGVAR | 1 |
| 3278 | GGWP . . . | 1 |
| 2913 | GMLAR | 1 |
| 2481 | GNLER | 1 |
| 139 | GNLMR | 1 |
| 2609 | GNLQR | 1 |
| 3279 | GSLRV | 1 |
| 2918 | GTLGR | 1 |
| 2919 | GTLHR | 1 |
| 3081 | GTLMR | 1 |
| 2747 | GTLNR | 1 |
| 2723 | GTLSR | 1 |
| 3280 | HAAQ . . . | 1 |
| 3281 | HALAS | 1 |

TABLE 18-continued

ZF5
selection on G:T
change at nt 8 of core motif in CBS.
Sequences reflect position 2 to 6.

| SEQ ID NO: | Sequence | Read # |
|---|---|---|
| 3282 | HALER | 1 |
| 3283 | HALVH | 1 |
| 3284 | HAMRR | 1 |
| 3285 | HAQHR | 1 |
| 3286 | HGLTL | 1 |
| 3287 | HGLVM | 1 |
| 2531 | HLLKR | 1 |
| 2661 | HNLAR | 1 |
| 2557 | HNLHR | 1 |
| 3050 | HNLKR | 1 |
| 2627 | HNLSR | 1 |
| 2644 | HNLVR | 1 |
| 3177 | HPAP . . . | 1 |
| 2645 | HQLIR | 1 |
| 3288 | HSLGR | 1 |
| 1936 | HTLRV | 1 |
| 2935 | HVLAR | 1 |
| 2710 | IGLRR | 1 |
| 2754 | IGLTG | 1 |
| 2711 | INLTR | 1 |
| 3184 | KGLPG | 1 |
| 3289 | MPLQR | 1 |
| 2937 | NALAR | 1 |
| 2663 | NGLHR | 1 |
| 2615 | NGLMR | 1 |
| 2555 | NGLSR | 1 |
| 2664 | NMLKR | 1 |
| 2543 | NNLAR | 1 |
| 2637 | NNLLR | 1 |
| 3006 | NTLTR | 1 |
|  | PWS . . . | 1 |
| 3290 | QAPWP . . . | 1 |
| 3023 | QDLRR | 1 |
| 2728 | QGLAR | 1 |
| 2574 | QMLKR | 1 |
| 2729 | QNLHR | 1 |

TABLE 18-continued

ZF5
selection on G:T
change at nt 8 of core motif in CBS.
Sequences reflect position 2 to 6.

| SEQ ID NO: | Sequence | Read # |
|---|---|---|
| 2646 | QNLQR | 1 |
| 2841 | QNLRW | 1 |
| 3104 | QTLSR | 1 |
| 3291 | RGLQR | 1 |
| 2629 | SALER | 1 |
| 2693 | SALGR | 1 |
| 2955 | SALMC | 1 |
| 3292 | SALQR | 1 |
| 3293 | SAQR . . . | 1 |
| 3294 | SARVR | 1 |
| 2957 | SDLAR | 1 |
| 3295 | SDLNR | 1 |
| 2958 | SDLQR | 1 |
| 2959 | SDLRR | 1 |
| 3105 | SELRR | 1 |
| 3296 | SGADA . . . | 1 |
| 3297 | SGLR . . . | 1 |
| 3298 | SGLVC | 1 |
| 3299 | SGPDP . . . | 1 |
| 2533 | SMLAR | 1 |
| 2487 | SNLDR | 1 |
| 2963 | SNLQR | 1 |
| 2544 | SNLSR | 1 |
| 2696 | SQLRR | 1 |
| 3300 | SSLPR | 1 |
| 2302 | STLKT | 1 |
| 2968 | STLRK | 1 |
| 3301 | STPSR | 1 |
| 2733 | SVLTR | 1 |
| 3302 | TALLR | 1 |
| 3303 | TAPTR | 1 |
| 2973 | TDLAR | 1 |
| 2974 | TDLRR | 1 |
| 3304 | TGLIK | 1 |
| 2977 | TGPAR | 1 |

TABLE 18-continued

ZF5  
selection on G:T  
change at nt 8 of core motif in CBS.  
Sequences reflect position 2 to 6.

| SEQ ID NO: | Sequence | Read # |
|---|---|---|
| 3217 | TGQRR | 1 |
| 2595 | TNLKR | 1 |
| 2526 | TNLNR | 1 |
| 2766 | TSLKR | 1 |
| 2983 | TSLQR | 1 |
| 2859 | TTLIR | 1 |
| 1849 | TTLKV | 1 |
| 2681 | TTLNR | 1 |
| 2861 | TVLRM | 1 |
| 3305 | TWLRR | 1 |
| 2985 | VALAR | 1 |
| 3306 | VALQR | 1 |
| 2652 | VGLQR | 1 |
| 2990 | VGLTM | 1 |
| 2605 | VNLKR | 1 |
| 3307 | VSLKR | 1 |
| 3308 | VSLRR | 1 |
| 3112 | VTLAR | 1 |
| 2994 | VTLGR | 1 |

TABLE 19

ZF4  
selection on G:T  
change at nt 10 of core motif in CBS.  
Sequences reflect position 2 to 6.

| SEQ ID NO: | Sequence | Read # |
|---|---|---|
| 60 | AHLRK | 4967 |
| 158 | GHLKK | 1446 |
| 3309 | THLRA | 1429 |
| 1386 | EHLRR | 1293 |
| 162 | GHLRK | 1082 |
| 3310 | HHLTK | 876 |
| 63 | AKLRI | 867 |
| 61 | AKLRV | 641 |
| 3311 | AKLRL | 625 |
| 3312 | AKLKI | 599 |

TABLE 19-continued

ZF4  
selection on G:T  
change at nt 10 of core motif in CBS.  
Sequences reflect position 2 to 6.

| SEQ ID NO: | Sequence | Read # |
|---|---|---|
| 3313 | SHLRK | 566 |
| 159 | AHLKK | 560 |
| 163 | THLKK | 496 |
| 160 | TKLRL | 486 |
| 92 | SKLRL | 475 |
| 2137 | SKLKV | 466 |
| 161 | TKLKL | 466 |
| 3314 | QHLRK | 457 |
| 3315 | AKLKL | 443 |
| 3316 | GHLVK | 419 |
| 3317 | GKLKI | 302 |
| 3318 | THLRK | 268 |
| 3319 | AKLKV | 258 |
| 106 | GKLRI | 246 |
| 3320 | GKLRL | 224 |
| 3321 | GHLRL | 213 |
| 3322 | TKLKI | 199 |
| 3323 | RSLGL | 178 |
| 90 | AHLRV | 177 |
| 3324 | AHLRL | 153 |
| 3325 | TKLRV | 152 |
| 3326 | SKLKI | 146 |
| 3327 | SHLVG | 132 |
| 3328 | GKLKL | 116 |
| 64 | TKLKV | 108 |
| 3329 | THLRT | 107 |
| 3330 | GHLRR | 102 |
|  | *R . . . | 92 |
| 3331 | SHLRL | 90 |
| 65 | SKLRV | 80 |
| 3332 | GALV . . . | 79 |
| 3333 | GHLKM | 75 |
| 3334 | SKLRI | 74 |
| 3335 | GILS . . . | 71 |
| 3336 | SK*VL | 63 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3337 | SKLVL | 62 |
|  | TR . . . | 61 |
| 3338 | IRLGV | 59 |
| 3339 | MALGL | 58 |
| 3340 | EHLRK | 54 |
| 3341 | GHLRM | 54 |
| 1407 | EHLKR | 50 |
| 3342 | ITLM . . . | 48 |
| 3343 | AHLVK | 40 |
| 3344 | THLRL | 40 |
| 3345 | GKLKV | 38 |
| 3346 | GHLKL | 34 |
| 3347 | AHLRR | 32 |
| 3348 | GHLIK | 30 |
| 3349 | EHLVR | 28 |
| 3350 | GKLRV | 27 |
| 3351 | TALSM | 26 |
| 3352 | EHLQR | 25 |
| 3353 | EKLKV | 25 |
| 3354 | QHLVK | 25 |
| 3355 | TKLNL | 25 |
| 3356 | GHLRA | 23 |
| 3357 | GRLPK | 21 |
|  | NGR . . . | 21 |
| 3358 | SKLKL | 21 |
| 3359 | THLTK | 21 |
| 3360 | RLLSG | 20 |
| 3361 | TKLRI | 19 |
| 3362 | AHLRI | 18 |
| 409 | GHLKV | 16 |
| 3363 | GHLRV | 16 |
| 3364 | GLLPG | 16 |
| 3365 | AKLRT | 14 |
| 3366 | RHLRV | 14 |
| 3367 | AALRK | 11 |
| 3368 | AHLHK | 11 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3369 | GHLTK | 11 |
| 3370 | QHLRR | 11 |
| 3371 | RSHS . . . | 11 |
| 3372 | SHLNK | 11 |
| 3373 | AHLQK | 10 |
| 3374 | GHLMK | 10 |
| 3375 | SKLRT | 10 |
| 287 | AHLKV | 9 |
| 3376 | AHLRA | 9 |
| 370 | AHLRT | 9 |
| 3377 | EHLRL | 9 |
| 3378 | GHLKI | 9 |
| 3379 | SHLKL | 9 |
| 3380 | EHLKK | 8 |
| 3381 | GHLRT | 8 |
| 3382 | GKLKM | 8 |
| 3383 | HHLKK | 8 |
| 3384 | SKLTI | 8 |
| 3385 | THEKP . . . | 8 |
|  | *G . . . | 7 |
| 3386 | AKLIL | 7 |
| 3387 | AKLTI | 7 |
| 3388 | HALAA | 7 |
| 3389 | TKLQV | 7 |
| 3390 | AKLRM | 6 |
| 3391 | EHLRI | 6 |
| 3392 | GHLAK | 6 |
| 3393 | GHLKR | 6 |
| 3394 | GKLTL | 6 |
| 3395 | SHLKK | 6 |
| 3396 | SHLRR | 6 |
| 3397 | AILKA | 5 |
| 89 | AKLRK | 5 |
| 3398 | AKLTL | 5 |
| 3399 | ASLTG | 5 |
| 201 | EHLRV | 5 |

TABLE 19-continued

ZF4 selection on G:T change at nt 10 of core motif in CBS. Sequences reflect position 2 to 6.

| SEQ ID NO: | Sequence | Read # |
|---|---|---|
| 3400 | EVLTM | 5 |
| 3401 | GHLKT | 5 |
| 3402 | NGRS . . . | 5 |
| 3403 | THLRR | 5 |
| 3404 | AHLKL | 4 |
| 3405 | GALVH | 4 |
| 3406 | GKLVL | 4 |
| 3407 | NGRSPV . . . | 4 |
| 3408 | QALSI | 4 |
| 3409 | SHLRT | 4 |
|  | TRS . . . | 4 |
| 3410 | AALRL | 3 |
| 3411 | AHLMK | 3 |
| 439 | AHLRE | 3 |
| 3412 | AHLRQ | 3 |
| 3413 | AKLNL | 3 |
| 3414 | AKLRA | 3 |
| 3415 | APLRK | 3 |
| 186 | EKLRI | 3 |
| 3416 | GALMG | 3 |
| 3417 | GALTG | 3 |
| 3418 | GHLRG | 3 |
| 3419 | GHLTL | 3 |
| 3420 | GKLRK | 3 |
| 3421 | GKLTV | 3 |
| 187 | GKLVT | 3 |
| 3422 | HHLRK | 3 |
| 3423 | MGLVG | 3 |
| 1848 | SHLKV | 3 |
| 3424 | SHLRI | 3 |
| 3425 | SKLIL | 3 |
| 3426 | SKLMV | 3 |
| 3427 | SLLAG | 3 |
| 3428 | THLKI | 3 |
| 3429 | THLQK | 3 |
| 3430 | VPLAG | 3 |

TABLE 19-continued

ZF4 selection on G:T change at nt 10 of core motif in CBS. Sequences reflect position 2 to 6.

| SEQ ID NO: | Sequence | Read # |
|---|---|---|
| 3431 | AGLLG | 2 |
| 3432 | AHLKM | 2 |
| 3433 | AHLRN | 2 |
| 3434 | AHLTK | 2 |
| 3435 | AKLIV | 2 |
| 3436 | AKLKA | 2 |
| 88 | AKLKK | 2 |
| 3437 | AKLTV | 2 |
| 3438 | AKLVL | 2 |
| 3439 | AKSRI | 2 |
| 3440 | AMLMQ | 2 |
| 3441 | AQLRI | 2 |
| 3442 | DALR . . . | 2 |
| 419 | EHLRA | 2 |
| 313 | EHLRT | 2 |
| 3443 | EKLKL | 2 |
| 3444 | GGLQK | 2 |
| 3445 | GGLTM | 2 |
|  | GH*R . . . | 2 |
| 3446 | GHLLR | 2 |
| 3447 | GHLRI | 2 |
| 3448 | GHLVG | 2 |
| 3449 | GHLVR | 2 |
| 3450 | GKLNL | 2 |
| 2912 | GKLRR | 2 |
| 3451 | GKLVP | 2 |
| 3452 | GLLGL | 2 |
| 3453 | GNLGM | 2 |
| 3454 | GVLQK | 2 |
| 3455 | HGLLP | 2 |
| 2043 | HHLRV | 2 |
| 3456 | HLLEN | 2 |
| 3457 | IGLQR | 2 |
| 3458 | KTLGV | 2 |
| 3459 | LSLLK | 2 |
| 3460 | MRLGE | 2 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3461 | NSLTR | 2 |
| 3462 | NVLNK | 2 |
| 3463 | PHLRK | 2 |
| 3464 | PLLMP | 2 |
| 3465 | PRLRH | 2 |
| 3466 | QKLHL | 2 |
| 3467 | QKLNL | 2 |
| 3468 | SHLRV | 2 |
| 3469 | SKLHL | 2 |
| 3470 | SKLKR | 2 |
| 3471 | SKLNL | 2 |
| 3472 | SPLAE | 2 |
| 3473 | SVLML | 2 |
|  | TH*R . . . | 2 |
| 2448 | THLKL | 2 |
| 3474 | THLRV | 2 |
| 3475 | TKLIL | 2 |
| 3476 | TKLMV | 2 |
| 3477 | TPLNI | 2 |
| 3478 | TRLQK | 2 |
| 3024 | TSLTR | 2 |
| 3479 | VGLGQ | 2 |
| 3480 | VHLRK | 2 |
| 3481 | AALES | 1 |
| 3482 | AALRI | 1 |
| 3483 | ADLRK | 1 |
| 3484 | AELLG | 1 |
| 3485 | AELRI | 1 |
| 3486 | AGLAA | 1 |
| 1986 | AGLKR | 1 |
| 3487 | AGLMD | 1 |
| 3488 | AHLGL | 1 |
| 3489 | AHLK . . . | 1 |
| 3490 | AHLKA | 1 |
| 3491 | AHLKI | 1 |
| 438 | AHLKT | 1 |
| 3492 | AHLNK | 1 |
| 3493 | AHLR . . . | 1 |
| 3494 | AHLSK | 1 |
| 3495 | AHLSP | 1 |
| 214 | AHLTV | 1 |
| 3496 | AHLWK | 1 |
| 3497 | AKFKI | 1 |
| 3498 | AKIKH | 1 |
| 3499 | AKIRI | 1 |
| 3500 | AKIRL | 1 |
| 3501 | AKIRV | 1 |
| 3502 | AKLHT | 1 |
| 3503 | AKLKE | 1 |
| 3504 | AKLKG | 1 |
| 3505 | AKLKM | 1 |
| 3506 | AKLMN | 1 |
| 3507 | AKLNI | 1 |
| 3508 | AKLQL | 1 |
| 3509 | AKLRG | 1 |
| 3510 | AKLRR | 1 |
| 3511 | AKLSM | 1 |
| 3512 | AKSRV | 1 |
| 3513 | AKVKL | 1 |
| 3514 | AKVRI | 1 |
| 3515 | ALLMA | 1 |
| 3516 | ALLRR | 1 |
| 3517 | AMLIM | 1 |
| 3518 | AMLKI | 1 |
| 3519 | AMLRG | 1 |
| 3520 | AMLRL | 1 |
| 3521 | ANLSN | 1 |
| 3522 | ANVAQ | 1 |
| 3523 | APLKK | 1 |
| 3524 | AQFRK | 1 |
| 3525 | AQLVD | 1 |
| 3526 | ARLAG | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3527 | ARLGT | 1 |
| 3528 | ARLRA | 1 |
| 3529 | ARLRK | 1 |
| 3530 | ASLRM | 1 |
| 3531 | ATLKL | 1 |
| 3532 | ATLRV | 1 |
| 3533 | C*LKI | 1 |
| 3534 | DELMR | 1 |
| 3535 | DELRV | 1 |
| 3536 | DGLES | 1 |
| 2005 | DGLLR | 1 |
| 3537 | DGLMD | 1 |
| 3538 | DGLVG | 1 |
| 3539 | DHLKK | 1 |
| 3540 | DHLRK | 1 |
| 3541 | DHLRR | 1 |
| 3542 | DKLRK | 1 |
| 3543 | DLLGV | 1 |
| 3544 | DLLLN | 1 |
| 3545 | DNLRE | 1 |
| 3546 | DPLAR | 1 |
| 3547 | DSLGE | 1 |
| 3548 | EALMA | 1 |
| 3549 | EDLVK | 1 |
| 3550 | EELGL | 1 |
| 3551 | EELMM | 1 |
| 3267 | EGLRG | 1 |
| 3552 | EGLVE | 1 |
| 3553 | EHLG . . . | 1 |
| 3554 | EHLHK | 1 |
| 3555 | EHLKL | 1 |
| 3556 | EHLKM | 1 |
| 2016 | EHLRQ | 1 |
| 3557 | EHLRS | 1 |
| 3558 | EHLSE | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3559 | EHLSR | 1 |
| 3560 | EHLTK | 1 |
| 3561 | EHLVK | 1 |
| 3562 | EQLGP | 1 |
| 3563 | ERLAA | 1 |
| 3564 | ERLGR | 1 |
| 1893 | ERLRR | 1 |
| 3565 | ESLMA | 1 |
| 3566 | ETLSH | 1 |
| 3567 | EVLGI | 1 |
| 3568 | FFLRV | 1 |
| 3569 | GALGR | 1 |
| 3570 | GALIM | 1 |
| 3571 | GDLSG | 1 |
| 3572 | GGLDL | 1 |
| 3573 | GGLDQ | 1 |
| 1957 | GGLKV | 1 |
| 3574 | GGLNM | 1 |
| 3575 | GGLPE | 1 |
| 2295 | GGLVV | 1 |
| 3576 | GHFKT | 1 |
| 3577 | GHFQN | 1 |
| 3578 | GHLK . . . | 1 |
| 3579 | GHLMN | 1 |
| 3580 | GHLMV | 1 |
| 3159 | GHLQR | 1 |
| 3581 | GHLR . . . | 1 |
| 3582 | GILAG | 1 |
| 3583 | GKLHE | 1 |
| 3584 | GKLKA | 1 |
| 3585 | GKLKF | 1 |
| 3586 | GKLKT | 1 |
| 3587 | GKLR . . . | 1 |
| 3588 | GKLRA | 1 |
| 3589 | GKLRM | 1 |
| 3590 | GKLVA | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3591 | GKLVV | 1 |
| 3592 | GLLGE | 1 |
| 3593 | GLLLD | 1 |
| 3594 | GLLMG | 1 |
| 3595 | GLLRG | 1 |
| 3596 | GMLGG | 1 |
| 3597 | GPLGV | 1 |
| 3598 | GPLRV | 1 |
| 3599 | GRLKI | 1 |
| 3600 | GRLKK | 1 |
| 3601 | GSLST | 1 |
| 3602 | GSLVK | 1 |
| 2554 | GTLKR | 1 |
| 3603 | GVLAG | 1 |
| 3604 | GVLLV | 1 |
| 3605 | GVLS . . . | 1 |
| 3606 | GYLRK | 1 |
| 3607 | HALRT | 1 |
| 3608 | HALVN | 1 |
| 3609 | HGLTG | 1 |
| 3610 | HHLAK | 1 |
| 3611 | HHLRR | 1 |
| 3612 | HIRS . . . | 1 |
| 3613 | HTHEK | 1 |
| 3614 | IELVQ | 1 |
| 3615 | IGLGL | 1 |
| 3616 | IKLRL | 1 |
| 3617 | IMLRE | 1 |
| 3618 | IMLVE | 1 |
| 3619 | IPLGD | 1 |
| 3620 | IQLRK | 1 |
| 3621 | IRLG . . . | 1 |
| 3622 | IRLGG | 1 |
| 3623 | IRLVV | 1 |
| 3624 | IVLAA | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3625 | KHLRA | 1 |
| 3626 | KHLRL | 1 |
| 3627 | KILPE | 1 |
| 3628 | KKLLE | 1 |
| 3629 | KMLPP | 1 |
| 3630 | KNLIK | 1 |
| 3631 | KSLMP | 1 |
| 3632 | LALGG | 1 |
| 3633 | LGLGA | 1 |
| 3634 | LGLVG | 1 |
| 3635 | LHLTK | 1 |
|  | LQ . . . | 1 |
| 3636 | LRLIG | 1 |
|  | LTE . . . | 1 |
| 3637 | LTLQR | 1 |
| 3638 | LVLRR | 1 |
| 3639 | MA*SHMK | 1 |
| 3640 | MALRL | 1 |
| 3641 | MALTR | 1 |
| 3642 | MGLDP | 1 |
| 3643 | MGLGE | 1 |
| 3644 | MGLQN | 1 |
| 3645 | MHLRM | 1 |
| 3646 | MKLEQ | 1 |
| 3647 | MLLRN | 1 |
| 3648 | MLLSH | 1 |
| 3649 | MLLVN | 1 |
| 3650 | MPLRA | 1 |
| 3651 | MQLGG | 1 |
| 3652 | MRLAR | 1 |
| 3653 | MRLMG | 1 |
| 3654 | MRLVG | 1 |
| 3655 | MSLER | 1 |
| 3656 | MTLPL | 1 |
| 3657 | MTLSD | 1 |
| 3658 | MVLAG | 1 |
|  | NG . . . | 1 |

TABLE 19-continued

ZF4 selection on G:T change at nt 10 of core motif in CBS. Sequences reflect position 2 to 6.

| SEQ ID NO: | Sequence | Read # |
|---|---|---|
| 2615 | NGLMR | 1 |
| 2504 | NGLQR | 1 |
| 3659 | NKLRL | 1 |
| 3660 | NLAH | 1 |
| 3661 | NLLPT | 1 |
| 3662 | NRLES | 1 |
| 3663 | NRLGG | 1 |
| 3664 | NTLPK | 1 |
| 3665 | PGLHG | 1 |
| 3666 | PGLRA | 1 |
| 3667 | PHFTK | 1 |
| 3668 | PILLQ | 1 |
| 3669 | PKLGL | 1 |
| 3670 | PLLKS | 1 |
| 3671 | PQLTG | 1 |
| 3672 | PREAM | 1 |
| 3673 | PTLQR | 1 |
| 3674 | QELGR | 1 |
| 3675 | QGLPV | 1 |
| 3676 | QHLKK | 1 |
| 3677 | QHLQR | 1 |
| 3678 | QHLR . . . | 1 |
| 3679 | QHLRI | 1 |
| 3680 | QHLRL | 1 |
| 3681 | QHLTK | 1 |
| 3682 | QILLH | 1 |
| 3683 | QKLRI | 1 |
| 3684 | QNLHK | 1 |
| 3685 | QPLIK | 1 |
| 3686 | QQVTA . . . | 1 |
| 3687 | QTLAE | 1 |
| 3688 | QVTLA | 1 |
| 3689 | RALSA | 1 |
|  | RGL . . . | 1 |
| 3690 | RGLGA | 1 |
| 3691 | RGLTA | 1 |
| 2953 | RGLVR | 1 |
| 3692 | RGLVV | 1 |
| 3693 | RHLRA | 1 |
| 3694 | RHLRE | 1 |
| 3695 | RHLRM | 1 |
| 3696 | RHLRR | 1 |
| 3697 | RILPR | 1 |
| 3698 | RKLIV | 1 |
| 3699 | RKLKL | 1 |
| 3700 | RLLGA | 1 |
| 3701 | RLLMP | 1 |
| 3702 | RLLRR | 1 |
| 3703 | RMLVP | 1 |
| 3704 | RRLEG | 1 |
| 3705 | RRLVN | 1 |
| 3706 | RTLML | 1 |
| 3707 | RTLTQ | 1 |
| 3708 | SDLHV | 1 |
| 3709 | SDLRK | 1 |
| 2581 | SGLGR | 1 |
| 3710 | SGLLV | 1 |
| 2486 | SGLVR | 1 |
| 3711 | SHLKM | 1 |
| 3712 | SHLRA | 1 |
| 3713 | SHLRE | 1 |
| 3714 | SHLRG | 1 |
| 3715 | SHLTK | 1 |
| 3716 | SHLTM | 1 |
| 3717 | SHLV . . . | 1 |
| 3718 | SHLVK | 1 |
| 3719 | SKIRL | 1 |
| 3720 | SKLEG | 1 |
| 3721 | SKLGA | 1 |
| 3722 | SKLKG | 1 |
| 2191 | SKLRM | 1 |
| 3723 | SKLRN | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3724 | SKLRR | 1 |
| 3725 | SLLEE | 1 |
| 3726 | SLLGT | 1 |
| 3727 | SLLNG | 1 |
| 2138 | SQLKV | 1 |
| 3728 | SQLLE | 1 |
| 3729 | SRLMA | 1 |
| 3730 | STLLM | 1 |
| 3731 | STLVG | 1 |
| 3732 | TALRG | 1 |
|  | TG . . . | 1 |
| 2469 | TGLAR | 1 |
| 3733 | TGLGL | 1 |
| 3734 | TGLLK | 1 |
| 2157 | TGLRV | 1 |
| 3735 | TGLVD | 1 |
| 3385 | THEKP | 1 |
| 3736 | THFRT | 1 |
| 3737 | THIR . . . | 1 |
| 3738 | THLAR | 1 |
| 2449 | THLKQ | 1 |
| 3739 | THLLK | 1 |
| 3740 | THLMK | 1 |
| 331 | THLRP | 1 |
| 3741 | THLVK | 1 |
| 3742 | THMK | 1 |
| 3743 | THVKK | 1 |
| 3744 | TKLKM | 1 |
| 3745 | TKLKR | 1 |
| 3746 | TKLNM | 1 |
| 3747 | TKLRK | 1 |
| 3748 | TKLRP | 1 |
| 3749 | TKLS . . . | 1 |
| 3750 | TKLTI | 1 |
| 3751 | TMLGG | 1 |
| 3752 | TMLKL | 1 |

TABLE 19-continued

ZF4
selection on G:T
change at nt 10 of core motif in CBS.
Sequences reflect position 2 to 6.

| SEQ ID NO: | Sequence | Read # |
|---|---|---|
| 3753 | TMLPG | 1 |
| 3754 | TPLKR | 1 |
| 3755 | TPLRA | 1 |
| 3756 | TQLKK | 1 |
| 3757 | TQLKL | 1 |
| 1941 | TQLKV | 1 |
| 3758 | TR*RL | 1 |
| 3759 | TRLKL | 1 |
| 110 | TRLRE | 1 |
|  | TS . . . | 1 |
| 3760 | TTLGI | 1 |
| 3761 | TYLKK | 1 |
| 3762 | VELDP | 1 |
| 3763 | VELVN | 1 |
| 3764 | VKLQQ | 1 |
| 3765 | VKLRL | 1 |
| 3766 | VKLRN | 1 |
| 3767 | VKLRV | 1 |
| 3768 | VLLKS | 1 |
| 3769 | VLLQM | 1 |
| 3770 | VMLKD | 1 |
| 3771 | VMLMG | 1 |
| 3772 | VPLAL | 1 |
| 3773 | VPLER | 1 |
| 3774 | VPLNT | 1 |
| 3775 | VPLSS | 1 |
| 3776 | VPLVP | 1 |
|  | VQ*G . . . | 1 |
| 3777 | VRLEE | 1 |
| 3778 | VRLQA | 1 |
| 3779 | VVTA . . . | 1 |
| 3780 | WHLKK | 1 |
|  | YG . . . | 1 |

TABLE 20

ZF4 selection on G:C change at nt 10 of core motif in CBS. Sequences reflect position 2 to 6.

| SEQ ID NO: | Sequence | Read # |
|---|---|---|
| 61 | AKLRV | 5924 |
| 3325 | TKLRV | 4888 |
| 64 | TKLKV | 3542 |
| 2137 | SKLKV | 3056 |
| 3319 | AKLKV | 2451 |
| 65 | SKLRV | 1583 |
| 3375 | SKLRT | 474 |
| 3350 | GKLRV | 320 |
| 63 | AKLRI | 254 |
| 3345 | GKLKV | 237 |
| 3312 | AKLKI | 164 |
| 1986 | AGLKR | 132 |
| 3322 | TKLKI | 129 |
| 1957 | GGLKV | 78 |
| 3326 | SKLKI | 76 |
| 3334 | SKLRI | 76 |
| 3527 | ARLGT | 64 |
| 3781 | VALGS | 48 |
| 3454 | GVLQK | 46 |
|  | TRS . . . | 39 |
| 60 | AHLRK | 30 |
| 3782 | AKLVV | 26 |
| 3783 | TKLRA | 24 |
| 3784 | LGLRG | 18 |
| 3652 | MRLAR | 15 |
| 3785 | TKLKA | 14 |
| 3722 | SKLKG | 13 |
| 3361 | TKLRI | 13 |
| 3365 | AKLRT | 12 |
|  | NGR . . . | 12 |
| 3786 | PNLAV | 12 |
| 3787 | GGLEV | 10 |
| 158 | GHLKK | 10 |
| 3788 | PREAI | 10 |
| 3789 | TKLKG | 10 |
| 3790 | TKLIV | 9 |
| 3791 | WILRA | 9 |

TABLE 20-continued

ZF4 selection on G:C change at nt 10 of core motif in CBS. Sequences reflect position 2 to 6.

| SEQ ID NO: | Sequence | Read # |
|---|---|---|
| 3792 | AK*RG | 8 |
| 3414 | AKLRA | 8 |
| 3311 | AKLRL | 8 |
| 3793 | EK*KV | 8 |
| 106 | GKLRI | 8 |
| 3310 | HHLTK | 8 |
| 3385 | THEKP . . . | 8 |
| 3794 | TK*RG | 8 |
| 3795 | TKLRT | 8 |
| 3315 | AKLKL | 7 |
| 3796 | AKLRE | 7 |
| 3437 | AKLTV | 7 |
| 3353 | EKLKV | 7 |
| 2187 | SKLKE | 7 |
| 3797 | TKLRG | 7 |
| 3509 | AKLRG | 6 |
| 1386 | EHLRR | 6 |
| 3798 | EKLRV | 6 |
| 3799 | RALW . . . | 6 |
| 2438 | SKLKA | 6 |
| 3504 | AKLKG | 5 |
| 3390 | AKLRM | 5 |
| 3400 | EVLTM | 5 |
| 3314 | QHLRK | 5 |
| 3800 | SKLVV | 5 |
| 1851 | STLKV | 5 |
| 3801 | TKLKE | 5 |
| 3802 | TKLNV | 5 |
| 3316 | GHLVK | 4 |
| 3320 | GKLRL | 4 |
| 3803 | KDALQYESECG . . . | 4 |
| 3804 | LSLVD | 4 |
| 3805 | QKLKV | 4 |
| 3806 | RELKE . . . | 4 |
| 3807 | RILGS | 4 |

TABLE 20-continued

ZF4
selection on G:C
change at nt 10 of core motif in CBS.
Sequences reflect position 2 to 6.

| SEQ ID NO: | Sequence | Read # |
|---|---|---|
| 163 | THLKK | 4 |
| 3309 | THLRA | 4 |
| 3808 | TKIRV | 4 |
| 160 | TKLRL | 4 |
| 3809 | TKLRM | 4 |
| 3810 | TKLVV | 4 |
| 3811 | TKVRV | 4 |
| 3812 | TRSHSR . . . | 4 |
| 159 | AHLKK | 3 |
| 3436 | AKLKA | 3 |
| 3813 | AKLRD | 3 |
| 1909 | ATLKV | 3 |
| 3532 | ATLRV | 3 |
| 3536 | DGLES | 3 |
| 3814 | GGLKG | 3 |
| 3418 | GHLRG | 3 |
| 162 | GHLRK | 3 |
| 3815 | GKLIV | 3 |
| 3816 | GKLKG | 3 |
| 3317 | GKLKI | 3 |
| 3451 | GKLVP | 3 |
| 3817 | KKLHW . . . | 3 |
| 3408 | QALSI | 3 |
| 3818 | RTLS . . . | 3 |
| 3819 | SKLRA | 3 |
| 3820 | SKVRV | 3 |
| 3427 | SLLAG | 3 |
| 3821 | TK*SV | 3 |
| 3822 | TKLAV | 3 |
| 3823 | TKLRE | 3 |
| 3824 | TKSRV | 3 |
| 3825 | TKVKV | 3 |
| 3826 | VMLMM | 3 |
| 3430 | VPLAG | 3 |
| 3431 | AGLLG | 2 |
| 3827 | AILQV | 2 |
| 3501 | AKIRV | 2 |
| 3435 | AKLIV | 2 |
| 3503 | AKLKE | 2 |
| 3828 | AKLMV | 2 |
| 3829 | AKLSV | 2 |
| 3830 | AKVKV | 2 |
| 3521 | ANLSN | 2 |
| 2315 | DKLRV | 2 |
| 3831 | ETLMH | 2 |
| 3416 | GALMG | 2 |
| 3444 | GGLQK | 2 |
| 3445 | GGLTM | 2 |
| 3333 | GHLKM | 2 |
| 3832 | GKSKV | 2 |
| 3592 | GLLGE | 2 |
| 3452 | GLLGL | 2 |
| 3453 | GNLGM | 2 |
| 2554 | GTLKR | 2 |
| 3456 | HLLEN | 2 |
| 3457 | IGLQR | 2 |
| 3833 | IKLRV | 2 |
| 3834 | KALHT | 2 |
| 3835 | KGLMM | 2 |
| 3836 | MELAE | 2 |
| 3423 | MGLVG | 2 |
| 3460 | MRLGE | 2 |
| 3656 | MTLPL | 2 |
| 2615 | NGLMR | 2 |
| 3402 | NGRS . . . | 2 |
| 3837 | NKLKV | 2 |
| 3838 | PRLLA | 2 |
| 3465 | PRLRH | 2 |
| 3839 | PRLSR | 2 |
| 3840 | QGLEA | 2 |
| 2434 | SELKV | 2 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3470 | SKLKR | 2 |
| 3841 | SKLRE | 2 |
| 3842 | SKLRG | 2 |
|  | TH*R... | 2 |
| 3843 | TKIKV | 2 |
| 161 | TKLKL | 2 |
| 3476 | TKLMV | 2 |
| 3389 | TKLQV | 2 |
| 3844 | TKLRD | 2 |
| 3845 | TKLSV | 2 |
| 3477 | TPLNI | 2 |
| 3478 | TRLQK | 2 |
| 3024 | TSLTR | 2 |
| 1919 | TTLRV | 2 |
|  | V | 2 |
| 3481 | AALES | 1 |
| 3846 | AELKA | 1 |
| 3847 | AELKV | 1 |
| 3484 | AELLG | 1 |
| 3486 | AGLAA | 1 |
| 3848 | AGLKH | 1 |
| 2475 | AGLRR | 1 |
| 2498 | AGLSR | 1 |
| 2473 | AGLTR | 1 |
| 1988 | AGLVR | 1 |
| 3490 | AHLKA | 1 |
| 287 | AHLKV | 1 |
| 90 | AHLRV | 1 |
| 3495 | AHLSP | 1 |
| 3849 | AKIRE | 1 |
| 3850 | AKLAV | 1 |
| 3851 | AKLGV | 1 |
| 3852 | AKLMI | 1 |
| 3853 | AKLNV | 1 |
| 3854 | AKLRF | 1 |
| 3855 | AKLRN | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3387 | AKLTI | 1 |
| 3856 | AKLWV | 1 |
| 3857 | AKRRV | 1 |
| 3858 | AKSKV | 1 |
| 3859 | AKVRG | 1 |
| 3860 | ALLKV | 1 |
| 3517 | AMLIM | 1 |
| 3861 | AMLKV | 1 |
| 3440 | AMLMQ | 1 |
| 3519 | AMLRG | 1 |
| 3862 | AQLKV | 1 |
| 3863 | AQLRV | 1 |
| 3525 | AQLVD | 1 |
| 1945 | ARLKV | 1 |
| 3864 | ARLRI | 1 |
| 1993 | ARLRM | 1 |
| 1947 | ARLRV | 1 |
| 3865 | ATLQV | 1 |
| 3866 | AVLKV | 1 |
| 3867 | AYPRE | 1 |
| 3868 | CGLHW... | 1 |
| 3869 | CKLRV | 1 |
| 1995 | DALDR | 1 |
| 3535 | DELRV | 1 |
| 1852 | DGLKV | 1 |
| 2005 | DGLLR | 1 |
| 3537 | DGLMD | 1 |
| 3870 | DGLTG | 1 |
| 3538 | DGLVG | 1 |
| 3871 | DHLKR | 1 |
| 206 | DHLNV | 1 |
| 3543 | DLLGV | 1 |
| 3544 | DLLLN | 1 |
| 3545 | DNLRE | 1 |
| 3546 | DPLAR | 1 |
| 3872 | DRLTI | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3873 | DVLKG | 1 |
| 3874 | DVLRG | 1 |
| 3875 | EALVH | 1 |
| 3551 | EELMM | 1 |
| 3267 | EGLRG | 1 |
| 3552 | EGLVE | 1 |
| 201 | EHLRV | 1 |
| 3349 | EHLVR | 1 |
| 3562 | EQLGP | 1 |
| 3876 | EQLMT | 1 |
| 3564 | ERLGR | 1 |
| 3565 | ESLMA | 1 |
| 3566 | ETLSH | 1 |
| 3877 | EVLAA | 1 |
| 3567 | EVLGI | 1 |
|  | G . . . | 1 |
| 3571 | GDLSG | 1 |
| 3573 | GGLDQ | 1 |
| 3878 | GGLKD | 1 |
| 3879 | GGLKI | 1 |
| 2659 | GGLNR | 1 |
| 3575 | GGLPE | 1 |
|  | GH*R . . . | 1 |
| 3393 | GHLKR | 1 |
| 3446 | GHLLR | 1 |
| 3580 | GHLMV | 1 |
| 3330 | GHLRR | 1 |
| 3363 | GHLRV | 1 |
| 3419 | GHLTL | 1 |
| 3448 | GHLVG | 1 |
| 3582 | GILAG | 1 |
| 3880 | GILRM | 1 |
| 3881 | GK*RG | 1 |
| 3584 | GKLKA | 1 |
| 3382 | GKLKM | 1 |
| 3882 | GKLML | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3883 | GKLQV | 1 |
| 3588 | GKLRA | 1 |
| 3884 | GKLRQ | 1 |
| 3885 | GKLRT | 1 |
| 3394 | GKLTL | 1 |
| 3593 | GLLLD | 1 |
| 3594 | GLLMG | 1 |
| 3364 | GLLPG | 1 |
| 3595 | GLLRG | 1 |
| 3886 | GPLGQ | 1 |
| 3597 | GPLGV | 1 |
| 3887 | GPLMG | 1 |
| 3888 | GQLKA | 1 |
| 3889 | GRLAV | 1 |
| 3890 | GRLNA | 1 |
| 3601 | GSLST | 1 |
| 3602 | GSLVK | 1 |
| 3603 | GVLAG | 1 |
| 3604 | GVLLV | 1 |
| 3607 | HALRT | 1 |
| 3455 | HGLLP | 1 |
| 3612 | HIRS . . . | 1 |
| 3891 | HPLTV | 1 |
| 3892 | HRLTR | 1 |
| 3614 | IELVQ | 1 |
| 3615 | IGLGL | 1 |
| 3893 | IKLKV | 1 |
| 3894 | IMLKS | 1 |
| 3618 | IMLVE | 1 |
| 3895 | IQSGE | 1 |
| 3896 | IQVTLA | 1 |
| 3897 | IRLAL | 1 |
| 3621 | IRLG . . . | 1 |
| 3338 | IRLGV | 1 |
| 3342 | ITLM . . . | 1 |
| 3624 | IVLAA | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3898 | KALRG | 1 |
| 3628 | KKLLE | 1 |
| 3899 | KKLRE | 1 |
| 3900 | KKLVR | 1 |
| 3629 | KMLPP | 1 |
| 3630 | KNLIK | 1 |
| 3631 | KSLMP | 1 |
| 3458 | KTLGV | 1 |
| 3632 | LALGG | 1 |
| 3633 | LGLGA | 1 |
| 3634 | LGLVG | 1 |
|  | LQ . . . | 1 |
| 3636 | LRLIG | 1 |
| 3901 | LSLDG | 1 |
| 3637 | LTLQR | 1 |
| 3638 | LVLRR | 1 |
|  | MA . . . | 1 |
| 3339 | MALGL | 1 |
| 3641 | MALTR | 1 |
| 3902 | MELDR | 1 |
| 3642 | MGLDP | 1 |
| 3643 | MGLGE | 1 |
| 3644 | MGLQN | 1 |
| 3646 | MKLEQ | 1 |
| 3903 | MKLQA | 1 |
| 3904 | MKLRV | 1 |
| 3647 | MLLRN | 1 |
| 3649 | MLLVN | 1 |
| 3905 | MPLLA | 1 |
| 3650 | MPLRA | 1 |
| 3906 | MRLARHIRSHTGERP . . . | 1 |
| 3653 | MRLMG | 1 |
| 3655 | MSLER | 1 |
| 3907 | MSLVN | 1 |
| 3657 | MTLSD | 1 |
| 3658 | MVLAG | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3908 | MVLQE | 1 |
| 3909 | MVLVG | 1 |
|  | N . . . | 1 |
| 3910 | NDALEYESECGP . . . | 1 |
| 3911 | NDALQYESVCVP . . . | 1 |
| 2504 | NGLQR | 1 |
| 3912 | NGLVV | 1 |
| 3913 | NK*NV | 1 |
| 3914 | NKLRV | 1 |
| 3660 | NLAH | 1 |
| 3661 | NLLPT | 1 |
| 3663 | NRLGG | 1 |
| 3664 | NTLPK | 1 |
|  | NV . . . | 1 |
| 3915 | NVLGG | 1 |
| 3462 | NVLNK | 1 |
| 3916 | PGLAA | 1 |
| 3665 | PGLHG | 1 |
| 3669 | PKLGL | 1 |
| 3917 | PKLRA | 1 |
| 3670 | PLLKS | 1 |
| 3464 | PLLMP | 1 |
| 3918 | PNLAG | 1 |
| 3919 | PNYW . . . | 1 |
| 3671 | PQLTG | 1 |
| 3672 | PREAM | 1 |
| 3673 | PTLQR | 1 |
| 3920 | PVLDH | 1 |
|  | Q | 1 |
| 3921 | QALTN | 1 |
| 3674 | QELGR | 1 |
| 3675 | QGLPV | 1 |
| 3682 | QILLH | 1 |
| 3467 | QKLNL | 1 |
| 3684 | QNLHK | 1 |
| 3685 | QPLIK | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3687 | QTLAE | 1 |
| 3922 | QVLRK | 1 |
| 3689 | RALSA | 1 |
| 3923 | RELVR | 1 |
|  | RGL . . . | 1 |
| 3924 | RGLDM | 1 |
| 3925 | RGLDR | 1 |
| 3691 | RGLTA | 1 |
| 3926 | RGLVA | 1 |
| 2953 | RGLVR | 1 |
| 3692 | RGLVV | 1 |
| 3694 | RHLRE | 1 |
| 3697 | RILPR | 1 |
| 3698 | RKLIV | 1 |
| 3927 | RKLKA | 1 |
| 3928 | RKLKV | 1 |
| 3929 | RKLRE | 1 |
| 3930 | RKLRV | 1 |
| 3931 | RKVRV | 1 |
| 3700 | RLLGA | 1 |
| 3701 | RLLMP | 1 |
| 3932 | RMLQE | 1 |
| 3703 | RMLVP | 1 |
| 3933 | RPLEV | 1 |
| 3705 | RRLVN | 1 |
| 3706 | RTLML | 1 |
| 3707 | RTLTQ | 1 |
|  | S*G . . . | 1 |
| 3708 | SDLHV | 1 |
| 2581 | SGLGR | 1 |
| 3710 | SGLLV | 1 |
| 2486 | SGLVR | 1 |
| 1848 | SHLKV | 1 |
| 3331 | SHLRL | 1 |
| 3934 | SKFKV | 1 |
| 3935 | SKFRV | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3936 | SKIRT | 1 |
| 3469 | SKLHL | 1 |
| 3937 | SKLKD | 1 |
| 3358 | SKLKL | 1 |
| 3938 | SKLKM | 1 |
| 3939 | SKLQI | 1 |
| 92 | SKLRL | 1 |
| 3940 | SKLSV | 1 |
| 3941 | SKLTV | 1 |
| 3337 | SKLVL | 1 |
| 3942 | SKSRT | 1 |
| 3943 | SKVKV | 1 |
| 3944 | SKVRT | 1 |
| 3725 | SLLEE | 1 |
| 3726 | SLLGT | 1 |
| 3945 | SNLKG | 1 |
| 3946 | SNLTH | 1 |
| 3728 | SQLLE | 1 |
| 1857 | SRLKV | 1 |
| 3730 | STLLM | 1 |
| 3947 | TALIS | 1 |
| 3732 | TALRG | 1 |
| 3948 | TELIG | 1 |
| 3949 | TELKV | 1 |
|  | TG*S . . . | 1 |
| 2469 | TGLAR | 1 |
| 3733 | TGLGL | 1 |
| 2157 | TGLRV | 1 |
| 3385 | THEKP | 1 |
| 3737 | THIR . . . | 1 |
| 3738 | THLAR | 1 |
| 3429 | THLQK | 1 |
| 3318 | THLRK | 1 |
| 3344 | THLRL | 1 |
| 3329 | THLRT | 1 |
| 3950 | TKLHV | 1 |

TABLE 20-continued

ZF4
selection on G:C
change at nt 10 of core motif in CBS.
Sequences reflect position 2 to 6.

| SEQ ID NO: | Sequence | Read # |
|---|---|---|
| 3951 | TKLKD | 1 |
| 3744 | TKLKM | 1 |
| 3745 | TKLKR | 1 |
| 3952 | TKLKT | 1 |
| 3953 | TKLMA | 1 |
| 3746 | TKLNM | 1 |
| 3954 | TKLQI | 1 |
| 3955 | TKLR . . . | 1 |
| 3956 | TKLTV | 1 |
| 3957 | TKLWV | 1 |
| 3958 | TKSRD | 1 |
| 3751 | TMLGG | 1 |
| 3959 | TMLKV | 1 |
| 3753 | TMLPG | 1 |
| 3960 | TMLRV | 1 |
| 3754 | TPLKR | 1 |
| 1864 | TRLKV | 1 |
| 110 | TRLRE | 1 |
| 2168 | TRLRG | 1 |
| 1883 | TRLRV | 1 |
| 3961 | TRSHS . . . | 1 |
| 3962 | TTIRV | 1 |
| 3760 | TTLGI | 1 |
| 1849 | TTLKV | 1 |
| 3963 | TTLSA | 1 |
| 3964 | TTLVP | 1 |
| 3965 | TVLAP | 1 |
| 3966 | TVLPM | 1 |
| 3967 | VALTK | 1 |
| 3763 | VELVN | 1 |
| 3479 | VGLGQ | 1 |
| 3968 | VGLLR | 1 |
| 3969 | VKLLV | 1 |
| 3764 | VKLQQ | 1 |
| 3766 | VKLRN | 1 |
| 3767 | VKLRV | 1 |
| 3768 | VLLKS | 1 |
| 3970 | VLLMA | 1 |
| 3971 | VLLPS | 1 |
| 3770 | VMLKD | 1 |
| 3771 | VMLMG | 1 |
| 3972 | VNLLE | 1 |
| 3772 | VPLAL | 1 |
| 3773 | VPLER | 1 |
| 3774 | VPLNT | 1 |
| 3775 | VPLSS | 1 |
| 3776 | VPLVP | 1 |
|  | VQ*G . . . | 1 |
| 3973 | VQLPV | 1 |
| 3777 | VRLEE | 1 |
| 3778 | VRLQA | 1 |
| 2994 | VTLGR | 1 |
| 3974 | YTHMK | 1 |

TABLE 21

ZF4
selection on G:A
change at nt 10 of core motif in CBS.
Sequences reflect position 2 to 6.

| SEQ ID NO: | Sequence | Read # |
|---|---|---|
| 61 | AKLRV | 408 |
| 3350 | GKLRV | 294 |
|  | TRS | 180 |
| 64 | TKLKV | 170 |
| 3320 | GKLRL | 166 |
| 3402 | NGRS | 155 |
| 3325 | TKLRV | 124 |
| 3390 | AKLRM | 109 |
| 160 | TKLRL | 109 |
| 3345 | GKLKV | 107 |
| 3312 | AKLKI | 92 |
| 3319 | AKLKV | 88 |

TABLE 21-continued

ZF4
selection on G:A
change at nt 10 of core motif in CBS.
Sequences reflect position 2 to 6.

| SEQ ID NO: | Sequence | Read # |
|---|---|---|
| 186 | EKLRI | 84 |
| 3655 | MSLER | 68 |
| 3975 | NGRSPVC | 67 |
| 3416 | GALMG | 66 |
| 3976 | AELIR | 63 |
| 2581 | SGLGR | 63 |
| 3915 | NVLGG | 61 |
| 3977 | RGLT | 61 |
| 3978 | TLLMG | 58 |
| 3451 | GKLVP | 57 |
| 3430 | VPLAG | 57 |
| 3682 | QILLH | 55 |
| 3979 | TLPL | 55 |
| 3980 | *MLTS | 54 |
| 3981 | EMLTS | 53 |
| 2137 | SKLKV | 53 |
| 3615 | IGLGL | 52 |
| 3322 | TKLKI | 52 |
| 3495 | AHLSP | 51 |
| 3828 | AKLMV | 51 |
| 3982 | DALRG | 51 |
| 3633 | LGLGA | 51 |
| 3805 | QKLKV | 51 |
| 3408 | QALSI | 50 |
| 3983 | PLLET | 49 |
| 3984 | PSLM | 49 |
| 3452 | GLLGL | 48 |
| 3985 | TLLVG | 48 |
| 3766 | VKLRN | 48 |
| 62 | GGLGL | 47 |
| 3419 | GHLTL | 47 |
| 3986 | GPLHI | 46 |
| 3649 | MLLVN | 46 |
| 3987 | VELNS | 46 |
| 3988 | AKLIT | 45 |
| 3394 | GKLTL | 45 |
| 3946 | SNLTH | 45 |
| 3989 | AT*RR | 44 |
| 3544 | DLLLN | 44 |
| 3596 | GMLGG | 44 |
| 3923 | RELVR | 44 |
| 3990 | SPLLS | 44 |
| 3991 | DKLRR | 43 |
| 3570 | GALIM | 43 |
| 3992 | GLLG | 43 |
| 3993 | GLMM | 42 |
| 3994 | IHLAD | 42 |
| 3995 | TLTQ | 42 |
| 3996 | TRSHSS | 42 |
| 3997 | ALMQ | 41 |
| 1947 | ARLRV | 41 |
| 3321 | GHLRL | 41 |
| 3456 | HLLEN | 41 |
| 3998 | HTLNM | 41 |
| 3999 | PMLVD | 41 |
| 3469 | SKLHL | 41 |
| 4000 | GK*KL | 40 |
| 3440 | AMLMQ | 39 |
| 3546 | DPLAR | 39 |
| 3328 | GKLKL | 39 |
| 3914 | NKLRV | 39 |
| 3732 | TALRG | 39 |
| 3827 | AILQV | 38 |
| 3435 | AKLIV | 38 |
| 3311 | AKLRL | 38 |
| 3612 | HIRS | 38 |
| 3382 | GKLKM | 37 |
| 3592 | GLLGE | 37 |
| 3453 | GNLGM | 37 |
| 3582 | GILAG | 36 |
| 4001 | GPLAL | 36 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3908 | MVLQE | 36 |
| 3669 | PKLGL | 36 |
| 4002 | ARLGL | 35 |
| 4003 | EELLK | 35 |
| 3647 | MLLRN | 35 |
| 3685 | QPLIK | 35 |
| 288 | AHLAV | 34 |
| 3400 | EVLTM | 34 |
| 3460 | MRLGE | 34 |
| 3548 | EALMA | 33 |
| 4004 | PLLGV | 33 |
| 3671 | PQLTG | 33 |
| 3877 | EVLAA | 32 |
| 4005 | HPLQQ | 32 |
| 3916 | PGLAA | 32 |
| 3467 | QKLNL | 32 |
| 4006 | SKLNN | 32 |
| 4007 | TRLRN | 32 |
| 3438 | AKLVL | 31 |
| 4008 | DLLV | 31 |
| 462 | DSLLA | 31 |
| 4009 | GELRT | 31 |
| 4010 | RLLGV | 31 |
| 2700 | AALTR | 30 |
| 3444 | GGLQK | 30 |
| 2615 | NGLMR | 30 |
| 4011 | NRLQ | 30 |
| 4012 | PALGN | 30 |
| 4013 | PLLGM | 30 |
| 4014 | PPLMQ | 30 |
| 4015 | TQLEE | 30 |
| 4016 | VGLEG | 30 |
| 3543 | DLLGV | 29 |
| 3572 | GGLDL | 29 |
| 3418 | GHLRG | 29 |
| 4017 | KTLRE | 29 |
| 4018 | PRLR | 29 |
| 4019 | PSLGV | 29 |
| 4020 | RR*PS | 29 |
| 3735 | TGLVD | 29 |
| 3429 | THLQK DGLMDHIRSH | 29 |
| 4021 | TGERPF | 28 |
| 3459 | LSLLK | 28 |
| 4022 | MVLVP | 28 |
| 4023 | SELTG | 28 |
| 4024 | SGLKH | 28 |
| 3754 | TPLKR | 28 |
| 4025 | VGLG | 28 |
| 60 | AHLRK | 27 |
| 3506 | AKLMN | 27 |
| 63 | AKLRI | 27 |
| 4026 | DRLGP | 27 |
| 4027 | GLLGR | 27 |
| 3617 | IMLRE | 27 |
| 4028 | KQLQP | 27 |
|  | MA*S | 27 |
|  | NGR | 27 |
| 3694 | RHLRE | 27 |
| 4029 | RPLLR | 27 |
| 4030 | RSLRL | 27 |
| 65 | SKLRV | 27 |
| 3427 | SLLAG | 27 |
| 3760 | TTLGI | 27 |
| 3484 | AELLG | 26 |
| 2473 | AGLTR | 26 |
| 3538 | DGLVG | 26 |
| 4031 | GALG | 26 |
| 4032 | GDLSP | 26 |
| 3573 | GGLDQ | 26 |
| 3580 | GHLMV | 26 |
| 3317 | GKLKI | 26 |
| 4033 | GKLSL | 26 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3603 | GVLAG | 26 |
| 4034 | LRLNL | 26 |
| 4035 | MTLGN | 26 |
| 4036 | PMLAA | 26 |
| 3375 | SKLRT | 26 |
| 3746 | TKLNM | 26 |
| 4037 | ALIG | 25 |
| 4038 | AQLAN | 25 |
| 4039 | DGLAM | 25 |
| 3575 | GGLPE | 25 |
| 4040 | GLPV | 25 |
| 3631 | KSLMP | 25 |
| 2601 | NGLNR | 25 |
| 4041 | SHMK | 25 |
| 3477 | TPLNI | 25 |
| 3965 | TVLAP | 25 |
| 4042 | VLLME | 25 |
| 3431 | AGLLG | 24 |
| 4043 | GALPR | 24 |
| 4044 | GKLIL | 24 |
| 3882 | GKLML | 24 |
| 3604 | GVLLV | 24 |
| 4045 | KQLTD | 24 |
| 4046 | LKLIG | 24 |
| 3636 | LRLIG | 24 |
| 4047 | LRLMS | 24 |
| 3663 | NRLGG | 24 |
| 4048 | PNYWP | 24 |
| 4049 | RHLVP | 24 |
| 4050 | SRLGA | 24 |
| 3855 | AKLRN | 23 |
| 4051 | DRLAS | 23 |
| 3547 | DSLGE | 23 |
| 3563 | ERLAA | 23 |
| 106 | GKLRI | 23 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4052 | GSLS | 23 |
| 664 | HRLGG | 23 |
| 4053 | MDLLL | 23 |
| 4054 | MTLGA | 23 |
| 4055 | PPLER | 23 |
| 4056 | PVLPG | 23 |
| 3674 | QELGR | 23 |
| 3818 | RTLS | 23 |
| 4057 | SLLQG | 23 |
| 2157 | TGLRV | 23 |
| 3476 | TKLMV | 23 |
| 3773 | VPLER | 23 |
| 4058 | APLGM | 22 |
| 1386 | EHLRR | 22 |
| 2607 | GALVR | 22 |
| 2659 | GGLNR | 22 |
| 3446 | GHLLR | 22 |
| 4059 | GILAK | 22 |
| 4060 | GMLPD | 22 |
| 3597 | GPLGV | 22 |
| 4061 | GSLPM | 22 |
| 3602 | GSLVK | 22 |
| 3166 | GVLAR | 22 |
| 3634 | LGLVG | 22 |
| 3637 | LTLQR | 22 |
| 4062 | NGRSPVET | 22 |
| 3666 | PGLRA | 22 |
| 4063 | PMLRV | 22 |
| 4064 | TLML | 22 |
| 90 | AHLRV | 21 |
| 3515 | ALLMA | 21 |
| 4065 | ASLGQ | 21 |
| 3870 | DGLTG | 21 |
| 3267 | EGLRG | 21 |
| 223 | EHLAV | 21 |
| 4066 | ELILE | 21 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4067 | GH*RS | 21 |
| 4068 | GHLAM | 21 |
| 3589 | GKLRM | 21 |
| 4069 | GLLP | 21 |
| 4070 | GTLAI | 21 |
| 4071 | IRLKK | 21 |
| 4072 | KELRR | 21 |
| 3627 | KILPE | 21 |
| 4073 | LHLPI | 21 |
| 3423 | MGLVG | 21 |
| 3905 | MPLLA | 21 |
| 4074 | NELRG | 21 |
| 3462 | NVLNK | 21 |
| 4075 | PHLNG | 21 |
| 3464 | PLLMP | 21 |
| 4076 | RLLGS | 21 |
| 4077 | RTLIS | 21 |
| 4078 | SC*AS | 21 |
| 3708 | SDLHV | 21 |
| 92 | SKLRL | 21 |
| 4079 | VKLMN | 21 |
| 4080 | VTLIG | 21 |
| 4081 | AGLQE | 20 |
| 4082 | ALHT | 20 |
| 4083 | DPLVD | 20 |
|  | E | 20 |
| 4084 | EALDA | 20 |
| 4085 | GALAT | 20 |
| 4052 | GSLS | 20 |
| 4086 | GTLLM | 20 |
| 4087 | IKLRP | 20 |
|  | LQ | 20 |
|  | NGP | 20 |
| 3684 | QNLHK | 20 |
| 4088 | RRLLD | 20 |
| 3726 | SLLGT | 20 |
| 3948 | TELIG | 20 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4089 | TGLMG | 20 |
| 4090 | TKLLL | 20 |
| 4091 | TTLGA | 20 |
| 4092 | VE*DP | 20 |
| 3968 | VGLLR | 20 |
| 4093 | AGLGI | 19 |
| 4094 | AGLLQ | 19 |
| 3526 | ARLAG | 19 |
| 4095 | AVLSH | 19 |
| 3535 | DELRV | 19 |
| 4096 | DRLAG | 19 |
| 4097 | ERLSN | 19 |
| 4098 | ETLM | 19 |
| 4099 | GELRG | 19 |
| 3590 | GKLVA | 19 |
| 4100 | GRLNR | 19 |
| 4101 | GRLRL | 19 |
| 4102 | IMLAG | 19 |
| 4103 | IVLDP | 19 |
| 4104 | KVLAP | 19 |
| 4105 | LMLGM | 19 |
| 3641 | MALTR | 19 |
| 4106 | MPLRE | 19 |
| 4107 | RLLGP | 19 |
| 3819 | SKLRA | 19 |
| 4108 | SMYRS | 19 |
| 4109 | THLAK | 19 |
| 3762 | VELDP | 19 |
| 4110 | VGLTR | 19 |
| 3775 | VPLSS | 19 |
| 4111 | VQLPT | 19 |
| 2538 | AALRR | 18 |
| 4112 | AGLD | 18 |
| 3517 | AMLIM | 18 |
| 3519 | AMLRG | 18 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4113 | DVLPG | 18 |
| 3562 | EQLGP | 18 |
| 3393 | GHLKR | 18 |
| 3880 | GILRM | 18 |
| 4114 | GLLV | 18 |
| 4115 | GLMN | 18 |
| 4116 | GMLVG | 18 |
| 4117 | GPLTI | 18 |
| 4118 | GRLE | 18 |
| 4119 | GSLQS | 18 |
| 4120 | GVLVS | 18 |
| 4121 | HKLLK | 18 |
| 3614 | IELVQ | 18 |
| 3619 | IPLGD | 18 |
| 3632 | LALGG | 18 |
| 3648 | MLLSH | 18 |
| 4122 | MRLKV | 18 |
| 4123 | MRLRS | 18 |
| 4124 | MSLSP | 18 |
| 4125 | PALGG | 18 |
| 3665 | PGLHG | 18 |
| 3673 | PTLQR | 18 |
| 4126 | QPLAG | 18 |
| 4127 | SK*VV | 18 |
| 3842 | SKLRG | 18 |
| 4128 | TLIN | 18 |
| 4129 | TLLTP | 18 |
| 4130 | DALME | 17 |
| 4131 | EALNK | 17 |
| 4132 | EGLPT | 17 |
| 4133 | ELLKS | 17 |
| 4134 | GELTD | 17 |
| 3884 | GKLRQ | 17 |
| 3161 | GMLRR | 17 |
| 4135 | GPLVS | 17 |
| 4136 | GQLMM | 17 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4137 | GQLVG | 17 |
| 4138 | KGLEG | 17 |
| 4139 | QGLDN | 17 |
| 4140 | RALVS | 17 |
| 4141 | RGLAT | 17 |
| 3426 | SKLMV | 17 |
| 3800 | SKLVV | 17 |
| 3729 | SRLMA | 17 |
| 4142 | TLHE | 17 |
| 2168 | TRLRG | 17 |
| 3864 | ARLRI | 16 |
| 201 | EHLRV | 16 |
| 4143 | GHLKS | 16 |
| 4144 | GLLKH | 16 |
| 3890 | GRLNA | 16 |
| 4145 | GVLSI | 16 |
| 4146 | GVLST | 16 |
| 3607 | HALRT | 16 |
| 3900 | KKLVR | 16 |
| 3638 | LVLRR | 16 |
| 4147 | MPLVP | 16 |
| 3661 | NLLPT | 16 |
| 4148 | PKLQP | 16 |
| 4149 | PVLMG | 16 |
| 4150 | QALIG | 16 |
| 4151 | RGLIT | 16 |
| 3691 | RGLTA | 16 |
| 3705 | RRLVN | 16 |
| 4152 | RVQD | 16 |
| 3725 | SLLEE | 16 |
| 4153 | TELPM TGL | 16 16 |
| 3751 | TMLGG | 16 |
| 3776 | VPLVP | 16 |
| 4154 | APLDL | 15 |
| 4155 | ARLGR | 15 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4156 | DALSA | 15 |
| 4157 | EGLAG | 15 |
| 50 | GGLVR | 15 |
| 4158 | GGLVS | 15 |
| 3363 | GHLRV | 15 |
| 3815 | GKLIV | 15 |
| 3595 | GLLRG | 15 |
| 4159 | GMLGT | 15 |
| 4160 | GPLLG | 15 |
| 4161 | HIRSH | 15 |
| 3457 | IGLQR | 15 |
| 4162 | IMLV | 15 |
| 3897 | IRLAL | 15 |
| 304 | KALGT | 15 |
| 3898 | KALRG | 15 |
| 4163 | LHLQG | 15 |
| 4164 | MELMT | 15 |
| 4165 | MPLGG | 15 |
| 4166 | PGLAD | 15 |
| 4167 | PTLEV | 15 |
| 4168 | RQLGM | 15 |
| 4169 | RVLRG | 15 |
| 2525 | SGLLR | 15 |
| 4170 | SVLRV | 15 |
| 3733 | TGLGL | 15 |
| 4171 | TVLAG | 15 |
| 4172 | VGLA | 15 |
| 4173 | VGLRG | 15 |
| 3770 | VMLKD | 15 |
| 3774 | VPLNT | 15 |
| 2994 | VTLGR | 15 |
|  | WR | 15 |
|  | A | 14 |
| 4174 | AALHH | 14 |
| 3490 | AHLKA | 14 |
| 4175 | ALLGV | 14 |
| 3525 | AQLVD | 14 |
| 4176 | ARLHA | 14 |
| 4177 | DGLG | 14 |
| 4178 | DHLVG | 14 |
| 4179 | DILRG | 14 |
| 4180 | DQLVE | 14 |
| 4181 | DQLVG | 14 |
| 4182 | EKLMM | 14 |
| 4183 | ELLTP | 14 |
| 3564 | ERLGR | 14 |
| 4184 | GALRS | 14 |
| 3445 | GGLTM | 14 |
| 3583 | GKLHE | 14 |
| 4185 | GKLNI | 14 |
| 3406 | GKLVL | 14 |
| 4186 | GRLLE | 14 |
| 3628 | KKLLE | 14 |
| 3458 | KTLGV | 14 |
| 4187 | MALPE | 14 |
| 3653 | MRLMG | 14 |
| 4188 | NDALQYES | 14 |
| 3662 | NRLES | 14 |
| 3461 | NSLTR | 14 |
| 4189 | PKLRS | 14 |
| 4190 | PRLPP | 14 |
| 4191 | PVLKL | 14 |
| 4192 | QKLAN | 14 |
| 4193 | QKLKL | 14 |
| 4194 | RALPK | 14 |
| 3697 | RILPR | 14 |
| 4195 | THLGR | 14 |
| 3753 | TMLPG | 14 |
| 4196 | VALGT | 14 |
| 4197 | VKLHE | 14 |
| 4198 | VTLG | 14 |
| 4199 | ARLLG | 13 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4200 | ARLTG | 13 |
| 4201 | ASLGA | 13 |
| 4202 | DLLSG | 13 |
| 3545 | DNLRE | 13 |
| 4203 | EALTI | 13 |
| 3551 | EELMM | 13 |
| 4204 | ETLS | 13 |
| 4205 | GALGS | 13 |
| 3381 | GHLRT | 13 |
| 4206 | GPLVL | 13 |
| 4207 | GRLGA | 13 |
| 4208 | GRSYMA | 13 |
| 4209 | GVLGS | 13 |
| 4210 | HPLLV | 13 |
| 4211 | ITLSP | 13 |
| 3642 | MGLDP | 13 |
| 4212 | MLLNG | 13 |
| 4213 | MRLAE | 13 |
| 4214 | NMLSR | 13 |
| 4215 | PGLGG | 13 |
| 4216 | PGLVP | 13 |
| 3670 | PLLKS | 13 |
| 3468 | SHLRV | 13 |
| 4217 | SRLGV | 13 |
| 2469 | TGLAR | 13 |
| 4218 | TLMG | 13 |
| 4219 | TRLMM TRLREHIRSHT | 13 |
| 4220 | GERPF | 13 |
| 4221 | VELGP | 13 |
| 4222 | VHLAR | 13 |
| 4223 | VKLVG | 13 |
| 3486 | AGLAA | 12 |
| 4224 | APLRV | 12 |
| 4225 | EALV | 12 |
| 4226 | EVLPE | 12 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4227 | GALMN | 12 |
| 4228 | GLQA | 12 |
| 4229 | GLTG | 12 |
| 4230 | GTLGD | 12 |
| 4231 | HLLGP | 12 |
| 4232 | LKLKL | 12 |
| 4233 | MALRK | 12 |
| 4234 | MVLTG | 12 |
| 4235 | NGLIE | 12 |
| 4236 | NKLVV | 12 |
| 4237 | PALNV | 12 |
| 4238 | PMLRL | 12 |
| 4239 | PQLLG | 12 |
| 4240 | PVLRV | 12 |
| 4241 | QPLKR | 12 |
| 3924 | RGLDM | 12 |
| 4242 | RGLEN | 12 |
| 3700 | RLLGA | 12 |
| 4243 | RRLMV | 12 |
| 2486 | SGLVR | 12 |
| 4244 | SPLSG | 12 |
| 3728 | SQLLE | 12 |
| 4245 | SRLGR | 12 |
| 4246 | TGLVG | 12 |
| 3403 | THLRR | 12 |
| 3809 | TKLRM | 12 |
| 4247 | TKLVM | 12 |
| 4248 | TLLG | 12 |
| 4249 | TMLPR | 12 |
| 4250 | TNLRL | 12 |
| 4251 | TPLGE | 12 |
| 4252 | TPLVG | 12 |
| 4253 | TRLLT | 12 |
| 4254 | VGLGR | 12 |
| 4255 | VKLQ | 12 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3768 | VLLKS | 12 |
| 4256 | AGLML | 11 |
| 3398 | AKLTL | 11 |
| 3521 | ANLSN | 11 |
| 4257 | ARLLT | 11 |
| 2880 | ATLLR | 11 |
| 4258 | EGLGG | 11 |
| 4259 | EGLHL | 11 |
| 3333 | GHLKM | 11 |
| 3889 | GRLAV | 11 |
| 4260 | GVLG | 11 |
| 4261 | LGLEG | 11 |
| 4262 | LNLQP | 11 |
| 4263 | LRLRT | 11 |
| 4264 | MELGD | 11 |
| 4265 | MLLQR | 11 |
| 4266 | MLPP | 11 |
| 4267 | MSLGG | 11 |
| 4268 | PKLII | 11 |
| 4269 | PNLQT | 11 |
| 4270 | PPLLS | 11 |
| 4271 | PTLGM | 11 |
| 4272 | QKLMT | 11 |
| 3687 | QTLAE | 11 |
| 3701 | RLLMP | 11 |
| 4273 | RRLVG | 11 |
| 4274 | SNLIM | 11 |
| 3730 | STLLM | 11 |
| 3738 | THLAR | 11 |
| 4275 | TLTM | 11 |
| 4276 | TRLGG | 11 |
| 3478 | TRLQK | 11 |
| 4277 | VGLLA | 11 |
| 4278 | VKLRM | 11 |
| 4279 | VLLGG | 11 |
| 4280 | VQ*GG | 11 |
| 3777 | VRLEE | 11 |
| 4281 | AGLSG | 10 |
| 4282 | AGLTE | 10 |
| 4283 | AGLVA | 10 |
| 4284 | ALSA | 10 |
| 4285 | ATLMK | 10 |
| 2468 | DGLAR | 10 |
| 206 | DHLNV | 10 |
| 4286 | EALAI | 10 |
| 4287 | EELVE | 10 |
| 4288 | EMLIP | 10 |
| 4289 | EPLAA | 10 |
| 4290 | ERLQE | 10 |
| 3878 | GGLKD | 10 |
| 3588 | GKLRA | 10 |
| 3591 | GKLVV | 10 |
| 4291 | GMLRV | 10 |
| 4292 | GPLME | 10 |
| 4293 | GVLSP | 10 |
| 4294 | IKLMG | 10 |
| 4295 | IPLNR | 10 |
| 4296 | MLLKG | 10 |
| 4297 | MRLPR | 10 |
| 4298 | MSLRE | 10 |
| 3918 | PNLAG | 10 |
| 4299 | PPLMV | 10 |
| 4300 | PTLGV | 10 |
| 4301 | RGLRN | 10 |
| 3692 | RGLVV | 10 |
| 4302 | RSLIV | 10 |
| 4303 | RTLGE | 10 |
| 4304 | SSLGV | 10 |
| 3947 | TALIS | 10 |
| 4305 | TGLGT | 10 |
| 3344 | THLRL | 10 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3822 | TKLAV | 10 |
| 4306 | TKLLG | 10 |
| 4307 | TLIG | 10 |
| 4308 | TNLLR | 10 |
| 4309 | TTLGG | 10 |
| 4310 | VILGA | 10 |
| 3972 | VNLLE | 10 |
| 3481 | AALES | 9 |
| 4311 | AALGL | 9 |
| 4312 | AELMR | 9 |
| 4313 | AGLDG | 9 |
| 1988 | AGLVR | 9 |
| 3534 | DELMR | 9 |
| 4314 | DSLVI | 9 |
| 4315 | EKLKA | 9 |
| 3798 | EKLRV | 9 |
| 4316 | GKLIA | 9 |
| 4317 | GNLVT | 9 |
| 4318 | GRLLI | 9 |
| 4319 | GRLRS | 9 |
| 3239 | GSLIR | 9 |
| 2554 | GTLKR | 9 |
| 4320 | HELMK | 9 |
| 4321 | KMLGG | 9 |
| 4322 | LGLIQ | 9 |
| 4323 | LKLER | 9 |
| 4324 | LPLNG | 9 |
| 4325 | MGLGV | 9 |
| 3658 | MVLAG | 9 |
| 3909 | MVLVG | 9 |
| 2540 | NGLAR | 9 |
| 3668 | PILLQ | 9 |
| 4326 | PMLTV | 9 |
| 4327 | PPLII | 9 |
| 4328 | QRLVE | 9 |
| 3698 | RKLIV | 9 |
| 4329 | RKLKE | 9 |
| 4330 | RRLHE | 9 |
| 4331 | RVLGA | 9 |
| 2532 | SALAR | 9 |
| 4332 | SC*RP | 9 |
| 4333 | SGLDA | 9 |
| 4334 | SQLDR | 9 |
| 2507 | TGLLR | 9 |
| 3952 | TKLKT | 9 |
| 4335 | TSLTE | 9 |
| 2342 | AGLKM | 8 |
| 4336 | AGLRS | 8 |
| 4337 | AHLGQ | 8 |
| 3493 | AHLR | 8 |
| 4338 | ALME | 8 |
| 2875 | ASLRR | 8 |
| 1995 | DALDR | 8 |
| 4339 | DGLHG | 8 |
| 4340 | DGLLQ | 8 |
| 3550 | EELGL | 8 |
| 4341 | EKLRS | 8 |
| 3876 | EQLMT | 8 |
| 4342 | ERLAR | 8 |
| 3569 | GALGR | 8 |
| 4343 | GELKA | 8 |
| 2295 | GGLVV | 8 |
| 3341 | GHLRM | 8 |
| 4344 | GLML | 8 |
| 4345 | GLQN | 8 |
| 4346 | GLTA | 8 |
| 4347 | GMLGE | 8 |
| 4348 | GPLRR | 8 |
| 4349 | GVLDT | 8 |
| 4350 | GVLNT | 8 |
| 4351 | IQLAD | 8 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4352 | KGLTM | 8 |
| 4353 | MELGN | 8 |
| 4354 | MPLMR | 8 |
| 3657 | MTLSD | 8 |
| 4355 | NGLAM | 8 |
| 4356 | NGLQD | 8 |
| 4357 | NTLDV | 8 |
| 4358 | PHLSM | 8 |
| 4359 | PILLG | 8 |
| 4360 | PVLQG | 8 |
| 4361 | QGLGG | 8 |
| 4362 | QKLQI | 8 |
| 4363 | QPLIA | 8 |
| 3926 | RGLVA | 8 |
| 3727 | SLLNG | 8 |
| 4364 | SRLTD | 8 |
| 4365 | TLLGD | 8 |
| 4366 | TRSHSSV | 8 |
| 3024 | TSLTR | 8 |
| 4367 | TTLGD | 8 |
| 4368 | VKLAP | 8 |
| 3973 | VQLPV | 8 |
| 3367 | AALRK | 7 |
| 159 | AHLKK | 7 |
| 4369 | AKLHP | 7 |
| 4370 | AVLEN | 7 |
| 3571 | GDLSG | 7 |
| 4371 | GELGV | 7 |
| 187 | GKLVT | 7 |
| 3593 | GLLLD | 7 |
| 3594 | GLLMG | 7 |
| 4372 | GLMA | 7 |
| 4373 | GLNR | 7 |
| 4374 | GLVV | 7 |
| 4375 | GPLPV | 7 |
| 4376 | GSLTQ | 7 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4377 | GVLRG | 7 |
| 4378 | HPLAV | 7 |
| 4379 | HTLGM | 7 |
| 4380 | IQLGG | 7 |
| 4381 | KLLGD | 7 |
| 3630 | KNLIK | 7 |
| 4382 | MALAR | 7 |
| 4383 | MELEP | 7 |
| 4384 | MGLAN | 7 |
| 3643 | MGLGE | 7 |
| 4385 | MPLDG | 7 |
| 4386 | NVLGR | 7 |
| 4387 | PGLPE | 7 |
| 4388 | PHLQN | 7 |
| 4389 | PRLGS | 7 |
| 4390 | PSLLV | 7 |
| 4391 | PTLAR | 7 |
| 4392 | QMLER | 7 |
| 4393 | RDLGS | 7 |
| 4394 | RGLGN | 7 |
| 4395 | RLLEK | 7 |
| 3703 | RMLVP | 7 |
| 4396 | SVLSG | 7 |
| 4397 | TGLVN | 7 |
| 4398 | TLA*SH | 7 |
| 4399 | TRLHT | 7 |
| 3967 | VALTK | 7 |
| 3771 | VMLMG | 7 |
| 4400 | VVLAG | 7 |
| 4401 | AGLVG | 6 |
| 3315 | AKLKL | 6 |
| 4402 | AR*PS | 6 |
| 1945 | ARLKV | 6 |
| 2005 | DGLLR | 6 |
| 4403 | DKLHR | 6 |

TABLE 21-continued

ZF4
selection on G:A
change at nt 10 of core motif in CBS.
Sequences reflect position 2 to 6.

| SEQ ID NO: | Sequence | Read # |
|---|---|---|
| 2203 | DKLKV | 6 |
| 4404 | ERLPV | 6 |
| 4405 | GDLVE | 6 |
| 4406 | GELGE | 6 |
| 4407 | GGLMQ | 6 |
| 4408 | GLLT | 6 |
| 4409 | GLPG | 6 |
| 4410 | GSLRT | 6 |
| 4411 | GTLQV | 6 |
| 4412 | GVLKS | 6 |
| 4413 | HGLVN | 6 |
| 4414 | IELGR | 6 |
| 4415 | KPLEL | 6 |
| 4416 | MKLE | 6 |
| 3664 | NTLPK | 6 |
| 4417 | PALMR | 6 |
| 303 | PHLVV | 6 |
| 4418 | PPLVV | 6 |
| 4419 | QALVP | 6 |
| 4420 | QELGG | 6 |
| 3370 | QHLRR | 6 |
| 4421 | QTLGV | 6 |
| 4422 | RILEP | 6 |
| 4423 | RLLMN | 6 |
| 4424 | RPLVG | 6 |
| 4425 | RRLEP | 6 |
| 4426 | SGLRA | 6 |
| 4427 | SKLMA | 6 |
| 3940 | SKLSV | 6 |
| 4428 | TMLEP | 6 |
| 4429 | TRSQ | 6 |
| 4430 | VALRK | 6 |
| 4431 | VDLSG | 6 |
| 4432 | VMLLG | 6 |
| 4433 | VPLSE | 6 |
| 2718 | AGLDR | 5 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4434 | ARLPV | 5 |
| 4435 | ARYGC | 5 |
| 1909 | ATLKV | 5 |
| 2317 | DGLRA | 5 |
| 4436 | ERLLQ | 5 |
| 4437 | ETLMG | 5 |
| 4438 | GHLML | 5 |
| 4439 | GHLQG | 5 |
| 4440 | GKLMV | 5 |
| 4441 | GPLG | 5 |
| 4442 | GPLTM | 5 |
| 4443 | GQLV | 5 |
| 4444 | GSLTL | 5 |
| 4445 | GTLRA | 5 |
| 4446 | GTLTG | 5 |
| 3310 | HHLTK | 5 |
| 4447 | IVLVR | 5 |
| 4448 | MALVR | 5 |
| 4449 | MELGK | 5 |
| 4450 | MGLEG | 5 |
| 4451 | MGLMA | 5 |
| 4452 | MPLNR | 5 |
| 4453 | NMLGG | 5 |
| 4454 | NPLEL | 5 |
| 4455 | NSLGG | 5 |
| 4456 | PRLLQ | 5 |
| 4457 | PRLVK | 5 |
| 2953 | RGLVR | 5 |
| 4458 | RHLRS | 5 |
| 4459 | RSLVV RSPV*ERMWI | 5 |
| 4460 | LRA | 5 |
| 4461 | RTLNA | 5 |
| 4462 | TELN | 5 |
| 4463 | VKLRA | 5 |
| 4464 | VLLQD | 5 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4465 | VMLG | 5 |
| 4466 | AGLNG | 4 |
| 4467 | AHLRM | 4 |
| 3414 | AKLRA | 4 |
| 4468 | AR*RA | 4 |
| 4469 | ARLPE | 4 |
| 4470 | AVLNKDALQYESECG | 4 |
| 4471 | GLNH | 4 |
| 3030 | DTLLR | 4 |
| 4472 | EGLRD | 4 |
| 4473 | ESLMGG | 4 4 |
| 4474 | GELV | 4 |
| 4475 | GGLRP | 4 |
| 158 | GHLKK | 4 |
| 3584 | GKLKA | 4 |
| 4476 | GLIG | 4 |
| 4477 | GLIS | 4 |
| 4478 | GLLGN | 4 |
| 4479 | GMLVN | 4 |
| 4480 | GPLED | 4 |
| 4481 | GPLQA | 4 |
| 4482 | GTLTV | 4 |
| 4483 | GVLGI | 4 |
| 4484 | IDLGM | 4 |
| 4485 | IELGG | 4 |
| 4486 | IGLAT | 4 |
| 4487 | KKLMP | 4 |
| 4488 | KLLGE | 4 |
| 4489 | KLLLG | 4 |
| 3629 | KMLPP | 4 |
| 4490 | MGLTL | 4 |
| 4491 | MNLGM | 4 |
| 4492 | MPLMV | 4 |
| 3650 | MPLRA | 4 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3651 | MQLGG | 4 |
| 2085 | MRLRM | 4 |
| 4493 | PALTV | 4 |
| 4494 | PGLAL | 4 |
| 4495 | PGLMG | 4 |
| 4496 | PHLMS | 4 |
| 4497 | PQLSA | 4 |
| 4498 | PRLKA | 4 |
| 4499 | QKLIR | 4 |
| 4500 | RELGV | 4 |
| 4501 | RGLHQ | 4 |
| 4502 | RGLIG | 4 |
| 4503 | RGLMG | 4 |
| 4504 | RTRSH | 4 |
| 4505 | SQLDT | 4 |
| 4506 | TELGG | 4 |
| 163 | THLKK | 4 |
| 3309 | THLRA | 4 |
| 4507 | TKLGV | 4 |
| 4508 | TMLEG | 4 |
| 4509 | VSLGV | 4 |
| 4510 | VSLTA | 4 |
| 4511 | VSLVG | 4 |
| 1986 | AGLKR | 3 |
| 4512 | AGLQN | 3 |
| 4513 | AGLRV | 3 |
| 3516 | ALLRR | 3 |
| 4514 | ARLRT | 3 |
| 4515 | ASLQK | 3 |
| 4516 | ASLR | 3 |
| 2772 | ATLSR | 3 |
| 4517 | DILGE | 3 |
| 4518 | EELRM | 3 |
| 4519 | EGLTG | 3 |
| 4520 | EMLKE | 3 |
| 4521 | ESLLG | 3 |

TABLE 21-continued

ZF4
selection on G:A
change at nt 10 of core motif in CBS.
Sequences reflect position 2 to 6.

| SEQ ID NO: | Sequence | Read # |
|---|---|---|
| 3565 | ESLMA | 3 |
| 4522 | ETLAG | 3 |
| 4523 | EVLVQ | 3 |
| 2521 | GALKR | 3 |
| 2745 | GGLGR | 3 |
| 162 | GHLRK | 3 |
| 4524 | GKLRS | 3 |
| 4525 | GLKT | 3 |
| 4526 | GLLGV | 3 |
| 4527 | GMLLP | 3 |
| 4528 | GMLSG | 3 |
| 3887 | GPLMG | 3 |
| 4529 | GRLAP | 3 |
| 4530 | GSLLR | 3 |
| 4531 | GTLTM | 3 |
|  | GVI | 3 |
| 4532 | ILLQQ | 3 |
| 4533 | KLLQM | 3 |
| 4534 | LGLPG | 3 |
| 4535 | MELVL | 3 |
| 4536 | MGLAG | 3 |
| 4537 | MGLPV | 3 |
| 3644 | MGLQN | 3 |
| 4538 | MQLAD | 3 |
| 4539 | MSLLR | 3 |
| 4540 | MSLPE | 3 |
| 4541 | NGLKQ | 3 |
| 2504 | NGLQR | 3 |
| 4542 | NGRSPV*E | 3 |
| 4543 | NPLSR | 3 |
| 4544 | NQLVA | 3 |
| 4545 | NTLGL | 3 |
| 4546 | PRLRV | 3 |
| 4547 | PVLLM | 3 |
| 4548 | PVLTG | 3 |
| 3314 | QHLRK | 3 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4549 | QQLL | 3 |
| 4550 | RGLVN | 3 |
| 4551 | RHLVV | 3 |
| 4552 | RLLAE | 3 |
| 4553 | RLLPG | 3 |
| 4554 | RPLIT | 3 |
| 4555 | RVLMN | 3 |
| 4556 | RVLQR | 3 |
| 2580 | SGLER | 3 |
| 161 | TKLKL | 3 |
| 4557 | TLLPG | 3 |
| 110 | TRLRE | 3 |
| 3249 | TSLER | 3 |
| 4558 | VGLPA | 3 |
| 4559 | VPLRP | 3 |
| 4560 | VRLMP | 3 |
| 4561 | VSLGE | 3 |
| 4562 | AALTK | 2 |
| 4563 | AALVK | 2 |
| 4564 | AHLTP | 2 |
| 4565 | AILRT | 2 |
| 4566 | AKLNS | 2 |
| 3853 | AKLNV | 2 |
| 3509 | AKLRG | 2 |
| 4567 | ALLGA | 2 |
| 4568 | ARLLR | 2 |
| 3528 | ARLRA | 2 |
| 4569 | DVLG | 2 |
| 4570 | EELQS | 2 |
| 3552 | EGLVE | 2 |
| 4571 | ELLGP | 2 |
| 4572 | ERMC | 2 |
| 4573 | EVLAG | 2 |
| 4574 | GALGE | 2 |
| 4575 | GDLVP | 2 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4576 | GELRI | 2 |
| 4577 | GGLEL | 2 |
| 4578 | GHLSP | 2 |
| 4579 | GKLEA | 2 |
| 4580 | GKLKR | 2 |
| 2912 | GKLRR | 2 |
| 4581 | GKLVI | 2 |
| 4582 | GLHQ | 2 |
| 4583 | GLLR | 2 |
| 4584 | GLMV | 2 |
| 4585 | GLTL | 2 |
| 117 | GNLVR | 2 |
| 4586 | GPLVG | 2 |
| 4587 | GQLVD | 2 |
| 4588 | GRLSV | 2 |
| 4589 | GVLAV | 2 |
| 3609 | HGLTG | 2 |
| 4590 | HVLEL | 2 |
| 4591 | IELEM | 2 |
| 4592 | IGLQA | 2 |
| 4593 | KGLGN | 2 |
| 4594 | KILPV | 2 |
| 4595 | KPLPG | 2 |
| 4596 | KSLRM | 2 |
| 4597 | KTLGT | 2 |
| 4598 | LGLAA | 2 |
| 4599 | LGLGG | 2 |
| 4600 | LVLQE | 2 |
| 4601 | MGLAS | 2 |
| 4602 | MLLEE | 2 |
| 771 | MLPA | 2 |
| 3652 | MRLAR | 2 |
| 4603 | MSLRQ | 2 |
| 4604 | MTLGT | 2 |
| 4605 | NGLIV | 2 |
| 4606 | NHLRM | 2 |

TABLE 21-continued

ZF4
selection on G:A
change at nt 10 of core motif in CBS.
Sequences reflect position 2 to 6.

| SEQ ID NO: | Sequence | Read # |
|---|---|---|
|  | NLA | 2 |
| 4607 | PALIM | 2 |
| 4608 | PGLAG | 2 |
| 4609 | PLLRA | 2 |
| 4610 | PPLDG | 2 |
| 4611 | PPLIM | 2 |
| 4612 | PPLLG | 2 |
| 4613 | PQLTE | 2 |
| 4614 | PVLDG | 2 |
| 4615 | QGLTT | 2 |
| 4616 | QRLAV | 2 |
| 4617 | RELGG | 2 |
| 4618 | RGLDG | 2 |
| 4619 | RGLTE | 2 |
| 4620 | RHLGA | 2 |
| 4621 | RSLMI | 2 |
| 4622 | RSLRP | 2 |
| 3721 | SKLGA | 2 |
| 4623 | SKLGE T*LT | 2 2 |
| 2443 | TALKV | 2 |
| 4624 | THLR | 2 |
| 1864 | TRLKV | 2 |
| 4625 | TRLPP | 2 |
| 4626 | VELGD | 2 |
| 3763 | VELVN | 2 |
| 2459 | VGLGG | 2 |
| 4627 | VGLKD | 2 |
| 4628 | VKLHV | 2 |
| 4629 | VKLLS | 2 |
| 4630 | VQLTK | 2 |
| 4631 | VRLK | 2 |
| 4632 | VRLPP | 2 |
| 4633 | AALEN | 1 |
| 4634 | AALGP | 1 |
| 4635 | AALGT | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4636 | AALKI | 1 |
| 4637 | AALMN | 1 |
| 4638 | AALMQ | 1 |
| 2865 | AALMR | 1 |
| 4639 | AALRV | 1 |
| 4640 | AALSS | 1 |
| 4641 | AELGP | 1 |
| 4642 | AELRA | 1 |
| 3485 | AELRI | 1 |
| 4643 | AGIAA | 1 |
| 4644 | AGILQ | 1 |
| 4645 | AGLDS | 1 |
| 4646 | AGLG | 1 |
| 4647 | AGLGG | 1 |
| 4648 | AGLGN | 1 |
| 4649 | AGLGP | 1 |
| 4650 | AGLGQ | 1 |
| 4651 | AHFRV | 1 |
| 4652 | AHLRG | 1 |
| 4653 | AHLRP | 1 |
| 4654 | AKFRM | 1 |
| 4655 | AKLE | 1 |
| 4656 | AKLGE | 1 |
| 4657 | AKLGL | 1 |
| 4658 | AKLHA | 1 |
| 3504 | AKLKG | 1 |
| 4659 | AKLLG | 1 |
| 4660 | AKLML | 1 |
| 4661 | AKLQP | 1 |
| 3854 | AKLRF | 1 |
| 4662 | AKLRQ | 1 |
| 4663 | AKLS | 1 |
| 4664 | AKLTN | 1 |
| 4665 | AKLWL | 1 |
| 4666 | ALDA | 1 |
| 4667 | ALIM | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4668 | ALKG | 1 |
| 4669 | ALLGE | 1 |
| 4670 | ALLRS | 1 |
| 4671 | ALTG | 1 |
| 4672 | ALTR | 1 |
| 4673 | AMLPD | 1 |
| 4674 | AMLR | 1 |
| 4675 | APLAG | 1 |
| 4676 | APLGP | 1 |
| 4677 | AQLAD | 1 |
| 4678 | AQLLL | 1 |
| 4679 | AR*RG | 1 |
| 4680 | ARLAA | 1 |
| 3527 | ARLGT | 1 |
| 4681 | ARLMS | 1 |
| 4682 | ARLRS | 1 |
| 4683 | ARLTE | 1 |
| 4684 | ARYGR | 1 |
| 4685 | ASLGP | 1 |
| 4686 | ASLRP | 1 |
| 4687 | AT*RS | 1 |
| 4688 | ATLAK | 1 |
| 4689 | ATLEV | 1 |
| 4690 | ATLKI | 1 |
| 4691 | ATLMG | 1 |
| 4692 | ATLNM | 1 |
| 4693 | ATLNV | 1 |
| 4694 | AVIG | 1 |
| 4695 | CGLGR | 1 |
| 4696 | DALQP | 1 |
| 1999 | DALTV | 1 |
| 4697 | DELM | 1 |
| 4698 | DELMN | 1 |
| 4699 | DELRA | 1 |
| 4700 | DGLE | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4701 | DGLEK | 1 |
| 3536 | DGLES | 1 |
| 4702 | DGLML DGLTGHIRSHT | 1 |
| 4703 | GERPF | 1 |
| 4704 | DGVAM | 1 |
| 4705 | DHLVD | 1 |
| 4706 | DILG | 1 |
| 4707 | DILRT | 1 |
| 2348 | DKLKG | 1 |
| 4708 | DKLMM | 1 |
| 4709 | DLLA | 1 |
| 4710 | DLLAR | 1 |
| 103 | DNLRV | 1 |
| 4711 | DRLAA | 1 |
| 4712 | DRLGG | 1 |
| 4713 | DSLPE | 1 |
| 4714 | DSLV | 1 |
| 3874 | DVLRG | 1 |
| 4715 | DYLNV | 1 |
| 4716 | EALA | 1 |
| 4717 | EALKV | 1 |
| 4718 | EALMV | 1 |
| 4719 | EALTN | 1 |
| 4720 | EELAP EELMMHIRSH | 1 |
| 4721 | TGERPF EELVEHIRSHT | 1 |
| 4722 | GERPF | 1 |
| 3377 | EHLRL | 1 |
| 3349 | EHLVR | 1 |
| 4723 | EKLIV | 1 |
| 3353 | EKLKV | 1 |
| 4724 | ELLAR | 1 |
| 4725 | ELLPS | 1 |
| 4726 | EMLVA | 1 |
| 4727 | EQLGT | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4728 | ERLAV | 1 |
| 93 | ERLRV | 1 |
| 4729 | ETLNS | 1 |
| 4730 | ETSSH | 1 |
| 4731 | EVLAV | 1 |
| 3567 | EVLGI | 1 |
| 4732 | EVLIQ | 1 |
| 4733 | EVLQE | 1 |
| 4734 | GALGL | 1 |
| 4735 | GALGV | 1 |
| 4736 | GALIS | 1 |
| 4737 | GALMQ | 1 |
| 4738 | GALRD | 1 |
| 4739 | GALRG | 1 |
| 4740 | GAVMN | 1 |
| 4741 | GE*GI | 1 |
| 4742 | GELKV | 1 |
| 4743 | GELML | 1 |
| 4744 | GELMR | 1 |
| 4745 | GELRV | 1 |
| 4746 | GELTG | 1 |
| 4747 | GFLAR | 1 |
| 4748 | GGFRD | 1 |
| 4749 | GGLA | 1 |
| 4750 | GGLAE | 1 |
| 368 | GGLGA | 1 |
| 4751 | GGLGE | 1 |
| 4752 | GGLGP | 1 |
| 4753 | GGLHP | 1 |
| 1957 | GGLKV | 1 |
| 4754 | GGLMD | 1 |
| 4755 | GGLMT | 1 |
| 4756 | GGLNI | 1 |
| 2357 | GGLRG | 1 |
| 4757 | GGLRL | 1 |
| 4758 | GGLSG | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4759 | GGLVG | 1 |
| 4760 | GGVGL | 1 |
| 4761 | GHLAI | 1 |
| 4762 | GHLQC | 1 |
| 3159 | GHLQR | 1 |
| 3330 | GHLRR | 1 |
| 4763 | GHLSV | 1 |
| 3448 | GHLVG | 1 |
| 3316 | GHLVK | 1 |
| 4764 | GILAR | 1 |
| 4765 | GILSG | 1 |
| 4766 | GKLAI | 1 |
| 4767 | GKLGG | 1 |
| 4768 | GKLIG | 1 |
| 4769 | GKLII | 1 |
| 4770 | GKLIT GKLKMHIRSH | 1 |
| 4771 | TGERPF | 1 |
| 4772 | GKLLK | 1 |
| 4773 | GKLNA | 1 |
| 4774 | GKLPT | 1 |
| 4775 | GKLQA | 1 |
| 3587 | GKLR | 1 |
| 3588 | GKLRA | 1 |
| 4776 | GKLRE | 1 |
| 4777 | GKLT | 1 |
| 4778 | GKLTM | 1 |
| 4779 | GLAA | 1 |
| 4780 | GLIV | 1 |
| 4781 | GLLEK | 1 |
| 4782 | GLLGG | 1 |
| 4783 | GLLMV | 1 |
| 3364 | GLLPG | 1 |
| 4784 | GLLQD | 1 |
| 4785 | GLLTG | 1 |
| 4786 | GLSG | 1 |
| 4787 | GLSGR | 1 |
| 4788 | GLSV | 1 |
| 4789 | GLVN | 1 |
| 4790 | GLVQ | 1 |
| 4791 | GMLAG | 1 |
| 4792 | GNLSN | 1 |
| 727 | GPLA | 1 |
| 4793 | GPLKP | 1 |
| 4794 | GPLRP | 1 |
| 4795 | GPLVP | 1 |
| 4796 | GQLGP | 1 |
| 4797 | GQLLE | 1 |
| 4798 | GR*ML | 1 |
| 4799 | GRLGG | 1 |
| 4800 | GRLLG | 1 |
| 4801 | GRLMP | 1 |
| 4802 | GRLVS | 1 |
| 4803 | GRYGC | 1 |
| 3279 | GSLRV | 1 |
| 4804 | GSLSK | 1 |
| 4805 | GSLSP | 1 |
| 4806 | GTLKL | 1 |
| 4807 | GTLLL | 1 |
| 2685 | GTLLV | 1 |
| 4808 | GTLMT | 1 |
| 2192 | GTLRV | 1 |
| 4809 | GTLTE | 1 |
| 4810 | GVIN | 1 |
|  | GVL | 1 |
| 4811 | GVLDN | 1 |
| 4812 | GVLE | 1 |
| 4813 | GVLKD | 1 |
| 3454 | GVLQK | 1 |
| 4814 | GVLRL | 1 |
| 4815 | GVLSG | 1 |
| 2220 | GVLTG | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4816 | GVMN | 1 |
| 4817 | GVPV | 1 |
| 4818 | HELMR | 1 |
| 4819 | HLLVP | 1 |
| 4820 | HPLDR | 1 |
| 4821 | HPLLS | 1 |
| 4822 | HPVKE | 1 |
| 4823 | HTLKM | 1 |
| 4824 | HTLLK | 1 |
| 4825 | HTLNI | 1 |
| 3178 | HTLNK | 1 |
| 4826 | HTLRP | 1 |
| 4827 | IALPG | 1 |
| 4828 | IELAL | 1 |
| 4829 | IELG | 1 |
| 4830 | IELHL | 1 |
| 4831 | IGIQR | 1 |
| 4832 | IGLGA | 1 |
| 4833 | IGLRL | 1 |
| 4834 | IHLAG | 1 |
| 4835 | IHLRM | 1 |
| 4836 | IKLTG | 1 |
| 4837 | IMLPR | 1 |
| 4838 | IQLMG | 1 |
| 4839 | IQLRL | 1 |
| 4840 | IRLAA | 1 |
| 4841 | IRLGP | 1 |
| 3338 | IRLGV | 1 |
| 4842 | IRLRR | 1 |
| 4843 | ISLVG | 1 |
| 4844 | ITLMV | 1 |
| 4845 | ITLRG | 1 |
| 4846 | ITLRP | 1 |
| 4847 | ITLVG | 1 |
| 4848 | IVLPGKG | 1 |
| 4849 | KGLAT | 1 |
| 4850 | KGLDL | 1 |
| 4851 | KGLMR | 1 |
| 4852 | KGRSPVET | 1 |
| 4853 | KIIV | 1 |
| 4854 | KILLA | 1 |
| 4855 | KKLAG | 1 |
| 4856 | KKLGV | 1 |
| 4857 | KKLRI | 1 |
| 4858 | KLLAG | 1 |
| 4859 | KLLRV | 1 |
| 4860 | KPLAA | 1 |
| 4861 | KPLMV | 1 |
| 4862 | KRLEG | 1 |
| 4863 | KSLVG | 1 |
| 4864 | KTLEG | 1 |
| 4865 | KTLRG | 1 |
| 2404 | KTLRV | 1 |
| 4866 | KTLVG | 1 |
| 4867 | KVLPV | 1 |
| 4868 | LAHGT | 1 |
| 4869 | LGLGP | 1 |
| 4870 | LGLGV | 1 |
| 4871 | LKVKL | 1 |
| 4872 | LNLHT | 1 |
| 4873 | LRLIM | 1 |
| 4874 | LRVIG | 1 |
| 4875 | LSLSG | 1 |
| 4876 | LTLQQ | 1 |
| 4877 | LVLRG | 1 |
| 4878 | MALRG | 1 |
| 4879 | MELIG | 1 |
| 4880 | MGLRV | 1 |
| 4881 | MLAA | 1 |
| 4882 | MLLIS | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4883 | MLLLP | 1 |
| 4884 | MLLMV | 1 |
| 4885 | MLLPP | 1 |
| 4886 | MLLPV | 1 |
| 4887 | MLLV | 1 |
| 4888 | MLLVG | 1 |
| 4889 | MLVG | 1 |
| 4890 | MMLDP | 1 |
| 4891 | MPLGA | 1 |
| 4892 | MPLGL | 1 |
| 4893 | MPLLG | 1 |
| 4894 | MRLEE | 1 |
| 4895 | MRLGA | 1 |
| 4896 | MRLGG | 1 |
| 4897 | MRLGR | 1 |
| 3654 | MRLVG | 1 |
| 4898 | MSLHG | 1 |
| 4899 | MSLQQ | 1 |
| 4900 | MTLER | 1 |
|  | MVL | 1 |
| 4901 | MVLMN | 1 |
| 4902 | MVLNT | 1 |
| 4903 | MVLRG | 1 |
| 4904 | MVLVT | 1 |
| 4905 | MVVAS | 1 |
| 4906 | NDALQYD | 1 |
| 4907 | NDALQYESECGP | 1 |
| 4908 | NELLR | 1 |
| 4909 | NELMR | 1 |
| 4910 | NELRV | 1 |
| 4911 | NGLG | 1 |
| 4912 | NGLIVHIRSHTGERPF | 1 |
|  | NGR | 1 |
| 4913 | NGRPPG*E | 1 |
| 4914 | NGRSPVR | 1 |
| 4915 | NILMG | 1 |
| 4916 | NKLAR | 1 |
| 4917 | NKLRA | 1 |
| 4918 | NKLRG | 1 |
| 4919 | NKLVA | 1 |
| 4920 | NKLVK | 1 |
| 4921 | NMLGV | 1 |
| 4922 | NNLIN | 1 |
| 1838 | NRLRE | 1 |
| 4923 | NRLRI | 1 |
| 4924 | NSLV | 1 |
| 4925 | NSLVA | 1 |
| 4926 | NVHP*VVGLAA | 1 |
| 4927 | NVLGE | 1 |
| 4928 | PALAG | 1 |
| 4929 | PALGP | 1 |
| 4930 | PALV | 1 |
| 4931 | PASV | 1 |
| 4932 | PDLRA | 1 |
| 4933 | PGITE | 1 |
| 4934 | PGLAP | 1 |
| 4935 | PGLHE | 1 |
| 4936 | PGVAA | 1 |
| 4937 | PGVVP | 1 |
| 4938 | PHLKR | 1 |
| 4939 | PKLIF | 1 |
| 4940 | PLRG | 1 |
| 4941 | PMLAG | 1 |
| 4942 | PMLTM | 1 |
| 4943 | PNLAS | 1 |
| 3786 | PNLAV | 1 |
| 3919 | PNYW | 1 |
| 4944 | PNYWS | 1 |
| 4945 | PQLVV | 1 |
| 4946 | PQSRG*RG | 1 |
| 4947 | PR*GA | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 4948 | PRLRL | 1 |
| 4949 | PSFQ | 1 |
| 4950 | PTLAK | 1 |
| 4951 | PVLKV | 1 |
| 4952 | PVLMT | 1 |
| 2602 | QALKR | 1 |
| 4953 | QALRG | 1 |
| 4954 | QALSP | 1 |
| 4955 | QGLHL | 1 |
| 3675 | QGLPV | 1 |
| 4956 | QILLQ QILLRHIRSHT | 1 |
| 4957 | GERPF | 1 |
| 4958 | QILLY | 1 |
| 4959 | QILPE | 1 |
| 4960 | QMLAR | 1 |
| 4961 | QPLAV | 1 |
| 4962 | QPLTM | 1 |
| 4963 | QRLGG | 1 |
| 4964 | QTLAV | 1 |
| 4965 | QTLGG | 1 |
| 4966 | QTLGP | 1 |
| 4967 | REIVR | 1 |
| 4968 | RELRR | 1 |
| 4969 | RGLAA | 1 |
| 4970 | RGLDN | 1 |
| 4971 | RGLNS | 1 |
| 4972 | RGLRS | 1 |
| 4973 | RGLTG | 1 |
| 4974 | RGLVE | 1 |
| 4975 | RGYGT RHE | 1 1 |
| 4976 | RHLKM | 1 |
| 4977 | RLLGL | 1 |
| 4978 | RP*SG | 1 |
| 4979 | RPLAG | 1 |
| 4980 | RQLGK | 1 |
| 4981 | RQLLE | 1 |
| 4982 | RRLEA | 1 |
| 4983 | RRLET | 1 |
| 2126 | RRLGD | 1 |
| 4984 | RRLGS | 1 |
| 4985 | RRLSE | 1 |
| 4986 | RRLTP | 1 |
| 4987 | RRVVG RSH | 1 1 |
| 4988 | RTLKL | 1 |
| 4989 | RTLVG | 1 |
| 4990 | RVLEP | 1 |
| 4991 | RVLRE SC**A | 1 1 |
| 4992 | SCLK | 1 |
| 4993 | SGILV | 1 |
| 4994 | SGLGG | 1 |
| 4995 | SGLGL | 1 |
| 4996 | SGLGT | 1 |
| 4997 | SGLLG | 1 |
| 4998 | SGLNL | 1 |
| 4999 | SGLRL | 1 |
| 5000 | SGLVG | 1 |
| 3331 | SHLRL | 1 |
| 3425 | SKLIL | 1 |
| 2438 | SKLKA | 1 |
| 3722 | SKLKG | 1 |
| 5001 | SKLLG | 1 |
| 3334 | SKLRI | 1 |
| 2191 | SKLRM | 1 |
| 3337 | SKLVL | 1 |
| 5002 | SL*HG | 1 |
| 5003 | SLLRT | 1 |
| 5004 | SNLTY | 1 |
| 5005 | SNYWP | 1 |
| 5006 | SPLIG | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 5007 | SPLKI | 1 |
| 5008 | SPLRN | 1 |
| 2138 | SQLKV | 1 |
| 5009 | SQMK | 1 |
|  | SR*G | 1 |
| 1857 | SRLKV | 1 |
| 5010 | SRLMT | 1 |
| 5011 | SRLVT | 1 |
| 5012 | SSLGA | 1 |
| 5013 | SSLGL | 1 |
| 5014 | STLQK | 1 |
| 5015 | SVLVG | 1 |
| 5016 | SVLVS | 1 |
|  | T | 1 |
| 5017 | TALEA | 1 |
| 5018 | TALKG | 1 |
| 5019 | TELE | 1 |
| 5020 | TELIR | 1 |
| 5021 | TELPR | 1 |
| 5022 | TELRV | 1 |
| 5023 | TGLAD | 1 |
| 5024 | TGLGA | 1 |
| 5025 | THLAN | 1 |
| 5026 | THLAV | 1 |
| 3318 | THLRK | 1 |
| 3808 | TKIRV | 1 |
| 3785 | TKLKA | 1 |
| 5027 | TKLLR | 1 |
| 5028 | TKLME | 1 |
| 3802 | TKLNV | 1 |
| 3955 | TKLR | 1 |
| 3783 | TKLRA | 1 |
| 3361 | TKLRI | 1 |
| 5029 | TKLRR | 1 |
| 5030 | TKLVL | 1 |
| 5031 | TKSGV | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 5032 | TLIS | 1 |
| 5033 | TLLIR | 1 |
| 5034 | TLLM | 1 |
| 5035 | TLLMQ | 1 |
| 5036 | TLNG | 1 |
| 5037 | TLQP | 1 |
| 5038 | TMLDP | 1 |
| 5039 | TMLRE | 1 |
| 5040 | TNLVG | 1 |
| 5041 | TPLIV | 1 |
| 5042 | TPLMQ | 1 |
| 5043 | TPLSD | 1 |
| 5044 | TPLSI | 1 |
| 5045 | TQLED | 1 |
| 5046 | TRLGA | 1 |
| 5047 | TRLMI | 1 |
| 5048 | TRLRL | 1 |
| 1883 | TRLRV | 1 |
| 5049 | TRLTG | 1 |
| 5050 | TSLSE | 1 |
| 5051 | TTLEP | 1 |
| 5052 | TTLGV | 1 |
| 1849 | TTLKV | 1 |
| 1919 | TTLRV | 1 |
| 5053 | TVLGG | 1 |
| 5054 | TVLT | 1 |
|  | V*KS | 1 |
| 5055 | VALHT | 1 |
| 5056 | VDLLL | 1 |
| 5057 | VELAP | 1 |
| 5058 | VELN | 1 |
| 5059 | VELNN | 1 |
| 5060 | VELRV | 1 |
| 5061 | VGLPV | 1 |
| 5062 | VGLQA | 1 |
| 2652 | VGLQR | 1 |

TABLE 21-continued

ZF4
selection on G:A
change at nt 10 of core motif in CBS.
Sequences reflect position 2 to 6.

| SEQ ID NO: | Sequence | Read # |
|---|---|---|
| 5063 | VGLRN | 1 |
| 5064 | VGLRV | 1 |
| 5065 | VGLSP | 1 |
| 5066 | VGLSQ | 1 |
| 5067 | VHLAL | 1 |
| 5068 | VKLMA | 1 |
| 5069 | VKLQN | 1 |
| 3765 | VKLRL | 1 |
| 5070 | VLLAA | 1 |
| 5071 | VLLIE | 1 |
| 5072 | VLLKI | 1 |
| 5073 | VLLTP | 1 |
| 5074 | VLMV | 1 |
| 5075 | VLQR | 1 |
| 5076 | VMLRG | 1 |
| 3772 | VPLAL | 1 |
| 5077 | VPLVG | 1 |
| 5078 | VQLPM | 1 |
| 5079 | VQLRV | 1 |
| 5080 | VRLEG | 1 |
| 5081 | VRLGG | 1 |
| 3778 | VRLQA | 1 |
| 5082 | VRLVR | 1 |
|  | VTG | 1 |
| 5083 | VTLER | 1 |
| 5084 | VTLGS | 1 |
|  | WRN | 1 |

TABLE 22

ZF4
selection on G:A
change at nt 11 of core motif in CBS.
Sequences reflect position 2 to 6.

| SEQ ID NO: | Sequence | Read # |
|---|---|---|
| 118 | GNLRR | 3407 |
| 69 | ANLRR | 1937 |

TABLE 22-continued

ZF4
selection on G:A
change at nt 11 of core motif in CBS.
Sequences reflect position 2 to 6.

| SEQ ID NO: | Sequence | Read # |
|---|---|---|
| 117 | GNLVR | 1794 |
| 116 | SNLRR | 1771 |
| 5085 | SNLKR | 1208 |
| 68 | TNLRR | 862 |
| 119 | GNLKR | 850 |
| 138 | GNLAR | 805 |
| 2582 | SNLVR | 764 |
| 2609 | GNLQR | 562 |
| 70 | GNLTR | 531 |
| 121 | NNLRR | 486 |
| 2914 | GNLIR | 475 |
| 2494 | ANLVR | 455 |
| 2706 | GNLNR | 373 |
| 2517 | GNLLR | 360 |
| 2620 | ANLKR | 326 |
| 2524 | SNLAR | 269 |
| 2963 | SNLQR | 261 |
| 139 | GNLMR | 251 |
| 2695 | SNLMR | 228 |
| 2746 | GNLHR | 220 |
| 5086 | SNLTR | 209 |
| 5087 | NNLKR | 202 |
| 5088 | SNLIR | 199 |
| 5089 | ANLMR | 191 |
| 2621 | ANLNR | 179 |
| 74 | TMLRR | 158 |
| 5090 | SNLNR | 155 |
| 5091 | ANLTR | 136 |
| 5092 | ANLQR | 125 |
| 2595 | TNLKR | 118 |
| 73 | AMLRR | 111 |
| 2567 | GNLSR | 107 |
| 2542 | ANLAR | 102 |
| 66 | ATLRR | 96 |

TABLE 22-continued

ZF4 selection on G:A change at nt 11 of core motif in CBS. Sequences reflect position 2 to 6.

| SEQ ID NO: | Sequence | Read # |
|---|---|---|
| 2558 | HNLRR | 90 |
| 2538 | AALRR | 81 |
| 2496 | SNLLR | 77 |
| 5093 | ANLER | 73 |
| 2556 | SMLRR | 62 |
| 5094 | ANLHR | 59 |
| 5095 | ANLLR | 58 |
| 3032 | SMLKR | 51 |
| 2544 | SNLSR | 47 |
| 2541 | TNLQR | 47 |
| 2521 | GALKR | 44 |
| 2641 | GALRR | 44 |
| 3347 | AHLRR | 42 |
| 2823 | HMLRR | 40 |
| 2047 | HMLKR | 36 |
| 5096 | RNLQR | 35 |
| 71 | AMLKR | 31 |
| 2722 | GMLKR | 31 |
| 3161 | GMLRR | 29 |
| 2131 | SALKR | 28 |
| 5097 | SNLER | 26 |
| 5098 | KNLQR | 25 |
| 5099 | RNLRR | 24 |
| 2584 | GTLRR | 21 |
| 2978 | TMLKR | 21 |
| 2481 | GNLER | 20 |
| 5100 | QNLKR | 19 |
| 67 | RRLDR | 19 |
| 2638 | STLRR | 19 |
| 2526 | TNLNR | 17 |
| 2575 | QNLRR | 16 |
| 2523 | SALRR | 16 |
| 2714 | TNLHR | 16 |
| 2551 | ANLIR | 15 |
| 1985 | AALKR | 14 |
| 48 | ATLKR | 14 |
| 2875 | ASLRR | 13 |
| 2587 | NTLRR | 13 |
| 2511 | TNLVR | 13 |
| 3330 | GHLRR | 12 |
| 2691 | NNLMR | 12 |
| 2617 | TALKR | 12 |
| 5101 | KNLER | 11 |
| 2518 | NNLVR | 11 |
| 3403 | THLRR | 11 |
| 5102 | SMLQR | 10 |
| 2561 | TNLMR | 10 |
| 2737 | TTLRR | 10 |
| 2475 | AGLRR | 9 |
| 2622 | ATLTR | 9 |
| 3050 | HNLKR | 9 |
| 5103 | KNLVR | 9 |
| 2464 | SGLRR | 9 |
| 2769 | VNLRR | 9 |
| 5104 | AMLTR | 8 |
| 2882 | AVLRR | 8 |
| 3393 | GHLKR | 8 |
| 5105 | TNLTR | 8 |
| 3017 | ATLNR | 7 |
| 2739 | ATLVR | 7 |
| 5106 | HNLMR | 7 |
| 2734 | TALRR | 7 |
| 4308 | TNLLR | 7 |
| 5107 | AMLQR | 6 |
| 52 | ANLSR | 6 |
| 2509 | ASLKR | 6 |
| 2876 | ASLTR | 6 |
| 2801 | ATLMR | 6 |
| 5108 | GMLER | 6 |

TABLE 22-continued

ZF4 selection on G:A change at nt 11 of core motif in CBS. Sequences reflect position 2 to 6.

| SEQ ID NO: | Sequence | Read # |
|---|---|---|
| 5109 | RLLIN | 6 |
| 5110 | SGLLK | 6 |
| 2649 | TNLAR | 6 |
| 5111 | AHLVR | 5 |
| 3012 | ATLHR | 5 |
| 2881 | ATLQR | 5 |
| 2599 | ENLRR | 5 |
| 3084 | HMLQR | 5 |
| 72 | HMLTR | 5 |
| 5112 | ISLRV | 5 |
| 2543 | NNLAR | 5 |
| 3205 | SNLHR | 5 |
| 2153 | STLKR | 5 |
| 5113 | AHLKR | 4 |
| 2879 | ATLIR | 4 |
| 2623 | DNLRR | 4 |
| 2592 | GALTR | 4 |
| 5114 | GNLRK | 4 |
| 5115 | KKLLR | 4 |
| 5116 | MNLRR | 4 |
| 5117 | MVLLR | 4 |
| 5118 | NNLQR | 4 |
| 5119 | QNLVR | 4 |
| 5120 | RNLAR | 4 |
| 3396 | SHLRR | 4 |
| 2962 | SMLHR | 4 |
| 2679 | TNLER | 4 |
| 5121 | TVLLV | 4 |
| 2738 | AALNR | 3 |
| 2770 | AALVR | 3 |
| 1986 | AGLKR | 3 |
| 2539 | ETLRR | 3 |
| 3159 | GHLQR | 3 |
| 3449 | GHLVR | 3 |
| 5122 | GMLNR | 3 |
| 5123 | GMLTR | 3 |
| 5124 | GMLVR | 3 |
| 2608 | GNLGR | 3 |
| 5125 | GNLRG | 3 |
| 5126 | GNLVK | 3 |
| 2600 | GSLRR | 3 |
| 2554 | GTLKR | 3 |
| 56 | HTLRR | 3 |
| 3010 | HVLRR | 3 |
| 5127 | KNLRR | 3 |
| 5128 | MNLKR | 3 |
| 3407 | NGRSPV... | 3 |
| 2712 | NMLRR | 3 |
| 2757 | PNLIR | 3 |
| 3370 | QHLRR | 3 |
| 2956 | SALNR | 3 |
| 5129 | STLEV | 3 |
| 2967 | STLNR | 3 |
| 5130 | TALRS | 3 |
| 1305 | THLKR | 3 |
| 5131 | TNLIR | 3 |
| 2700 | AALTR | 2 |
| 5132 | AMLNR | 2 |
| 5133 | ANLRL | 2 |
| 5134 | ANLRW | 2 |
| 2654 | ATLAR | 2 |
| 5135 | DALLV | 2 |
| 2528 | GGLIR | 2 |
| 4764 | GILAR | 2 |
| 3160 | GILRR | 2 |
|  | GN*S... | 2 |
| 2522 | GNLDR | 2 |
| 5136 | GNLNK | 2 |
| 5137 | GNLRP | 2 |
| 5138 | GNLRS | 2 |

TABLE 22-continued

ZF4
selection on G:A
change at nt 11 of
core motif in CBS.
Sequences reflect
position 2 to 6.

| SEQ ID NO: | Sequence | Read # |
|---|---|---|
| 5139 | GTLIR | 2 |
| 3081 | GTLMR | 2 |
| 2626 | GTLVR | 2 |
| 5140 | HGLET | 2 |
| 5141 | HMLNR | 2 |
| 2644 | HNLVR | 2 |
| 5142 | KNLMR | 2 |
| 2637 | NNLLR | 2 |
| 2756 | NSLRR | 2 |
| 5143 | PGLLG | 2 |
| 5144 | RNLVR | 2 |
| 5145 | SMLNR | 2 |
| 2677 | SMLTR | 2 |
| 2487 | SNLDR | 2 |
| 2850 | STLMR | 2 |
| 2970 | SVLRR | 2 |
| 2462 | TGLRR | 2 |
| 5146 | TMLQR | 2 |
| 2766 | TSLKR | 2 |
| 2860 | TTLKR | 2 |
| 3075 | TVLRR | 2 |
| 5147 | AALRS | 1 |
| 5148 | ADLER | 1 |
| 3089 | ADLVR | 1 |
| 2798 | AGLMR | 1 |
| 1431 | AHLTR | 1 |
| 2871 | AILTR | 1 |
| 5149 | AMLAR | 1 |
| 5150 | AMLHR | 1 |
| 5151 | AMLIR | 1 |
| 5152 | ANFRR | 1 |
| 5153 | ANIQR | 1 |
| 5154 | ANLDR | 1 |
| 2771 | ANLGR | 1 |
| 5155 | ANLVG | 1 |
| 5156 | ANSRR | 1 |
| 5157 | ANVRR | 1 |
| 5158 | APLRR | 1 |
| 2799 | ASLQR | 1 |
| 2880 | ATLLR | 1 |
| 5159 | ATLRS | 1 |
| 5160 | AYFRR | 1 |
| 5161 | CNLAR | 1 |
| 5162 | CNLNR | 1 |
| 5163 | CNLVR | 1 |
| 2591 | DNLKR | 1 |
| 2506 | DNLVR | 1 |
| 2778 | GALNR | 1 |
| 3035 | GDLAR | 1 |
| 2816 | GDLRR | 1 |
| 2780 | GDLTR | 1 |
| 2027 | GGLKR | 1 |
| 2461 | GGLRR | 1 |
| 2909 | GGVRR | 1 |
| 5164 | GHLNR | 1 |
| 5165 | GNFRR | 1 |
| 5166 | GNFVG | 1 |
| 5167 | GNLAG | 1 |
| 5168 | GNLAS | 1 |
| 5169 | GNLHK | 1 |
| 5170 | GNLLS | 1 |
| 5171 | GNLMS | 1 |
| 5172 | GNLNH | 1 |
| 5173 | GNLQS | 1 |
| 5174 | GNLRH | 1 |
| 5175 | GNLS... | 1 |
| 5176 | GNLTK | 1 |
| 5177 | GNLTQ | 1 |
| 5178 | GNLTW | 1 |

TABLE 22-continued

ZF4 selection on G:A change at nt 11 of core motif in CBS. Sequences reflect position 2 to 6.

| SEQ ID NO: | Sequence | Read # |
|---|---|---|
| 5179 | GNLVW | 1 |
| 5180 | GNLWR | 1 |
| 5181 | GNSKR | 1 |
| 5182 | GNSQR | 1 |
| 5183 | GNSRR | 1 |
| 5184 | GNVQR | 1 |
| 5185 | GNVTR | 1 |
| 5186 | GQLAL | 1 |
| 2819 | GSLKR | 1 |
| 2747 | GTLNR | 1 |
| 5187 | GY*LR | 1 |
| 2661 | HNLAR | 1 |
| 2752 | HNLQR | 1 |
| 5188 | ITLQR | 1 |
| 5189 | KILGN | 1 |
| 5190 | KNLKR | 1 |
| 1356 | KNLTR | 1 |
| 5191 | KSLRR | 1 |
| 5192 | LNLRR | 1 |
| 5193 | LNLVR | 1 |
| 2664 | NMLKR | 1 |
| 2690 | NNLIR | 1 |
| 5194 | NNLNR | 1 |
| 2726 | NNLTR | 1 |
| 5195 | NNSRR | 1 |
| 2788 | NTLAR | 1 |
| 2939 | NTLIR | 1 |
| 2628 | NTLKR | 1 |
| 2940 | NTLNR | 1 |
| 5196 | PRLRG | 1 |
| 5197 | QHLKR | 1 |
| 2574 | QMLKR | 1 |
| 2593 | QTLRR | 1 |
| 5198 | RLIIN | 1 |
| 5199 | RNLKR | 1 |
| 3292 | SALQR | 1 |
| 2559 | SGLKR | 1 |
| 5200 | SHLKR | 1 |
| 3202 | SILNR | 1 |
| 5201 | SKLTR | 1 |
| 2647 | SMLIR | 1 |
| 5202 | SMLVR | 1 |
| 5203 | SNLFR | 1 |
| 5204 | SNLIH | 1 |
| 5205 | SNLRK | 1 |
| 5206 | SNLRQ | 1 |
| 5207 | SNLSG | 1 |
| 5208 | SNLTS | 1 |
| 5209 | SNLVW | 1 |
| 5210 | SNSRR | 1 |
| 5211 | SNVKR | 1 |
| 5212 | SNVRG | 1 |
| 2698 | STLVR | 1 |
| 5213 | TMFRR | 1 |
| 3109 | TMLNR | 1 |
| 2680 | TNLGR | 1 |
| 5214 | TNLLS | 1 |
| 5215 | TPTRS | 1 |
| 5216 | TQLVL | 1 |
| 2589 | TSLRR | 1 |
| 5217 | VNLTR | 1 |
| 2997 | VTLRR | 1 |

TABLE 23

ZF4 selection on G:C change at nt 11 of core motif in CBS. Sequences reflect position 2 to 6.

| SEQ ID NO: | Sequence | Read # |
|---|---|---|
| 73 | AMLRR | 3064 |
| 74 | TMLRR | 2212 |
| 2556 | SMLRR | 1556 |
| 3161 | GMLRR | 1320 |
| 2722 | GMLKR | 1160 |
| 3032 | SMLKR | 1049 |
| 71 | AMLKR | 797 |
| 2978 | TMLKR | 515 |
| 2823 | HMLRR | 478 |
| 2047 | HMLKR | 429 |
| 66 | ATLRR | 261 |
| 5102 | SMLQR | 248 |
| 5107 | AMLQR | 212 |
| 5132 | AMLNR | 125 |
| 5104 | AMLTR | 124 |
| 5146 | TMLQR | 123 |
| 2712 | NMLRR | 119 |
| 2664 | NMLKR | 102 |
| 2677 | SMLTR | 98 |
| 72 | HMLTR | 93 |
| 5123 | GMLTR | 88 |
| 5150 | AMLHR | 72 |
| 5122 | GMLNR | 68 |
| 2962 | SMLHR | 63 |
| 5145 | SMLNR | 59 |
| 48 | ATLKR | 58 |
| 5124 | GMLVR | 50 |
| 5141 | HMLNR | 47 |
| 3084 | HMLQR | 47 |
| 5149 | AMLAR | 46 |
| 5218 | AMLVR | 45 |
| 3109 | TMLNR | 38 |
| 5219 | GMLHR | 34 |
| 5202 | SMLVR | 34 |
| 2533 | SMLAR | 29 |

TABLE 23-continued

ZF4 selection on G:C change at nt 11 of core motif in CBS. Sequences reflect position 2 to 6.

| SEQ ID NO: | Sequence | Read # |
|---|---|---|
| 2638 | STLRR | 27 |
| 2970 | SVLRR | 27 |
| 67 | RRLDR | 26 |
| 118 | GNLRR | 24 |
| 2737 | TTLRR | 24 |
| 2882 | AVLRR | 23 |
| 5151 | AMLIR | 22 |
| 2913 | GMLAR | 22 |
| 5220 | GMLQR | 22 |
| 2584 | GTLRR | 19 |
| 2875 | ASLRR | 18 |
| 5221 | HMLAR | 17 |
| 2587 | NTLRR | 17 |
| 69 | ANLRR | 16 |
| 2713 | QMLRR | 16 |
| 3017 | ATLNR | 15 |
| 2574 | QMLKR | 15 |
| 5222 | RRLKN | 15 |
| 5223 | AMLMR | 14 |
| 2801 | ATLMR | 14 |
| 5224 | GMLIR | 14 |
| 5225 | EMLRR | 13 |
| 117 | GNLVR | 13 |
| 5226 | RTLAL | 13 |
| 5227 | SMLSR | 13 |
| 116 | SNLRR | 13 |
| 2647 | SMLIR | 12 |
| 1986 | AGLKR TRS | 11 11 |
| 2739 | ATLVR TRS... | 10 10 |
| 2538 | AALRR | 9 |
| 3012 | ATLHR | 9 |
| 2582 | SNLVR | 9 |
| 5228 | TMLTR | 9 |

TABLE 23-continued

ZF4 selection on G:C change at nt 11 of core motif in CBS. Sequences reflect position 2 to 6.

| SEQ ID NO: | Sequence | Read # |
|---|---|---|
| 68 | TNLRR | 9 |
| 5229 | TMLVR | 8 |
| 3075 | TVLRR | 8 |
| 2027 | GGLKR | 7 |
| 2914 | GNLIR | 7 |
| 2609 | GNLQR | 7 |
| 3407 | NGRSPV... | 7 |
| 2559 | SGLKR | 7 |
| 5230 | TMLMR | 7 |
| 2860 | TTLKR | 7 |
| 2881 | ATLQR | 6 |
| 2622 | ATLTR | 6 |
| 5231 | GMLMR | 6 |
| 70 | GNLTR | 6 |
| 2554 | GTLKR | 6 |
| 5085 | SNLKR | 6 |
| 2965 | SSLKR | 6 |
| 5232 | AMLER | 5 |
| 5233 | AMVRR | 5 |
| 2494 | ANLVR | 5 |
| 119 | GNLKR | 5 |
| 5086 | SNLTR | 5 |
| 5234 | TMLAR | 5 |
| 3987 | VELNS | 5 |
| 2654 | ATLAR | 4 |
| 2879 | ATLIR | 4 |
| 2606 | EMLKR | 4 |
| 138 | GNLAR | 4 |
| 139 | GNLMR | 4 |
| 5087 | NNLKR | 4 |
| 5235 | SMLMR | 4 |
| 2153 | STLKR | 4 |
| 2462 | TGLRR | 4 |
| 5093 | ANLER | 3 |
| 2620 | ANLKR | 3 |

TABLE 23-continued

ZF4 selection on G:C change at nt 11 of core motif in CBS. Sequences reflect position 2 to 6.

| SEQ ID NO: | Sequence | Read # |
|---|---|---|
| 2621 | ANLNR | 3 |
| 5092 | ANLQR | 3 |
| 2509 | ASLKR | 3 |
| 2520 | DMLRR | 3 |
| 2641 | GALRR | 3 |
| 2706 | GNLNR | 3 |
| 5236 | HLLRR | 3 |
| 5237 | HMLHR | 3 |
| 3010 | HVLRR | 3 |
| 5238 | KTLRR LL... | 3 3 |
| 121 | NNLRR | 3 |
| 2477 | SGLTR | 3 |
| 5239 | SMLKN | 3 |
| 3203 | SMLLR | 3 |
| 2963 | SNLQR | 3 |
| 2967 | STLNR | 3 |
| 1985 | AALKR | 2 |
| 2738 | AALNR | 2 |
| 3516 | ALLRR | 2 |
| 5240 | AMLLR | 2 |
| 5241 | AMLRH | 2 |
| 5242 | AMLRS | 2 |
| 5243 | AMLRW | 2 |
| 5244 | AMLSR | 2 |
| 5094 | ANLHR | 2 |
| 2802 | AVLKR | 2 |
| 5108 | GMLER | 2 |
| 5245 | GMLKN | 2 |
| 5246 | GMLRW | 2 |
| 5247 | GMVRR | 2 |
| 2600 | GSLRR | 2 |
| 2921 | GVLRR | 2 |
| 3039 | HILKR | 2 |
| 5248 | HILRR | 2 |

TABLE 23-continued

ZF4 selection on G:C change at nt 11 of core motif in CBS. Sequences reflect position 2 to 6.

| SEQ ID NO: | Sequence | Read # |
|---|---|---|
| 5249 | HMLRS | 2 |
| 3040 | HMLVR | 2 |
| 2558 | HNLRR | 2 |
| 56 | HTLRR | 2 |
| 5250 | MGLST | 2 |
| 5251 | NMLIR | 2 |
| 2628 | NTLKR | 2 |
| 2593 | QTLRR | 2 |
| 5252 | RMLKR | 2 |
| 5253 | RMLQR | 2 |
|  | RN*P... | 2 |
| 5254 | SMFKR | 2 |
| 2524 | SNLAR | 2 |
| 2850 | STLMR | 2 |
| 5255 | TLLRR | 2 |
| 5256 | TMIRR | 2 |
| 5257 | TMVRR | 2 |
| 5258 | VIKR... | 2 |
| 5259 | AKLQR | 1 |
| 3062 | ALLKR | 1 |
| 5260 | AMFRR | 1 |
| 5261 | AMIRR | 1 |
| 5262 | AMITR | 1 |
| 5263 | AMKTR | 1 |
| 5264 | AMLCR | 1 |
| 5265 | AMLHS | 1 |
| 5266 | AMLPR | 1 |
| 4674 | AMLR... | 1 |
| 3519 | AMLRG | 1 |
| 5267 | AMLRK | 1 |
| 5268 | AMLTM | 1 |
| 5269 | AMLWR | 1 |
| 5270 | AMYT... | 1 |
| 2542 | ANLAR | 1 |
| 5271 | ARLRR | 1 |
| 4682 | ARLRS | 1 |
| 1947 | ARLRV | 1 |
| 3251 | ASLNR | 1 |
| 2878 | ATLER | 1 |
| 3025 | ATLGR | 1 |
| 5159 | ATLRS | 1 |
| 2772 | ATLSR | 1 |
| 5272 | CMLRR | 1 |
| 2640 | DMLKR | 1 |
| 3078 | DMLQR | 1 |
| 5273 | DMVKR | 1 |
| 5274 | EMLNS | 1 |
| 2539 | ETLRR | 1 |
| 5275 | GLLKR | 1 |
| 5276 | GLLQS | 1 |
| 5277 | GLLSR | 1 |
| 5278 | GMIKR | 1 |
| 5279 | GMLKT | 1 |
| 5280 | GMLRM | 1 |
| 5281 | GMLTW | 1 |
| 2746 | GNLHR | 1 |
| 2517 | GNLLR | 1 |
| 5282 | GRLKR | 1 |
| 5283 | GRLKS | 1 |
| 5284 | GRLRV | 1 |
| 2747 | GTLNR | 1 |
| 2626 | GTLVR | 1 |
| 3001 | GVLKR | 1 |
| 2483 | HALRR | 1 |
| 2531 | HLLKR | 1 |
| 5285 | HLLNS... | 1 |
| 5286 | HMLLR | 1 |
| 5287 | HMLMR | 1 |
| 5288 | HMVRR | 1 |

TABLE 23-continued

ZF4 selection on G:C change at nt 11 of core motif in CBS. Sequences reflect position 2 to 6.

| SEQ ID NO: | Sequence | Read # |
|---|---|---|
| 5106 | HNLMR | 1 |
| 2784 | HVLKR | 1 |
| 5189 | KILGN | 1 |
| 5289 | KMLKR | 1 |
| 5290 | LMLGK | 1 |
| 5291 | MLRR | 1 |
| 5292 | NLLKR | 1 |
| 5293 | NMLGR | 1 |
| 5294 | NTFRR | 1 |
| 2939 | NTLIR | 1 |
| 2940 | NTLNR | 1 |
| 5295 | PMLMR | 1 |
| 5296 | PVVKR | 1 |
| 2692 | QSLKR | 1 |
| 5297 | RMFRR | 1 |
| 5298 | RMLRR | 1 |
| 2956 | SALNR | 1 |
| 2523 | SALRR | 1 |
| 2464 | SGLRR | 1 |
| 3004 | SILKR | 1 |
| 3470 | SKLKR | 1 |
| 5201 | SKLTR | 1 |
| 5299 | SLLNR | 1 |
| 5300 | SMFRR | 1 |
| 5301 | SMIKR | 1 |
| 5302 | SMLGR | 1 |
| 5303 | SMLKW | 1 |
| 5304 | SMSRR | 1 |
| 5305 | SMVKR | 1 |
| 2496 | SNLLR | 1 |
| 5090 | SNLNR | 1 |
| 2792 | SQLKR | 1 |
| 1876 | SRLKR | 1 |
| 5306 | SRLRR | 1 |
| 2845 | SSLAR | 1 |
| 2698 | STLVR | 1 |
| 2699 | SVLKR | 1 |
| 5307 | TILRR | 1 |
| 5308 | TMLER | 1 |
| 5309 | TMLGR | 1 |
| 5310 | TMLHR | 1 |
| 5311 | TMLLR | 1 |
| 5312 | TMLRH | 1 |
| 5313 | TMLWR | 1 |
| 2595 | TNLKR | 1 |
| 2856 | TNLSR | 1 |
| 5215 | TPTRS | 1 |
| 5314 | VMLKR | 1 |
| 5315 | VSLRK | 1 |
| 2997 | VTLRR | 1 |
| 5316 | WMLKR | 1 |
| 5317 | WMLRR | 1 |
| 5318 | YMLKR | 1 |
| 5319 | YMLRR | 1 |

TABLE 24

ZF4 selection on G:T change at nt 11 of core motif in CBS. Sequences reflect position 2 to 6.

| SEQ ID NO: | Sequence | Read # |
|---|---|---|
| 66 | ATLRR | 6399 |
| 67 | RRLDR | 1155 |
| 2584 | GTLRR | 1073 |
| 2737 | TTLRR | 1024 |
| 2638 | STLRR | 970 |
| 3017 | ATLNR | 770 |
| 2739 | ATLVR | 727 |

TABLE 24-continued

ZF4 selection on G:T change at nt 11 of core motif in CBS. Sequences reflect position 2 to 6.

| SEQ ID NO: | Sequence | Read # |
|---|---|---|
| 48 | ATLKR | 708 |
| 2587 | NTLRR | 670 |
| 2538 | AALRR | 657 |
| 2801 | ATLMR | 456 |
| 2654 | ATLAR | 418 |
| 2554 | GTLKR | 399 |
| 2875 | ASLRR | 366 |
| 2622 | ATLTR | 363 |
| 2593 | QTLRR | 298 |
| 2539 | ETLRR | 292 |
| 2881 | ATLQR | 291 |
| 2879 | ATLIR | 261 |
| 2153 | STLKR | 252 |
| 2628 | NTLKR | 237 |
| 56 | HTLRR | 227 |
| 2882 | AVLRR | 208 |
| 2880 | ATLLR | 171 |
| 1985 | AALKR | 141 |
| 2878 | ATLER | 134 |
| 3012 | ATLHR | 130 |
| 2860 | TTLKR | 125 |
| 2509 | ASLKR | 95 |
| 73 | AMLRR | 93 |
| 3010 | HVLRR | 81 |
| 2523 | SALRR | 63 |
| 5248 | HILRR | 60 |
| 74 | TMLRR | 59 |
| 2967 | STLNR | 58 |
| 2131 | SALKR | 47 |
| 2738 | AALNR | 46 |
| 2483 | HALRR | 44 |
| 2641 | GALRR | 41 |
| 2843 | QTLKR | 41 |
| 2783 | HTLKR | 39 |
| 3032 | SMLKR | 39 |
| 1930 | HALKR | 36 |
| 2970 | SVLRR | 36 |
| 2802 | AVLKR | 35 |
| 2556 | SMLRR | 34 |
| 3161 | GMLRR | 33 |
| 2722 | GMLKR | 31 |
| 2850 | STLMR | 31 |
| 2698 | STLVR | 31 |
| 2626 | GTLVR | 28 |
| 2521 | GALKR | 27 |
| 2747 | GTLNR | 27 |
| 2590 | TTLQR | 27 |
| 2921 | GVLRR | 25 |
| 118 | GNLRR | 24 |
| 116 | SNLRR | 24 |
| 2589 | TSLRR | 24 |
| 69 | ANLRR | 23 |
| 2997 | VTLRR | 23 |
| 2700 | AALTR | 22 |
| 71 | AMLKR | 22 |
| 2697 | STLQR | 22 |
| 5320 | ATLRK | 21 |
| 117 | GNLVR | 21 |
| 2823 | HMLRR | 20 |
| 2772 | ATLSR | 17 |
| 5321 | RTLQR | 17 |
| 2734 | TALRR | 17 |
| 2819 | GSLKR | 16 |
| 3018 | STLIR | 16 |
| 2717 | AALQR | 15 |
| 2800 | ASLVR | 15 |
| 2849 | STLHR | 15 |
| 2489 | SSLRR | 14 |
| 2978 | TMLKR | 14 |

TABLE 24-continued

ZF4 selection on G:T change at nt 11 of core motif in CBS. Sequences reflect position 2 to 6.

| SEQ ID NO: | Sequence | Read # |
|---|---|---|
| 3075 | TVLRR | 14 |
| 2876 | ASLTR | 13 |
| 3081 | GTLMR | 13 |
| 2047 | HMLKR | 13 |
| 2966 | STLLR | 13 |
| 2762 | STLTR | 13 |
| 2681 | TTLNR | 13 |
| 70 | GNLTR | 12 |
| 5189 | KILGN | 12 |
| 68 | TNLRR | 11 |
| 3864 | ARLRI | 10 |
| 2502 | ETLKR | 10 |
| 2600 | GSLRR | 10 |
| 2684 | GTLAR | 10 |
| 5322 | KTLER | 10 |
| 5323 | QTLMR | 10 |
| 3028 | SILRR | 10 |
| 5085 | SNLKR | 10 |
| 2617 | TALKR | 10 |
| 2799 | ASLQR | 9 |
| 3001 | GVLKR | 9 |
| 121 | NNLRR | 9 |
| 2877 | ATLDR | 8 |
| 138 | GNLAR | 8 |
| 2914 | GNLIR | 8 |
| 5324 | KTLQR | 8 |
| 5325 | RTLRR | 8 |
| 5102 | SMLQR | 8 |
| 2965 | SSLKR | 8 |
| 1947 | ARLRV | 7 |
| 2607 | GALVR | 7 |
| 5139 | GTLIR | 7 |
| 2784 | HVLKR | 7 |
| 3067 | MTLRR | 7 |
| 5086 | SNLTR | 7 |
| 2582 | SNLVR | 7 |
| 2620 | ANLKR | 6 |
| 119 | GNLKR | 6 |
| 5326 | HILNR | 6 |
| 5327 | MTLMR | 6 |
| 2770 | AALVR | 5 |
| 5107 | AMLQR | 5 |
| 2609 | GNLQR | 5 |
| 2940 | NTLNR | 5 |
| 3027 | NTLVR | 5 |
| 3196 | QTLTR | 5 |
| 5328 | RTLKR | 5 |
| 2666 | SALTR | 5 |
| 2699 | SVLKR | 5 |
| 5104 | AMLTR | 4 |
| 2621 | ANLNR | 4 |
| 2494 | ANLVR | 4 |
| 5158 | APLRR | 4 |
| 3025 | ATLGR | 4 |
| 5329 | ATVRR | 4 |
| 2530 | DTLRR | 4 |
| 3160 | GILRR | 4 |
| 5122 | GMLNR | 4 |
| 3033 | GTLLR | 4 |
| 2707 | GTLQR | 4 |
| 5330 | GVLSR | 4 |
| 5331 | HRLKI | 4 |
| 2830 | HTLVR | 4 |
| 5332 | KTLIR | 4 |
| 5238 | KTLRR | 4 |
| 5087 | NNLKR | 4 |
| 2756 | NSLRR | 4 |
| 2939 | NTLIR | 4 |
| 2677 | SMLTR | 4 |

TABLE 24-continued

ZF4 selection on G:T change at nt 11 of core motif in CBS. Sequences reflect position 2 to 6.

| SEQ ID NO: | Sequence | Read # |
|---|---|---|
| 2524 | SNLAR | 4 |
| 2963 | SNLQR | 4 |
| 2550 | STLAR | 4 |
| 5333 | TILAR | 4 |
| 2766 | TSLKR | 4 |
| 2857 | TTLAR | 4 |
| 2618 | TTLMR | 4 |
| 3117 | AILRR | 3 |
| 5089 | ANLMR | 3 |
| 3090 | ASLAR | 3 |
| 5334 | ASLHR | 3 |
| 5335 | ATLNK | 3 |
| 5336 | ATLRG | 3 |
| 2583 | EALRR | 3 |
| 3049 | GILKR | 3 |
| 5123 | GMLTR | 3 |
| 2706 | GNLNR | 3 |
| 4375 | GPLPV | 3 |
| 5337 | GPLVR | 3 |
| 3245 | GSLSR | 3 |
| 72 | HMLTR | 3 |
| 2827 | HSLRR | 3 |
| 5338 | HVLNR | 3 |
| 5339 | NSLKR | 3 |
| 5340 | NTLMR | 3 |
| 5341 | NVLRR | 3 |
| 2950 | QTLQR | 3 |
| 5342 | RRLNR | 3 |
| 2956 | SALNR | 3 |
| 3292 | SALQR | 3 |
| 2733 | SVLTR | 3 |
| 1986 | AGLKR | 2 |
| 2475 | AGLRR | 2 |
| 1988 | AGLVR | 2 |
| 5150 | AMLHR | 2 |

TABLE 24-continued

ZF4 selection on G:T change at nt 11 of core motif in CBS. Sequences reflect position 2 to 6.

| SEQ ID NO: | Sequence | Read # |
|---|---|---|
| 5151 | AMLIR | 2 |
| 5343 | ARLKI | 2 |
| 3251 | ASLNR | 2 |
| 3244 | ASLSR | 2 |
| 5344 | ATFRR | 2 |
| 5345 | ATLNW | 2 |
| 5346 | ATLRW | 2 |
| 2634 | ESLRR | 2 |
| 3151 | ETLVR | 2 |
| 2778 | GALNR | 2 |
| 2815 | GALQR | 2 |
| 5124 | GMLVR | 2 |
| 2517 | GNLLR | 2 |
| 3230 | HALTR | 2 |
| 5141 | HMLNR | 2 |
| 2558 | HNLRR | 2 |
| 2586 | HTLMR | 2 |
| 2613 | HTLQR | 2 |
| 5347 | IALAG | 2 |
| 5348 | MSLRR | 2 |
| 5349 | MTLLR | 2 |
| 5350 | MTLVR | 2 |
| 3407 | NGRSPV... | 2 |
| 2664 | NMLKR | 2 |
| 2712 | NMLRR | 2 |
| 3191 | PTLRR | 2 |
| 5351 | QRLSV | 2 |
| 4424 | RPLVG | 2 |
| 5352 | RRIDR | 2 |
| 5353 | RRLDS | 2 |
| 5354 | RRVDR | 2 |
| 5355 | RSLIR | 2 |
| 5356 | RTLIR | 2 |
| 5357 | SDLTV | 2 |

TABLE 24-continued

ZF4 selection on G:T change at nt 11 of core motif in CBS. Sequences reflect position 2 to 6.

| SEQ ID NO: | Sequence | Read # |
|---|---|---|
| 2962 | SMLHR | 2 |
| 5358 | SRLKI | 2 |
| 2564 | SSLVR | 2 |
| 5359 | STVRR | 2 |
| 2651 | TTLTR | 2 |
| 2767 | TTLVR | 2 |
| 57 | TVLKR | 2 |
| 2546 | AALAR | 1 |
| 2864 | AALLR | 1 |
| 5360 | AALNS | 1 |
| 3367 | AALRK | 1 |
| 3410 | AALRL | 1 |
| 5147 | AALRS | 1 |
| 5361 | AAVRR | 1 |
| 5259 | AKLQR | 1 |
| 3510 | AKLRR | 1 |
| 3062 | ALLKR | 1 |
| 5149 | AMLAR | 1 |
| 5132 | AMLNR | 1 |
| 5218 | AMLVR | 1 |
| 5094 | ANLHR | 1 |
| 5092 | ANLQR | 1 |
| 5091 | ANLTR | 1 |
|  | AP*C... | 1 |
| 5362 | APLHR | 1 |
| 5363 | APLKR | 1 |
| 5364 | APLMR | 1 |
| 5365 | APLVR | 1 |
| 5366 | APYP... | 1 |
| 5271 | ARLRR | 1 |
| 2874 | ARLTR | 1 |
| 5367 | ARLVG | 1 |
| 5368 | ASFRR | 1 |
| 5369 | ASLER | 1 |
| 3250 | ASLMR | 1 |
|  | AT*G... | 1 |
| 5370 | ATFKR | 1 |
| 5371 | ATFRT | 1 |
| 5372 | ATFTR | 1 |
| 5373 | ATIRR | 1 |
| 5374 | ATLES | 1 |
| 5375 | ATLFR | 1 |
| 5376 | ATLHW | 1 |
| 5377 | ATLIS | 1 |
| 5378 | ATLNH | 1 |
| 5379 | ATLNS | 1 |
| 5380 | ATLQG | 1 |
| 5381 | ATLQW | 1 |
| 5382 | ATLRI | 1 |
| 5383 | ATLRP | 1 |
| 5384 | ATLWR | 1 |
| 5385 | ATSVR | 1 |
| 5386 | ATVAR | 1 |
| 5387 | AVLGR | 1 |
| 5388 | AVLLR | 1 |
| 5389 | AVLNR | 1 |
| 3121 | AVLTR | 1 |
| 3991 | DKLRR | 1 |
| 2640 | DMLKR | 1 |
| 5390 | DRLRA | 1 |
| 2656 | DTLNR | 1 |
| 5391 | EPLVM | 1 |
| 3038 | ETLAR | 1 |
| 3043 | ETLQR | 1 |
| 2592 | GALTR | 1 |
| 2816 | GDLRR | 1 |
| 2913 | GMLAR | 1 |
| 139 | GNLMR | 1 |
| 5392 | GPFKR | 1 |
| 5393 | GPLGL | 1 |

TABLE 24-continued

ZF4 selection on G:T change at nt 11 of core motif in CBS. Sequences reflect position 2 to 6.

| SEQ ID NO: | Sequence | Read # |
|---|---|---|
| 5394 | GPLKR | 1 |
| 5395 | GSLGA | 1 |
| 2781 | GSLQR | 1 |
| 2660 | GSLTR | 1 |
| 5396 | GTFRR | 1 |
| 3014 | GTLDR | 1 |
| 2917 | GTLER | 1 |
| 2918 | GTLGR | 1 |
| 5397 | GTLMW | 1 |
| 5398 | GTLRK | 1 |
| 2562 | GTLTR | 1 |
| 386 | GTLVS | 1 |
| 5399 | GTSNR | 1 |
| 5400 | GTSRR | 1 |
| 5401 | GVLRK | 1 |
| 5402 | GVVRR | 1 |
| 2749 | HALMR | 1 |
| 3246 | HALQR | 1 |
| 3039 | HILKR | 1 |
| 5403 | HILQR | 1 |
| 2578 | HTLAR | 1 |
| 2689 | HTLLR | 1 |
| 2828 | HTLNR | 1 |
| 3180 | HTLRG | 1 |
| 3181 | HTLSR | 1 |
| 3099 | HVLHR | 1 |
| 5404 | KTLLR | 1 |
| 5405 | KTLVR | 1 |
| 5406 | MALRM | 1 |
| 5407 | MPLAR | 1 |
| 4452 | MPLNR | 1 |
| 5408 | MPLVR | 1 |
|  | MRS | 1 |
| 2833 | MTLKR | 1 |
| 4923 | NRLRI | 1 |

TABLE 24-continued

ZF4 selection on G:T change at nt 11 of core motif in CBS. Sequences reflect position 2 to 6.

| SEQ ID NO: | Sequence | Read # |
|---|---|---|
| 2788 | NTLAR | 1 |
| 2837 | NTLHR | 1 |
| 3015 | NTLLR | 1 |
| 2941 | NTLQR | 1 |
| 5409 | NTLRW | 1 |
| 3006 | NTLTR | 1 |
| 5410 | NTLVS | 1 |
| 5411 | NTVRR | 1 |
| 2942 | NVLKR | 1 |
| 5412 | PPLKR | 1 |
| 5413 | PSLKR | 1 |
| 5414 | PTFHR | 1 |
| 5415 | QKLA... | 1 |
| 2574 | QMLKR | 1 |
| 2692 | QSLKR | 1 |
| 3195 | QTLHR | 1 |
| 5416 | QTLIR | 1 |
| 5417 | QTLRQ | 1 |
| 3248 | QTLVR | 1 |
|  | RN*P... | 1 |
| 5418 | RRLAG | 1 |
| 5419 | RRLAR | 1 |
| 5420 | RRLDG | 1 |
| 5421 | RRLHR | 1 |
| 5422 | RRLVR | 1 |
| 5423 | RRSDR | 1 |
| 5424 | RRVEK | 1 |
| 5425 | RTLER | 1 |
| 5426 | RTLNR | 1 |
| 5427 | RTLRG | 1 |
| 5428 | SAVKR | 1 |
| 2559 | SGLKR | 1 |
| 5201 | SKLTR | 1 |
| 2647 | SMLIR | 1 |
| 5145 | SMLNR | 1 |

TABLE 24-continued

ZF4 selection on G:T change at nt 11 of core motif in CBS. Sequences reflect position 2 to 6.

| SEQ ID NO: | Sequence | Read # |
|---|---|---|
| 5304 | SMSRR | 1 |
| 5088 | SNLIR | 1 |
| 5429 | SPLRR | 1 |
| 5430 | SRLRI | 1 |
| 5431 | STLCR | 1 |
| 2848 | STLER | 1 |
| 5432 | STLKS | 1 |
| 5433 | STLRI | 1 |
| 5434 | STSRR | 1 |
| 5435 | SVLRK | 1 |
| 5436 | TALIR | 1 |
| 5437 | TALMR | 1 |
| 2764 | TALTR | 1 |
| 5146 | TMLQR | 1 |
| 5438 | TMLRG | 1 |
| 5131 | TNLIR | 1 |
| 2595 | TNLKR | 1 |
| 5439 | TPIMM | 1 |
| 5215 | TPTRS | 1 |
| 1883 | TRLRV | 1 |
| 5440 | TRSP... | 1 |
| 2858 | TTLGR | 1 |
| 2859 | TTLIR | 1 |
| 5441 | TTLRS | 1 |
| 5442 | TVLNR | 1 |
| 3308 | VSLRR | 1 |
| 2995 | VTLKR | 1 |
| 5443 | VTLQR | 1 |
| 5444 | VVLGN | 1 |
| 5445 | WRLDR | 1 |
| 5446 | WTLRR | 1 |

TABLE 25

ZF3 selection on G:A change at nt 13 of core motif in CBS. Sequences reflect position 2 to 6.

| SEQ ID NO: | Sequence | Read # |
|---|---|---|
| 81 | GQLTV | 1094 |
| 5447 | GQLVV | 906 |
| 78 | GELVV | 766 |
| 5448 | AELIV | 643 |
| 5449 | TELIV | 552 |
| 5450 | QELLV | 528 |
| 5451 | GELIV | 525 |
| 5452 | GELTV | 505 |
| 80 | GQLIV | 476 |
| 5453 | QELLT | 457 |
| 5454 | SELIV | 416 |
| 5455 | GQLLV | 372 |
| 5456 | SGLIV | 372 |
| 5457 | GQLII | 361 |
| 5458 | AELLV | 311 |
| 5459 | VELLI | 277 |
| 5460 | AELVV | 271 |
| 5461 | AQLIV | 267 |
| 76 | SQLIV | 265 |
| 82 | TELII | 251 |
| 83 | QGLLV | 247 |
| 5462 | SQLII | 243 |
| 79 | QQLLI | 224 |
| 5463 | AGLIV | 221 |
| 5464 | QELVV | 209 |
| 5465 | GELLV | 206 |
| 86 | GELLT | 202 |
| 5466 | SQLLV | 199 |
| 5467 | GELVI | 194 |
| 75 | QQLIV | 179 |
| 5468 | QELII | 177 |
| 5469 | TQLIV | 176 |
| 5470 | VELII | 172 |
| 5471 | VELLV | 160 |
| 5472 | GELLI | 151 |

TABLE 25-continued

ZF3 selection on G:A change at nt 13 of core motif in CBS. Sequences reflect position 2 to 6.

| SEQ ID NO: | Sequence | Read # |
|---|---|---|
| 85 | GQLLT | 150 |
| 5473 | NELLI | 149 |
| 5474 | GQLLI | 148 |
| 5475 | SQLLI | 140 |
| 5476 | AQLLV | 136 |
| 5477 | GQLIT | 132 |
| 5478 | GQLTI | 129 |
| 5479 | TELIT | 122 |
| 5480 | TELLI | 118 |
| 5481 | TELLV | 116 |
| 5482 | QELLI | 112 |
| 5483 | AQLVV | 106 |
| 5484 | GSLLV | 104 |
| 5485 | AQLLI | 102 |
| 5486 | HPPEE | 100 |
| 5487 | SQLVV | 100 |
| 77 | QQLLV | 98 |
| 5488 | QELIV | 95 |
| 5489 | SELII | 91 |
| 5490 | AQLII | 90 |
| 5491 | QQLVV | 90 |
| 5492 | TGLLV | 88 |
| 5493 | NQLII | 88 |
| 5494 | GQLVI | 81 |
| 5495 | AGLLV | 80 |
| 5496 | NQLLV | 73 |
| 5497 | QELGV | 69 |
| 5498 | GALVV | 68 |
| 5499 | SQLTV | 67 |
| 5500 | GELTT | 67 |
| 5501 | GELII | 65 |
| 3710 | SGLLV | 63 |
| 5502 | AELII | 60 |
| 5503 | TQLII | 59 |
| 5504 | QQLII | 59 |
| 5505 | AQLIT | 58 |
| 5506 | SQLIT | 58 |
| 5507 | SSLIV | 57 |
| 5508 | SELTV | 57 |
| 5509 | NELLV | 57 |
| 5510 | TQLLV | 56 |
| 5511 | QGLIV | 55 |
| 5512 | QELVI | 55 |
| 5513 | NELIV | 55 |
| 5514 | TELLT | 53 |

TABLE 26

ZF3 selection on G:T change at nt 13 of core motif in CBS. Sequences reflect position 2 to 6.

| SEQ ID NO: | Sequence | Read # |
|---|---|---|
| 79 | QQLLI | 1145 |
| 5452 | GELTV | 1108 |
| 81 | GQLTV | 933 |
| 5474 | GQLLI | 748 |
| 5447 | GQLVV | 545 |
| 5457 | GQLII | 518 |
| 80 | GQLIV | 479 |
| 78 | GELVV | 477 |
| 5515 | GELIT | 438 |
| 5466 | SQLLV | 432 |
| 5462 | SQLII | 431 |
| 85 | GQLLT | 404 |
| 5516 | SQLSM | 365 |
| 84 | QQLLT | 349 |
| 75 | QQLIV | 312 |
| 5486 | HPPEE | 308 |

TABLE 26-continued

ZF3 selection on G:T change at nt 13 of core motif in CBS. Sequences reflect position 2 to 6.

| SEQ ID NO: | Sequence | Read # |
|---|---|---|
| 5453 | QELLT | 300 |
| 5475 | SQLLI | 282 |
| 4773 | GKLNA | 281 |
| 5451 | GELIV | 263 |
| 5455 | GQLLV | 225 |
| 76 | SQLIV | 219 |
| 5517 | RALLI | 216 |
| 5518 | ENLLI | 201 |
| 5476 | AQLLV | 174 |
| 5519 | PDLKR | 174 |
| 86 | GELLT | 172 |
| 5505 | AQLIT | 164 |
| 5520 | GQLVT | 138 |
| 5521 | GQLLS | 116 |
| 5450 | QELLV | 112 |
| 5522 | GELNP | 112 |
| 5523 | GQLIQ | 98 |
| 5524 | PTLVG | 98 |
| 5525 | LVLAD | 95 |
| 5526 | EALRA | 94 |
| 5467 | GELVI | 87 |
| 1926 | STLKA | 87 |
| 5494 | GQLVI | 85 |
| 5463 | AGLIV | 82 |
| 5527 | GQLTL | 82 |
| 5528 | NVLGT | 81 |
| 5529 | KGLGP | 79 |
| 5530 | MQLRR | 79 |
| 3026 | GDLQR | 75 |
| 5531 | VLLPN | 71 |
| 5532 | MRLGD | 69 |
| 5533 | GQLAQ | 67 |
| 4074 | NELRG | 67 |
| 5500 | GELTT | 66 |

TABLE 26-continued

ZF3 selection on G:T change at nt 13 of core motif in CBS. Sequences reflect position 2 to 6.

| SEQ ID NO: | Sequence | Read # |
|---|---|---|
| 5534 | GELVT | 64 |
| 333 | STLVV | 63 |
| 5535 | VDLAV | 61 |
| 5536 | AQLTI | 59 |
| 5537 | DALPA | 57 |
| 5538 | SVLQL | 57 |
| 5539 | GPLGN | 56 |
| 5540 | GHLLL | 52 |
| 5541 | DVLDP | 51 |
| 5542 | SSLSI | 50 |
| 5543 | KM LAD | 50 |

TABLE 27

ZF3 selection on G:C change at nt 13 of core motif in CBS. Sequences reflect position 2 to 6.

| SEQ ID NO: | Sequence | # Reads |
|---|---|---|
| 173 | RKHD | 4641 |
| 175 | RKAD | 1938 |
| 174 | RRSD | 1299 |
| 681 | RRHD | 868 |
| 682 | RKTD | 182 |
| 683 | NVSM | 146 |
| 684 | RQSD | 76 |
| 685 | RKND | 69 |
| 686 | SENV | 69 |
| 687 | VDHR | 60 |
| 688 | AQIV | 58 |
| 689 | KTPH | 56 |
| 690 | PKIV | 51 |
| 691 | GAEP | 42 |
| 692 | MLVE | 40 |
| 693 | VVGN | 40 |

TABLE 27-continued

ZF3 selection on G:C change at nt 13 of core motif in CBS. Sequences reflect position 2 to 6.

| S

TABLE 27-continued

ZF3
selection on G:C
change at nt 13 of
core motif in CBS.
Sequences reflect
position 2 to 6.

| SEQ ID NO: | Sequence | # Reads |
|---|---|---|
| 762 | SSHD | 1 |
| 763 | TTHV | 1 |
| 764 | VHHV | 1 |
| 765 | WKAD | 1 |
| 766 | WKHD | 1 |

REFERENCES

1. Ong, Chin-Tong & Corces, V. P., *Nat Rev Genet.* 2014 April; 15(4):234-46.
2. Phillips, J. & Corces, V. P., *Cell.* 2009 Jun. 26; 137(7): 1194-1211.
3. Ali, T. et al., *Curr Opin Genet Dev.* 2016 April; 37:17-26.
4. Nora, E. P. et al., *Nature.* 2012 Apr. 11; 485(7398):381-5.
5. Rao, S. S. et al., *Cell.* 2014 Dec. 18; 159(7): 1665-1680.
6. Phillip, J., et al., *Cell.* 2013 Jun. 6; 153(6): 1281-1295.
7. Shukla, S., et al., *Nature.* 2011 Nov. 3; 479(7371):74-9.
8. Hilmi, K., et al. *Sci Adv.* 2017 May 24; 3(5):e1601898.
9. Han, D., et al. *Sci Rep.* 2017 Mar. 6; 7:43530.
10. Rhee, S., & Pugh, F. B., *Cell.* 2011 Dec. 9; 147(6):1408-19.
11. Nakahashi, H., et al., *Cell Rep.* 2013 May 30; 3(5):1678-1689.
12. Hashimoto, et al., *Mol Cell.* 2017 Jun. 1; 66(5):711-720.e3.
13. Guo, A. et al., *Nat Commun.* 2018 Apr. 18; 9(1):1520.
14. Schuijers, J. et al., *Cell Reports* (2018). *Cell Rep.* 2018 Apr. 10; 23(2):349-360.
15. Kang, J. Y. et al., *Oncogene.* 2015 Nov. 5; 34(45):5677-84.
16. Wright, D., et al. *Nat Protoc.* 2006; 1(3):1637-52.
17. Sander, J., et al. *Nat Methods.* 2011 January; 8(1):67-9.
18. Maeder, M., et al. *Mol Cell.* 2008 Jul. 25; 31(2):294-301.
19. Joung J. K. et al., *Proc Natl Acad Sci USA.* 2000 Jun. 20; 97(13):7382-7.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11041155B2). An electronic copy of the "Sequence Listing" will also be available from the USPTO upon request and payment of the fee set forth in 37 CFR 1.19(b)(3).

What is claimed is:

1. An engineered CCCTC-binding factor (CTCF) variant comprising at least one amino acid residue in at least one zinc finger that differs in sequence from the amino acid sequence of a wild-type CTCF, wherein the engineered CTCF variant binds to a mutant CTCF binding sequence (CBS) with a higher affinity than wild-type CTCF,
    wherein the mutant CBS has G, G, and A residues at positions 2, 5, and 11 of the consensus CBS motif, respectively, and the engineered CTCF comprises:
       (i) the amino acid sequence GNLVR (SEQ ID NO: 117), GNLRR (SEQ ID NO: 118), GNLAR (SEQ ID NO: 138), GNLMR (SEQ ID NO: 139), ANLRR (SEQ ID NO: 69), SNLRR (SEQ ID NO: 116), or NNLRR (SEQ ID NO: 121) at ZF4 positions +2 to +6 of the engineered CTCF;
       (ii) the amino acid sequence EHMNR (SEQ ID NO: 126), EHMKR (SEQ ID NO: 123), EHMRR (SEQ ID NO: 34), SHMNR (SEQ ID NO: 146), SHMRR (SEQ ID NO: 147), THMKR (SEQ ID NO: 33), or DHMNR (SEQ ID NO: 32) at ZF6 positions +2 to +6 of the engineered CTCF; and
       (iii) the amino acid sequence EHLKV (SEQ ID NO: 13), EHLAE (SEQ ID NO: 151), STLNE (SEQ ID NO: 152), DHLQV (SEQ ID NO: 12), EHLNV (SEQ ID NO: 9), DHLNT (SEQ ID NO: 155), EHLQA (SEQ ID NO: 156), or HHLMH (SEQ ID NO: 157) at ZF7 positions +2 to +6 of the engineered CTCF.

2. A pharmaceutical composition comprising an engineered CTCF variant according to claim 1.

3. A gene expression system for regulation of a gene, the system comprising a nucleic acid encoding an engineered CTCF variant according to claim 1.

4. A kit comprising an engineered CTCF variant according to claim 1.

5. A nucleic acid encoding an engineered CTCF variant according to claim 1.

6. A method of altering expression of a gene under the control of a mutant CBS, wherein the mutant CBS has G, G, and A residues at positions 2, 5, and 11 of the consensus CBS motif, respectively, the method comprising contacting the mutant CBS with an engineered CTCF according to claim 1, thereby regulating the expression of the gene.

* * * * *

UNITED STATES PATENT AND TRADEMARK OFFICE
CERTIFICATE OF CORRECTION

PATENT NO. : 11,041,155 B2
APPLICATION NO. : 16/415989
DATED : June 22, 2021
INVENTOR(S) : Rebecca Tayler Cottman and J. Keith Joung It is certified that error appears in the above-identified patent and that said Letters Patent is hereby corrected as shown below:

In the Specification

In Column 1, Line 15 (approx.), delete "Grant No. GM118158" and insert -- Grant Nos. GM118158 and HG009490 --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*